(12) United States Patent
Iwahashi et al.

(10) Patent No.: US 7,704,692 B1
(45) Date of Patent: Apr. 27, 2010

(54) PROCESS FOR DETECTING TOXIC SUBSTANCES

(75) Inventors: Hitoshi Iwahashi, Tsukuba (JP); Yuko Momose, Tsukuba (JP); Emiko Kitagawa, Tsukuba (JP); Junko Takahashi, Tsukuba (JP)

(73) Assignee: Daiken Industries, Ltd., Osaka-shi, Osaka-fu (JP)

( * ) Notice: Subject to any disclaimer, the term of this patent is extended or adjusted under 35 U.S.C. 154(b) by 302 days.

(21) Appl. No.: 11/758,288

(22) Filed: Jun. 5, 2007

Related U.S. Application Data

(62) Division of application No. 10/487,438, filed as application No. PCT/JP02/08495 on Aug. 23, 2002, now abandoned.

(30) Foreign Application Priority Data

Aug. 24, 2001 (JP) .............................. 2001-255379

(51) Int. Cl.
C12Q 1/64 (2006.01)
(52) U.S. Cl. ......................................... 435/6
(58) Field of Classification Search ........................ None
See application file for complete search history.

(56) References Cited

FOREIGN PATENT DOCUMENTS

| JP | 2001-286281 A | 10/2001 |
|---|---|---|
| JP | 3446042 B2 | 7/2003 |
| WO | WO 99/09202 A1 | 2/1999 |
| WO | WO-00/58520 A1 | 10/2000 |
| WO | WO-01/38549 | 5/2001 |

OTHER PUBLICATIONS

Grigoryev et al. (Genome Biol. 2004;5(5):R34. Epub Apr. 27, 2004).*
Database EMBL (online) (May 10, 1994), "S. cerevisiae chromosome XI reading frame ORF YKL071w" XP002317607 retrieved from EBI accession No. EM_PRO:SCYKL071W Database accession No. SCYKL071W.
Database Swissprot, accession No. P15992, sequence updated. Nov. 1, 1990.
Database EMBL, Online Hsp26p, (Saccharomyces cerevisiae), Feb. 25, 2005, XP002319286, Database accession No. NP_009628.
Emiko Kitagawa et al., Environ. Sci. Technol., vol. 36, (2002), pp. 3908-3915.
Audrey P. Gasch et al., Molecular Biology of the Cell, vol. 11, (Dec. 2000), pp. 4243-4257.
K. Fujita et al., Wat. Res., vol. 30, No. 9, (1996), pp. 2102-2106.
Momose et al., Chem-Bio Informatics Journal, vol. 1, No. 1, pp. 41-50 (2001).
Iwahashi et al., Applied and Environmental Microbiology, vol. 66, No. 12, p. 5182-5185 (Dec. 2000).
Iwahashi, Biotechnol. Bioprocess Eng., vol. 5, pp. 400-406 (2000).
Prein, B. et al., "A novel strategy for constructing N-terminal chromosomal fusions to green fluorescent protein in the yeast *Saccharomyces cerevisiae*", FEBS Letters, 2000, Vo. 485, No. 1, pp. 29 to 34, abstract, Materials and Methods.
Casalone, E. et al., "Disruption and phenotypic analysis of six novel genes from chromosome IV of *Saccharomyces cerevisiae* revieal YDL060w as an essential gene for vegetative growth", Yeast, 1999, vol. 15, No. 15, pp. 1691 to 1701, abstract, table 1.
Sartori, G. et al., "Inactivation of six genes from chromosomes VII and XIV of *Saccharomyces cerevisiae* and basic phenotypic analysis of the mutant strains", Yeast, 2000, vol 16, No. 3, pp. 255 to 265, abstract, table 1.
Fujita, K. et al., "Hsp104 expression and morphological changes associated with disinfectants in *Saccharomyces cerevisiae*: Environmental bioassay using stress response", Water Science and Technology, 1998, vol. 38, No. 7, pp. 237 to 243, abstract.
Miura, S. et al,, "Screening of genes involved in Isooctane tolerance in *Saccharomyces cerevisiae* by suing MRNA differential display", Applied and Environmental Microbiology, 2000, vol. 66, No. 11, pp. 4883 to 4889, abstract.
Parry, J.M., "The use of yeast cultures for the detection of environmental mutagens using a fluctuation test", Mutation Research, 1977, vol. 46, No. 3, pp. 165 to 175, abstract.
Alberts, B. et al,, "Essential Cell Biology", New York: Garland Publishing, Inc., 1998, p. 323, Fig. 10-9.
Lashkari, D.A. et al., "Yeast microarrays for genome wide parallel genetic and gene expression analysis", Proc. Natl. Acad. Sci. USA, 1997, Vo. 94, pp. 13057 to 13062, abstract; table 1.
Genbank Accession No. NC_001144 (Nov. 1999).
Genbank Accession No. Z47973 (Jan. 1995).
Belli, G. et al., "Functional analysis of yeast essential genes using a promoter-substitution cassette and the tetracycline-regulatable dual expression system", Yeast, 1998, vol. 14, No. 12, pp. 1127 to 1138. abstract, table 3.
Huang, M.E., "Disruption of six novel yeast genes reveals three genes essential for vegetative growth and one required for growth at low temperature", Yeast, 1997, vol. 13, No. 12, pp. 1181 to 1194, abstract; table 2.
Gasch et al., Molecular Biology of the Cell, vol. 11, No. 12, pp. 4241-4257, (2000), XP-002259051.
Database EMBL (online), (1996), XP-002475245.
Foury et al., The Journal of Biological Chemistry, vol. 276, No. 11, pp. 7762-7768, (2000), XP-002475244.

* cited by examiner

*Primary Examiner*—Christopher M. Babic
(74) *Attorney, Agent, or Firm*—Birch, Stewart, Kolasch & Birch, LLP

(57) ABSTRACT

Biology-based processes for detecting toxic substances are provided. The processes comprise transforming cells with a vector comprising a polynucleotide which comprises a promoter of certain yeast gene operably linked to a polynucleotide encoding a marker protein; contacting the transformed cells to test sample; and detecting the expression of mRNA encoding the marker protein, thus detecting a toxic compound in the test sample.

4 Claims, No Drawings

SEQUENCE LISTING

<160> NUMBER OF SEQ ID NOS: 16

<210> SEQ ID NO 1
<211> LENGTH: 1682
<212> TYPE: DNA
<213> ORGANISM: Saccharomyces cerevisiae

<400> SEQUENCE: 1

```
cgcaataata ctggaaacat caacgaatgc tataataatg cgcatttact ttgggcaaaa      60
gaactattta aaattacgca ttacgtagtt tattttgaca ttatgatcat aaacatgcgc     120
aaatcctaag atcgtgaatt acctctactg cgagaataca aattataaca tatgactaac     180
gttacacaac attgtattac atttctgact aatttgaagt ctgggagtta attgtagtag     240
cctactaaat agcgcggtta tttataaagc taacattacc atgttacatg acatgctatt     300
tctagcgagg taaaagcatt gctccggctt ttcgaagata agtattcctt caatttccaa     360
atgtcacaac ataaaatttt gatttgcgtt atctctcgtt ctctttaatc actacaatag     420
catcaaccaa gtcaataaaa catgttgtga agagactacg cagacgtgac ggtcatctag     480
caactctcca tcttttgatg cagccatcca cagtttatcg tgagttatgg caaaatccaa     540
aaatgtaccg taccatttcc tctttaatcc tgtattcaat aagcaagttc cccatttcaa     600
ttgatctaca catcactgcg cgttaaagcg cacctaattt attcggtagg aaacagaaat     660
agtctgcaaa gtcattcaag cacctttctt taccaaatga aaggatttaa tagtacctat     720
gaaacaatag ttcgaacttt tgccatttcc cggtttttt ggccagcttg tataaaagtg     780
caccttaccc ttatattggg ctcttattga atgccttccg aagaactgac tattcaaaaa     840
atagaaacaa gtacgtcaat aaaaaatttt gcaattctac gaataattat tcctgtttct     900
ttaacctggt aaaaaaaagt acaaacactt aagctttttg aaacagcttt attttgcttc     960
attaaatagc taggataaga aatccctcat ccgaaaggtt ttgtatctaa ctaccctaga    1020
gaacatttgt cctgatcagg ttcatttgga gtttatattt tttagaagct caaagtttgt    1080
tggactcatt accatggaag aaaaaaagaa gatactacga aatattggtt tctcaggtta    1140
aataagggac accattttcc tattaggcta gtcgagctta gttcttctaa tttcttcaga    1200
tcttctataa tttcctatct tctacctgat gtgtgcatga tatatctatg agctcctgat    1260
attgcttgtt ttactttagc ttgcatgact tgcaataatc taatcatata tgttcccgat    1320
```

-continued

| | |
|---|---|
| taatatactg tgcacaaatt gcaggacata taattttttcc gtggattata tcttcgatta | 1380 |
| acgtccgcgg gtctcataaa aagcaaacca acttcgcaat tccctagaaa tacctcaata | 1440 |
| gaaagttatt tgtaatgaga ttagtaatga gattagcaat gagattagta atgagattag | 1500 |
| taatgagatt agtaatgtga ttagtaatgc atagcggtat aaatggtagt actaataagt | 1560 |
| aagatagtat accagttata ataaataggc ggcgatgctt caaaactaat ttttgacgtt | 1620 |
| tttaagaata aagcctttac cagtggcata atcagtaga attctaagca aacaaagtcg | 1680 |
| at | 1682 |

<210> SEQ ID NO 2
<211> LENGTH: 1072
<212> TYPE: DNA
<213> ORGANISM: Saccharomyces cerevisiae

<400> SEQUENCE: 2

| | |
|---|---|
| aggtgcgata gtggggaata agaattggaa atccgcttga taatcaggga aaacttaaag | 60 |
| aacgggtgt taaaagtctg tgaagtatag atcaaactcg cactagctag caatactcat | 120 |
| gagaacctag gtgagtgtaa agcagtgaac cttctttaga aagcagagaa aaatcctcca | 180 |
| agttaacagt cttccatact tactcagtat ggatcaagtt ccacagtttg tccacttctg | 240 |
| tagaataaac ttgtagtgct tttccgatga aaagggatag agtctttaaa agacttgatc | 300 |
| ttggcatttt tatcctcctt caagcagaat ggctccagta gagttgttct gaacgcttct | 360 |
| gggcagtgag cagcattgaa gaaaaagtac tcagcattcc aagctttgtc ttcatataat | 420 |
| tataaattaa aactcatagc caccaatttc caggttttgg tcgcaatatg ctgcagaatc | 480 |
| aatggcttgt ttcgttacta tactggtccg acggagttta cttactctaa atttgctgaa | 540 |
| atagcaaggc cacacgccat acaattaaca atagttcatt cagttgaaag gtttccgaga | 600 |
| tagaaagtgc ggtagtagag aagaacaata aacgtatcaa actttgcgca gtcatggaat | 660 |
| ttccaggaaa cattttttagg ttttcatatg acagcagttc ctgtccgaga gctgtgcctt | 720 |
| cttgtctcag ctgactaaga tgtctcggat ccgcccggct ggcgcgcggc tccgtctagt | 780 |
| gggataggct ttcaacacat aggaaaccct tcagatgatg agaacacatc gaatcccaga | 840 |
| gagtaatatc accaagaata aagcaaccat gatagacaat attactaagt gttcctcaac | 900 |
| agatattgag aaaagttctt ataaagcggg caggcttttt tctattttttt tcttttttctt | 960 |
| tatctagctt aagatccttc taaccatatt ctataaaatg gcaagctgaa tacagattat | 1020 |
| caacgacaat tacatataac ctacaaacag gcaagttgca attccagaaa cc | 1072 |

<210> SEQ ID NO 3
<211> LENGTH: 1477
<212> TYPE: DNA
<213> ORGANISM: Saccharomyces cerevisiae

<400> SEQUENCE: 3

| | |
|---|---|
| gcttttctcg cttcgttatc acctaaccac taagaacata ctaataatac aaaattttta | 60 |
| tccacttttt accaacagat tttcatgaaa tatccatctt ctttccgaat tctgtataaa | 120 |
| atgaaagaga gatttttttgc tctcaatcca ggctcaaggc tcttgagaac aggtaattgt | 180 |
| tgtttagcac gttttcaaca catttatcag aaaacgacag ttaaaaataa gacgagcggc | 240 |
| gttatcatcc tgatagtcac taaatgaaaa gcaggtactt tgaagagca catgtaatat | 300 |
| ttgctcaact gataatacct tcatttttata cacacttcta attttttttttt taaaatcaga | 360 |
| tacgcattga tgttcaatgt agcattacca tcacaagaca aaaaatcaga attttacaag | 420 |

```
caaaagcgct tatctttaag gaccaacata ttagatgaat tcttaagggt tgccaaaacg      480
caagacaaca ggcaaaataa tttcgtttct cagtaccgaa atgacgaaat atactgaggc      540
aaatgcgatc atcatgcctt tgcgccaaga aactcccttg tgaagaactt caaaccgaaa      600
tgggaaaact ttgagttatt gacagggaat acggaggggga agatcacact taaatccgta     660
tgagccgcgc acataatggt attcaaatac acaagaacat tcatgagcta ttttcatcc      720 gtgcaaacga atttactaca attggaccag agggcaccat aactggagac tttgctactg     780
actcaacgtt gatgatgcga gtagtgggtg tactgtgatt tgctcatttt ttttttata      840 gaaagattcg attaatgaaa gtcacaggag acattttac atagacattc cgtatatgtt     900
gcgggtatcg cggatgcgga ttagtgatgc ctttaactac atttcataga tttctgtata     960
ccaattgaaa tgagtgaagt aagctcctac agtgaaatat ctgggtgcta ctgacgccaa    1020
gccctacagc gatcggaatg cgggaacgga agttaacggg gcttccagaa cggcggaagc    1080
gaattgaacg aggacggcaa acaaaaacac ccaaaatttc attacttaga atgaccctca    1140
agagcagggt gcaatttatc aagcgatcat tgaactaact aagttcatat cctgtatagg    1200
atttaaaaca atgcaccta agttcaaatg cacccccccct cgccccgcag cggacccttg    1260
aacagagaac tgtttcgagg ttcacccaat tggatcactt gtataatttg taatcgagtt    1320
cggataagat gtatacgaat ctaactgggt gcagtataat tagcatttta tattacctag    1380
caatatatgt ataaaacagg aatgtgtgcg tgcttcaggc agaatttac ggtccttgta     1440 aaaaagtcta tcataaagcc atcacaaaac aataata                              1477

<210> SEQ ID NO 4
<211> LENGTH: 948
<212> TYPE: DNA
<213> ORGANISM: Saccharomyces cerevisiae

<400> SEQUENCE: 4
gctaacgaac aggatggtat tgatgaagat tccaaaattt tgcgtgctgt cactgaacag       60
gttgccttga gttacaaaga caaaggtgtt tcagcaagaa ttgtcagact cccattctcg      120
gttcatggca aggggggacaa ggcttttgta ccaatattaa tgaatattgc caaagctgcc    180
ggaaaatctg gctatgtcgg acaaggcaca aacgcttggg cggctgtaca tcgtttggat     240
acggctcctc tgttcagact tgttttagag aaaggaaaaa caggacaagt gtatcattgc     300
gttggtgaac aagtatacc attcaaagat attgcgcgtg tgattggaga aattttgaat      360
gttcccgtgg cctctatccc tgttgatgac gcggaaagtc attttggctt cctcacttgt    420
tttgtcacta gagatggccc agtttcaagc gaaggtacca gaaaaagagct gggatggcag    480 ccacaacaaa tcggtcttct tgaagatatc cgtgcgaact atagcttaaa ctgacttgaa     540
gcttatatta tgcgtttttt ctaagagcgc atagcatgt aacgtttttt acatactagt      600
tagctttatc tatatagtct actgtgcagc ttaaaatacc caactcatgc gtctcattgg    660
acgagctctt ggcccttgga aaggtgctat attagtatat aggggaatga tgacaaaagc    720
ctcaatgtgg cttgagtcga tttcttattt ggcgccacag ggcacatgga gtttattat     780 catactacta acataaagaa ggtatgtagg caatacaaca agaatgctgg aaaagttaag    840
gagtcagtaa cagttcttga tgacagaaac atataaaaag gtgtactatt gctgtataat     900 cggcccttc atacttgtac aaacatagca cagtaaccca gttaaaat                    948

<210> SEQ ID NO 5
```

```
<211> LENGTH: 968
<212> TYPE: DNA
<213> ORGANISM: Saccharomyces cerevisiae

<400> SEQUENCE: 5
tcgttttcta ctttcttctg ctgctataat aagcacctat gggatctata tagtattttt      60
ataacgatag actttataaa agaaaatacc taagtgaaaa tttggtgaat tttgagataa     120
ttgttgggat tccattttta ataaggcaat aatattaggt atgtagaata tactagaagt     180
tctcctcgag gatttaggaa tccataaaag ggaatctgca attctacaca attctataaa     240
tattattatc atcgttttat atgttaatat tcattgatcc tattcatta tcaatccttg      300
cgtttcagct tccactaatt tagatgacta tttctcatca tttgcgtcat cttctaacac     360
cgtatatgat aatatactag taacgtaaat actagttagt agatgatagt tgattttat      420
tccaacacta agaaataatt tcgccatttc ttgaatgtat ttaaagatat ttaatgctat     480
aatagacatt taaatccaat tcttccaaca tacaatggga gtttggccga gtggtttaag     540
gcgtcagatt taggtggatt taacctctaa atctctgat atcttcggat gcaagggttc      600
gaatccctta gctctcatta ttttttgctt tttctcttga ggtcacatga tcgcaaaatg     660
gcaaatggca cgtgaagctg tcgatattgg ggaactgtgg tggttggcaa atgactaatt     720
aagttagtca aggcgccatc ctcatgaaaa ctgtgtaaca taataaccga agtgtcgaaa     780
aggtggcacc ttgtccaatt gaacacgctc gatgaaaaaa ataagatata tataaggtta     840
agtaaagcgt ctgttagaaa ggaagttttt cctttttctt gctctcttgt cttttcatct     900
actatttcct tcgtgtaata cagggtcgtc agatacatag atacaattct attaccccca     960
tccataca                                                              968

<210> SEQ ID NO 6
<211> LENGTH: 720
<212> TYPE: DNA
<213> ORGANISM: Aequorea victoria

<400> SEQUENCE: 6
tcagttgtac agttcatcca tgccatgtgt aatcccagca gctgttacaa actcaagaag      60
gaccatgtgg tctctctttt cgttgggatc tttcgaaagg gcagattgtg tggacaggta     120
atggttgtct ggtaaaagga cagggccatc gccaattgga gtattttgtt gataatggtc     180
tgctagttga acgcttccat cttcaatgtt gtggcgggtc ttgaagttca ctttgattcc     240
attcttttgt ttgtctgcca tgatgtatac attgtgtgag ttatagttgt attccaattt     300
gtgtcccaga atgttgccat cttccttgaa gtcaatacct tttaactcga ttctattaac     360
aagggtatca ccttcaaact tgacttcagc acgtgtcttg tagttgccgt catctttgaa     420
gaagatggtc ctttcctgta cataaccttc gggcatggca ctcttgaaaa agtcatgccg     480
tttcatatga tccgggtatc ttgaaaagca ttgaacacca tagcacagag tagtgactag     540
tgttggccat ggaacaggca gtttgccagt agtgcagatg aacttcaggg taagttttcc     600
gtatgttgca tcaccttcac cctctccact gacagagaac ttgtgccgt taacatcacc      660
atctaattca acaagaattg ggacaactcc agtgaagagt tcttctcctt gctagccat      720

<210> SEQ ID NO 7
<211> LENGTH: 23
<212> TYPE: DNA
<213> ORGANISM: Saccharomyces cerevisiae

<400> SEQUENCE: 7
```

-continued cgcaataata ctggaaacat caa                23

<210> SEQ ID NO 8
<211> LENGTH: 22
<212> TYPE: DNA
<213> ORGANISM: Saccharomyces cerevisiae

<400> SEQUENCE: 8
atcgactttg tttgcttaga at                 22

<210> SEQ ID NO 9
<211> LENGTH: 23
<212> TYPE: DNA
<213> ORGANISM: Saccharomyces cerevisiae

<400> SEQUENCE: 9
aggtgcgata gtggggaata aga                23

<210> SEQ ID NO 10
<211> LENGTH: 22
<212> TYPE: DNA
<213> ORGANISM: Saccharomyces cerevisiae

<400> SEQUENCE: 10
ggtttctgga attgcaactt gc                 22

<210> SEQ ID NO 11
<211> LENGTH: 23
<212> TYPE: DNA
<213> ORGANISM: Saccharomyces cerevisiae

<400> SEQUENCE: 11
gcttttctcg cttcgttatc acc                23

<210> SEQ ID NO 12
<211> LENGTH: 22
<212> TYPE: DNA
<213> ORGANISM: Saccharomyces cerevisiae

<400> SEQUENCE: 12
tattattgtt ttgtgatggc tt                 22

<210> SEQ ID NO 13
<211> LENGTH: 23
<212> TYPE: DNA
<213> ORGANISM: Saccharomyces cerevisiae

<400> SEQUENCE: 13
gctaacgaac aggatggtat tga                23

<210> SEQ ID NO 14
<211> LENGTH: 22
<212> TYPE: DNA
<213> ORGANISM: Saccharomyces cerevisiae

<400> SEQUENCE: 14
attttaactg ggttactgtg ct                 22

<210> SEQ ID NO 15
<211> LENGTH: 23
<212> TYPE: DNA
<213> ORGANISM: Saccharomyces cerevisiae

```
-continued

<400> SEQUENCE: 15
tcgttttcta ctttcttctg ctg                                             23

<210> SEQ ID NO 16
<211> LENGTH: 22
<212> TYPE: DNA
<213> ORGANISM: Saccharomyces cerevisiae

<400> SEQUENCE: 16
tgtatggatg ggggtaatag aa                                              22
```

PROCESS FOR DETECTING TOXIC SUBSTANCES

CROSS-REFERENCE TO RELATED APPLICATIONS

The present application is a 37 C.F.R. § 1.53(b) divisional of U.S. application Ser. No. 10/487,438 filed May 21, 2004, now abandoned, which claims priority on PCT International Application No. PCT/JP02/08495 filed Aug. 23, 2002, which in turn claims priority on Japanese Application No. JP 2001-255379 filed Aug. 24, 2001. The entire contents of each of these applications is hereby incorporated by reference.

FIELD OF THE INVENTION

This invention relates to biology-based processes for detecting toxic substances. It also relates to polynucleotides, vectors, and cells as used for the processes.

BACKGROUND ART

Environmental chemical fate search has been conducted every year for 24 years from 1974 through 1998 by the Environmental Agency, and revealed that about 40% of 775 chemical substances that have been searched so far are emitted into the environment. Chemical substances that are industrially produced at the present in Japan are estimated about 50,000, and the production scale and the kinds of chemical substances are increasing year by year. It is known that chemical substances that are accidentally produced by water treatment with chlorine and incineration pollute the environment. Although such facts allow us to predict that there are a large number of chemical substances that have been accumulated in the environment, it is extremely difficult to search and examine individually all chemical substances.

Conventional bioassays (approaches to evaluate the harmful effects on biological materials on the basis of their responses) wherein inhibited growth and particular biological responses in individuals and cells of fishes, daphnia and shellfish are used as indicators make it possible to determine the presence or absence of the toxicity of chemical substances in the environment, but neither possible to evaluate the characters nor origins of the toxicity. The evaluation methods based on the activity of nitrite-forming bacteria or nitrate-forming bacteria (Japanese Patent Publication (kokai) No. 123705/1994, Japanese Patent Publication (kokai) No. 2000-206087) and the activity of iron bacteria have been proposed, and devices such as Acute toxicants monitor (Fuji Electric Corporate Research and Development, Ltd. Japan) are marketed. In foreign countries, the devices for evaluation based on emission intensity of luminous bacteria are commercially available (MICROTOX, azur, Co., USA; LUMIS, drlange, Co. Germany). However, those devices still involve conventional bioassays, and never provide any detailed information of toxic chemical substances.

In Japan, the risk control of chemical substances is reconsidered every time a chemical substance pollution is newly found, and official regulations and self-imposed regulations are combined to organize the system for risk control. However, any system has not been yet organized that could quickly respond to the present complicated and diversified conditions, including accidental productions and environmental emission of toxic chemical substances as typified by trihalomethane and dioxin. Animal experiments as used in the method for evaluation of toxic substance of "Law Concerning Examination and Manufacture, etc. of Chemical Substances" are expensive and time-consuming, and are not accepted across the world. Although, as such, the control system has been continuously discussed, it has not been successfully accomplished because there is no way to solve the problem. Thus, a method for readily detecting chemical substances that occur in the environment is desired.

DISCLOSURE OF THE INVENTION

The inventors of the present application found that a toxic substance activates the promoter of a particular yeast gene to induce the transcription of mRNA from the polynucleotide encoding a marker protein operably linked to the promoter, and accomplished the present invention.

Specifically, the invention of the present application relates, as the first embodiment, to a polynucleotide which comprises a polynucleotide sequence operably linked to a polynucleotide encoding a marker protein, wherein the polynucleotide sequence comprises a promoter from yeast genes that is selected from a group consisting of the following, or a promoter from a gene that is homologous to the yeast genes and is derived from other species; YBR072W, YCR102C, YCR107W, YDL218W, YDL243C, YDR453C, YDR533C, YFL014W, YFL056C, YFL057C, YGR110W, YJR155W, YKL071W, YKR076W, YLL060C, YLR460C, YMR090W, YNL331C, YNL332W, YNL335W, YOL150C, YOL165C, YPL171C, YPR167C, YBL048W, YBL064C, YBL107C, YBR008C, YBR173C, YBR256C, YBR296C, YDL021W, YFL022C, YFL024C, YFL061W, YGL121C, YGL158W, YGR043C, YHR029C, YHR112C, YHR139C, YHR179W, YHR209W, YIR030C, YJR010W, YJR048W, YKL001C, YKL107W, YKR075C, YKR097W, YLL056C, YLR297W, YLR303W, YML087C, YMR096W, YNL274C, YOL151W, YOR226C, YOR338W, YOR391C, YPL280W, YDR406W, YJL153C, YLR346C, YOR049C, YOR153W, YPL088W, YAL034C, YDL124W, YDL174C, YDR476C, YGL156W, YGR035C, YGR157W, YGR213C, YGR281W, YGR284C, YHL047C, YHR043C, YHR044C, YHR054C, YJR073C, YKL165C, YLR008C, YMR315W, YNL211C, YOL031C, YOL101C, YOR303W, YAL005C, YAR031W, YBL005W-A, YBL022C, YBL041W, YBL049W, YBL075C, YBL078C, YBR062C, YBR169C, YBR294W, YCL020W, YCL035C, YCL043C, YCL050C, YCL057W, YCR012W, YCR013C, YCR060W, YDL007W, YDL027C, YDL097C, YDL110C, YDL126C, YDL169C, YDR070C, YDR155C, YDR158W, YDR204W, YDR210W, YDR214W, YDR258C, YDR313C, YDR368W, YDR435C, YER012W, YER037W, YER091C, YER103W, YFL044C, YFR003C, YFR010W, YFR020W, YFR024C, YFR044C, YFR053C, YGL006W, YGL048C, YGL062W, YGL141W, YGL157W, YGL163C, YGL180W, YGL184C, YGR010W, YGR028W, YGR032W, YGR048W, YGR124W, YGR135W, YGR142W, YGR161C, YGR192C, YGR197C, YGR201C, YGR212W, YGR231C, YGR244C, YGR254W, YGR268C, YHL030W, YHR016C, YHR018C, YHR055C, YHR087W, YHR166C, YIL160C, YIR017C, YJL034W, YJL048C, YJL052W, YJL144W, YJL163C, YJR009C, YJR069C, YJR074W, YJR130C, YJR149W, YKL065C, YKL073W, YKL103C, YKL142W, YKL210W, YKL218C, YKR011C, YKR018C, YKR046C, YKR049C, YLL024C, YLL026W, YLR027C, YLR080W, YLR107W, YLR121C, YLR132C, YLR133W, YLR155C, YLR158C, YLR161W, YLR195C, YLR217W, YLR328W, YLR336C, YLR345W, YLR370C, YLR423C, YML004C, YML092C, YML128C, YML130C, YML131W, YMR040W, YMR118C, YMR214W, YMR251W, YMR297W, YMR322C, YNL036W, YNL055C, YNL071W, YNL094W, YNL134C, YNL155W, YNL160W, YNL239W, YNL241C, YOL005C, YOR020C, YOR027W, YOR037W, YOR059C, YOR120W, YOR134W, YOR152C, YOR173W, YOR289W, YOR362C, YPL240C, YPR030W, YAL008W, YAL023C, YAL060W, YAL062W, YAR009C, YBL101C, YBR006W, YBR046C, YBR052C, YBR053C, YBR056W, YBR099C, YBR137W, YBR139W, YBR149W, YBR170C, YBR177C, YBR203W, YBR207W, YBR212W, YBR239C, YBR284W, YBR293W, YCL018W, YCL033C, YCL040W, YCL049C, YCR062W, YCR067C, YCR082W, YDL010W, YDL020C, YDL024C, YDL054C, YDL095W, YDL100C, YDL115C, YDL144C, YDL198C, YDL223C, YDL245C, YDL246C, YDR001C, YDR032C, YDR058C, YDR072C, YDR127W, YDR168W, YDR169C, YDR188W, YDR231C, YDR261C, YDR264C, YDR272W, YDR293C, YDR304C, YDR330W, YDR403W, YDR411C, YDR427W, YDR436W, YDR497C, YDR511W, YDR516C, YDR519W, YDR545W, YEL012W, YEL030W, YER004W, YER009W, YER021W, YER035W, YER053C, YER079W, YER094C, YER096W, YER125W, YER158C, YER163C, YER175C, YER177W, YER178W, YER185W, YFL006W, YFL010C, YFL016C, YFL029C, YFL030W, YFL031W, YFL032W, YFL038C, YFL041W, YFR004W, YFR047C, YFR050C, YFR052W, YGL011C, YGL013C, YGL037C, YGL047W, YGL053W, YGL091C, YGL094C, YGL127C, YGL150C, YGL199C, YGL207W, YGL248W, YGR008C, YGR037C, YGR055W, YGR101W, YGR130C, YGR154C, YGR194C, YGR221C, YGR232W, YGR248W, YGR253C, YGR256W, YHL008C, YHR027C, YHR053C, YHR057C, YHR111W, YHR138C, YHR161C, YHR164C, YHR169W, YHR174W, YHR176W, YHR199C, YIL010W, YIL034C, YIL041W, YIL045W, YIL087C, YIL107C, YIL142W, YIL155C, YIR034C, YIR036C, YIR037W, YIR038C, YIR039C, YJL001W, YJL031C, YJL035C, YJL053W, YJL057C, YJL066C, YJL068C, YJL082W, YJL099W, YJL102W, YJL151C, YJL152W, YJL161W, YJL164C, YJL171C, YJL172W, YJL210W, YJL219W, YJR008W, YJR045C, YJR046W, YJR106W, YJR117W, YJR137C, YKL007W, YKL026C, YKL035W, YKL091C, YKL104C, YKL117W, YKL145W, YKL146W, YKL151C, YKL152C, YKL153W, YKL193C, YKL195W, YKL213C, YKL215C, YLL028W, YLL039C, YLL058W, YLR054C, YLR103C, YLR120C, YLR136C, YLR149C, YLR152C, YLR178C, YLR259C, YLR299W, YLR324W, YLR327C, YLR348C, YLR350W, YLR356W, YLR362W, YLR387C, YLR429W, YML054C, YML070W, YML100W, YML117W, YML125C, YMR004W, YMR008C, YMR009W, YMR020W, YMR067C, YMR089C, YMR097C, YMR102C, YMR105C, YMR107W, YMR152W, YMR180C, YMR184W, YMR191W, YMR219W, YMR271C, YMR275C, YMR295C, YMR314W, YMR316W, YNL006W, YNL007W, YNL012W, YNL044W, YNL045W, YNL074C, YNL092W, YNL093W, YNL104C, YNL115C, YNL156C, YNL231C, YNL234W, YNL237W, YNL281W, YNL305C, YNL333W, YNR010W, YNR019W, YNR033W, YNR059W, YNR068C, YNR069C, YOL032W, YOL036W, YOL047C, YOL071W, YOL082W, YOL083W, YOL117W, YOL119C, YOL126C, YOL131W, YOL153C, YOL162W, YOL163W, YOL164W, YOR019W, YOR035C, YOR036W, YOR099W, YOR117W, YOR124C, YOR130C, YOR132W, YOR157C, YOR185C, YOR197W, YOR259C, YOR261C, YOR273C, YOR288C, YOR332W, YOR336W, YOR347C, YPL017C, YPL087W, YPL106C, YPL109C, YPL149W, YPL154C, YPL196W, YPL206C, YPL222W, YPR023C, YPR024W, YPR026W, YPR067W, YPR103W, YPR108W, YPR151C, YAL012W, YBR029C, YBR222C, YCL009C, YCL027W, YCL064C, YCR098C, YDL222C, YDR055W, YDR077W, YDR502C, YEL001C, YEL042W, YER026C, YER106W, YGR136W, YGR138C, YHR137W, YHR142W, YIL023C, YIL153W, YJL073W, YJR004C, YJR054W, YKL039W, YKL086W, YKL163W, YKR091W, YLR109W, YLR194C, YLR250W, YMR095C, YMR189W, YNL106C, YNL169C, YNL322C, YOR181W, YOR198C, YOR208W, YOR247W, YPL089C, YAL038W, YAL053W, YBR023C, YBR214W, YBR295W, YCR048W, YDL072C, YDL204W, YDR085C, YDR098C, YDR259C, YDR380W, YDR388W, YDR391C, YDR432W, YDR481C, YDR510W, YER069W, YGL022W, YGL126W, YGL209W, YGL255W, YGR189C, YGR282C, YHL035C, YHR030C, YIL022W, YIL024C, YIL117C, YIL123W, YIL140W, YIL154C, YJL088W, YJL108C, YJL149W, YJL159W, YJL186W, YJR148W, YKL096W, YLR180W, YLR273C, YLR300W, YLR307W, YLR378C, YLR391W, YMR094W, YMR104C, YMR276W, YMR296C, YNL190W, YNL208W, YNL300W, YNR064C, YOL013C, YOL058W, YOR248W, YOR355W, YPL052W, YPL163C, YPR079W, YAR028W, YBR146W, YBR183W, YCL038C, YCR071C, YDL008W, YDR019C, YDR031W, YDR115W, YDR486C, YER038C, YER130C, YFL054C, YGL136C, YGR146C, YGR207C, YHL040C, YIL167W, YJL020C, YKR039W, YLR031W, YLR205C, YMR072W, YMR140W, YMR173W, YMR195W, YMR226C, YNL037C, YNR002C, YOL143C, YOR136W, YOR215C, YOR382W, YOR383C, YPL054W, YPL271W, YPR127W, YAL044C, YAL054C, YAR010C, YAR027W, YAR071W, YBL001C, YBL043W, YBL057C, YBR014C, YBR024W, YBR035C, YBR068C, YBR111C, YBR116C, YBR147W, YBR168W, YBR246W, YBR273C, YCR004C, YCR021C, YCR037C, YCR088W, YDL022W, YDL128W, YDL238C, YDR003W, YDR009W, YDR033W, YDR084C, YDR104C, YDR270W, YDR315C, YDR340W, YDR357C, YDR358W, YDR396W, YDR405W, YDR410C, YDR434W, YDR482C, YDR487C, YDR520C, YDR534C, YDR539W, YEL011W, YEL065W, YEL066W, YER039C, YER044C, YER067W, YER080W, YER107C, YFL020C, YFL028C, YFL043C, YFR015C, YGL001C, YGL008C, YGL068W, YGL073W, YGL104C, YGL113W, YGL154C, YGL167C, YGL229C, YGL242C, YGL249W, YGL253W, YGR052W, YGR060W, YGR065C, YGR106C, YGR111W, YGR220C, YGR257C, YHL023C, YHL048W, YHR004C, YHR037W, YHR071W, YHR092C, YHR190W, YIL007C, YIL033C, YIL070C, YIL088C, YIL111W, YIR002C, YIR016W, YIR035C, YIR043C, YJL012C, YJL083W, YJL089W, YJL116C, YJL131C, YJL132W, YJL196C, YJR061W, YJR086W, YJR142W, YJR161C, YKL008C, YKL013C, YKL041W, YKL067W, YKL138C, YKL139W, YKL150W, YKL175W, YKR006C, YKR014C, YKR070W, YLL023C, YLR023C, YLR093C, YLR118C, YLR142W, YLR225C, YLR241W, YLR251W, YLR252W, YLR270W, YML030W, YML110C, YMR021C, YMR027W, YMR148W, YMR181C, YMR262W, YMR272C, YMR298W, YNL011C, YNL130C, YNL214W, YNL259C, YOL129W, YOR042W, YOR052C, YOR137C, YOR149C, YOR165W, YOR270C, YOR285W, YOR367W, YPL018W, YPL156C, YPL186C, YPL203W, YPL216W, YPL255W, YPR006C, YPR073C, YPR098C, YBR050C, YBR145W, YBR299W, YDR518W, YEL020C, YFL062W, YGL039W, YGL134W, YJL217W, YJR159W, YLR126C, YNL249C, YNL284C, YNL336W, YOL157C, YOR344C, YOR381W, YPL265W, YPR124W, YBR074W, YBR109C, YBR126C, YBR201W, YCR005C, YDL248W, YDR041W, YDR105C, YDR268W, YDR452W, YEL075C, YER046W, YER050C, YER136W, YER159C, YGL250W, YGR019W, YGR042W, YGR053C, YGR066C, YGR247W, YGR255C, YGR295C, YHL044W, YHR145C, YIL058W, YIL065C, YIL083C, YIL098C, YIL172C, YJL030W, YJL185C, YJL213W, YJR029W, YJR099W, YJR122W, YJR125C, YKL190W, YKR020W, YLL025W, YLL051C, YLR043C, YLR090W, YLR100W, YLR108C, YLR290C, YML068W, YMR051C, YMR139W, YMR178W, YMR193W, YNL015W, YNL079C, YNL122C, YNL223W, YNL285W, YNL293W, YNR007C, YNR035C, YNR061C, YOL016C, YOL104C, YOR220W, YOR221C, YOR374W, YPL123C, YPR077C, YPR107C, YPR147C, YBR093C, YBR196C, YEL041W, YEL047C, YER023W, YER119C, YFL055W, YGR209C, YIL124W, YKL187C, YLL055W, YMR318C, YOL152W, YAL007C, YBR067C, YBR115C, YBR285W, YBR292C, YDL043C, YDL123W, YDL131W, YDL168W, YDL212W, YDR056C, YDR132C, YDR154C, YDR183W, YDR216W, YDR253C, YDR295C, YDR494W, YDR513W, YEL072W, YER045C, YER061C, YER181C, YFL052W, YFL058W, YFR030W, YGL089C, YGL096W, YGL114W, YGL193C, YGL202W, YGL204C, YGL259W, YGR006W, YGR070W, YGR088W, YHL034C, YHL036W, YHR048W, YHR104W, YHR163W, YIL060W, YIL136W, YIR024C, YJL036W, YJL045W, YJL060W, YJL101C, YJL155C, YJR085C, YJR109C, YJR156C, YKL070W, YKL161C, YKL221W, YKR071C, YLL009C, YLL050C, YLR092W, YLR145W, YLR156W, YLR163C, YLR220W, YLR280C, YLR311C, YLR390W, YML116W, YMR034C, YMR038C, YMR081C, YMR250W, YNL240C, YNL260C, YNL277W, YNR074C, YOL044W, YOL084W, YOL147C, YOL159C, YOR184W, YOR228C, YOR255W, YPL223C, YPR160W, YDL182W, YBR047W, YBR054W, YBR291C, YDR069C, YER124C, YER131W, YGR044C, YIL094C, YKR007W, YMR240C, YNR050C, YOR007C, YAL015C, YBL065W, YBR105C, YBR182C, YBR186W, YBR244W, YBR272C, YCL069C, YDL025C, YDL059C, YDL085W, YDL113C, YDL244W, YDR018C, YDR054C, YDR202C, YDR223W, YDR350C, YDR353W, YDR374C, YDR512C, YEL052W, YEL070W, YER098W, YFR017C, YGL046W, YGL067W, YGL098W, YGL117W, YGL146C, YGL240W, YGR011W, YGR067C, YGR133W, YGR153W, YGR223C, YHR116W, YHR124W, YIL097W, YIL168W, YJL103C, YJL221C, YJR036C, YJR095W, YKL085W, YKL133C, YKL162C, YKL188C, YKL217W, YKR061W, YKR105C, YLL062C, YLR174W, YLR216C, YLR247C, YLR260W, YLR267C, YLR389C, YML007W, YMR041C, YMR177W, YMR253C, YNL009W, YNL117W, YNL128W, YNL183C, YNR073C, YOL133W, YOL158C, YOR133W, YOR225W, YOR227W, YPL161C, YPL166W, YPL202C, YPL224C, YPR015C, YPR086W, YPR201W, YAL061W, YAL067C, YAR007C, YBL033C, YBL056W, YBL086C, YBR026C, YBR073W, YBR101C, YBR117C, YBR123C, YBR213W, YBR269C, YBR280C, YCR036W, YDL132W, YDL149W, YDL200C, YDL234C, YDL242W, YDR099W, YDR177W, YDR256C, YDR392W, YDR394W, YDR531W, YEL071W, YER014W, YER042W, YER090W, YER184C, YFL059W, YFR042W, YFR046C, YFR049W, YGL026C, YGL058W, YGL185C, YGL227W, YGL252C, YGL254W, YGR089W, YGR112W, YGR134W, YGR276C, YHL019C, YHR012W, YHR017W, YHR028C, YHR106W, YHR109W, YHR156C, YIL036W, YIL046W, YIL143C, YIL152W, YIL159W, YIL164C, YJL071W, YJL094C, YJL154C, YJR056C, YJR072C, YJR110W, YJR139C, YKL025C, YKL034W, YKL064W, YKL171W, YKL196C, YKR012C, YKR068C, YKR069W, YLL001W, YLL057C, YLL061W, YLR064W, YLR070C, YLR099C, YLR144C, YLR157C, YLR160C, YLR164W, YLR364W, YLR421C, YML032C, YML042W, YML112W, YML118W, YMR114C, YMR115W, YMR258C, YNL181W, YNL191W, YNL212W, YNL213C, YNL250W, YNL265C, YNL312W, YNR032W, YOL038W, YOL049W, YOL064C, YOR088W, YOR155C, YOR257W, YOR265W, YOR377W, YOR386W, YPL031C, YPL113C, YPL124W, YPL151C, YPL249C, YPL260W, YPL274W, YPR048W, YPR061C, YPR093C, YPR125W, YPR158W, YPR168W, YPR169W, YPR174C, YPR180W, YPR193C, YPR200C, YAL014C, YAL017W, YAL049C, YBL019W, YBL058W, YBR001C, YBR013C, YBR018C, YBR037C, YBR045C, YBR051W, YBR063C, YBR128C, YBR129C, YBR204C, YBR241C, YBR255W, YBR281C, YCL044C, YCL055W, YCR014C, YCR019W, YCR024C, YCR105W, YDL065C, YDL089W, YDL143W, YDL173W, YDL193W, YDL197C, YDL206W, YDL230W, YDL233W, YDR040C, YDR071C, YDR078C, YDR109C, YDR140W, YDR194C, YDR212W, YDR221W, YDR257C, YDR271C, YDR287W, YDR294C, YDR316W, YDR329C, YDR338C, YDR369C, YDR421W, YDR425W, YDR485C, YDR488C, YDR504C, YDR505C, YDR506C, YDR515W, YEL005C, YEL037C, YEL044W, YER017C, YER048C, YER052C, YER078C, YER089C, YER092W, YER100W, YER162C, YER182W, YFL021W, YFL042C, YFR045W, YFR051C, YFR056C, YGL040C, YGL041C, YGL045W, YGL057C, YGL093W, YGL105W, YGL125W, YGL166W, YGL181W, YGL183C, YGL215W, YGL216W, YGL221C, YGL223C, YGR007W, YGR029W, YGR155W, YGR156W, YGR186W, YGR198W, YGR210C, YGR211W, YGR237C, YGR250C, YGR258C, YGR266W, YGR270W, YGR274C, YGR277C, YHL021C, YHL037C, YHL038C, YHR082C, YHR083W, YHR134W, YHR160C, YHR171W, YHR180W, YHR205W, YIL062C, YIL072W, YIL075C, YIL099W, YIL108W, YIL165C, YIL170W, YIR009W, YIR018W, YIR030C, YIR032C, YJL032W, YJL049W, YJL128C, YJL165C, YJR044C, YJR052W, YJR090C, YJR091C, YJR103W, YJR104C, YJR153W, YKL059C, YKL079W, YKL090W, YKL094W, YKL192C, YKL209C, YKR052C, YKR102W, YKR106W, YLL054C, YLR025W, YLR097C, YLR200W, YLR226W, YLR248W, YLR266C, YLR392C, YLR427W, YML013W, YML029W, YML041C, YML051W, YML078W, YML079W, YML088W, YML099C, YMR056C, YMR068W, YMR091C, YMR110C, YMR160W, YMR186W, YMR255W, YNL005C, YNL026W, YNL039W, YNL063W, YNL064C, YNL077W, YNL083W, YNL147W, YNL176C, YNL194C, YNL253W, YNL257C, YNL261W, YNL264C, YNL276C, YNR006W, YNR034W, YNR047W, YNR051C, YNR071C, YOL066C, YOL067C, YOR005C, YOR008C, YOR022C, YOR023C, YOR058C, YOR069W, YOR087W, YOR138C, YOR229W, YOR256C, YOR267C, YPL005W, YPL020C, YPL022W, YPL105C, YPL147W, YPL150W, YPL152W, YPL164C, YPL168W, YPL180W, YPL188W, YPL194W, YPR025C, YPR047W, YPR049C, YPR066W, YPR081C, YPR134W, YPR140W, YPR148C, YPR155C, YPR172W, YPR185W, YAL018C, YAR064W, YBR012C, YBR076W, YBR287W, YDR043C, YDR250C, YDR373W, YFR014C, YGL191W, YGR180C, YHR136C, YJL026W, YJL037W, YLR038C, YNL058C, YOR031W, YGR087C, YIL166C, YHR008C, YIL129C, YGL256W, YJR030C, YMR077C, YBR264C, YPL177C, YKR040C, YGL056C, YDR128W, YGR139W, YBL101W-A, YOR253W, YOL026C, YDR278C, YHR095W, YCL042W, YNL200C, YPL221W, YLR415C, YMR058W, YPR037C, YER072W, YML028W, YOR325W, YAL039C, YMR112C, YJR107W, YGL088W, YJR058C, YNL142W, YDR090C, YMR071C, YBL093C, YGR293C, YML055W, YDL017W, YDL210W, YGL055W, YCL025C, YDR080W, YDL181W, YNR030W, YJL017W, YIL127C, YDR281C, YDR366C, YFR026C, YJL212C, YPL215W, YEL019C, YBR132C, YHL018W, YNL196C, YPL038W, YAR047C, YPL262W, YHL006C, YPL225W, YBR124W, YOR148C, YKR053C, YBL044W, YER029C, YLR360W, YCL056C, YCR007C, YGR239C, YNL256W, YPR146C, YLR377C, YKL097C, YBR066C, YLR338W, YDL229W, YBR253W, YJR027W, YKL198C, YBL030C, YBR031W, YBR118W, YBR162C, YBR221C, YCR024C-A, YCR106W, YDL046W, YDR012W, YDR133C, YDR134C, YDR276C, YDR342C, YDR343C, YEL027W, YEL034W, YGR038W, YGR243W, YGR279C, YHR094C, YHR105W, YHR175W, YHR181W, YIL056W, YIL162W, YJL059W, YJL097W, YJL158C, YJR105W, YKL051W, YKL056C, YKL097W-A, YKL100C, YKL141W, YKR066C, YLR134W, YLR258W, YLR339C, YML058W, YMR083W, YMR203W, YNL209W, YNL307C, YOL030W, YOR178C, YPL028W, YPR028W, YPR113W, YPR149W, YPR150W, YPR183W, YAL016W, YBL099W, YBL100C, YBR011C, YBR096W, YBR100W, YBR127C, YBR283C, YBR286W, YCL008C, YCL058C, YCR030C, YCR034W, YCR069W, YDL015C, YDL023C, YDL061C, YDL086W, YDR038C, YDR039C, YDR050C, YDR151C, YDR178C, YDR233C, YDR284C, YDR298C, YDR345C, YDR359C, YDR382W, YDR385W, YDR400W, YDR407C, YDR538W, YEL024W, YEL033W, YEL063C, YER057C, YER081W, YER120W, YFL011W, YGL012W, YGL206C, YGR022C, YGR026W, YGR082W, YGR107W, YGR172C, YGR191W, YGR204W, YGR260W, YHL005C, YHL046C, YHR025W, YHR026W, YHR123W, YHR126C, YHR143W, YIL011W, YIL015W, YIL018W, YIL157C, YIR041W, YJL016W, YJL121C, YJL133W, YJL138C, YJL191W, YJR018W, YJR047C, YJR077C, YJR119C, YJR121W, YJR123W, YJR143C, YJR145C, YKL060C, YKL147C, YKL148C, YKL157W, YKL164C, YKL169C, YKR033C, YLL041C, YLL064C, YLR041W, YLR044C, YLR056W, YLR058C, YLR081W, YLR089C, YLR110C, YLR177W, YLR264W, YLR284C, YLR304C, YLR340W, YLR354C, YLR372W, YLR388W, YML022W, YMR007W, YMR011W, YMR015C, YMR092C, YMR101C, YMR156C, YMR205C, YMR215W, YMR261C, YMR323W, YNL069C, YNL135C, YNL195C, YNR076W, YOL039W, YOL073C, YOL086C, YOL120C, YOL156W, YOL161C, YOR002W, YOR009W, YOR010C, YOR085W, YOR108W, YOR128C, YOR129C, YOR142W, YOR161C, YOR176W, YOR230W, YOR298W, YPL004C, YPL036W, YPL048W, YPL057C, YPL059W, YPL061W, YPL135W, YPL179W, YPL218W, YPL220W, YPL246C, YPL272C, YPR063C, YPR080W, YPR181C, YBR290W, YCR010C, YCR091W, YDL107W, YDL129W, YDR066C, YDR529C, YFL026W, YGL018C, YGL059W, YNL144C, YOR003W, YAL037W, YAR023C, YBR003W, YBR020W, YBR044C, YBR091C, YBR185C, YBR282W, YCR015C, YCR038C, YCR043C, YDL119C, YDL146W, YDL220C, YDR057W, YDR123C, YDR125C, YDR222W, YDR225W, YDR277C, YDR286C, YDR347W, YDR408C, YDR438W, YDR479C, YDR483W, YEL039C, YEL057C, YEL073C, YER066W, YER076C, YER084W, YER121W, YER189W, YFL017C, YFL046W, YFR006W, YFR008W, YGL115W, YGL208W, YGL214W, YGL218W, YGR021W, YGR023W, YGR024C, YGR064W, YGR076C, YGR096W, YGR108W, YGR174C, YGR182C, YGR236C, YGR288W, YHL042W, YHR195W, YHR210C, YIL006W, YIL012W, YIL028W, YIL050W, YIL057C, YIL089W, YIL102C, YIL113W, YIL122W, YJL100W, YJL169W, YJL199C, YJR039W, YJR050W, YJR101W, YKL003C, YKL016C, YKL061W, YKL093W, YKL121W, YKL160W, YKL170W, YKL194C, YKR034W, YKR067W, YLR006C, YLR016C, YLR030W, YLR036C, YLR112W, YLR125W, YLR128W, YLR204W, YLR211C, YLR233C, YLR257W, YLR288C, YLR326W, YLR334C, YLR395C, YLR408C, YLR414C, YLR444C, YML050W, YML107C, YML120C, YMR031C, YMR053C, YMR073C, YMR162C, YMR204C, YMR206W, YMR284W, YNL010W, YNL025C, YNL127W, YNL139C, YNL217W, YOL116W, YOL118C, YOR053W, YOR100C, YOR103C, YOR122C, YOR150W, YOR187W, YOR251C, YOR312C, YOR327C, YOR348C, YOR352C, YOR388C, YOR394W, YPL001W, YPL033C, YPL066W, YPL148C, YPL230W, YPL275W, YPL276W, YPR005C, YPR014C, YPR192W, YPR194C, YBR005W, YER025W, YFL027C, YGL080W, YGL205W, YHL028W, YHR185C, YIL076W, YJL166W, YLR046C, YMR035W, YMR238W, YMR252C, YNL192W, YNL202W, YOL108C, YOR385W, YPR165W, YAR033W, YBL038W, YBR009C, YBR010W, YBR151W, YCL067C, YCR096C, YDL137W, YDL192W, YDR073W, YDR086C, YDR224C, YDR377W, YDR378C, YER015W, YGL187C, YHR162W, YJL167W, YJL216C, YKR009C, YLR165C, YMR197C, YNL157W, YOL002C, YOL109W, YOR180C, YPL010W, YPL233W, YBR036C, YDR297W, YGR149W, YGR224W, YNL043C, YPL067C, YPL170W, YCR046C, YDR387C, YFL050C, YGL051W, YHR132C, YIL112W, YJL141C, YKR098C, YLR052W, YLR206W, YML129C, YNL203C, YNR014W, YOL043C, YOL096C, YPR184W, YAL028W, YAL055W, YAR062W, YBL095W, YBL102W, YBR122C, YBR157C, YBR161W, YBR251W, YBR298C, YCR039C, YCR083W, YDL018C, YDL067C, YDL078C, YDL091C, YDL215C, YDL216C, YDR022C, YDR067C, YDR079W, YDR181C, YDR186C, YDR196C, YDR262W, YDR306C, YDR319C, YER188W, YGL004C, YGL035C, YGR036C, YGR062C, YGR120C, YGR131W, YGR141W, YGR167W, YGR287C, YHL024W, YHR080C, YHR097C, YIL077C, YJL046W, YJL070C, YJL096W, YJL113W, YJL146W, YJL180C, YJR019C, YJR049C, YKR058W, YLL005C, YLR078C, YLR151C, YLR271W, YLR295C, YLR351C, YLR375W, YMR023C, YMR025W, YMR135C, YMR210W, YMR267W, YMR278W, YMR293C, YNL073W, YNR037C, YNR040W, YNR072W, YOR028C, YOR316C, YOR328W, YOR363C, YPL039W, YPL040C, YPL099C, YPL107W, YPL134C, YPL138C, YPL140C.

The base sequences and the amino acid sequences of the yeast genes are disclosed in public databases such as MIPS in Germany: Munich Information Center for Protein Sequence, and SGD in USA: *Saccharomyces* Genome Database, and are known via the internet. The sequences of promoters are also disclosed in a public database of SCPD: The Promoter Database of *Saccharomyces cerevisiae*.

In addition to the promoters from yeast genes as described above, promoters from a gene that is homologous to the yeast genes and is derived from other species may be used in the invention. In this context, "a gene that is homologous to the yeast genes" means a gene that comprises a base sequence having a 50% or more, preferably 80% or more of the base sequences of yeast genes, wherein the base sequence encodes a protein having the same functions as the proteins encoded by the yeast genes.

A polynucleotide encoding a marker protein is operably linked to a polynucleotide of a promoter from the gene as described above so as to provide a polynucleotide construct. Processes to link a polynucleotide encoding a protein operably to a promoter is well known in the art. See, for example, R. W. Old, S. B. Primrose Principles of Gene Manipulation 5th Ed., BAIFUKAN CO., LTD, pp 138-165, pp. 234-263, 2000.

Examples of marker proteins include GFP (Green Fluorescence Protein) (Heim, R., Cubitt, A. B. and Tsien, R. Y. (1995) Nature 373, 663-664; Heim, R., Prasher D C. and Tsien, R. Y. (1994) Proc. Natl. Acad. Sci., 91, 12501-12504; Warg, S. and Hazerigg, T. (1994) Nature 639, 400-403; Youvan, D. C. and Michel-Beyerle, M. E. (1996) Nature Biotechnology 14 1219-1220; Chalfie, M., Tu, Y., Euskirchen, G., Ward, W. W. and Prasher, D. C. (1994) Science 263, 802-805), β-galactosidase (Canestro C, Albalat R, Escriva H, Gonzalez-Duarte R. Endogenous beta-galactosidase activity in amphioxus: a useful histochemical marker for the digestive system. Dev Genes Evol 2001 March 211(3):154-6), luciferases (Arch Toxicol 2002 June; 76(5-6):257-61, Estrogenic activity of IJV filters determined by an in vitro reporter gene assay and an in vivo transgenic zebrafish assay. Schreurs R, Lanser P, Seinen W, Van Der Burg B.), and acetyltransferase (J Recept Signal Transduct Res 2001 February; 21(1):71-84, A simplified method for large scale quantification of transcriptional activity and its use in studies of steroids and steroid receptors. Zhang S, Lu J, Iyama K, Lo S C, Danielsen M.).

The present invention also relates to a vector that comprises a polynucleotide construct as described above.

A polynucleotide comprising a promoter sequence from yeast genes is obtained by preparing a primer that transcribes a likely necessary portion on the basis of the base sequence of the yeast genes as known in the public database, and amplifying the same by PCR using the genomic DNA of yeast as a template. Further, a plasmid that is capable of replicating in an intended cell is selected, and a base sequence of a marker protein is introduced into the plasmid. The polynucleotide comprising a promoter sequence as shown above is inserted upstream the marker gene to obtain an intended vector.

The present invention also relates to a host cell that is transformed with the vector as described above. It is natural to use preferably human cells as a host cell, and cells from other mammalian such as mouse may be used. Also, cells from fishes, nematode or the like as used in bioassay so far may be used in view of environmental toxic evaluation. Further, it is preferred to use microbiological cells since cultivation of them are easy. It is more preferred to use yeast cells because the present method is based on the use of genes from yeast cells, and because yeast is grown irrespective of variable environmental conditions such as salt concentration. Transformation of cells are well known. For example, see Kaiser C, Michaelis S, Mitchell A: Lithium acetate yeast transformation, Methods in Yeast Genetics, A Cold Spring Harbor Laboratory Course Manual 1994 edition (Cold Spring Harbor Laboratory Press) pp. 133-134, 1994. The purpose may be attained without vector when the encoding region of the yeast gene is replaced with a polynucleotide sequence encoding a marker protein. The polynucleotide construct can be directly introduced into cells, and the method therefore is also well known.

The invention also relates to a process for detecting a toxic compound in a test material, which comprises:

(1) contacting the test material to the transformed cells as described above, and (2) detecting the expression of mRNA encoding a marker protein.

The step to contact a test material to a cell comprises for example culturing the transformed cell in liquid at an appropriate condition for the cultivation of the cell, and adding the test material directly to the culture liquid.

Then, the expression level of a marker protein or a mRNA encoding the protein is determined.

The determination of the expression level of a marker protein may be conducted by destroying the cells, obtaining an extract containing the protein, and determining the level of marker protein in the extract. For example, when a marker protein is GFP, the fluorescence level in the protein extract is determined with a spectrofluorometer. Also, even when the cells are not destroyed, it is possible to determine them by observation and image processing with fluorescence microscopes and laser microscopes, determination with flow cytometry, and detection with evanescent lights.

The level of an expressed mRNA may be detected by 1) northern blotting (OGATA Nobukuni, NOJIMA Hiroshi: Genetic Engineering Keywords Book, revised 2nd ed., Yodosha, co.jp, 2000, pp 299-301), 2) reverse transcription-PCR (RT-PCR) (NAKABEPPU Yusaku, et al.: Cell Technology, suppl. Tips series, Modified PCR Tips, Shujunsha Co. Ltd., 1999, pp 25-43) and the like.

Procedures of northern blotting comprises electrophoresing the RNA, transferring the pattern to a filter, and hybridizing it with a specific probe labeled with an isotope, thereby analyzing the presences and the amount of mRNA in the sample as well as the length of the same. RT-PCR is a procedure for detection and quantitative determination of an intended RNA in a form of the amplified cDNA, which comprises forming cDNA from the RNA by reverse-transcription with reverse transcriptase, and conducting PCR using the cDNA as a starting material as well as specific primer sets and a thermostable DNA polymerase.

Toxic substances to be detected according to the present invention include, but are not limited to, $Na_2As$, $CdCl_2$, $HgCl_2$, $PbCl_2$, 4-nitroquinolin-N-oxide, 2,4,5-trichlorophenol, γ-hexachlorocyclohexane, manganese ethylenebis (dithiocarbamate), 2,4,5,6-tetrachloro-1,3-benzenedicarbonitrile, tetramethylthiuram disulfide, zinc N,N'-ethylenebis (dithiocarbamate), 8-methyl-N-vanillyl-6-nonenamide, gingerol, acrolein, dimethylsulfoxide, Roundup (trademark, herbicide) (N-(phosphomethyl) glycinate ammonium 41.0%, surfactant 59.0%), sodium dodecylbenzosulfonate, sodium lauryl sulfate, 2,4-dichlorophenoxyacetic acid, potassium cyanide, benzo(a)pyrene, formaldehyde, bisphenol-A, 2,5-dichlorophenol, methylmercury chloride, p-nonylphenol, pentachlorophenol, nickel (II) chloride, potassium bichromate, triphenyltin chloride, phenol, S-4-chlorobenzyl-N,N-diethylcarbamate, hexachlorophene, triclosan, and copper sulfate.

When the method as described above is conducted using two or more cells, both of which are transformed with a vector comprising a polynucleotide of a promoter from different yeast genes operably linked to a polynucleotide encoding a marker protein, then toxic substances can be further examined. For example, as shown in the working examples hereinafter, YLL057C can be used as a yeast gene promoter to detect 2,4-dichlorophenoxyacetic acid, arsenious acid or a salt thereof, cadmium salt, and cyanide or a salt thereof, and YLR303W can be used as a yeast gene promoter to detect 2,4-dichlorophenoxyacetic acid, arsenious acid or a salt thereof, cadmium salt, cyanide or a salt thereof, benzo(a) pyrene, formaldehyde, manganese ethylenebis (dithiocarbamate), and a mercuric salt. Accordingly, when for example the expression of a marker protein is induced by using YLR303W as yeast gene, and not induced by YLL057C, then toxic substances are identified as benzo(a)pyrene, mercuric salt, manganese ethylenebis(dithiocarbamate) or formaldehyde. When the expression of a marker protein is induced by using both yeast genes, then toxic substances are identified as 2,4-dichlorophenoxyacetic acid, arsenious acid or a salt thereof, cadmium salt, or cyanide or a salt thereof.

The following examples are presented for purpose of further illustration of the invention, and such examples are not intended to be limiting the invention in any respect.

EXAMPLES

Example 1

The following experiment was conducted to examine which yeast gene is useful for the detection of a toxic substance.

Yeast (*Saccharomyces cerevisiae* S288C (α SUC2mal mel gap2 CUP1)) were cultured at 25° C. on YPD medium (yeast extract 1%, polypepton 2%, glucose 2%). One of toxic chemical substances was added to the cell at logarithmic growth phase, and the cell was further cultured for two hours. Cell was cultured without any chemical substance in the same condition, and was used as control. Concentrations of the chemical substances were defined to inhibit the growth of the yeast but not lead to death.

| Chemical Substances | Concentrations |
| --- | --- |
| (1) $Na_2As$ | 0.3 mM |
| (2) $CdCl_2$ | 0.3 mM |
| (3) $HgCl_2$ | 0.7 mM |
| (4) $PbCl_2$ | 2 mM |
| (5) 4-nitroquinolin-N-oxide | 0.2 μM |
| (6) 2,4,5-trichlorophenol | 16 μM |
| (7) γ-hexachlorocyclohexane | 1.3 mM |
| (8) manganese ethylenebis(dithiocarbamate) | 2 ppm |
| (9) 2,4,5,6-tetrachloro-1,3-benzenedicarbonitrile | 10 μM |
| (10) Tetramethylthiuram disulfide | 75 μM |
| (11) zinc N,N'-ethylenebis(dithiocarbamate) | 2 ppm |
| (12) 8-methyl-N-vanillyl-6-nonenamide | 0.82 mM |
| (13) gingerol | 1.36 mM |
| (14) acrolein | 0.20 mM |
| (15) dimethylsulfoxide | 1.41 M |
| (16) Roundup (trademark, herbicide)[1] | 1500-fold dilution |
| (17) sodium dodecylbenzosulfonate | 0.02% |
| (18) sodium lauryl sulfate | 0.01% |

[1] N-(phosphomethyl) glycinate ammonium 41.0%, surfactant 59.0%

After the completion of cultivation, the culture was centrifuged to collect the cells. To the cells, sodium acetate buffer (50 mM sodium acetate, 10 mM EDTA, 1% SDS) was added, and the mixture was shaken at 65° C. for five minutes, followed by returning to room temperature, and obtaining the supernatant, which procedure was repeated two times. To the supernatant, ½ amount of a solution of phenol/chloroform was added, and the mixture was centrifuged to give a supernatant, which was added with an equal amount of chloroform, and the mixture was centrifuged to give a supernatant. To the supernatant, an equal amount of isopropanol containing 0.3 M sodium acetate was added, and the mixture was allowed to stand at room temperature for 30 minutes, after which the mixture was centrifuged to give a sediment of the whole RNAs. Seventy % ethanol was added to the sediment, and the mixture was again centrifuged to give a sediment, which was then dried and dissolved in water. mRNA was isolated from the whole RNAs as followings. In view of the fact that a poly A chain is attached to the 3' terminus of mRNA, a polynucleotide having a poly T structure which was immobilized on the surface of latex beads was used to trap the mRNA, and then the mRNA was washed and eluted with spine column (Oligotex-dT30<Super>mRNA Purification Kit, Takara). Reverse transcription of the mRNA was conducted with a reverse transcriptase (Super Script II Reverse Transcriptase; catalogue No. 18064-014, GibcoBRL) using fluorescence-labeled nucleotides to give cDNAs that were introduced with Cy3-dUTP or Cy5-dUTP during the reverse transcription.

The labeled cDNAs were dissolved in TE buffer (10 mM Tris-HCl/1 mM EDTA, pH8.0), and the solution was dropped on the DNA chip containing the whole genes of yeast (DNA Chip Research Inc. Japan) so that the cDNAs were hybridized on the DNA chip at 65° C. for over 12 hours. The fluoresces intensity of the DNA chip was read with a scanner, and the ratio relative to the fluorescence intensity resulting from the absence of chemical substance was estimated as the following, which is shown in Tables 1 to 9:

$$\frac{\text{The level of expressed } mRNA \text{ in the presence of chemical substance}}{\text{The level of expressed } mRNA \text{ in the absence of chemical substance}}$$

In the Tables, "Intensity" indicated in the rightmost column is a value of the level of expressed mRNA of each gene in control cells as divided by the average level of the expressions of the whole genes. A gene of which mRNA level is lower in control, and is higher in cases of addition of chemical substance, is especially useful in the detection of toxic substances.

TABLE 1

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR102C | 3.4 | 3.2 | 2.4 | 1.1 | 0.7 | 0.4 | 1.1 | 4.9 | 9.8 | 61.5 | 13.5 | 0.5 | 1.1 | 4.1 | 0.9 | 1.2 | 1.1 | 1.2 | 0.53 |
| YDL218W | 3.5 | 1.2 | 2.6 | 1.4 | 0.7 | 0.9 | 1.1 | 1.5 | 72.5 | 12.6 | 5.7 | 0.9 | 1.1 | 4.8 | 1.1 | 3.5 | 1.1 | 0.9 | 0.42 |
| YDR533C | 3.4 | 4.9 | 3.5 | 1.8 | 1.3 | 2.2 | 1.7 | 5.4 | 7.3 | 12.7 | 7.7 | 1.4 | 3.0 | 2.9 | 2.5 | 6.7 | 2.3 | 2.7 | 1.82 |
| YGR110W | 1.6 | 3.1 | 2.2 | 5.9 | 0.9 | 0.9 | 1.7 | 1.5 | 6.4 | 4.8 | 0.5 | 1.4 | 3.6 | 2.8 | 1.2 | 17.1 | 0.9 | 2.1 | 0.19 |
| YKL071W | 8.3 | 3.8 | 5.4 | 2.8 | 1.1 | 18.6 | 3.7 | 24.7 | 162.2 | 109.2 | 40.3 | 1.0 | 8.4 | 21.9 | 1.7 | 2.2 | 1.0 | 0.9 | 0.31 |
| YLR460C | 2.1 | 2.1 | 2.0 | 1.1 | 1.3 | 0.6 | 1.1 | 8.1 | 13.9 | 31.6 | 14.3 | 0.4 | 0.7 | 3.5 | 0.7 | 1.8 | 1.0 | 1.1 | 0.48 |
| YMR090W | 6.9 | 9.5 | 2.3 | 3.5 | 0.7 | 3.8 | 2.7 | 3.9 | 16.7 | 6.1 | 8.8 | 2.2 | 6.9 | 6.5 | 1.9 | 5.1 | 1.8 | 2.8 | 1.30 |
| YOL150C | 4.1 | 3.7 | 9.9 | 0.9 | 1.0 | 5.2 | 2.4 | 3.7 | 10.8 | 8.3 | 9.4 | 2.9 | 8.9 | 5.7 | 1.8 | 3.1 | 2.7 | 2.2 | 0.47 |
| YBL048W | 2.0 | 7.9 | 2.3 | 2.8 | 1.3 | 2.0 | 1.9 | 1.2 | 7.2 | 4.4 | 2.0 | 1.2 | 2.7 | 2.0 | 4.1 | 5.7 | 1.3 | 1.0 | 0.29 |
| YBL107C | 1.4 | 1.1 | 0.4 | 1.5 | 1.2 | 1.1 | 2.1 | 1.9 | 1.0 | 3.1 | 2.9 | 1.4 | 2.6 | 2.5 | 1.4 | 1.5 | 0.9 | 1.4 | 1.03 |
| YFL024C | 1.0 | 1.1 | 1.1 | 0.7 | 1.1 | 2.0 | 3.3 | 0.9 | 0.5 | 0.5 | 0.6 | 0.8 | 0.9 | 3.3 | 0.9 | 1.1 | 0.9 | 0.8 | 0.37 |
| YGL121C | 2.6 | 5.0 | 1.4 | 4.2 | 0.9 | 9.8 | 4.7 | 3.0 | 7.0 | 15.0 | 6.1 | 1.6 | 7.8 | 5.8 | 1.6 | 8.5 | 2.7 | 3.5 | 0.60 |
| YHR029C | 2.8 | 1.8 | 1.8 | 1.8 | 1.0 | 2.7 | 2.0 | 2.7 | 13.6 | 8.6 | 3.8 | 1.5 | 4.7 | 3.5 | 1.0 | 1.0 | 2.1 | 2.1 | 0.87 |
| YHR209W | 2.8 | 1.1 | 0.8 | 4.5 | 1.8 | 3.2 | 5.0 | 2.0 | 2.9 | 6.4 | 3.3 | 1.0 | 2.0 | 2.2 | 5.0 | 3.5 | 2.6 | 2.6 | 0.56 |
| YKL107W | 2.4 | 2.5 | 0.5 | 0.8 | 1.1 | 2.0 | 1.1 | 0.9 | 28.2 | 8.3 | 2.0 | 1.0 | 1.9 | 3.4 | 1.7 | 3.5 | 1.6 | 0.9 | 0.17 |
| YKR075C | 1.5 | 0.7 | 2.7 | 4.5 | 1.2 | 1.5 | 1.4 | 2.0 | 0.2 | 0.6 | 1.3 | 2.3 | 3.8 | 2.7 | 0.4 | 4.3 | 2.4 | 1.9 | 1.15 |
| YLL056C | 2.1 | 2.3 | 3.0 | 2.0 | 1.1 | 0.6 | 1.0 | 1.3 | 58.8 | 8.8 | 1.7 | 1.3 | 6.8 | 11.0 | 1.5 | 4.8 | 5.3 | 2.5 | 0.32 |
| YLR297W | 2.4 | 2.1 | 3.5 | 1.7 | 1.3 | 0.8 | 1.1 | 1.3 | 2.1 | 5.5 | 3.5 | 0.8 | 0.8 | 2.3 | 0.7 | 1.8 | 0.7 | 1.0 | 0.81 |
| YOR338W | 1.8 | 1.8 | 0.5 | 1.7 | 1.6 | 2.6 | 1.3 | 2.2 | 0.6 | 3.5 | 0.8 | 1.2 | 1.4 | 2.5 | 1.8 | 1.0 | 1.1 | 0.5 | 0.52 |
| YOR391C | 2.1 | 2.0 | 0.9 | 1.2 | 1.3 | 1.6 | 2.0 | 2.8 | 18.8 | 18.1 | 3.2 | 1.1 | 2.3 | 2.4 | 5.8 | 2.2 | 1.0 | 0.9 | 0.22 |
| YPL280W | 1.7 | 1.9 | 1.9 | 2.0 | 1.4 | 1.9 | 1.8 | 2.3 | 49.8 | 14.0 | 1.9 | 0.9 | 2.4 | 2.4 | 4.3 | 1.5 | 1.2 | 0.9 | 0.22 |
| YLR346C | 4.4 | 2.0 | 2.1 | 4.5 | 1.4 | 5.5 | 5.6 | 1.3 | 8.6 | 6.6 | 0.5 | 4.2 | 6.2 | 2.2 | 1.0 | 2.4 | 10.6 | 7.8 | 0.53 |
| YOR049C | 2.5 | 0.9 | 12.8 | 1.4 | 1.3 | 8.4 | 4.2 | 0.9 | 1.1 | 1.9 | 1.1 | 6.7 | 7.1 | 1.5 | 1.3 | 4.3 | 2.6 | 2.9 | 0.22 |
| YAL034C | 1.1 | 1.8 | 2.8 | 1.1 | 1.0 | 1.5 | 1.8 | 1.0 | 3.0 | 3.3 | 1.5 | 2.8 | 4.9 | 1.2 | 1.4 | 1.0 | 1.2 | 1.3 | 0.52 |
| YDR476C | 0.7 | 1.8 | 6.0 | 1.2 | 0.5 | 3.1 | 1.5 | 1.3 | 1.7 | 3.4 | 1.6 | 2.1 | 2.8 | 1.1 | 2.2 | 2.0 | 2.4 | 1.5 | 0.58 |
| YGR035C | 1.6 | 0.6 | 1.2 | 0.6 | 1.3 | 3.3 | 1.1 | 0.9 | 1.1 | 0.5 | 0.4 | 3.3 | 2.1 | 0.8 | 0.3 | 1.9 | 2.5 | 4.3 | 1.04 |
| YGR284C | 1.0 | 2.0 | 4.0 | 1.4 | 1.2 | 1.4 | 2.2 | 1.1 | 4.3 | 1.8 | 1.7 | 2.1 | 3.6 | 1.2 | 3.9 | 1.9 | 1.3 | 2.1 | 2.57 |
| YHR054C | 1.7 | 0.9 | 2.2 | 1.0 | 1.0 | 2.9 | 1.6 | 1.8 | 2.6 | 7.7 | 0.9 | 3.6 | 5.8 | 1.0 | 0.8 | 2.2 | 5.1 | 3.4 | 0.80 |
| YLR008C | 0.9 | 0.5 | 0.7 | 0.9 | 1.3 | 2.7 | 2.0 | 1.0 | 0.4 | 0.7 | 0.8 | 3.5 | 6.2 | 1.6 | 0.7 | 1.7 | 5.4 | 4.9 | 2.00 |
| YMR315W |  | 4.3 | 1.8 | 1.7 |  | 4.2 | 2.9 | 2.0 | 2.4 | 2.6 | 3.2 | 2.0 | 2.5 | 1.3 | 2.5 | 1.6 | 2.1 | 2.8 | 1.76 |
| YNL211C | 1.2 | 1.0 | 0.8 | 1.0 | 1.0 | 7.4 | 3.1 | 1.1 | 0.8 | 1.1 | 1.1 | 3.2 | 9.9 | 1.1 | 0.8 | 9.3 | 4.2 | 6.8 | 0.52 |
| YOL031C | 0.9 | 1.9 | 1.0 | 1.7 | 1.2 | 1.0 | 2.5 | 2.1 | 2.3 | 1.4 | 1.3 | 2.1 | 2.4 | 1.1 | 4.4 | 1.5 | 1.2 | 1.9 | 1.20 |
| YOL101C | 0.9 | 0.8 | 0.4 | 1.7 | 1.6 | 0.5 | 0.7 | 0.9 | 0.1 | 0.3 | 0.9 | 2.4 | 0.2 | 0.8 | 0.6 | 3.5 | 0.6 | 0.6 | 1.37 |
| YAR031W | 1.5 | 1.1 | 1.1 | 1.7 | 1.1 | 2.9 | 1.6 | 1.2 | 2.7 | 1.6 | 1.4 | 1.2 | 3.3 | 1.4 | 0.9 | 3.5 | 1.6 | 2.5 | 1.00 |
| YBL049W | 2.9 | 11.8 | 2.1 | 2.9 | 1.1 |  | 1.7 | 1.9 | 5.2 | 5.2 | 2.2 | 0.7 | 3.9 | 1.5 | 7.2 | 6.4 | 1.1 | 1.1 | 0.47 |
| YBR062C | 1.3 | 1.7 | 0.4 | 1.2 | 1.4 | 1.9 | 1.5 | 1.9 | 5.4 | 2.2 | 2.3 | 1.2 | 2.8 | 2.6 | 0.7 | 2.2 | 1.4 | 1.6 | 0.93 |
| YCR013C | 1.3 | 1.4 | 5.0 | 1.1 | 1.1 | 1.8 | 1.6 | 0.7 | 0.8 | 1.3 | 2.4 | 1.4 | 3.9 | 1.5 | 1.6 | 1.6 | 1.1 | 1.3 | 2.80 |
| YDL027C | 1.2 | 2.0 | 1.7 | 1.7 | 1.2 | 2.1 | 2.9 | 1.5 | 2.0 | 2.3 | 1.7 | 1.7 | 3.2 | 1.1 | 1.4 | 1.8 | 1.4 | 2.0 | 0.69 |
| YDL110C | 1.5 | 1.4 | 1.1 | 2.1 | 0.8 | 1.7 | 2.5 | 1.8 | 3.0 | 2.3 | 1.9 | 1.5 | 2.7 | 2.7 | 1.3 | 3.6 | 2.0 | 4.4 | 1.27 |
| YDL169C | 1.7 | 1.7 | 1.1 | 1.3 | 1.1 | 2.6 | 2.1 | 1.3 | 7.3 | 4.7 | 1.2 | 1.2 | 3.7 | 2.7 | 2.2 | 3.8 | 1.5 | 1.6 | 0.42 |
| YDR070C | 2.2 | 6.4 | 3.6 | 3.5 | 0.9 | 6.2 | 1.4 | 1.9 | 13.9 | 6.0 | 4.1 | 4.3 | 6.6 | 2.0 | 2.1 | 15.1 | 1.2 | 3.1 | 0.44 |
| YDR210W | 1.1 | 1.0 | 0.9 | 1.0 | 2.0 | 1.2 | 1.5 | 1.4 | 0.5 | 1.0 | 1.0 | 1.0 | 2.3 | 1.1 | 1.0 | 1.5 | 1.9 | 1.9 | 1.82 |
| YDR214W | 1.3 | 4.0 | 4.5 | 1.3 | 1.1 | 1.7 | 1.5 | 1.5 | 5.5 | 2.4 | 1.9 | 1.1 | 5.3 | 1.2 | 1.1 | 0.7 | 1.2 | 1.0 | 1.07 |
| YDR435C | 1.2 | 1.1 | 1.2 | 1.4 | 1.2 | 2.5 | 2.1 | 1.2 | 0.8 | 2.1 | 1.3 | 1.1 | 2.5 | 1.3 | 0.6 | 2.0 | 1.3 | 2.0 | 1.30 |
| YER037W | 2.0 | 2.1 | 0.8 | 1.1 | 1.3 | 3.2 | 2.6 | 1.0 | 1.0 | 5.5 | 1.5 | 1.2 | 3.0 | 1.7 | 0.8 | 1.8 | 1.7 | 2.6 | 1.17 |
| YFL044C | 1.0 | 1.5 | 0.8 | 2.3 | 1.6 | 1.3 | 1.6 | 1.4 | 5.2 | 3.7 | 2.2 | 1.2 | 4.7 | 1.2 | 1.0 | 1.8 | 1.3 | 1.4 | 0.50 |
| YFR003C | 1.2 | 1.5 | 0.8 | 1.6 | 1.0 | 2.2 | 1.4 | 1.4 | 8.3 | 3.1 | 1.4 | 0.9 | 2.5 | 2.1 | 1.0 | 1.4 | 1.3 | 1.8 | 1.01 |
| YFR020W | 1.0 | 0.9 | 1.2 | 1.0 | 0.9 | 1.4 | 1.1 | 0.9 | 3.7 | 3.5 | 1.4 | 0.9 | 2.3 | 1.8 | 2.6 | 1.0 | 1.2 | 0.9 | 0.61 |
| YFR044C | 0.9 | 1.3 | 3.8 | 1.1 | 0.9 | 2.1 | 1.2 | 0.8 | 2.1 | 2.2 | 1.9 | 1.2 | 3.1 | 0.8 | 1.5 | 1.2 | 1.0 | 1.0 | 1.99 |
| YGR010W | 1.2 | 1.6 | 0.9 | 1.2 | 0.8 | 1.2 | 1.7 | 1.6 | 13.6 | 8.9 | 1.5 | 0.9 | 5.2 | 1.9 | 1.3 | 1.4 | 0.8 | 1.3 | 0.55 |
| YGR142W | 2.7 | 6.2 | 15.3 | 1.3 | 1.3 | 0.9 | 1.4 | 1.5 | 36.8 | 12.2 | 2.3 | 2.0 | 8.9 | 0.9 | 1.3 | 0.3 | 1.9 | 1.5 | 1.28 |
| YGR161C | 2.0 | 2.2 | 5.4 | 3.8 | 1.0 | 1.4 | 1.4 | 1.3 | 2.0 | 3.8 | 0.8 | 1.7 | 2.8 | 0.9 | 1.7 | 1.1 | 1.5 | 1.8 | 0.65 |
| YGR212W | 1.5 | 1.7 | 1.5 | 1.3 | 1.2 |  |  | 1.0 | 1.1 | 3.8 | 0.9 | 1.5 | 10.0 | 1.1 | 1.1 | 2.1 | 3.9 | 2.2 | 0.28 |
| YGR268C | 1.1 | 2.3 | 2.0 | 2.5 | 1.1 | 1.1 | 1.0 | 1.1 | 4.1 | 1.6 | 0.8 | 1.0 | 2.8 | 1.0 | 1.5 | 1.2 | 1.5 | 1.4 | 0.48 |
| YHR016C | 0.8 | 1.5 | 1.7 | 1.5 |  | 1.8 | 3.7 | 0.8 | 2.8 | 2.0 | 2.2 | 1.3 | 3.3 | 0.9 | 0.6 | 2.1 | 1.2 | 1.4 | 0.51 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YHR087W | 1.2 | 2.7 | 8.6 | 2.8 | 0.7 | 4.2 | 3.4 | 1.2 | 4.1 | 3.9 | 3.7 | 1.4 | 4.0 | 1.5 | 1.9 | 3.8 | 1.2 | 2.9 | 1.34 |
| YJL048C | 1.7 | 2.5 | 2.0 | 2.9 | 0.9 | 1.5 | 0.7 | 1.5 | 1.2 | 3.8 | 3.2 | 1.1 | 2.4 | 1.7 | 0.6 | 2.3 | 1.6 | 2.5 | 0.82 |
| YJL144W | 1.9 | 1.6 | 2.2 | 1.6 | 1.2 | 1.7 | 1.7 | 1.3 | 14.6 | 8.9 | 3.0 | 0.8 | 3.9 | 1.6 | 1.0 | 2.5 | 2.2 | 2.4 | 0.60 |
| YJL163C | 1.2 | 1.9 | 1.7 | 1.5 | 0.9 | 2.8 | 2.3 | 0.7 | 14.5 | 2.5 | 3.1 | 2.0 | 4.5 | 1.0 | 2.0 | 2.8 | 1.5 | 1.7 | 0.28 |
| YJR074W | 1.0 | 1.4 | 2.0 | 2.0 | 0.7 | 1.2 | 1.8 | 1.3 | 3.7 | 3.1 | 1.2 | 2.0 | 2.8 | 1.7 | 3.4 | 1.5 | 1.8 | 1.9 | 0.68 |
| YKL065C | 1.9 | 2.0 | 1.3 | 1.7 | 1.0 | 2.3 | 3.8 | 1.8 | 3.1 | 3.9 | 1.3 | 1.3 | 3.0 | 2.1 | 1.7 | 2.8 | 2.8 | 4.6 | 2.29 |
| YKR011C | 1.1 | 1.6 | 0.9 | 1.6 | 1.2 | 2.3 | 2.7 | 2.0 | 4.7 | 4.4 | 1.5 | 1.1 | 3.5 | 1.4 | 1.8 | 1.3 | 1.3 | 1.9 | 0.66 |
| YKR018C | 0.7 | 1.1 | 1.7 | 0.7 | 0.9 | 1.7 | 1.0 | 0.7 | 3.9 | 1.7 | 1.4 | 1.0 | 3.0 | 1.1 | 1.0 | 1.8 | 1.0 | 1.2 | 0.98 |
| YKR046C | 1.9 | 7.8 | 2.8 | 1.8 | 0.6 | 1.9 | 1.3 | 0.8 | 3.9 | 2.0 | 2.6 | 1.3 | 2.8 | 1.9 | 2.9 | 3.5 | 1.2 | 1.9 | 0.73 |
| YKR049C | 1.6 | 4.2 | 1.0 | 3.2 | 0.9 | 3.0 | 2.4 | 1.3 | 2.2 | 3.2 | 2.2 | 1.2 | 4.1 | 2.1 | 0.9 | 4.2 | 1.6 | 3.3 | 1.17 |
| YLR132C | 1.0 | 1.1 | 0.3 | 1.1 | 1.2 | 1.1 | 1.1 | 0.7 | 4.5 | 2.5 | 0.5 | 1.0 | 2.7 | 1.3 | 2.3 | 1.6 | 1.2 | 1.6 | 0.36 |
| YLR161W | 0.9 | 0.8 | 0.8 | 0.7 | 0.9 | 1.2 | 1.3 | 0.8 | 1.0 | 1.5 | 1.5 | 0.8 | 2.1 | 1.0 | 0.6 | 1.1 | 1.1 | 0.9 | 0.33 |
| YLR217W | 0.9 | 2.0 | 2.1 | 0.7 | 1.4 | 1.4 | 1.5 | 1.0 | 3.2 | 8.2 |  | 0.9 | 3.8 | 0.9 | 0.9 | 0.8 | 1.0 | 1.2 | 0.35 |
| YLR328W | 1.3 | 1.2 | 1.3 | 0.9 | 0.9 | 4.8 | 5.4 | 1.1 | 0.9 | 1.2 | 1.4 | 1.2 | 4.3 | 0.5 | 0.8 | 1.4 | 1.1 | 0.8 | 1.04 |
| YML128C | 1.5 | 3.3 | 4.1 | 4.1 | 0.5 | 5.1 | 2.8 | 1.1 | 5.1 | 3.1 | 2.9 | 1.4 | 4.9 | 1.4 | 2.6 | 5.6 | 2.0 | 5.5 | 1.66 |
| YMR040W | 3.1 | 2.9 | 0.9 | 2.8 | 1.7 | 2.8 | 5.1 | 1.7 | 1.4 | 1.4 | 1.5 | 2.1 | 5.2 | 1.8 | 2.0 | 2.7 | 3.1 | 3.7 | 0.62 |
| YMR251W | 1.3 | 1.3 | 1.8 | 0.6 | 2.2 | 1.6 | 3.1 | 1.7 | 3.1 | 11.6 | 2.8 | 1.2 | 2.5 | 1.5 | 0.4 | 1.3 | 1.5 | 0.9 | 0.20 |
| YMR322C | 2.0 | 4.3 | 1.5 | 2.9 | 1.4 | 1.8 | 1.7 | 2.1 | 21.3 | 10.3 | 3.2 | 1.1 | 2.1 | 2.7 | 3.6 | 1.8 | 1.4 | 0.8 | 0.18 |
| YNL094W | 0.9 | 1.4 | 1.1 | 1.0 | 1.4 | 2.9 | 1.2 | 2.0 | 3.5 | 2.6 | 1.7 | 1.2 | 3.4 | 1.0 | 1.5 | 1.5 | 1.1 | 1.3 | 0.66 |
| YNL134C | 2.3 | 6.0 | 4.5 | 0.9 | 1.7 | 1.4 | 1.5 | 3.2 | 6.1 | 5.9 | 5.0 | 1.1 | 3.1 | 1.4 | 0.8 | 2.1 | 1.3 | 2.0 | 2.51 |
| YNL155W | 1.1 | 1.2 | 1.1 | 0.9 | 1.4 | 3.0 | 1.3 | 1.7 | 5.8 | 2.7 | 2.2 | 1.1 | 4.4 | 2.1 | 2.0 | 2.0 | 1.1 | 1.6 | 1.89 |
| YOR059C | 1.2 | 1.2 | 0.4 | 0.9 | 1.4 | 1.1 | 2.2 | 1.3 | 7.6 | 4.6 | 1.0 | 1.0 | 3.3 | 2.2 | 3.5 | 1.8 | 1.3 | 1.7 | 0.71 |
| YOR152C | 4.5 | 2.5 | 3.4 | 2.9 | 0.8 | 4.5 | 3.2 | 1.2 | 10.0 | 5.0 | 2.7 | 2.9 | 7.4 | 1.7 | 3.6 | 2.1 | 4.0 | 2.2 | 0.42 |
| YOR173W | 0.7 | 2.3 | 6.3 | 2.0 | 0.9 | 3.5 | 4.9 | 1.4 | 5.2 | 3.7 | 2.3 | 1.9 | 3.8 | 2.8 | 0.7 | 5.7 | 1.7 | 3.8 | 0.54 |
| YOR289W | 1.6 | 1.5 | 1.0 | 2.0 | 1.2 | 4.2 | 6.1 | 2.4 | 2.4 | 1.7 | 2.6 | 1.5 | 4.3 | 2.0 | 1.6 | 3.0 | 2.3 | 3.9 | 0.74 |
| YPR030W | 1.7 | 1.4 | 1.4 | 1.0 | 1.2 | 1.3 | 1.2 | 0.9 | 2.5 | 2.4 | 1.2 | 1.4 | 3.2 | 1.5 | 1.5 | 3.1 | 1.4 | 2.1 | 0.30 |
| YAL008W | 1.4 | 2.4 | 2.0 | 2.4 | 0.7 | 1.6 | 1.9 | 1.3 | 1.8 | 1.5 | 2.2 | 1.3 | 2.2 | 2.6 | 0.9 | 4.2 | 1.4 | 1.9 | 1.04 |
| YBR053C | 1.0 | 1.6 | 2.4 | 2.4 | 1.6 | 2.7 | 4.1 | 1.2 | 2.9 | 2.1 | 2.3 | 1.1 | 2.4 | 1.0 | 0.7 | 2.8 | 1.9 | 2.4 | 1.25 |
| YBR099C | 1.0 | 1.4 | 7.2 | 1.8 | 1.0 | 0.5 | 0.9 | 1.5 | 3.4 | 12.9 | 0.4 | 1.0 | 2.1 | 1.6 | 0.8 | 0.5 | 0.8 | 0.9 | 0.47 |
| YBR137W | 1.1 | 2.2 | 1.4 | 3.5 | 0.9 | 2.4 | 2.7 | 2.0 | 2.2 | 1.8 | 2.4 | 1.4 | 2.1 | 1.8 | 0.6 | 2.8 | 1.4 | 2.6 | 1.40 |
| YBR203W | 1.4 | 1.4 | 1.6 | 2.4 | 0.9 | 0.6 | 0.9 | 1.3 | 1.1 | 1.8 | 1.3 | 1.6 | 2.4 | 1.3 | 1.0 | 18.0 | 1.4 | 2.2 | 0.38 |
| YCL049C | 1.9 | 1.3 | 1.4 | 1.2 | 1.6 | 2.3 | 2.1 | 1.0 | 2.0 | 1.9 | 1.6 | 1.4 | 2.4 | 1.8 | 1.4 | 2.1 | 1.4 | 1.4 | 0.86 |
| YCR082W | 1.4 | 1.2 | 0.7 | 1.2 | 1.3 | 1.3 | 1.5 | 1.5 | 4.3 | 2.3 | 2.0 | 1.0 | 2.0 | 2.4 | 1.6 | 2.2 | 1.2 | 1.7 | 1.62 |
| YDL054C | 1.3 | 2.2 | 2.7 | 1.1 | 1.2 | 1.2 | 0.9 | 0.7 | 3.5 | 2.1 | 2.1 | 1.1 | 2.7 | 1.2 | 1.0 | 1.0 | 1.0 | 1.0 | 0.92 |
| YDL115C | 1.4 | 1.0 | 0.5 | 1.8 | 0.8 | 1.5 | 1.8 | 1.6 | 6.6 | 3.6 | 1.8 | 1.1 | 1.9 | 2.3 | 1.2 | 1.6 | 1.3 | 1.8 | 0.83 |
| YDL144C | 0.8 | 0.9 | 1.2 | 1.5 | 1.0 | 1.8 | 1.0 | 0.9 | 3.6 | 1.2 | 1.9 | 1.0 | 2.1 | 1.2 | 1.0 | 1.1 | 0.9 | 0.9 | 0.52 |
| YDL223C | 0.7 | 1.1 | 5.0 | 2.5 | 0.9 | 0.8 | 1.0 | 0.3 | 3.8 | 1.5 | 5.2 | 1.0 | 3.1 | 1.3 | 3.1 | 7.2 | 0.9 | 1.0 | 0.32 |
| YDR032C | 1.7 | 2.2 | 3.5 | 2.5 | 1.4 | 2.7 | 2.8 | 2.4 | 3.1 | 2.9 | 3.3 | 1.8 | 2.9 | 2.8 | 1.3 | 3.8 | 1.9 | 3.5 | 3.50 |
| YDR330W | 0.8 | 1.5 | 1.2 | 0.8 | 1.2 | 2.3 | 1.3 | 1.1 | 3.9 | 2.6 | 0.9 | 1.0 | 2.2 | 1.1 | 1.6 | 1.4 | 1.5 | 1.3 | 0.53 |
| YDR411C | 0.9 | 2.8 | 1.8 | 1.2 | 1.6 | 0.8 | 2.0 | 0.9 | 0.7 | 1.0 | 1.3 | 1.5 | 1.9 | 0.8 | 4.1 | 1.5 | 1.5 | 1.3 | 0.56 |
| YDR511W | 1.3 | 1.7 | 0.9 | 2.3 | 1.0 | 2.0 | 1.5 | 1.7 | 2.5 | 2.2 | 1.2 | 0.8 | 3.1 | 2.2 | 0.8 | 2.2 | 1.3 | 1.5 | 0.66 |
| YDR545W | 0.6 | 1.2 | 0.6 | 0.7 | 1.4 | 1.0 | 1.2 | 0.6 | 1.8 | 0.7 | 0.7 | 0.9 | 2.0 | 0.7 | 0.9 | 0.9 | 0.9 | 0.9 | 1.06 |
| YER004W | 1.0 | 1.5 | 1.9 | 1.4 | 1.5 | 1.2 | 1.4 | 1.1 | 4.5 | 2.9 | 2.2 | 1.7 | 4.6 | 1.8 | 1.4 | 2.3 | 1.4 | 1.2 | 1.48 |
| YER035W | 1.4 | 1.6 | 1.6 | 1.9 | 1.5 | 0.9 | 1.9 | 1.2 | 1.2 | 1.4 | 1.4 | 1.1 | 1.9 | 1.0 | 0.9 | 2.1 | 2.2 | 2.1 | 0.85 |
| YER079W | 1.1 | 1.6 | 1.9 | 2.0 | 0.8 | 1.5 | 1.9 | 1.4 | 5.3 | 3.4 | 2.1 | 0.9 | 2.1 | 1.6 | 0.5 | 1.4 | 1.0 | 1.6 | 0.69 |
| YER158C | 1.2 | 0.9 | 0.9 | 3.1 | 0.8 | 0.7 | 1.2 | 0.9 | 2.1 | 1.6 | 2.3 | 1.0 | 3.1 | 0.9 | 0.6 | 1.6 | 1.6 | 1.2 | 0.61 |
| YER163C | 1.1 | 2.4 | 1.2 | 1.6 | 0.8 | 2.0 | 1.5 | 1.4 | 5.4 | 3.4 | 1.6 | 1.0 | 2.9 | 1.9 | 1.6 | 2.4 | 1.2 | 1.2 | 0.62 |
| YER175C | 0.9 | 1.2 | 1.3 | 2.2 | 0.9 | 0.8 | 2.3 | 1.1 | 11.5 | 1.1 | 0.9 | 4.3 | 1.1 | 1.3 | 2.8 | 0.9 | 1.2 | | 0.53 |
| YFL006W | 0.8 | 2.8 | 1.6 | 1.0 | 1.4 | 1.2 | 1.0 | 1.0 | 3.2 | 1.7 | 1.2 | 1.2 | 3.1 | 1.7 | 2.4 | 1.1 | 1.0 | 0.8 | 0.82 |
| YFL010C | 1.0 | 4.8 | 1.3 | 1.0 | 1.3 | 1.9 | 1.5 | 1.0 | 3.1 | 1.4 | 1.4 | 1.5 | 3.3 | 1.4 | 1.7 | 1.4 | 1.9 | 1.6 | 0.77 |
| YFL032W | 0.4 | 1.5 | 1.6 | 0.8 | 0.9 | 0.6 | 1.1 | 0.4 | 0.5 | 0.6 | 1.1 | 0.7 | 2.4 | 0.6 | 2.0 | 0.7 | 1.7 | 0.8 | 1.62 |
| YGL037C | 1.5 | 2.7 | 6.5 | 2.1 | 0.9 | 1.3 | 2.9 | 1.2 | 2.1 | 1.6 | 3.9 | 0.8 | 2.3 | 1.0 | 0.8 | 1.5 | 1.3 | 2.6 | 4.58 |
| YGL047W | 1.0 | 1.9 | 1.6 | 2.3 | 1.3 | 1.5 | 1.7 | 1.1 | 4.5 | 5.7 | 1.9 | 1.1 | 2.6 | 2.3 | 1.7 | 2.9 | 1.1 | 1.2 | 0.97 |
| YGL053W | 1.5 | 1.5 | 1.2 | 2.5 | 2.0 | 2.7 | 3.7 | 1.2 | 3.3 | 2.4 | 1.3 | 1.3 | 3.3 | 1.1 | 1.1 | 3.9 | 2.2 | 3.7 | 1.26 |
| YGL199C | 1.1 | 1.7 | 1.7 | 1.0 | 0.7 | 0.7 | 1.3 | 0.7 | | 0.1 | | 0.9 | 2.0 | 0.8 | 1.6 | 1.6 | 1.2 | 1.0 | 0.36 |
| YGR101W | 1.0 | 1.3 | 1.2 | 1.1 | 1.2 | 0.9 | 1.5 | 0.8 | 4.0 | 1.4 | 2.0 | 1.0 | 2.4 | 0.9 | 1.1 | 2.0 | 1.0 | 1.1 | 1.04 |
| YGR130C | 0.9 | 0.7 | 0.6 | 1.6 | 1.4 | 0.9 | 1.3 | 0.9 | 2.0 | 1.5 | 0.8 | 0.7 | 1.9 | 0.9 | 1.2 | 2.2 | 1.3 | 1.6 | 0.78 |
| YGR154C | 1.8 | 2.9 | 2.2 | 0.5 | 1.2 | 1.4 | 2.0 | 1.7 | 25.2 | 9.1 | 1.5 | 0.9 | 2.5 | 2.2 | 0.7 | 2.0 | 1.0 | 1.2 | 0.36 |
| YGR221C | 0.9 | 2.2 | 0.9 | 1.4 | 0.9 | 3.0 | 1.2 | 1.1 | | 0.7 | 0.5 | 1.6 | 2.3 | 1.4 | 1.5 | 2.7 | 1.3 | 1.3 | 0.29 |
| YHR138C | 2.8 | 1.8 | 2.2 | 2.8 | 1.5 | 3.8 | 3.0 | 1.4 | 5.3 | 4.6 | 1.6 | 1.8 | 4.0 | 3.4 | 2.2 | 3.3 | 5.0 | 7.1 | 1.89 |
| YHR199C | 1.9 | 2.0 | 3.2 | 2.0 | 1.2 | 1.1 | 1.1 | 1.0 | 8.6 | 6.0 | 1.9 | 1.1 | 2.1 | 2.0 | 2.8 | 3.3 | 1.1 | 0.9 | 0.63 |
| YIL041W | 1.0 | 1.2 | 2.1 | 1.3 | 0.5 | 1.0 | 0.8 | 0.9 | 1.8 | 1.4 | 1.4 | 1.0 | 2.3 | 1.3 | 1.3 | 0.7 | 0.8 | 1.1 | 1.33 |
| YIL087C | 1.3 | 1.9 | 3.4 | 1.6 | 1.4 | 4.1 | 1.8 | 1.1 | 2.4 | 1.8 | 2.8 | 1.1 | 2.4 | 1.3 | 0.4 | 5.6 | 1.7 | 1.6 | 0.68 |
| YJL057C | 1.5 | 1.2 | 1.6 | 1.7 | 1.5 | 1.4 | 2.7 | 1.5 | 7.3 | 6.1 | 2.0 | 1.0 | 2.5 | 1.6 | 1.4 | 1.9 | 1.4 | 1.5 | 0.51 |
| YJL066C | 0.9 | 1.2 | 1.2 | 2.5 | 0.8 | 1.4 | 1.6 | 0.8 | 2.0 | 2.1 | 0.8 | 1.0 | 2.2 | 1.0 | 1.3 | 2.8 | 1.4 | 1.5 | 0.43 |
| YJL082W | 1.4 | 0.8 | 2.4 | 1.1 | 1.7 | 0.2 | 0.4 | 0.9 | 1.4 | 2.9 | 1.0 | 1.3 | 2.1 | 0.5 | 3.2 | 0.2 | 0.6 | 0.3 | 2.07 |
| YJL151C | 1.0 | 2.4 | 3.2 | 1.2 | 1.3 | 2.2 | 1.4 | 0.8 | 0.5 | 1.6 | 1.0 | 1.3 | 2.4 | 1.3 | 1.0 | 2.5 | 3.5 | 2.4 | 1.69 |
| YJL152W | 0.9 | 1.5 | 1.8 | 1.6 | 1.5 | 1.2 | 1.2 | 0.7 | 0.3 | 1.0 | 1.0 | 1.0 | 1.8 | 1.4 | 0.8 | 1.6 | 2.5 | 1.7 | 0.80 |
| YJL161W | 1.7 | 2.2 | 1.5 | 4.6 | 1.1 | 8.0 | 3.6 | 1.4 | 3.1 | 2.1 | 3.7 | 1.0 | 2.5 | 2.2 | 0.6 | 4.4 | 1.9 | 2.1 | 0.44 |
| YJL171C | 2.3 | 0.7 | 2.8 | 1.4 | 1.0 | 2.7 | 1.4 | 0.9 | 1.0 | 1.7 | 2.2 | 1.0 | 2.9 | 1.0 | 1.8 | 1.0 | 3.6 | 2.9 | 1.94 |
| YJR008W | 1.6 | 1.5 | 1.2 | 1.7 | 1.4 | 2.2 | 2.9 | 1.1 | 1.8 | 1.9 | 1.4 | 1.3 | 2.0 | 1.2 | 0.9 | 3.3 | 1.5 | 2.7 | 0.87 |
| YKL151C | 1.2 | 3.1 | 1.7 | 2.5 | 1.0 | 2.0 | 5.6 | 1.0 | 3.3 | 3.5 | 2.3 | 1.0 | 2.0 | 1.3 | 1.4 | 3.7 | 1.4 | 1.8 | 1.02 |
| YKL153W | 1.1 | 1.4 | 2.0 | 0.7 | 1.0 | 2.9 | 1.1 | 0.7 | 0.8 | 1.4 | 2.1 | 1.1 | 2.4 | 1.1 | 1.5 | 1.1 | 0.9 | 1.3 | 1.60 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YKL195W | 0.8 | 0.5 | 0.4 | 1.1 | 1.9 | 2.5 | 2.1 | 1.2 | 3.6 | 2.1 | 1.0 | 1.1 | 2.4 | 1.6 | 0.9 | 1.7 | 1.4 | 1.6 | 1.58 |
| YLR054C | 2.0 | 1.5 | 0.4 | 2.4 | 1.3 | 1.2 | 1.1 | 1.1 | 2.7 | 1.1 | 0.7 | 1.1 | 3.2 | 1.1 | 0.7 | 0.9 | 1.6 | 1.1 | 0.14 |
| YLR149C | 1.4 | 1.9 | 3.4 | 2.3 | 0.8 | 1.4 | 1.6 | 1.1 | 6.2 | 5.2 | 2.8 | 2.0 | 3.0 | 1.2 | 1.3 | 2.8 | 1.3 | 3.0 | 0.33 |
| YLR152C | 0.7 | 1.3 | 1.1 | 0.9 | 1.1 | 2.1 | 1.4 | 1.2 | 0.6 | 1.1 | 3.6 | 1.0 | 2.8 | 1.2 | 0.8 | 2.8 | 1.5 | 1.8 | 0.46 |
| YLR324W | 0.7 | 1.2 | 0.9 | 1.0 | 1.3 | 1.2 | 1.0 | 1.0 | 3.1 | 1.4 | 0.9 | 0.8 | 2.3 | 1.4 | 1.6 | 1.7 | 1.2 | 1.2 | 0.49 |
| YLR350W | 1.2 | 1.9 | 3.2 | 2.3 | 0.8 | 1.6 | 1.2 | 1.0 | 0.6 | 1.4 | 0.9 | 1.8 | 4.5 | 2.8 | 1.6 | 2.9 | 1.6 | 1.1 | 1.52 |
| YLR387C | 0.9 | 1.6 | 0.8 | 0.6 | 1.3 | 1.9 | 1.1 | 1.4 | 7.8 | 3.0 | 0.9 | 1.1 | 3.6 | 1.7 | 1.9 | 1.0 | 1.0 | 1.4 | 1.20 |
| YML117W | 0.9 | 2.2 | 0.9 | 1.6 | 0.8 | 1.0 | 0.7 | 0.7 | 1.0 | 1.4 | 0.8 | 0.8 | 2.0 | 0.8 | 2.8 | 0.7 | 1.1 | 1.3 | 0.70 |
| YMR009W | 2.3 | 1.9 | 0.5 | 1.9 | 1.9 | 1.2 | 1.9 | 1.4 | 3.4 | 2.2 | 2.1 | 0.6 | 2.3 | 1.9 | 0.6 | 2.3 | 2.7 | 2.5 | 0.75 |
| YMR067C | 0.9 | 0.9 | 1.1 | 0.4 | 1.1 | 1.4 | 1.2 | 1.1 | 4.0 | 3.5 | 1.1 | 1.1 | 2.2 | 1.5 | 1.4 | 1.0 | 1.0 | 1.0 | 0.49 |
| YMR097C | 1.5 | 1.0 | 0.7 | 1.6 | 0.7 | 1.2 | 1.5 | 1.5 | 2.1 | 2.1 | 1.5 | 1.2 | 2.1 | 2.1 | 1.7 | 1.7 | 1.4 | 1.8 | 0.59 |
| YMR102C | 1.0 | 2.9 | 1.1 | 0.8 | 1.2 | 6.3 | 1.8 | 1.0 | 1.7 | 2.6 | 1.5 | 2.4 | 4.4 | 0.7 | 0.7 | 1.1 | 2.4 | 2.8 | 0.94 |
| YMR107W | 5.0 | 3.9 | 1.7 | 18.4 | 1.1 | 1.0 | 1.2 | 1.3 | 6.0 | 17.1 | 3.0 | 0.8 | 1.8 | 8.1 | 1.9 | 12.0 | 1.3 | 8.1 | 0.49 |
| YMR180C | 1.2 | 0.9 | 1.0 | 1.3 | 1.0 | 2.4 | 1.7 | 1.8 | 1.8 | 2.2 | 0.7 | 1.2 | 3.1 | 1.7 | 1.0 | 1.8 | 1.4 | 1.7 | 0.57 |
| YMR184W | 1.3 | 5.4 | 1.0 | 1.1 | 0.8 | 0.9 | 1.6 | 1.9 | 2.1 | 0.9 | 1.5 | 1.7 | 2.3 | 1.5 | 1.1 | 1.2 | 1.4 | 2.0 | 0.68 |
| YMR191W | 1.3 | 2.4 | 1.9 | 1.6 | 1.5 | 1.0 | 2.0 | 1.1 | 2.2 | 3.5 | 2.3 | 1.8 | 3.4 | 1.5 | 2.7 | 1.7 | 1.2 | 2.1 | 0.99 |
| YMR295C | 1.7 | 1.0 | 1.2 | 1.6 | 1.4 | 1.9 | 1.3 | 1.0 | 1.0 | 0.8 | 1.2 | 1.1 | 2.3 | 1.3 | 0.9 | 1.9 | 2.1 | 3.4 | 3.43 |
| YMR316W | 3.2 | 2.9 | 1.1 | 1.9 | 1.1 | 0.7 | 2.0 | 1.6 | 2.1 | 3.0 | 1.5 | 1.9 | 2.9 | 1.3 | 0.5 | 1.3 | 6.9 | 6.4 | 1.25 |
| YNL044W | 1.3 | 0.9 | 2.3 | 1.3 | 1.2 | 0.9 | 0.9 | 1.8 | 0.8 | 0.8 | 1.1 | 1.0 | 3.1 | 1.2 | 2.4 | 1.0 | 3.1 | 3.4 | 2.56 |
| YNL074C | 0.9 | 1.3 | 1.8 | 1.2 | 1.3 | 1.7 | 1.1 | 0.6 | 1.5 | 2.0 | 1.3 | 0.9 | 2.3 | 0.6 | 1.0 | 0.7 | 1.1 | 1.3 | 0.68 |
| YNL092W | 1.3 | 1.4 | 2.4 | 1.8 | 0.9 | 1.2 | 1.6 | 0.9 | 2.3 | 1.5 | 0.7 | 1.1 | 2.3 | 1.2 | 2.7 | 1.3 | 1.7 | 1.6 | 0.16 |
| YNL115C | 0.7 | 1.8 | 1.6 | 1.4 | 0.8 | 9.1 | 2.4 | 0.8 | 2.6 | 1.9 | 1.1 | 0.8 | 2.5 | 1.0 | 1.6 | 3.1 | 1.6 | 2.6 | 0.80 |
| YNL156C | 1.1 | 1.2 | 0.9 | 1.3 | 1.6 | 1.3 | 1.9 | 1.2 | 2.4 | 1.9 | 1.4 | 0.9 | 2.0 | 1.4 | 1.8 | 2.1 | 1.8 | 1.9 | 1.85 |
| YNL234W | 1.1 | 1.1 | 0.6 | 1.8 | 1.7 | 1.3 | 1.2 | 1.3 | 2.6 | 3.3 | 1.3 | 1.1 | 2.5 | 1.5 | 1.4 | 2.6 | 1.0 | 1.0 | 0.49 |
| YNL281W | 1.0 | 1.3 | 2.0 | 1.4 | 1.7 | 0.9 | 1.2 | 1.2 | 2.8 | 1.6 | 1.6 | 0.7 | 2.0 | 1.2 | 1.2 | 0.5 | 0.9 | 0.9 | 1.79 |
| YNL305C | 0.9 | 2.2 | 2.7 | 1.4 | 1.3 | 1.1 | 1.7 | 0.7 | 2.9 | 2.1 | 1.8 | 1.1 | 2.6 | 1.3 | 1.6 | 2.5 | 1.7 | 1.6 | 1.35 |
| YNR068C | 1.2 | 1.5 | 2.3 | 2.6 | 1.7 | 0.4 | 1.8 | 1.1 | 6.7 | 14.4 | 1.1 | 1.3 | 3.7 | 1.8 | 1.0 | 1.4 | 1.0 | 1.0 | 0.24 |
| YOL032W | 1.3 | 0.8 | 2.0 | 1.3 | 1.4 | 2.1 | 1.4 | 1.5 | 4.5 | 3.0 | 1.4 | 1.0 | 2.3 | 1.3 | 0.9 | 2.4 | 1.7 | 1.8 | 0.77 |
| YOL036W | 0.8 | 0.9 | 1.3 | 0.8 | 1.2 | 1.2 | 1.0 | 0.8 | 3.1 | 2.8 | 2.2 | 1.0 | 2.5 | 1.0 | 2.0 | 1.0 | 1.1 | 0.9 | 0.48 |
| YOL047C | 1.4 | 1.1 | 1.1 | 2.5 | 1.4 | 1.5 | 1.3 | 1.1 | 0.6 | 2.3 | 0.9 | 0.8 | 2.0 | 1.2 | 12.3 | 1.3 | 1.5 | 1.0 | 0.19 |
| YOL071W | 1.3 | 2.0 | 1.7 | 2.0 | 0.9 | 1.7 | 2.0 | 1.6 | 4.4 | 2.3 | 4.3 | 1.0 | 2.5 | 2.5 | 0.7 | 4.6 | 1.3 | 2.0 | 1.08 |
| YOL082W | 1.0 | 1.6 | 1.6 | 2.1 | 1.5 | 1.8 | 2.5 | 1.1 | 3.4 | 2.0 | 1.6 | 1.0 | 2.4 | 1.4 | 1.0 | 2.4 | 1.6 | 2.5 | 0.60 |
| YOL083W | 1.1 | 2.3 | 1.2 | 2.8 | 1.4 | 4.5 | 3.1 | 1.3 | 2.7 | 2.3 | 1.3 | 1.2 | 2.3 | 1.4 | 1.0 | 3.8 | 1.4 | 3.2 | 0.41 |
| YOL117W | 1.0 | 1.1 | 0.5 | 1.4 | 1.7 | 2.0 | 1.6 | 1.1 | 1.3 | 4.1 | 1.0 | 0.9 | 2.2 | 1.7 | 1.1 | 2.2 | 1.3 | 1.4 | 0.21 |
| YOL131W | 1.0 | 1.5 | 0.6 | 1.0 | 1.5 | 1.1 | 1.3 | 1.1 | 8.4 | 8.1 | 1.4 | 0.9 | 3.1 | 2.3 | 1.4 | 0.7 | 1.1 | 0.9 | 0.15 |
| YOL162W | 2.0 | 6.9 | 1.7 | 1.4 | 0.9 | 1.2 | 2.0 | 1.6 | 12.0 | 6.8 | 4.3 | 1.4 | 3.8 | 1.4 | 0.6 | 0.9 | 1.2 | 0.9 | 0.26 |
| YOR019W | 2.9 | 1.2 | 0.8 | 4.7 | 1.4 | 1.3 | 2.8 | 1.1 | 3.5 | 7.1 | 1.7 | 1.0 | 2.2 | 1.4 | 0.7 | 2.6 | 1.7 | 2.8 | 0.40 |
| YOR197W | 0.8 | 1.0 | 1.1 | 1.4 | 0.6 | 1.3 | 0.9 | 0.9 | 0.8 | 0.7 | 1.0 | 1.0 | 2.1 | 0.7 | 1.7 | 1.0 | 1.5 | 1.5 | 1.30 |
| YPL087W | 1.0 | 5.1 | 3.0 | 7.3 | 0.6 | 4.3 | 4.2 | 1.0 | 1.0 | 2.2 | 2.5 | 1.8 | 4.4 | 1.2 | 1.3 | 1.8 | 2.1 | 2.7 | 1.49 |
| YPL196W | 1.3 | 1.6 | 1.3 | 1.7 | 1.5 | 2.0 | 2.4 | 1.2 | 10.9 | 2.8 | 1.7 | 0.9 | 2.1 | 1.6 | 0.7 | 4.3 | 1.4 | 2.3 | 0.92 |
| YPL206C | 1.0 | 2.9 | 1.4 | 1.9 | 0.7 | 1.8 | 1.2 | 1.0 | 1.7 | 1.1 | 1.5 | 0.8 | 2.5 | 1.1 | 0.8 | 1.2 | 1.4 | 1.9 | 1.22 |
| YPL222W | 0.9 | 3.5 | 0.8 | 1.3 | 1.2 | 2.2 | 1.1 | 0.7 | 7.4 | 3.4 | 1.2 | 1.3 | 3.0 | 1.1 | 0.9 | 2.2 | 1.1 | 0.9 | 0.26 |
| YPR023C | 1.2 | 1.4 | 1.2 | 0.8 | 1.1 | 1.4 | 1.2 | 0.9 | 4.4 | 2.8 | 1.7 | 0.9 | 2.0 | 0.9 | 0.8 | 1.4 | 1.0 | 1.1 | 0.81 |
| YPR151C | 2.3 | 2.0 | 1.5 | 4.1 | 1.3 | 1.6 | 4.4 | 1.4 | 3.0 | 9.5 | 1.4 | 0.9 | 2.0 | 1.4 | 0.7 | 2.8 | 1.3 | 1.4 | 0.16 |
| YDL222C | 0.9 | 1.1 | 1.5 | 3.9 | 1.0 | 1.4 | 1.0 | 0.7 | 1.9 | 1.0 | 2.6 | 1.0 | 2.2 | 1.3 | 7.1 | 6.5 | 0.9 | 1.3 | 0.50 |
| YEL001C | 1.0 | 1.0 | 1.4 | 0.7 | 0.9 | 1.3 | 1.1 | 1.2 | 2.0 | 1.2 | 1.2 | 1.1 | 0.9 | 1.3 | 3.0 | 1.2 | 0.7 | 1.3 | 2.81 |
| YER106W | 1.3 | 0.7 | 1.3 | 1.2 | 1.6 | 1.1 | 1.0 | 1.2 | 0.4 | 1.8 | 1.0 | 0.9 | 1.0 | 1.5 | 6.8 | 0.9 | 0.8 | 0.8 | 0.25 |
| YIL023C | 1.1 | 1.2 | 2.1 | 1.8 | 1.3 | 0.9 | 1.2 | 0.7 | 3.5 | 1.6 | 1.1 | 0.9 | 1.1 | 0.7 | 5.6 | 1.1 | 1.2 | 1.0 | 0.93 |
| YJR054W | 0.8 | 0.9 | 0.3 | 0.9 | 1.0 | 0.7 | 0.9 | 1.6 |  | 0.6 | 0.7 | 0.9 | 0.4 | 1.2 | 3.1 | 0.6 | 0.9 | 0.9 | 0.52 |
| YKL086W | 1.0 | 1.1 | 2.4 | 2.6 | 0.8 | 1.0 | 0.7 | 1.1 | 8.2 | 20.5 | 0.7 | 0.6 | 1.3 | 2.9 | 5.0 | 0.6 | 0.9 | 1.0 | 0.28 |
| YKR091W | 1.5 | 2.3 | 0.9 | 3.5 | 1.6 | 1.0 | 1.3 | 1.3 | 1.0 | 1.6 | 1.1 | 0.9 | 1.0 | 1.9 | 6.3 | 1.6 | 1.6 | 1.3 | 0.45 |
| YLR194C | 2.1 | 2.2 | 1.3 | 3.6 | 1.0 | 0.9 | 1.0 | 1.0 | 0.9 | 1.1 | 1.4 | 1.6 | 4.0 | 1.2 | 3.6 | 0.9 | 1.0 | 0.9 | 0.60 |
| YMR095C | 1.1 | 2.0 | 1.6 | 1.0 | 0.9 | 0.7 | 1.2 | 1.2 |  | 1.4 | 2.1 | 0.8 | 3.4 | 2.2 | 41.7 | 1.0 | 1.0 | 1.0 | 0.23 |
| YAL053W | 0.9 | 0.9 | 1.3 | 2.1 | 0.8 | 1.1 | 0.7 | 0.8 | 1.4 | 0.9 | 2.3 | 0.6 | 1.1 | 0.7 | 2.9 | 1.1 | 1.2 | 1.6 | 1.60 |
| YDL072C | 1.3 | 1.1 | 3.5 | 2.1 | 1.4 | 1.5 | 1.8 | 0.8 | 1.1 | 1.5 | 1.4 | 1.2 | 1.6 | 1.8 | 2.6 | 2.6 | 1.6 | 2.8 | 3.25 |
| YDL204W | 1.4 | 1.9 | 4.8 | 3.4 | 1.0 | 5.6 | 3.2 | 1.1 | 2.3 | 2.0 | 3.2 | 0.9 | 3.2 | 2.4 | 3.6 | 8.6 | 1.8 | 2.7 | 0.73 |
| YDR391C | 1.2 | 2.0 | 1.3 | 1.6 | 1.2 | 2.8 | 2.0 | 1.4 | 1.5 | 2.7 | 1.9 | 1.4 | 1.8 | 2.3 | 3.5 | 3.0 | 1.8 | 2.4 | 1.05 |
| YIL024C | 1.4 | 1.3 | 1.1 | 2.1 | 1.3 | 1.0 | 1.3 | 1.1 | 2.2 | 1.8 | 0.6 | 0.7 | 1.0 | 1.5 | 3.1 | 1.0 | 1.1 | 1.0 | 0.35 |
| YIL117C | 2.5 | 1.2 | 1.0 | 3.3 | 0.8 | 1.2 | 1.5 | 1.8 | 2.3 | 3.5 | 1.8 | 1.4 | 1.3 | 2.6 | 7.5 | 1.0 | 2.6 | 2.6 | 1.22 |
| YJL108C | 1.2 | 1.2 | 1.0 | 2.2 | 1.5 | 0.6 | 0.6 | 1.0 | 0.3 | 0.7 | 1.0 | 0.4 | 0.5 | 1.0 | 4.0 | 0.6 | 1.0 | 0.9 | 0.40 |
| YJL149W | 1.2 | 1.8 | 1.5 | 6.8 | 0.8 | 0.7 | 1.3 | 1.0 | 1.5 | 3.8 | 1.5 | 1.1 | 1.9 | 1.1 | 9.0 | 1.4 | 0.8 | 1.2 | 0.28 |
| YJL186W | 0.6 | 0.9 | 1.2 | 0.8 | 0.7 | 0.7 | 0.6 | 0.6 | 0.2 | 0.5 | 0.6 | 0.6 | 0.4 | 0.8 | 2.5 | 1.0 | 0.7 | 0.8 | 1.07 |
| YNL190W | 1.0 | 1.4 | 2.6 | 0.9 | 1.0 | 0.5 | 0.8 | 0.8 | 1.1 | 1.1 | 1.0 | 1.0 | 1.3 | 0.6 | 2.6 | 1.3 | 0.7 | 0.8 | 4.72 |
| YNL208W | 1.5 | 3.2 | 2.9 | 2.1 | 1.2 | 1.4 | 0.9 | 1.5 | 2.3 | 3.1 | 2.5 | 0.8 | 1.7 | 1.0 | 2.6 | 0.9 | 1.0 | 1.0 | 1.55 |
| YNL300W | 0.7 | 0.3 | 2.9 | 1.5 | 0.9 | 0.4 | 0.4 | 0.9 |  | 0.2 | 0.9 | 0.8 | 0.7 | 0.8 | 3.3 | 1.0 | 1.0 | 0.8 | 0.39 |
| YNR064C | 0.9 | 0.6 | 0.9 | 1.8 | 1.5 | 2.1 | 0.8 | 0.9 |  | 2.1 | 0.7 | 0.7 | 1.6 | 0.8 | 6.1 | 1.4 | 1.1 | 1.9 | 2.17 |
| YOR248W | 2.4 | 0.7 | 2.9 | 1.3 | 0.7 | 0.2 | 0.3 | 0.7 | 0.1 | 0.4 | 2.3 | 0.5 | 0.4 | 0.5 | 8.8 | 0.3 | 1.0 | 0.8 | 2.47 |
| YPL052W | 1.8 | 1.7 | 0.4 | 1.0 | 1.7 | 1.9 | 1.4 | 1.7 | 2.0 | 4.8 | 1.2 | 1.1 | 1.6 | 3.2 | 3.3 | 1.1 | 1.3 | 1.5 | 0.88 |
| YPR079W | 1.0 | 1.8 | 1.3 | 1.5 | 0.9 | 1.0 | 2.3 | 1.1 | 1.7 | 2.8 | 0.8 | 1.0 | 1.3 | 2.9 | 1.9 | 1.9 | 1.4 | 1.5 | 0.42 |
| YAR028W | 1.2 | 1.0 | 0.7 | 1.2 | 0.9 | 3.3 | 1.8 | 1.3 | 1.0 | 0.9 | 0.9 | 0.8 | 1.4 | 1.2 | 0.9 | 1.5 | 1.9 | 2.1 | 1.40 |
| YDR031W | 1.5 | 1.1 | 1.7 | 1.5 | 1.2 | 3.6 | 1.9 | 1.4 | 1.1 | 2.7 | 1.2 | 0.9 | 1.3 | 2.5 | 0.8 | 2.4 | 1.3 | 2.5 | 1.23 |
| YDR486C | 1.1 | 1.5 | 1.2 | 0.9 | 1.2 | 2.7 | 1.8 | 1.8 | 2.5 | 5.8 | 1.4 | 1.3 | 1.7 | 2.4 | 1.1 | 2.6 | 1.1 | 1.7 | 1.18 |
| YER038C | 1.2 | 1.4 | 0.6 | 1.2 | 1.4 | 2.8 | 1.5 | 1.1 | 0.7 | 2.5 | 0.6 | 0.9 | 2.2 | 1.3 | 0.8 | 1.6 | 1.2 | 1.4 | 0.51 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGL136C | 1.1 | 1.0 | 1.2 | 1.1 | 1.0 | 3.1 | 0.7 | 1.1 | 1.3 | 1.0 | 1.4 | 1.1 | 1.1 | 2.3 | 0.9 | 1.4 | 1.3 | 1.1 | 0.64 |
| YGR146C | 1.6 | 2.0 | 2.0 | 2.0 | 0.9 | 4.1 | 2.7 | 1.4 | 0.8 | 3.8 | 0.9 | 1.4 | 1.7 | 1.3 | 1.4 | 1.8 | 1.3 | 0.9 | 0.75 |
| YJL020C | 0.7 | 1.2 | 0.8 | 0.8 | 1.0 | 2.1 | 1.3 | 0.6 | 1.3 | 1.0 | 0.6 | 0.7 | 1.6 | 1.2 | 1.4 | 0.8 | 2.0 | 1.3 | 0.95 |
| YLR031W | 1.3 | 1.0 | 0.7 | 1.3 | 1.3 | 3.0 | 1.5 | 0.9 | 0.9 | 1.4 | 0.7 | 1.0 | 1.6 | 1.5 | 0.7 | 1.6 | 1.2 | 1.2 | 0.30 |
| YLR205C | 1.2 | 5.1 | 0.7 | 1.3 | 1.3 | 4.4 | 9.0 | 1.7 | 1.5 | 5.7 | 0.4 | 1.3 | 1.4 | 2.4 | 2.5 | 2.3 | 2.0 | 1.4 | 0.29 |
| YMR140W | 1.0 | 0.9 | 0.7 | 1.1 | 1.2 | 17.1 | 4.3 | 0.8 | 1.8 | 2.3 | 0.7 | 0.9 | 1.6 | 1.2 | 1.4 | 2.8 | 1.4 | 2.0 | 0.54 |
| YMR195W | 1.7 | 3.1 | 1.2 | 2.2 | 1.1 | 2.6 | 1.1 | 1.0 | 0.2 | 0.7 | 1.1 | 0.9 | 0.7 | 1.3 | 0.6 | 2.5 | 1.6 | 2.2 | 1.28 |
| YOR215C | 1.5 | 1.3 | 0.7 | 1.8 | 1.8 | 2.6 | 2.6 | 1.7 | 2.1 | 1.3 | 1.6 | 1.1 | 1.3 | 1.7 | 0.8 | 3.3 | 1.3 | 2.9 | 2.08 |
| YOR382W | 0.7 | 7.6 | 3.3 | 0.5 | 1.2 | 13.1 | 28.4 | 2.0 | 1.1 | 12.8 | 2.5 | 2.8 | 1.7 | 0.4 | 2.1 | 4.3 | 1.9 | 1.9 | 0.79 |
| YPL054W | 4.2 | 5.3 | 4.9 | 3.1 | 1.1 | 2.3 | 1.8 | 1.3 | 2.5 | 9.2 | 1.9 | 1.3 | 1.5 | 1.4 | 1.0 | 1.3 | 1.5 | 1.4 | 0.25 |
| YPR127W | 1.1 | 1.4 | 1.0 | 1.6 | 1.1 | 3.2 | 1.7 | 1.2 | 1.9 | 2.4 | 1.6 | 0.9 | 1.3 | 1.4 | 0.4 | 2.4 | 1.3 | 1.2 | 0.65 |
| YAR027W | 1.8 | 1.0 | 1.3 | 1.4 | 1.2 | 2.3 | 2.2 | 1.3 | 2.3 | 1.7 | 1.7 | 1.2 | 2.6 | 1.3 | 1.2 | 2.8 | 2.0 | 4.7 | 2.15 |
| YBL057C | 1.1 | 0.9 | 0.6 | 1.0 | 1.3 | 2.2 | 1.1 | 1.4 | 1.6 | 1.2 | 0.9 | 1.0 | 1.0 | 1.6 | 1.0 | 1.1 | 1.2 | 1.2 | 1.88 |
| YBR116C | 0.9 | 4.8 | 2.4 | 1.2 | 1.1 | 2.8 | 1.5 | 1.1 | 9.0 | 8.7 | 3.1 | 1.1 | 2.0 | 2.7 | 1.7 | 9.9 | 0.9 | 1.0 | 0.45 |
| YBR147W | 2.2 | 1.1 | 1.5 | 3.2 | 1.2 | 2.2 | 1.2 | 1.9 | 0.9 | 3.6 | 4.0 | 1.3 | 1.2 | 1.1 | 2.1 | 6.0 | 1.3 | 1.9 | 0.63 |
| YBR168W | 0.9 | 0.8 | 1.0 | 1.3 | 1.6 | 3.5 | 1.6 | 1.0 | 1.1 | 1.7 | 0.8 | 0.9 | 1.9 | 1.8 | 0.9 | 1.0 | 1.1 | 1.5 | 0.56 |
| YBR246W | 1.0 | 0.8 | 1.7 | 0.6 | 1.1 | 3.1 | 1.1 | 0.9 | 0.5 | 0.9 | 0.8 | 0.9 | 1.1 | 1.3 | 0.9 | 1.8 | 1.4 | 1.7 | 0.82 |
| YBR273C | 0.8 | 0.6 | 0.6 | 1.3 | 1.9 | 2.2 | 1.4 | 1.4 | 2.2 | 2.0 | 0.6 | 0.8 | 2.1 | 0.9 | 0.8 | 0.9 | 1.4 | 1.4 | 1.33 |
| YDR003W | 2.0 | 2.4 | 1.6 | 1.5 | 1.8 | 1.8 | 1.8 | 1.0 | 6.6 | 3.6 | 1.8 | 0.8 | 1.5 | 1.2 | 1.0 | 1.8 | 1.4 | 2.0 | 0.95 |
| YDR340W | 1.2 | 1.4 | 0.7 | 0.8 | 1.1 | 1.9 | 2.3 | 1.3 | 1.4 | 2.4 | 1.4 | 0.9 | 1.3 | 2.0 | 1.4 | 1.0 | 1.1 | 1.6 | 1.90 |
| YDR357C | 1.3 | 1.5 | 0.3 | 1.3 | 2.0 | 1.9 | 2.2 | 1.7 | 1.0 | 0.9 | 1.1 | 0.6 | 1.0 | 1.4 | 0.5 | 2.2 | 1.3 | 1.7 | 0.73 |
| YDR396W | 0.7 | 1.3 | 0.6 | 0.7 | 1.4 | 2.0 | 1.5 | 1.4 | 0.3 | 1.2 | 1.0 | 1.2 | 0.6 | 1.4 | 0.9 | 1.3 | 1.1 | 1.3 | 0.63 |
| YDR434W | 0.8 | 0.8 | 1.5 | 1.2 | 1.0 | 2.2 | 1.4 | 0.9 | 0.8 | 1.2 | 0.8 | 0.9 | 1.2 | 0.9 | 1.3 | 0.8 | 1.2 | 1.5 | 1.53 |
| YDR482C | 1.1 | 0.9 | 0.7 | 1.1 | 1.5 | 1.7 | 1.2 | 1.0 | 0.9 | 0.8 | 0.8 | 0.8 | 1.1 | 1.0 | 0.5 | 1.7 | 1.6 | 1.2 | 0.85 |
| YDR520C | 0.9 | 2.1 | 0.9 | 0.6 | 1.3 | 2.3 | 1.2 | 1.0 | 0.8 | 0.7 | 0.6 | 1.2 | 1.4 | 1.0 | 1.3 | 0.9 | 1.1 | 1.0 | 0.46 |
| YOR534C | 0.8 | 4.8 | 1.8 | 0.9 | 1.0 | 2.1 | 9.7 | 1.0 | 0.6 | 7.5 | 1.7 | 1.5 | 1.8 | 0.7 | 4.2 | 1.0 | 0.6 | 1.0 | 0.34 |
| YOR539W | 0.7 | 2.0 | 1.1 | 1.0 | 1.8 | 2.1 | 2.3 | 1.3 | 0.7 | 1.2 | 1.3 | 1.2 | 1.3 | 1.1 | 1.5 | 1.6 | 1.2 | 1.4 | 0.61 |
| YER044C | 1.2 | 1.0 | 2.1 | 1.3 | 1.8 | 3.0 | 1.8 | 0.9 | 0.3 | 0.7 | 1.7 | 0.7 | 0.9 | 1.4 | 0.7 | 3.0 | 1.3 | 2.1 | 1.62 |
| YER067W | 4.0 | 1.9 | 5.2 | 6.0 | 1.1 | 2.1 | 4.9 | 2.1 | 1.8 | 3.8 | 2.2 | 1.1 | 1.2 | 1.7 | 0.5 | 3.5 | 1.5 | 3.0 | 1.57 |
| YER080W | 0.8 | 0.8 | 1.5 | 0.5 | 1.1 | 5.3 | 3.0 | 1.4 | 4.0 | 2.7 | 1.2 | 0.9 | 1.8 | 1.1 | 0.8 | 1.9 | 1.2 | 1.3 | 0.55 |
| YGL113W | 0.7 | 0.9 | 0.9 | 0.4 | 1.5 | 2.1 | 0.9 | 0.9 | 0.7 | 0.8 | 0.7 | 0.8 | 1.2 | 0.9 | 1.0 | 1.0 | 1.5 | 0.9 | 0.35 |
| YGL242C | 0.8 | 0.9 | 0.6 | 0.8 | 1.4 | 1.9 | 2.0 | 1.5 | 0.9 | 1.3 | 1.4 | 0.9 | 1.6 | 1.6 | 1.2 | 1.1 | 1.5 | 1.4 | 1.32 |
| YGR052W | 1.6 | 0.8 | 3.9 | 4.6 | 1.4 | 2.6 | 0.8 | 1.1 | 0.6 | 1.7 | 0.6 | 0.7 | 1.5 | 1.3 | 0.6 | 7.6 | 1.8 | 4.0 | 0.48 |
| YGR106C | 1.2 | 0.8 | 1.9 | 1.3 | 0.9 | 2.0 | 1.1 | 1.0 | 0.7 | 1.0 | 1.2 | 1.1 | 1.0 | 1.2 | 0.9 | 1.1 | 1.0 | 1.7 | 4.60 |
| YGR111W | 1.1 | 2.0 | 1.0 | 1.7 | 1.0 | 2.4 | 1.8 | 1.8 | 3.3 | 2.5 | 1.6 | 0.9 | 2.2 | 1.5 | 0.9 | 2.2 | 1.1 | 2.1 | 0.79 |
| YHL023C | 0.7 | 0.6 | 1.3 | 0.7 | 1.1 | 1.8 | 1.0 | 1.0 | 1.3 | 1.1 | 1.0 | 1.1 | 1.9 | 1.0 | 1.0 | 1.1 | 0.9 | 0.9 | 0.32 |
| YHL048W | 1.3 | 1.6 | 2.8 | 1.3 | 1.1 | 3.7 | 2.3 | 1.2 | 0.8 | 1.2 | 0.9 | 1.1 | 1.7 | 1.0 | 2.3 | 2.5 | 1.9 | 3.2 | 4.10 |
| YIL007C | 1.2 | 1.0 | 1.1 | 1.0 | 1.4 | 2.0 | 1.3 | 1.2 | 1.1 | 1.4 | 1.2 | 1.0 | 1.1 | 1.7 | 1.1 | 1.9 | 1.2 | 1.5 | 0.69 |
| YIR016W | 1.1 | 1.1 | 1.4 | 1.6 | 1.2 | 2.3 | 1.7 | 0.8 | 1.4 | 1.3 | 1.4 | 1.3 | 1.6 | 1.3 | 1.0 | 2.7 | 1.9 | 2.0 | 0.67 |
| YIR043C | 1.2 | 1.6 | 2.2 | 1.8 | 1.3 | 2.4 | 2.2 | 1.0 | 0.8 | 1.3 | 1.4 | 1.3 | 2.0 | 1.4 | 2.5 | 2.6 | 1.4 | 2.5 | 3.90 |
| YJL012C | 0.7 | 0.6 | 1.6 | 0.7 | 1.5 | 1.9 | 0.5 | 1.0 | 0.6 | 1.0 | 0.7 | 1.2 | 1.3 | 1.0 | 1.1 | 0.3 | 0.9 | 0.8 | 1.77 |
| YJL083W | 0.9 | 1.3 | 0.8 | 0.9 | 1.1 | 2.8 | 0.7 | 0.7 | 0.0 | 0.4 | 0.3 | 0.9 | 0.8 | 1.1 | 0.9 | 0.6 | 1.4 | 1.0 | 0.34 |
| YJL131C | 0.9 | 0.8 | 0.5 | 1.1 | 1.7 | 2.2 | 1.9 | 1.2 | 0.5 | 1.0 | 0.3 | 0.8 | 1.8 | 1.5 | 1.0 | 2.2 | 1.3 | 1.2 | 0.54 |
| YJR061W | 1.0 | 2.1 | 1.0 | 0.7 | 1.1 | 2.0 | 0.9 | 1.9 | 1.6 | 1.4 | 0.8 | 0.9 | 0.8 | 1.5 | 1.6 | 1.1 | 1.3 | 1.1 | 0.34 |
| YJR161C | 1.2 | 2.0 | 2.8 | 1.8 | 0.8 | 2.2 | 2.6 | 1.0 | 0.5 | 1.2 | 1.7 | 1.2 | 2.1 | 1.0 | 2.9 | 2.6 | 2.1 | 3.4 | 3.62 |
| YKL175W | 0.7 | 1.1 | 2.1 | 0.9 | 1.4 | 2.2 | 1.3 | 0.9 | 1.1 | 1.9 | 0.8 | 0.9 | 1.7 | 1.0 | 1.6 | 1.1 | 0.9 | 1.0 | 1.71 |
| YKR070W | 1.3 | 0.8 | 1.4 | 1.4 | 1.1 | 2.2 | 1.4 | 1.3 | 3.4 | 2.0 | 1.6 | 0.9 | 1.7 | 1.2 | 0.8 | 2.1 | 1.0 | 1.4 | 0.99 |
| YLL023C | 0.7 | 1.3 | 5.9 | 0.9 | 1.0 | 2.6 | 1.5 | 0.5 | 1.1 | 1.5 | 1.6 | 1.2 | 1.6 | 1.1 | 2.5 | 2.8 | 1.6 | 1.4 | 1.66 |
| YLR023C | 1.3 | 1.5 | 0.9 | 1.2 | 1.1 | 2.6 | 1.2 | 0.9 | 0.7 | 1.7 | 1.1 | 0.6 | 1.0 | 1.1 | 0.9 | 0.8 | 0.7 | 0.8 | 0.92 |
| YLR225C | 0.8 | 0.7 | 0.4 | 0.7 | 1.6 | 2.4 | 1.6 | 1.2 | 1.0 | 1.2 | 0.8 | 1.2 | 1.3 | 1.4 | 1.6 | 0.8 | 1.2 | 1.2 | 1.41 |
| YLR241W | 0.9 | 1.7 | 1.6 | 2.1 | 0.8 | 1.7 | 0.9 | 1.0 | 1.8 | 1.5 | 0.7 | 0.9 | 2.0 | 0.9 | 2.4 | 1.1 | 1.4 | 1.6 | 1.03 |
| YLR252W | 1.3 | 1.3 | 4.6 | 3.0 | 1.0 | 2.8 | 1.6 | 1.1 | 3.1 | 1.4 | 2.5 | 0.7 | 1.3 | 1.3 | 0.9 | 2.7 | 2.2 | 2.9 | 0.96 |
| YLR270W | 1.2 | 1.1 | 2.3 | 1.2 | 1.1 | 3.5 | 3.9 | 1.1 | 3.3 | 2.1 | 2.8 | 1.1 | 2.1 | 1.3 | 1.4 | 2.6 | 1.4 | 2.3 | 1.00 |
| YML030W | 1.3 | 0.8 | 0.8 | 1.4 | 1.9 | 3.0 | 2.1 | 1.4 | 0.8 | 0.8 | 1.2 | 0.7 | 1.0 | 1.3 | 0.6 | 2.7 | 1.2 | 1.3 | 1.35 |
| YMR148W | 1.0 | 1.0 | 1.6 | 0.9 | 1.2 | 2.9 | 0.8 | 0.6 | 1.0 | 0.8 | 1.0 | 0.5 | 1.0 | 1.0 | 0.7 | 1.4 | 1.1 | 0.9 | 0.28 |
| YMR181C | 1.3 | 1.6 | 1.8 | 1.1 | 1.2 | 2.1 | 2.0 | 0.9 | 1.9 | 1.4 | 1.7 | 1.4 | 2.8 | 1.0 | 1.4 | 2.8 | 1.1 | 2.0 | 0.79 |
| YMR298W | 1.3 | 1.3 | 2.9 | 0.8 | 1.5 | 2.3 | 1.3 | 1.1 | 2.4 | 2.6 | 1.7 | 0.9 | 1.0 | 2.0 | 2.0 | 1.7 | 1.4 | 1.6 | 1.37 |
| YNL011C | 1.1 | 1.5 | 0.8 | 0.9 | 0.9 | 2.9 | 2.9 | 1.5 | 3.8 | 1.6 | 1.4 | 0.6 | 1.2 | 1.2 | 0.8 | 3.1 | 1.2 | 1.8 | 0.68 |
| YOL129W | 1.0 | 1.1 | 2.5 | 1.2 | 1.6 | 2.2 | 1.6 | 0.7 | 1.2 | 1.2 | 0.7 | 0.8 | 1.8 | 1.5 | 1.0 | 1.9 | 2.6 | 2.4 | 2.61 |
| YOR042W | 0.6 | 1.4 | 0.7 | 0.7 | 1.3 | 2.1 | 1.1 | 0.9 | 2.1 | 1.2 | 0.9 | 0.8 | 1.3 | 1.2 | 1.1 | 1.1 | 1.4 | 1.1 | 0.54 |
| YOR052C | 1.5 | 1.3 | 0.5 | 2.4 | 2.3 | 2.4 | 1.4 | 1.4 | 1.4 | 1.3 | 0.8 | 1.0 | 2.6 | 1.6 | 1.2 | 1.3 | 1.2 | 2.3 | 2.64 |
| YOR137C | 1.1 | 1.0 | 0.9 | 1.2 | 1.3 | 2.1 | 1.6 | 0.6 | 0.7 | 0.7 | 0.9 | 0.8 | 1.6 | 0.9 | 1.4 | 1.0 | 1.6 | 1.5 | 0.78 |
| YPL156C | 1.4 | 1.4 | 0.9 | 2.9 | 1.2 | 2.4 | 3.2 | 1.2 | 0.5 | 2.8 | 0.9 | 1.5 | 1.7 | 1.6 | 0.8 | 2.4 | 1.6 | 1.9 | 0.70 |
| YPL186C | 1.6 | 1.7 | 1.4 | 4.5 | 1.3 | 3.2 | 3.2 | 1.9 | 2.4 | 1.5 | 3.7 | 1.0 | 1.4 | 2.0 | 0.7 | 6.2 | 1.2 | 2.9 | 0.60 |
| YPL216W | 0.7 | 0.8 | 1.3 | 0.9 | 0.9 | 1.8 | 0.8 | 0.9 | 1.8 | 1.9 | 0.9 | 0.9 | 1.1 | 1.2 | 1.0 | 1.1 | 1.1 | 0.9 | 0.47 |
| YPR098C | 1.6 | 2.6 | 1.7 | 1.9 | 2.0 | 3.0 | 2.9 | 1.1 | 1.4 | 1.7 | 1.9 | 0.9 | 1.2 | 1.8 | 0.9 | 2.9 | 2.2 | 2.2 | 1.10 |
| YFL062W | 1.3 | 2.7 | 1.7 | 2.4 | 1.6 | 1.8 | 3.5 | 1.1 | 0.6 | 1.2 | 2.2 | 1.1 | 1.6 | 1.1 | 1.6 | 2.7 | 2.1 | 3.0 | 3.43 |
| YJL217W | 0.6 | 0.7 | 3.1 | 2.5 | 0.7 | 1.7 | 3.2 | 4.5 | 0.7 | 1.7 | 4.6 | 0.7 | 0.5 | 0.7 | 0.8 | 5.1 | 1.4 | 2.5 | 2.19 |
| YLR126C | 0.9 | 1.5 | 0.4 | 0.8 | 1.3 | 1.7 | 3.4 | 1.4 | 1.8 | 1.3 | 3.4 | 1.3 | 1.4 | 1.6 | 1.4 | 1.4 | 1.3 | 1.2 | 0.61 |
| YNL249C | 1.3 | 1.7 | 0.3 | 1.5 | 1.2 | 0.7 | 2.3 | 1.7 | 2.6 | 1.7 | 1.4 | 1.0 | 1.4 | 1.3 | 0.9 | 1.3 | 1.1 | 1.1 | 0.56 |
| YNL336W | 1.2 | 1.0 | 3.4 | 1.3 | 1.3 | 1.4 | 2.5 | 0.9 | 0.7 | 1.9 | 0.8 | 1.1 | 1.3 | 1.1 | 1.9 | 2.8 | 2.0 | 3.1 | 3.74 |
| YBR074W | 0.7 | 1.3 | 0.9 | 0.8 | 1.3 | 1.5 | 2.2 | 0.7 | 0.4 | 0.5 | 0.5 | 1.0 | 1.2 | 1.5 | 0.8 | 1.3 | 1.4 | 1.0 | 0.52 |
| YDL248W | 1.1 | 1.7 | 2.8 | 1.7 | 1.5 | 2.0 | 2.5 | 1.1 | 0.9 | 1.4 | 1.4 | 1.2 | 2.0 | 0.9 | 1.8 | 1.9 | 1.6 | 2.4 | 4.35 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR105C | 0.7 | 1.1 | 2.3 | 1.0 | 0.8 | 1.4 | 2.1 | 0.8 | 2.3 | 1.7 | 1.4 | 0.9 | 1.8 | 1.1 | 0.9 | 1.4 | 1.1 | 1.4 | 1.09 |
| YEL075C | 1.1 | 1.1 | 0.7 | 1.0 | 1.1 | 1.4 | 1.9 | 0.7 | 0.6 | 0.7 | 0.7 | 1.1 | 1.7 | 1.9 | 0.8 | 1.2 | 1.4 | 1.1 | 1.19 |
| YER046W | 1.3 | 1.9 | 0.5 | 1.1 | 1.6 | 1.8 | 2.6 | 1.5 | 1.5 | 1.7 | 1.1 | 1.0 | 1.0 | 1.4 | 0.7 | 2.7 | 2.0 | 1.9 | 0.53 |
| YER050C | 1.3 | 0.9 | 0.5 | 2.3 | 2.2 | 1.0 | 2.2 | 1.5 | 1.4 | 1.6 | 1.4 | 0.7 | 1.0 | 2.1 | 1.0 | 2.1 | 1.0 | 1.8 | 1.40 |
| YGL250W | 1.1 | 1.4 | 1.9 | 1.8 | 1.6 | 1.4 | 2.0 | 1.1 | 1.5 | 1.2 | 2.4 | 0.7 | 1.2 | 1.0 | 1.1 | 2.3 | 1.2 | 1.9 | 0.45 |
| YGR042W | 1.5 | 1.1 | 1.2 | 2.0 | 1.5 | 2.2 | 2.2 | 1.8 | 1.3 | 3.2 | 1.6 | 1.1 | 1.6 | 2.2 | 1.4 | 2.6 | 1.3 | 1.9 | 0.79 |
| YGR053C | 1.3 | 0.7 | 0.6 | 2.7 | 2.1 | 1.9 | 3.4 | 1.5 | 4.5 | 2.2 | 1.6 | 0.7 | 1.2 | 1.7 | 0.7 | 2.7 | 1.5 | 2.4 | 0.39 |
| YGR066C | 1.6 | 2.5 | 1.3 | 2.5 | 1.2 | 1.7 | 2.1 | 1.3 | 2.3 | 5.0 | 2.6 | 0.8 | 1.2 | 1.9 | 0.7 | 2.6 | 1.0 | 1.1 | 0.17 |
| YGR247W | 0.8 | 1.1 | 0.8 | 1.0 | 1.0 | 0.9 | 1.8 | 0.9 | 1.1 | 1.1 | 1.1 | 0.6 | 0.8 | 1.0 | 0.4 | 1.2 | 1.0 | 1.0 | 0.45 |
| YGR295C | 1.0 | 1.6 | 2.8 | 2.0 | 0.9 | 1.9 | 2.8 | 1.1 | 0.5 | 1.2 | 1.1 | 1.1 | 1.9 | 1.0 | 2.4 | 2.4 | 1.6 | 2.8 | 4.78 |
| YHL044W | 0.9 | 1.3 | 1.5 | 1.4 | 0.7 | 1.9 | 2.0 | 1.4 | 1.1 | 1.9 | 0.7 | 1.2 | 1.6 | 1.7 | 1.1 | 3.9 | 0.8 | 1.2 | 0.45 |
| YHR145C | 1.5 | 1.6 | 0.6 | 0.9 | 1.4 | 1.3 | 2.1 | 1.6 | 0.8 | 2.4 | 2.0 | 0.9 | 1.5 | 1.8 | 1.3 | 1.1 | 1.3 | 1.1 | 1.70 |
| YIL058W | 2.0 | 0.9 | 1.4 | 0.5 | 1.3 | 1.4 | 2.2 | 0.8 | 1.1 | 1.0 | 0.0 | 0.6 | 1.0 | 2.0 | 0.9 | 2.1 | 1.4 | 1.3 | 0.39 |
| YIL065C | 1.0 | 1.3 | 0.8 | 1.6 | 1.9 | 1.6 | 2.0 | 1.4 | 3.8 | 2.1 | 1.1 | 0.9 | 1.8 | 1.7 | 0.8 | 2.4 | 2.1 | 1.4 | 0.94 |
| YIL083C | 0.8 | 1.0 | 0.9 | 0.8 | 1.2 | 1.4 | 2.2 | 1.0 | 1.0 | 1.1 | 1.2 | 1.0 | 1.0 | 1.0 | 0.9 | 1.4 | 0.9 | 1.1 | 0.76 |
| YJL185C | 0.9 | 1.0 | 1.9 | 1.6 | 1.0 | 1.4 | 2.3 | 1.0 | 0.9 | 1.2 | 1.2 | 0.8 | 1.0 | 1.4 | 1.6 | 2.3 | 1.0 | 1.1 | 0.30 |
| YJL213W | 0.8 | 1.1 | 0.2 | 1.2 | 1.5 | 2.6 | 2.1 | 1.2 | 1.3 | 1.5 | 0.7 | 0.7 | 1.0 | 0.8 | 2.8 | 3.6 | 2.1 | 2.8 | 0.33 |
| YKR020W | 1.1 | 1.8 | 0.9 | 1.6 | 1.0 | 4.5 | 2.2 | 1.5 | 1.9 | 2.8 | 1.0 | 0.8 | 1.7 | 1.4 | 1.2 | 2.5 | 1.3 | 2.0 | 0.44 |
| YLL025W | 0.8 | 1.3 | 1.8 | 0.8 | 1.1 | 1.5 | 1.9 | 1.0 | 1.5 | 2.0 | 1.4 | 1.0 | 1.3 | 1.0 | 1.2 | 1.7 | 1.0 | 0.9 | 0.40 |
| YLR108C | 3.2 | 1.8 | 4.7 | 1.8 | 1.9 | 1.3 | 2.6 | 2.0 | 7.4 | 10.4 | 2.6 | 0.8 | 1.9 | 3.4 | 1.2 | 2.3 | 1.0 | 1.5 | 0.39 |
| YLR290C | 1.3 | 1.2 | 0.8 | 1.9 | 2.1 | 1.7 | 2.3 | 1.1 | 1.2 | 1.1 | 1.5 | 0.8 | 1.0 | 1.3 | 0.8 | 3.2 | 1.3 | 2.4 | 1.49 |
| YML068W | 1.0 | 3.7 | 1.0 | 1.2 | 1.0 | 0.9 | 4.1 | 1.3 | 1.3 | 1.4 | 0.6 | 0.4 | 0.8 | 1.1 | 1.1 | 1.9 | 1.0 | 1.3 | 0.41 |
| YMR178W | 1.6 | 1.0 | 0.8 | 0.9 | 1.1 | 1.6 | 2.1 | 1.6 | 1.6 | 1.6 | 1.0 | 0.9 | 1.0 | 1.2 | 0.9 | 2.1 | 1.4 | 2.3 | 1.36 |
| YNL122C | 1.2 | 0.9 | 1.2 | 1.3 | 1.6 | 1.8 | 2.1 | 1.4 | 1.0 | 1.2 | 1.3 | 0.7 | 1.0 | 1.2 | 0.6 | 1.8 | 1.0 | 1.4 | 1.07 |
| YNL285W | 1.1 | 1.2 | 0.6 | 1.1 | 1.4 | 0.8 | 2.3 | 1.2 | 1.4 | 1.7 | 1.2 | 0.6 | 1.1 | 1.8 | 0.9 | 1.3 | 1.2 | 1.3 | 0.43 |
| YNL293W | 1.3 | 0.8 | 0.8 | 1.8 | 1.3 | 0.9 | 2.1 | 1.0 | 1.6 | 2.4 | 0.8 | 0.7 | 1.4 | 1.1 | 1.2 | 2.1 | 1.0 | 1.4 | 0.58 |
| YNR061C | 0.8 | 1.1 | 2.5 | 0.8 | 1.0 | 1.3 | 2.6 | 0.8 | 0.8 | 0.9 | 1.2 | 0.9 | 1.1 | 1.3 | 0.9 | 1.1 | 1.6 | 1.1 | 1.52 |
| YOR220W | 1.5 | 1.4 | 1.7 | 2.4 | 1.3 | 1.2 | 2.1 | 0.9 | 1.8 | 2.5 | 1.2 | 1.2 | 2.9 | 0.8 | 0.7 | 2.0 | 3.5 | 3.4 | 1.44 |
| YPR077C | 1.4 | 1.4 | 1.2 | 2.7 | 1.4 | 1.2 | 2.0 | 1.5 | 0.6 | 2.5 | 0.8 | 1.0 | 0.8 | 1.6 | 2.9 | 0.6 | 1.4 | 1.2 | 0.24 |
| YPR147C | 0.9 | 0.8 | 1.1 | 1.4 | 1.6 | 2.1 | 1.8 | 1.1 | 1.2 | 2.4 | 1.3 | 0.9 | 1.6 | 1.1 | 1.4 | 1.9 | 1.1 | 1.3 | 1.18 |
| YEL041W | 1.4 | 1.4 | 0.8 | 2.5 | 0.8 | 1.2 | 1.9 | 1.9 | 2.4 | 3.6 | 3.5 | 0.9 | 1.9 | 2.0 | 1.4 | 1.9 | 1.5 | 1.9 | 0.39 |
| YKL187C | 0.9 | 1.0 | 1.4 | 1.5 | 0.8 | 0.8 | 0.7 | 1.1 | 5.2 | 8.6 | 3.3 | 0.9 | 1.4 | 1.6 | 1.2 | 4.8 | 0.7 | 1.2 | 0.36 |
| YBR285W | 1.6 | 1.6 | 0.9 | 6.2 | 1.3 | 2.2 | 1.5 | 1.0 | 4.0 | 3.1 | 4.6 | 0.5 | 0.9 | 1.6 | 0.4 | 7.8 | 2.5 | 2.3 | 0.27 |
| YBR292C | 0.8 | 4.3 | 1.2 | 0.6 | 1.0 | 0.8 | 0.7 | 0.8 | 2.1 | 1.3 | 1.8 | 0.4 | 0.7 | 1.1 | 1.0 | 1.0 | 0.9 | 0.9 | 0.30 |
| YDL123W | 1.0 | 1.3 | 3.7 | 1.4 | 0.8 | 0.7 | 1.0 | 0.8 | 2.0 | 2.0 | 4.6 | 1.1 | 1.5 | 0.9 | 3.3 | 1.5 | 1.1 | 1.0 | 0.52 |
| YDR056C | 1.4 | 1.3 | 2.0 | 2.0 | 0.9 | 1.0 | 1.4 | 1.4 | 1.3 | 2.3 | 2.3 | 1.2 | 1.0 | 2.3 | 1.1 | 2.5 | 1.2 | 2.0 | 1.83 |
| YDR132C | 3.7 | 1.6 | 1.4 | 2.1 | 1.2 | 1.9 | 1.7 | 2.3 | 5.9 | 7.3 | 3.3 | 0.9 | 1.5 | 1.4 | 1.2 | 1.2 | 1.0 | 1.3 | 0.40 |
| YDR154C | 1.0 | 2.1 | 2.5 | 1.7 | 0.8 | 1.5 | 0.9 | 1.1 | 1.5 | 1.2 | 3.2 | 1.0 | 2.6 | 1.0 | 1.8 | 1.3 | 1.5 | 2.0 | 2.69 |
| YDR295C | 0.8 | 1.0 | 0.6 | 1.0 | 0.9 | 1.0 | 0.8 | 1.3 | 2.6 | 1.3 | 1.9 | 0.7 | 1.8 | 1.1 | 1.4 | 0.6 | 0.8 | 1.0 | 0.49 |
| YDR494W | 0.9 | 0.9 | 0.2 | 1.3 | 1.3 | 1.4 | 1.7 | 1.2 | 1.2 | 0.9 | 1.6 | 0.8 | 1.0 | 1.0 | 0.6 | 1.9 | 1.1 | 1.3 | 1.39 |
| YEL072W | 3.2 | 3.5 | 1.6 | 1.8 | 1.5 | 0.6 | 1.3 | 1.6 | 4.7 | 4.3 | 1.7 | 0.9 | 1.0 | 2.0 | 0.5 | 1.5 | 0.8 | 1.1 | 0.39 |
| YER045C | 1.6 | 2.1 | 1.2 | 1.0 | 0.9 | 0.8 | 1.1 | 1.4 | 2.0 | 1.5 | 2.3 | 0.8 | 1.2 | 1.3 | 1.4 | 1.6 | 1.1 | 1.1 | 0.34 |
| YER181C | 1.1 | 0.4 | 1.7 | 2.2 | 1.0 | 0.7 | 1.0 | 0.9 |  | 0.8 | 0.1 | 0.6 | 1.3 | 1.0 | 0.7 | 0.7 | 0.7 | 1.1 | 0.42 |
| YGL114W | 1.5 | 0.8 | 3.6 | 1.3 | 1.3 | 0.7 | 1.0 | 1.1 | 2.7 | 5.6 | 3.2 | 0.6 | 1.2 | 1.1 | 1.2 | 1.4 | 0.9 | 0.8 | 0.60 |
| YGL193C | 1.1 | 0.9 | 0.9 | 1.4 | 0.7 | 0.7 | 1.0 | 0.7 | 0.8 | 1.0 | 2.1 | 0.7 | 1.1 | 1.0 | 1.1 | 1.7 | 1.1 | 0.9 | 0.62 |
| YGL204C | 0.9 | 2.2 | 1.2 | 1.2 | 0.7 | 0.3 | 1.3 | 0.8 | 1.0 | 0.9 | 1.9 | 0.8 | 1.4 | 1.8 | 0.8 | 1.1 | 0.9 | 0.9 | 0.38 |
| YGL259W | 1.1 | 1.6 | 1.4 | 1.5 | 1.1 | 0.8 | 1.6 | 1.3 | 2.6 | 2.2 | 2.7 | 1.1 | 1.9 | 1.1 | 1.3 | 4.1 | 0.9 | 0.9 | 0.49 |
| YIL060W | 1.0 | 2.3 | 0.8 | 1.2 | 0.7 | 0.9 | 1.8 | 0.9 | 3.0 | 1.9 | 0.7 | 0.6 | 0.9 | 1.3 | 1.1 | 1.2 | 0.9 | 0.9 | 1.22 |
| YJL036W | 1.3 | 1.0 | 0.6 | 1.6 | 0.7 | 1.1 | 1.5 | 1.5 | 6.6 | 3.5 | 1.7 | 1.2 | 2.2 | 1.5 | 1.1 | 2.1 | 1.4 | 1.6 | 0.88 |
| YJR085C | 1.0 | 1.9 | 2.8 | 4.5 | 0.6 | 1.5 | 1.4 | 0.9 | 3.7 | 2.6 | 2.9 | 1.1 | 1.9 | 1.9 | 0.5 | 2.0 | 1.4 | 1.9 | 2.19 |
| YKR071C | 3.6 | 1.6 | 1.0 | 1.1 | 1.9 | 0.6 | 0.9 | 2.1 | 4.7 | 4.9 | 2.3 | 0.8 | 1.5 | 1.6 | 0.7 | 0.8 | 0.9 | 1.0 | 1.05 |
| YLR145W | 0.9 | 1.1 | 0.6 | 1.5 | 1.1 | 0.6 | 0.9 | 1.1 | 1.9 | 1.2 | 2.4 | 0.8 | 0.7 | 1.6 | 1.0 | 2.5 | 1.0 | 0.8 | 0.62 |
| YLR156W | 1.3 | 1.0 | 0.7 | 0.8 | 0.8 | 0.6 | 1.3 | 1.0 | 1.1 | 2.2 | 1.9 | 0.8 | 1.9 | 1.0 | 1.1 | 1.7 | 1.1 | 0.9 | 0.31 |
| YLR280C | 0.6 | 1.4 | 0.4 | 0.6 | 1.3 | 0.9 | 1.5 | 1.0 | 0.5 | 1.3 | 2.1 | 0.8 | 1.6 | 0.5 | 0.6 | 1.2 | 1.2 | 0.9 | 0.19 |
| YLR311C | 1.5 | 1.9 | 2.8 | 2.9 | 0.9 | 0.4 | 1.1 | 1.0 | 0.9 | 3.0 | 7.8 | 0.9 | 0.9 | 1.6 | 0.5 | 1.9 | 1.3 | 1.1 | 0.33 |
| YMR034C | 1.5 | 1.3 | 1.0 | 6.5 | 1.3 | 1.1 | 1.9 | 1.2 | 0.7 | 2.7 | 2.1 | 0.9 | 1.8 | 1.4 | 1.7 | 1.3 | 1.8 | 1.6 | 0.43 |
| YNL240C | 0.8 | 0.8 | 0.8 | 0.6 | 0.8 | 0.7 | 0.7 | 0.9 | 5.4 | 3.1 | 3.4 | 0.7 | 1.1 | 0.8 | 1.4 | 0.8 | 0.8 | 0.7 | 0.37 |
| YNL260C | 1.7 | 1.8 | 0.5 | 1.0 | 1.6 | 0.8 | 1.1 | 1.2 | 3.8 | 2.0 | 2.5 | 0.6 | 0.7 | 1.4 | 0.7 | 1.2 | 0.9 | 1.0 | 0.75 |
| YNR074C | 1.3 | 1.7 | 3.1 | 1.4 | 1.2 | 0.7 | 1.4 | 1.5 | 3.9 | 3.0 | 2.7 | 0.6 | 1.5 | 1.7 | 0.8 | 0.9 | 0.9 | 0.8 | 0.66 |
| YQL084W | 1.0 | 1.4 | 1.6 | 3.6 | 0.6 | 1.6 | 0.8 | 1.0 | 2.6 | 3.4 | 6.1 | 1.7 | 6.4 | 0.9 | 1.6 | 6.6 | 1.3 | 1.6 | 0.28 |
| YOL159C | 1.9 | 2.4 | 1.7 | 2.0 | 0.9 | 1.0 | 2.1 | 1.2 | 1.1 | 2.4 | 6.6 | 1.2 | 1.4 | 1.8 | 1.1 | 2.3 | 2.0 | 1.6 | 0.61 |
| YOR228C | 1.3 | 1.1 | 1.8 | 1.4 | 1.2 | 1.0 | 1.2 | 0.7 | 1.4 | 1.1 | 2.8 | 0.9 | 1.1 | 1.0 | 0.6 | 3.4 | 1.0 | 1.4 | 0.44 |
| YOR25SW | 2.5 | 2.7 | 1.0 | 1.5 | 1.0 | 0.5 | 0.9 | 1.2 | 0.3 | 0.8 | 2.0 | 0.7 | 1.6 | 1.3 | 4.9 | 1.2 | 1.0 | 1.0 | 0.19 |
| YBR047W | 2.7 | 2.4 | 1.1 | 0.9 | 1.1 |  |  | 2.2 | 11.0 | 10.0 | 3.4 | 0.8 | 1.7 | 1.0 | 0.8 | 1.1 | 1.3 | 1.0 | 0.25 |
| YER124C | 0.5 | 17.3 | 0.7 | 1.2 | 1.4 | 2.1 | 1.0 | 1.8 | 0.4 | 1.4 | 1.5 | 0.6 | 0.7 | 0.5 | 0.5 | 1.5 | 0.9 | 1.1 | 2.22 |
| YKR007W | 0.8 | 0.9 | 0.8 | 0.9 | 1.1 | 1.6 | 1.5 | 1.9 | 1.1 | 1.8 | 1.3 | 0.8 | 0.9 | 1.2 | 1.2 | 1.1 | 0.8 | 0.9 | 0.73 |
| YOR007C | 1.1 | 3.3 | 1.4 | 0.9 | 1.1 | 1.2 | 0.4 | 2.1 | 5.6 | 2.5 | 1.8 | 0.7 | 0.7 | 0.8 | 1.3 | 1.0 | 1.2 | 0.8 | 2.26 |
| YBL065W | 1.2 | 2.9 | 1.0 | 3.5 | 1.1 | 0.7 | 1.0 | 1.9 | 20.8 | 4.2 | 1.3 | 0.7 | 1.8 | 1.9 | 3.1 | 0.9 | 1.1 | 0.9 | 0.15 |
| YDL113C | 1.0 | 1.4 | 1.2 | 1.0 | 1.0 | 1.2 | 2.2 | 1.7 | 3.8 | 3.0 | 1.1 | 1.3 | 1.5 | 1.2 | 1.7 | 1.2 | 1.5 |  | 0.58 |
| YDR018C | 1.5 | 1.3 | 3.3 | 2.6 | 1.3 | 1.5 | 1.4 | 1.4 | 2.3 | 4.4 | 1.4 | 1.1 | 1.8 | 1.7 | 1.0 | 2.6 | 0.9 | 1.2 | 0.22 |
| YDR202C | 1.1 | 1.2 | 1.1 | 1.3 | 1.3 | 1.7 | 1.6 | 1.4 | 4.8 | 2.4 | 1.3 | 0.8 | 1.2 | 2.0 | 0.5 | 2.8 | 1.0 | 1.6 | 0.79 |
| YDR223W | 1.3 | 4.6 | 2.0 | 1.9 | 1.1 | 1.4 | 1.0 | 1.0 | 2.7 | 4.6 | 1.4 | 1.0 | 1.5 | 1.2 | 1.2 | 3.5 | 0.9 | 1.0 | 0.29 |
| YDR350C | 0.9 | 1.5 | 0.4 | 1.3 | 1.3 | 1.3 | 1.5 | 0.9 | 2.8 | 2.5 | 0.9 | 0.9 | 1.0 | 1.1 | 1.6 | 1.3 | 1.4 | 1.2 | 0.53 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR374C | 1.9 | 2.9 | 1.5 | 0.8 | 1.3 | 1.1 | 0.9 | 1.8 | 10.4 | 3.9 | 1.4 | 1.0 | 2.5 | 4.0 | 2.0 | 1.3 | 1.0 | 1.0 | 0.36 |
| YDR512C | 1.8 | 4.3 | 2.5 | 2.3 | 0.7 | 2.1 | 2.0 | 1.6 | 3.6 | 4.0 | 1.8 | 1.1 | 1.9 | 2.7 | 1.1 | 3.0 | 1.3 | 2.0 | 0.82 |
| YFR017C | 1.1 | 1.4 | 4.4 | 4.4 | 1.2 | 1.2 | 1.3 | 0.8 | 1.0 | 7.1 | 3.1 | 1.8 | 1.7 | 1.3 | 1.4 | 3.7 | 0.9 | 1.1 | 0.49 |
| YGL046W | 1.6 | 1.2 | 1.5 | 1.4 | 0.9 | 1.2 | 1.0 | 1.2 | 0.8 | 4.5 | 1.5 | 1.1 | 1.6 | 0.9 | 2.0 | 1.2 | 1.5 | 1.3 | 0.42 |
| YGL067W | 1.6 | 1.3 | 1.7 | 1.1 | 0.6 | 1.0 | 1.1 | 1.2 | 1.0 | 2.3 | 1.7 | 0.9 | 3.7 | 1.6 | 0.7 | 1.0 | 0.9 | 1.1 | 0.63 |
| YGL098W | 1.2 | 0.8 | 0.5 | 1.7 | 0.8 | 0.7 | 1.2 | 1.3 | 1.2 | 2.4 | 1.3 | 0.8 | 0.8 | 1.1 | 0.7 | 1.3 | 1.1 | 1.5 | 0.77 |
| YGL117W | 2.3 | 0.6 | 0.5 | 2.0 | 0.9 | 0.9 | 1.3 | 1.9 | 0.5 | 5.8 | 1.4 | 1.5 | 1.4 | 2.0 | 1.4 | 0.6 | 2.1 | 1.1 | 1.05 |
| YGL146C | 0.9 | 1.0 | 1.1 | 3.3 | 1.3 | 1.2 | 1.3 | 1.2 | 0.9 | 3.2 | 1.3 | 0.9 | 1.1 | 1.2 | 1.1 | 2.2 | 1.0 | 1.0 | 0.43 |
| YGR011W | 1.1 | 1.5 | 1.0 | 1.3 | 0.9 | 1.1 | 1.8 | 1.4 | 7.4 | 9.4 | 2.3 | 0.8 | 1.6 | 3.9 | 1.8 | 1.6 | 0.9 | 1.0 | 0.40 |
| YGR153W | 1.5 | 0.9 | 1.0 | 1.1 | 1.6 | 0.9 | 1.4 | 1.8 | 2.7 | 2.5 | 1.0 | 0.7 | 1.1 | 1.9 | 1.3 | 1.1 | 1.3 | 1.7 | 0.39 |
| YGR223C | 1.8 | 1.2 | 1.5 | 1.3 | 1.3 | 1.2 | 1.2 | 1.4 | 6.2 | 3.8 | 1.9 | 0.8 | 1.8 | 1.6 | 1.2 | 1.8 | 1.1 | 1.8 | 0.66 |
| YHR116W | 0.9 | 1.2 | 0.9 | 2.1 | 1.6 | 1.5 | 1.8 | 1.1 | 1.5 | 2.7 | 0.9 | 0.8 | 1.9 | 1.4 | 1.2 | 1.9 | 0.9 | 1.5 | 0.60 |
| YIL097W | 1.2 | 1.0 | 1.3 | 1.2 | 1.2 | 2.0 | 1.6 | 1.7 | 4.9 | 3.4 | 1.4 | 1.1 | 1.4 | 1.4 | 1.2 | 2.1 | 1.1 | 1.7 | 0.52 |
| YKL133C | 1.3 | 12.7 | 2.4 | 2.0 | 1.0 | 1.7 | 3.2 | 1.5 | 4.1 | 5.9 | 1.4 | 1.3 | 1.4 | 1.6 | 1.7 | 3.8 | 1.2 | 2.4 | 0.35 |
| YKL162C | 1.3 | 1.0 | 1.9 | 0.9 | 1.1 | 1.7 | 1.4 | 1.5 | 6.7 | 4.7 | 1.6 | 1.1 | 1.1 | 1.9 | 1.6 | 2.0 | 0.8 | 1.1 | 0.25 |
| YLL062C | 6.5 | 6.7 | 4.6 | 1.1 | 0.8 | 0.9 | 0.7 | 1.8 | 14.9 | 5.4 | 1.7 | 0.6 | 1.4 | 1.7 | 1.6 | 1.0 | 0.9 | 0.9 | 0.29 |
| YLR247C | 0.8 | 1.5 | 1.0 | 1.0 | 1.2 | 1.2 | 1.2 | 1.3 | 2.5 | 2.9 | 1.6 | 1.0 | 1.8 | 1.0 | 1.4 | 1.4 | 1.2 | 1.3 | 0.48 |
| YLR267W | 0.9 | 1.7 | 1.3 | 1.4 | 1.2 | 1.3 | 1.4 | 1.4 | 1.1 | 4.6 | 1.7 | 0.8 | 1.5 | 2.3 | 0.7 | 3.6 | 1.2 | 2.8 | 0.24 |
| YMR041C | 1.2 | 2.8 | 1.4 | 1.2 | 1.1 | 0.5 | 0.5 | 1.4 | 6.5 | 6.0 | 1.6 | 1.0 | 1.1 | 0.6 | 0.5 | 0.3 | 0.8 | 0.4 | 0.84 |
| YMR253C | 0.9 | 1.7 | 2.0 | 1.3 | 0.8 | 1.7 | 2.3 | 1.0 | 1.5 | 2.8 | 1.0 | 0.5 | 1.2 | 1.3 | 0.9 | 1.3 | 1.2 | 1.4 | 0.42 |
| YOR225W | 1.1 | 2.8 | 1.4 | 1.0 | 1.3 | 0.7 | 0.8 | 0.8 | 0.8 | 3.3 | 1.2 | 0.5 | 0.6 | 2.2 | 0.7 | 0.6 | 0.9 | 0.9 | 0.26 |
| YPL166W | 1.0 | 1.4 | 1.4 | 1.4 | 1.2 | 0.7 | 1.8 | 1.2 | 1.5 | 3.1 | 1.4 | 0.8 | 1.4 | 0.8 | 1.2 | 2.3 | 1.1 | 1.6 | 0.39 |
| YPL202C | 1.1 | 1.6 | 1.0 | 0.7 | 1.9 | 1.4 | 1.6 | 1.1 | 1.8 | 3.5 | 1.0 | 0.7 | 1.1 | 0.9 | 1.0 | 1.2 | 1.1 | 1.0 | 0.56 |
| YBR101C | 1.3 | 2.2 | 1.7 | 1.1 | 1.2 | 0.8 | 0.6 | 1.0 | 6.9 | 3.0 | 1.3 | 0.7 | 1.6 | 0.7 | 0.5 | 0.3 | 0.9 | 1.0 | 1.83 |
| YBR269C | 1.2 | 5.7 | 2.2 | 1.1 | 1.3 | 1.8 | 1.3 | 0.8 | 2.7 | 2.6 | 1.2 | 1.0 | 1.3 | 1.4 | 0.4 | 1.6 | 1.5 | 1.6 | 0.58 |
| YBR280C | 1.2 | 1.0 | 2.7 | 2.0 | 1.3 | 1.6 | 1.7 | 1.0 | 5.3 | 1.9 | 1.3 | 1.3 | 2.8 | 1.3 | 1.0 | 3.2 | 1.1 | 1.7 | 0.33 |
| YDL234C | 1.9 | 0.9 | 0.5 | 1.4 | 1.0 | 1.1 | 1.9 | 1.3 | 4.6 | 2.1 | 1.5 | 0.9 | 3.5 | 0.7 | 1.0 | 2.5 | 2.3 | 3.6 | 0.94 |
| YOL242W | 1.3 | 1.3 | 1.6 | 1.5 | 1.3 | 0.7 | 1.1 | 0.5 | 4.0 | 4.1 | 1.3 | 1.0 | 1.0 | 1.0 | 1.2 | 1.3 | 0.9 | 1.0 | 0.38 |
| YDR531W | 0.8 | 0.9 | 0.7 | 1.0 | 2.0 | 1.2 | 1.6 | 1.4 | 2.9 | 1.5 | 1.3 | 0.9 | 1.4 | 1.2 | 0.9 | 1.2 | 1.5 | 1.2 | 1.32 |
| YFR042W | 1.5 | 1.2 | 1.9 | 1.9 | 1.8 | 0.8 | 1.6 | 1.0 | 2.8 | 2.6 | 1.7 | 1.1 | 1.9 | 1.7 | 1.4 | 1.4 | 1.7 | 1.7 | 1.17 |
| YFR046C | 1.1 | 2.3 | 1.1 | 1.6 | 1.2 | 1.0 | 1.0 | 1.5 | 5.8 | 1.5 | 1.0 | 0.9 | 1.1 | 1.4 | 0.9 | 1.3 | 1.2 | 1.2 | 0.29 |
| YGL227W | 1.0 | 0.8 | 0.9 | 0.7 | 1.2 | 1.1 | 1.2 | 1.0 | 2.4 | 1.9 | 1.1 | 0.8 | 1.0 | 1.3 | 0.9 | 1.5 | 1.1 | 1.3 | 0.59 |
| YGR089W | 0.8 | 0.8 | 0.9 | 0.5 | 1.1 | 1.2 | 0.9 | 0.8 | 4.0 | 1.4 | 0.9 | 0.7 | 0.8 | 1.1 | 0.8 | 0.9 | 0.9 | 1.1 | 0.50 |
| YGR134W | 1.1 | 1.5 | 0.5 | 1.3 | 1.3 | 1.0 | 1.0 | 1.5 | 2.4 | 1.9 | 0.9 | 0.7 | 1.5 | 1.1 | 1.1 | 0.7 | 0.9 | 0.8 | 0.33 |
| YHR017W | 0.8 | 1.0 | 1.3 | 1.4 | 1.1 | 1.1 | 1.5 | 1.5 | 2.9 | 1.7 | 1.5 | 1.0 | 1.2 | 1.2 | 0.8 | 2.5 | 1.1 | 1.7 | 0.90 |
| YIL152W | 1.1 | 1.3 | 1.0 | 1.7 | 1.0 | 0.8 | 1.2 | 1.0 | 3.1 | 1.8 | 0.9 | 1.1 | 1.4 | 1.7 | 0.9 | 1.5 | 1.1 | 1.1 | 0.81 |
| YIL164C | 1.2 | 1.2 | 1.0 | 1.2 | 1.0 | 1.1 | 2.0 | 1.2 | 4.2 | 3.0 | 1.0 | 1.0 | 1.8 | 2.0 | 0.9 | 2.5 | 1.4 | 1.4 | 0.54 |
| YJR056C | 1.0 | 2.4 | 0.8 | 1.2 | 0.9 | 0.5 | 0.9 | 1.2 | 3.5 | 1.4 | 0.8 | 0.8 | 0.9 | 1.4 | 1.6 | 1.3 | 0.9 | 1.1 | 0.44 |
| YJR072C | 0.7 | 2.5 | 1.0 | 0.8 | 1.1 | 0.7 | 0.8 | 1.3 | 3.1 | 1.6 | 0.9 | 1.0 | 1.1 | 1.2 | 0.6 | 0.9 | 0.8 | 0.8 | 0.78 |
| YKL034W | 0.8 | 1.4 | 1.0 | 0.9 | 1.1 | 1.9 | 1.4 | 0.7 | 2.6 | 3.7 | 1.2 | 1.0 | 1.9 | 1.0 | 1.6 | 1.5 | 1.3 | 1.2 | 0.41 |
| YKR012C | 0.7 | 1.4 | 1.0 | 1.0 | 1.2 | 1.4 | 1.0 | 1.0 | 3.9 | 1.2 | 0.8 | 0.7 | 1.5 | 1.4 | 1.2 | 0.9 | 1.0 | 0.9 | 0.61 |
| YLR064W | 1.1 | 1.1 | 2.9 | 1.3 | 0.8 | 1.2 | 0.8 | 1.0 | 3.3 | 2.1 | 1.6 | 0.7 | 1.6 | 1.4 | 1.5 | 1.0 | 0.9 | 1.0 | 1.49 |
| YLR364W | 3.3 | 8.0 | 1.2 | 1.5 | 1.3 | 1.0 | 1.0 | 1.1 | 8.3 | 1.3 | 1.5 | 0.7 | 1.0 | 3.0 | 1.9 | 1.0 | 1.0 | 0.9 | 0.37 |
| YLR421C | 1.1 | 1.3 | 0.9 | 1.2 | 0.9 | 2.6 | 1.5 | 1.5 | 4.5 | 3.3 | 1.2 | 0.9 | 1.6 | 1.6 | 1.6 | 1.9 | 1.2 | 1.8 | 2.07 |
| YML118W | 1.5 | 0.5 | 0.7 | 2.7 | 0.7 | 0.8 | 1.5 | 0.9 | 6.6 | 1.6 | 1.3 | 0.9 | 1.7 | 1.0 | 2.2 | 1.6 | 1.5 | 1.5 | 0.26 |
| YMR114C | 1.2 | 1.4 | 0.5 | 2.4 | 1.2 | 1.2 | 1.7 | 1.1 | 2.5 | 1.7 | 1.0 | 0.9 | 1.1 | 1.5 | 1.2 | 3.0 | 1.0 | 1.3 | 0.62 |
| YMR115W | 1.0 | 0.6 | 1.3 | 1.1 | 0.9 | 1.5 | 1.0 | 1.2 | 5.8 | 2.1 | 1.1 | 1.0 | 1.3 | 1.3 | 1.2 | 1.1 | 1.0 | 1.2 | 0.61 |
| YMR258C | 0.9 | 1.4 | 1.2 | 0.7 | 1.2 | 1.5 | 1.5 | 0.9 | 2.3 | 1.8 | 1.4 | 0.9 | 1.6 | 1.0 | 0.6 | 1.2 | 1.1 | 1.3 | 0.60 |
| YNL181W | 1.2 | 1.2 | 0.6 | 1.2 | 1.4 | 1.6 | 0.9 | 1.9 | 5.3 | 2.8 | 1.2 | 0.8 | 1.8 | 1.9 | 1.0 | 1.0 | 0.8 | 1.3 | 0.86 |
| YNL191W | 1.5 | 5.1 | 4.7 | 0.7 | 0.9 | 0.6 | 3.0 | 1.2 | 3.9 | 3.2 | 1.0 | 0.5 | 0.6 | 1.0 | 1.0 | 0.6 | 0.5 | 0.6 | 0.45 |
| YNL212W | 1.1 | 1.1 | 1.1 | 0.5 | 0.9 | 0.8 | 1.3 | 1.3 | 4.6 | 2.3 | 1.3 | 0.8 | 1.3 | 1.0 | 0.9 | 1.3 | 0.9 | 1.2 | 0.67 |
| YNL265C | 1.0 | 1.3 | 0.5 | 1.3 | 0.9 | 1.9 | 1.5 | 1.4 | 5.0 | 2.6 | 0.9 | 0.8 | 2.0 | 1.9 | 0.6 | 1.7 | 0.9 | 1.8 | 0.85 |
| YOR088W | 0.7 | 0.9 | 1.7 | 0.9 | 1.2 | 0.7 | 0.3 | 0.7 | 2.5 | 1.3 | 0.8 | 0.6 | 0.4 | 0.4 | 0.8 | 0.4 | 0.7 | 0.7 | 3.56 |
| YOR155C | 0.8 | 1.2 | 1.7 | 1.0 | 1.4 |  |  | 0.8 | 3.6 | 1.7 | 1.6 | 0.5 |  | 1.5 | 0.9 |  | 0.8 | 0.9 | 0.46 |
| YPL151C | 1.0 | 0.8 | 1.2 | 1.2 | 1.0 | 0.7 | 0.7 | 1.0 | 4.2 | 2.0 | 0.9 | 0.8 | 1.4 | 0.9 | 1.8 | 0.9 | 0.8 | 1.0 | 0.51 |
| YPL249C | 0.8 | 0.9 | 1.1 | 0.6 | 0.8 | 2.5 | 1.0 | 1.0 | 3.0 | 1.2 | 0.9 | 0.9 | 1.8 | 1.0 | 1.0 | 1.0 | 0.8 | 1.2 | 0.36 |
| YPL260W | 0.9 | 3.9 | 1.4 | 0.8 | 0.8 | 1.4 | 1.2 | 1.1 | 2.6 | 2.1 | 1.0 | 0.8 | 1.4 | 1.1 | 1.3 | 1.2 | 0.8 | 1.3 | 0.82 |
| YPR061C | 1.3 | 3.2 | 1.2 | 4.9 | 1.4 | 0.5 | 1.8 | 1.2 | 3.2 | 1.9 | 1.6 | 0.8 | 1.1 | 1.7 | 0.4 | 2.7 | 1.1 | 0.9 | 0.40 |
| YPR093C | 1.1 | 1.1 | 0.7 | 1.3 | 1.0 | 0.7 | 0.8 | 1.1 | 6.6 | 2.3 | 1.2 | 0.9 | 1.4 | 1.1 | 0.8 | 1.4 | 1.4 | 1.1 | 0.39 |
| YPR158W | 1.5 | 1.5 | 3.7 | 0.9 | 1.6 | 0.7 | 1.2 | 1.2 | 5.0 | 3.5 | 1.5 | 0.6 | 1.6 | 1.1 | 0.9 | 0.6 | 0.9 | 0.7 | 0.96 |
| YPR169W | 0.9 | 0.9 | 0.5 | 0.6 | 1.0 | 1.5 | 0.9 | 1.0 | 3.5 | 1.4 | 1.0 | 0.5 | 1.0 | 1.0 | 0.9 | 1.4 | 1.1 | 1.1 | 0.86 |
| YPR174C | 0.8 | 0.9 | 0.8 | 0.6 | 1.3 | 1.1 | 0.8 | 1.2 | 3.2 | 1.0 | 0.7 | 1.1 | 1.4 | 0.9 | 1.2 | 0.4 | 1.4 | 0.9 | 0.55 |
| YAL014C | 1.0 | 1.6 | 1.4 | 1.2 | 0.8 | 0.6 | 1.2 | 1.2 | 3.1 | 2.0 | 1.7 | 1.2 | 1.5 | 1.8 | 2.3 | 0.9 | 1.1 | 1.1 | 0.56 |
| YAL017W | 0.6 | 1.4 | 2.3 | 1.2 | 1.0 | 1.1 | 1.3 | 0.6 | 1.9 | 1.6 | 0.7 | 1.0 | 2.2 | 1.1 | 1.0 | 1.3 | 1.0 | 1.2 | 0.79 |
| YAL049C | 1.0 | 2.0 | 1.7 | 1.0 | 0.7 | 1.5 | 3.4 | 1.4 | 3.0 | 1.4 | 1.0 | 1.1 | 1.6 | 2.0 | 1.4 | 2.9 | 1.6 | 1.8 | 1.13 |
| YBR013C | 1.1 | 2.7 | 1.8 | 1.4 | 0.9 | 1.8 | 1.0 | 1.4 | 2.2 | 2.2 | 1.2 | 1.2 | 2.0 | 2.5 | 1.1 | 1.5 | 1.4 | 1.1 | 0.68 |
| YBR051W | 1.2 | 0.8 | 1.5 | 0.3 | 1.1 |  | 1.1 | 1.1 | 1.5 | 1.5 | 0.1 | 0.7 | 1.2 | 1.0 | 0.8 | 1.2 | 1.1 | 0.8 | 0.40 |
| YBR063C | 0.8 | 0.8 | 0.4 | 0.6 | 1.2 | 1.6 | 1.6 | 1.3 | 2.2 | 1.6 | 0.6 | 1.1 | 1.7 | 1.7 | 1.6 | 1.0 | 1.2 | 1.2 | 0.38 |
| YBR129C | 1.1 | 0.8 | 0.6 | 1.0 | 1.2 | 1.9 | 1.0 | 1.4 | 2.3 | 1.4 | 1.4 | 1.0 | 1.3 | 1.6 | 0.9 | 1.7 | 1.0 | 1.5 | 1.25 |
| YBR255W | 1.1 | 1.6 | 0.4 | 0.7 | 1.2 | 1.0 | 1.1 | 1.8 | 1.8 | 1.5 | 1.5 | 0.7 | 1.4 | 1.5 | 1.0 | 1.5 | 1.0 | 1.0 | 0.27 |
| YBR281C | 0.8 | 1.1 | 3.0 | 0.5 | 0.8 |  | 0.6 | 1.2 | 1.8 | 1.4 | 1.4 | 0.5 | 1.2 | 0.9 | 1.0 | 0.8 | 0.7 | 0.8 | 0.44 |
| YCL044C | 0.8 | 1.4 | 2.4 | 0.6 | 1.1 | 1.0 | 1.0 | 1.0 | 3.3 | 4.1 | 1.1 | 0.9 | 1.7 | 1.0 | 4.4 | 0.8 | 0.9 | 0.6 | 0.21 |
| YDL089W | 1.1 | 1.3 | 1.4 | 0.9 | 1.2 | 2.0 | 2.0 | 1.1 | 2.3 | 2.5 | 2.0 | 0.9 | 1.9 | 1.2 | 1.6 | 1.3 | 1.0 | 1.1 | 0.45 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDL173W | 1.0 | 1.2 | 1.0 | 0.8 | 1.3 | 1.1 | 1.6 | 1.5 | 1.8 | 1.6 | 1.2 | 1.1 | 1.7 | 2.1 | 1.1 | 1.3 | 1.3 | 1.8 | 1.19 |
| YDL193W | 0.9 | 1.5 | 1.4 | 0.8 | 1.1 | 2.0 | 1.5 | 1.6 | 2.5 | 1.4 | 1.1 | 1.1 | 1.4 | 1.1 | 1.2 | 1.8 | 0.9 | 1.4 | 0.93 |
| YDL233W | 0.8 | 2.0 | 1.0 | 3.8 | 0.9 | 1.0 | 0.8 | 1.0 | 2.1 | 1.1 | 0.7 | 0.9 | 1.8 | 1.1 | 1.3 | 0.9 | 1.1 | 1.4 | 0.33 |
| YDR071C | 1.4 | 1.1 | 0.7 | 1.3 | 1.1 | 1.5 | 1.3 | 1.6 | 2.6 | 1.6 | 1.4 | 0.9 | 1.3 | 2.0 | 0.9 | 1.2 | 0.9 | 1.6 | 3.08 |
| YDR078C | 1.1 | 1.6 | 3.5 | 0.8 | 0.9 | 0.8 | 2.8 | 1.4 | 2.1 | 1.4 | 1.1 | 0.7 | 1.1 | 1.8 | 0.5 | 1.3 | 0.9 | 1.2 | 0.53 |
| YDR109C | 0.8 | 1.0 | 1.0 | 1.3 | 1.0 | 0.9 | 1.2 | 1.5 | 1.9 | 1.3 | 0.9 | 1.0 | 1.4 | 1.0 | 1.7 | 1.5 | 1.2 | 0.9 | 0.38 |
| YDR140W | 1.7 | 1.4 | 0.9 | 1.8 | 0.7 | 0.9 | 1.2 | 1.5 | 2.2 | 2.5 | 1.7 | 1.1 | 2.0 | 3.2 | 0.9 | 1.9 | 1.3 | 1.3 | 0.78 |
| YDR221W | 0.8 | 1.3 | 0.3 | 0.8 | 1.1 | 1.5 | 0.9 | 1.0 | 2.3 | 1.4 | 0.7 | 0.6 | 1.0 | 1.0 | 1.0 | 1.0 | 1.1 | 1.0 | 0.34 |
| YDR271C | 1.0 | 0.8 | 0.7 | 1.7 | 0.8 | 1.4 | 1.3 | 0.8 | 5.4 | 0.9 | 0.6 | 0.7 | 1.5 | 1.4 | 1.3 | 0.6 | 1.2 | 0.9 | 0.32 |
| YDR316W | 1.0 | 0.8 | 0.6 | 0.9 | 1.5 | 0.7 | 0.3 | 1.4 | 2.5 | 1.0 | 1.3 | 0.6 | 0.6 | 0.7 | 1.3 | 0.3 | 0.6 | 0.5 | 0.69 |
| YDR338C | 1.1 | 1.3 | 1.4 | 1.0 | 0.7 | 0.9 | 1.1 | 0.9 | 2.7 | 1.7 | 1.9 | 0.8 | 1.3 | 1.0 | 0.8 | 0.8 | 0.9 | 1.1 | 0.40 |
| YDR421W | 1.1 | 1.0 | 1.0 | 1.1 | 0.9 | 0.5 | 0.2 | 0.9 | 3.8 | 1.2 | 1.0 | 0.7 | 0.6 | 1.2 | 1.9 | 1.0 | 0.7 | 0.8 | 0.42 |
| YDR425W | 1.3 | 1.7 | 1.0 | 2.2 | 1.4 | 1.7 | 1.8 | 1.2 | 2.6 | 2.2 | 0.9 | 1.1 | 1.4 | 1.3 | 1.3 | 1.1 | 1.2 | 1.2 | 0.31 |
| YDR485C | 0.8 | 0.9 | 0.7 | 0.9 | 1.6 | 1.2 | 1.2 | 1.1 | 2.7 | 2.0 | 0.9 | 0.9 | 1.2 | 1.1 | 1.3 | 1.5 | 0.8 | 1.0 | 0.59 |
| YDR504C | 1.0 | 1.0 | 0.9 | 0.8 | 1.1 | 1.2 | 1.1 | 0.8 | 2.3 | 1.1 | 1.2 | 0.7 | 2.2 | 1.3 | 1.2 | 1.2 | 1.2 | 1.2 | 0.70 |
| YEL044W | 0.8 | 1.5 | 0.7 | 0.9 | 1.2 | 0.8 | 0.8 | 0.8 | 2.1 | 1.2 | 1.6 | 0.6 | 1.3 | 0.6 | 0.6 | 0.7 | 1.4 | 1.0 | 0.93 |
| YER092W | 1.3 | 1.3 | 1.2 | 1.1 | 1.2 | 1.5 | 1.3 | 1.1 | 1.9 | 1.6 | 0.9 | 0.9 | 1.2 | 1.2 | 1.0 | 1.9 | 1.4 | 1.7 | 1.13 |
| YER182W | 1.2 | 0.8 | 1.1 | 1.9 | 1.2 | 0.6 | 0.8 | 1.4 | 2.2 | 1.2 | 1.5 | 1.0 | 0.9 | 1.9 | 0.5 | 3.6 | 0.8 | 1.2 | 0.87 |
| YFL042C | 0.8 | 0.9 | 0.6 | 1.1 | 1.4 | 1.5 | 1.1 | 0.8 | 2.0 | 2.0 | 5.4 | 0.9 | 1.7 | 1.2 | 1.1 | 1.0 | 1.1 | 1.2 | 0.43 |
| YFR056C | 0.9 | 1.5 | 0.7 | 0.5 | 1.2 | 0.3 | 0.9 | 1.0 | 2.4 | 2.7 | 1.3 | 0.5 | 0.3 | 0.6 | 0.9 | 0.5 | 1.1 | 0.8 | 0.59 |
| YGL041C | 0.9 | 0.6 | 1.3 | 1.0 | 0.6 | 1.4 | 1.0 | 0.8 | 1.3 | 0.4 | 0.6 | 0.6 | 1.0 | 1.2 | 0.7 | 0.8 | 1.0 | 1.1 | 0.51 |
| YGL045W | 1.4 | 1.1 | 1.9 | 3.4 | 1.0 | 0.8 | 1.7 | 1.2 | 2.8 | 4.2 | 1.2 | 1.1 | 1.3 | 1.1 | 1.5 | 3.4 | 1.3 | 1.2 | 0.47 |
| YGL057C | 1.3 | 1.1 | 1.4 | 1.4 | 1.3 | 1.3 | 1.1 | 1.1 | 2.1 | 1.1 | 1.3 | 1.1 | 1.3 | 1.5 | 0.7 | 1.2 | 0.9 | 1.1 | 0.56 |
| YGL183C | 1.1 | 1.4 | 0.8 | 0.5 | 1.6 | 1.2 | 1.2 | 0.8 | 3.4 | 2.5 | 0.8 | 0.9 | 1.5 | 1.7 | 1.7 | 0.6 | 1.4 | 1.0 | 0.18 |
| YGL223C | 1.1 | 1.7 | 1.0 | 0.7 | 1.4 | 1.1 | 1.2 | 1.0 | 2.6 | 2.0 | 1.3 | 0.9 | 1.7 | 0.9 | 0.7 | 1.1 | 0.8 | 1.0 | 0.60 |
| YGR156W | 0.9 | 1.3 | 1.7 | 1.2 | 1.0 | 1.2 | 1.3 | 1.3 | 4.0 | 2.4 | 0.5 | 1.2 | 1.8 | 1.6 | 1.3 | 0.5 | 0.8 | 0.8 | 0.26 |
| YGR198W | 0.7 | 0.9 | 0.7 | 1.0 | 0.8 | 0.8 | 0.8 | 1.0 | 2.9 | 1.8 | 1.0 | 0.7 | 1.3 | 0.8 | 0.9 | 1.2 | 1.1 | 1.0 | 0.87 |
| YGR210C | 0.9 | 1.4 | 1.1 | 0.9 | 0.8 | 0.8 | 0.8 | 1.0 | 3.5 | 1.8 | 1.0 | 0.6 | 1.0 | 0.8 | 1.3 | 0.7 | 1.1 | 0.7 | 0.56 |
| YGR211W | 0.7 | 1.0 | 2.0 | 1.0 | 0.9 | 0.6 | 0.5 | 1.0 | 2.9 | 2.5 | 0.8 | 0.6 | 0.8 | 0.4 | 0.5 | 0.3 | 0.5 | 0.5 | 1.99 |
| YGR237C | 0.8 | 1.3 | 2.5 | 0.8 | 1.2 | 0.7 | 1.4 | 1.0 | 1.8 | 1.4 | 1.6 | 0.8 | 1.6 | 0.6 | 1.1 | 1.2 | 0.9 | 1.0 | 0.50 |
| YGR250C | 1.3 | 1.4 | 1.4 | 1.5 | 1.4 | 1.6 | 1.2 | 1.1 | 2.4 | 2.8 | 1.6 | 0.6 | 1.7 | 1.3 | 1.2 | 1.2 | 1.3 | 2.1 | 1.21 |
| YGR266W | 0.7 | 0.5 | 1.0 | 0.9 | 0.8 | 1.2 | 0.9 | 0.9 | 2.0 | 1.1 | 1.2 | 0.6 | 1.1 | 0.8 | 1.1 | 1.3 | 0.7 | 1.0 | 0.59 |
| YGR277C | 1.0 | 1.9 | 1.1 | 0.8 | 0.8 | 0.8 | 1.9 | 1.3 | 2.8 | 1.5 | 1.2 | 0.9 | 1.6 | 1.5 | 0.9 | 1.0 | 1.3 | 1.1 | 0.81 |
| YHL021C | 1.6 | 3.9 | 5.9 | 3.2 | 0.9 | 1.4 | 2.7 | 1.0 | 2.7 | 1.1 | 1.4 | 1.1 | 2.6 | 1.1 | 1.2 | 2.4 | 1.3 | 3.6 | 1.27 |
| YHL037C | 1.2 | 1.4 | 0.9 |  | 1.0 | 0.7 | 1.0 | 1.1 | 0.4 | 1.1 | 1.0 | 0.6 | 1.0 | 0.9 | 0.8 | 0.7 | 0.9 | 0.9 | 0.28 |
| YHR083W | 1.0 | 0.9 | 1.4 | 1.3 | 0.9 | 0.9 | 1.0 | 1.0 | 2.0 | 2.1 | 1.3 | 0.9 | 1.1 | 1.6 | 1.3 | 2.4 | 0.8 | 1.0 | 0.90 |
| YHR134W | 1.1 | 0.7 | 0.4 | 1.1 | 1.1 | 2.0 | 1.3 | 1.2 | 3.5 | 1.5 | 0.7 | 1.0 | 1.2 | 1.6 | 1.0 | 1.2 | 1.3 | 1.3 | 0.81 |
| YHR180W | 1.5 | 0.7 | 1.1 | 1.5 | 0.9 | 1.1 | 1.1 | 1.2 | 4.8 | 3.5 | 1.4 | 0.7 | 1.3 | 1.5 | 0.8 | 1.3 | 0.8 | 1.0 | 0.36 |
| YIL108W | 1.0 | 1.7 | 2.2 | 0.7 | 1.3 | 0.6 | 0.9 | 0.8 | 2.4 | 2.0 | 1.2 | 0.7 | 1.3 | 1.0 | 1.8 | 0.7 | 1.2 | 0.7 | 0.51 |
| YIL165C | 1.2 | 2.3 | 0.9 | 1.6 | 1.6 | 0.8 | 1.5 | 1.1 | 3.2 | 3.4 | 1.1 | 0.9 | 1.5 | 1.3 | 0.8 | 1.9 | 1.4 | 1.3 | 0.74 |
| YJL032W | 1.1 | 1.0 | 0.8 | 0.9 | 0.9 | 0.6 | 0.9 | 1.3 | 3.3 | 2.0 | 1.8 | 0.5 | 1.4 | 1.6 | 1.0 | 1.2 | 1.1 | 1.1 | 0.33 |
| YJL049W | 1.3 | 0.8 | 0.5 | 1.8 | 1.6 | 1.5 | 1.2 | 1.5 | 2.0 | 1.9 | 1.5 | 0.8 | 0.9 | 1.8 | 0.8 | 1.6 | 0.9 | 1.1 | 0.75 |
| YJR044C | 1.1 | 1.2 | 5.1 | 1.0 | 1.0 | 1.5 | 2.0 | 1.0 | 2.2 | 1.6 | 1.9 | 0.7 | 2.0 | 1.3 | 1.6 | 2.7 | 1.8 | 1.6 | 1.18 |
| YKL059C | 0.8 | 1.0 | 0.9 | 0.7 | 1.3 | 0.9 | 1.0 | 1.0 | 2.6 | 1.2 | 0.9 | 0.9 | 1.3 | 1.1 | 0.8 | 1.1 | 0.8 | 0.9 | 0.53 |
| YKL090W | 1.0 | 0.9 | 1.0 | 1.2 | 1.1 | 1.0 | 1.1 | 1.2 | 3.9 | 1.6 | 2.3 | 0.6 | 0.8 | 1.4 | 0.8 | 1.6 | 0.7 | 0.9 | 0.37 |
| YKL094W | 1.2 | 1.6 | 1.2 | 1.9 | 0.9 | 1.0 | 1.1 | 1.3 | 3.1 | 1.8 | 1.3 | 0.9 | 1.7 | 1.3 | 1.0 | 2.0 | 1.2 | 1.9 | 1.60 |
| YLR097C | 1.1 | 1.5 | 1.0 | 1.6 | 1.6 | 1.7 | 1.8 | 1.4 | 2.2 | 1.1 | 1.7 | 0.8 | 1.1 | 1.7 | 0.9 | 2.5 | 1.1 | 1.7 | 0.76 |
| YLR226W | 1.0 | 1.8 | 0.3 | 1.0 | 1.7 | 1.1 | 1.9 | 1.3 | 2.1 | 1.4 | 0.8 | 0.7 | 0.7 | 1.1 | 1.3 | 0.9 | 1.1 | 1.0 | 0.56 |
| YLR392C | 1.1 | 0.9 | 0.8 | 1.9 | 1.0 | 1.2 | 1.0 | 1.3 | 2.4 | 2.1 | 1.4 | 0.6 | 1.4 | 1.1 | 0.5 | 2.1 | 0.8 | 1.6 | 0.46 |
| YLR427W | 0.6 | 1.0 | 0.2 | 0.5 | 1.6 | 1.0 | 1.2 | 1.1 | 2.1 | 1.3 | 0.8 | 0.9 | 2.5 | 0.8 | 0.8 | 1.3 | 1.0 | 1.0 | 0.49 |
| YML013W | 0.8 | 1.0 | 0.4 | 0.6 | 1.3 | 0.6 | 1.3 | 0.6 | 2.1 | 1.2 | 1.1 | 0.9 | 1.2 | 1.1 | 2.2 | 1.3 | 1.1 | 0.8 | 0.27 |
| YML029W | 0.6 | 1.5 | 1.3 | 1.0 | 1.2 | 1.6 | 1.1 | 0.9 | 2.3 | 1.8 | 1.2 | 1.1 | 2.0 | 1.6 | 0.8 | 1.1 | 1.2 | 1.0 | 0.46 |
| YML041C | 1.2 | 1.0 | 0.6 | 1.0 | 1.3 | 1.9 | 1.4 | 1.8 | 3.0 | 1.5 | 0.9 | 0.8 | 1.2 | 2.2 | 1.0 | 1.4 | 1.3 | 1.3 | 0.59 |
| YML079W | 1.0 | 1.7 | 1.1 | 1.5 | 0.8 | 1.4 | 1.2 | 1.2 | 1.9 | 1.4 | 1.2 | 1.1 | 1.6 | 1.4 | 0.3 | 2.0 | 1.4 | 1.4 | 1.18 |
| YMR068W | 0.9 | 0.7 | 0.8 | 1.5 | 1.6 | 1.1 | 1.5 | 0.8 | 2.4 | 1.4 | 1.1 | 0.7 | 1.4 | 1.1 | 2.2 | 0.8 | 1.3 | 1.1 | 0.24 |
| YMR160W | 0.8 | 1.3 | 1.2 | 1.2 | 1.4 | 2.2 | 1.0 | 0.9 | 2.2 | 1.8 | 1.0 | 1.0 | 1.6 | 1.1 | 1.5 | 1.4 | 0.9 | 1.3 | 0.37 |
| YNL026W | 0.7 | 1.0 | 1.3 | 0.8 | 1.4 | 1.1 | 1.5 | 1.0 | 2.7 | 1.8 | 1.1 | 0.9 | 1.7 | 0.8 | 0.8 | 1.5 | 1.0 | 1.4 | 0.86 |
| YNL063W | 0.9 | 1.9 | 0.9 | 1.4 | 1.1 | 1.1 | 1.4 | 1.5 | 3.0 | 1.8 | 1.1 | 1.0 | 1.5 | 1.1 | 0.7 | 1.8 | 0.9 | 1.0 | 0.54 |
| YNL176C | 1.1 | 1.3 | 2.9 | 1.0 | 0.8 | 0.7 | 0.7 | 0.9 | 2.4 | 2.1 | 1.2 | 0.6 | 0.6 | 0.9 | 0.8 | 1.3 | 0.6 | 0.8 | 0.66 |
| YNL194C | 1.6 | 0.7 | 2.0 | 15.2 | 0.7 | 0.7 | 1.5 | 0.9 | 2.2 | 6.4 | 17.1 | 0.5 | 1.5 | 3.0 | 0.5 | 4.3 | 0.8 | 2.4 | 0.34 |
| YNL253W | 1.3 | 1.3 | 0.6 | 1.0 | 1.5 | 1.3 | 1.3 | 1.1 | 2.8 | 2.6 | 0.8 | 0.8 | 1.1 | 1.4 | 0.5 | 1.1 | 1.1 | 1.2 | 0.54 |
| YNL276C | 1.3 | 13.1 | 1.9 | 0.3 | 1.1 | 1.3 | 0.9 | 0.7 | 3.1 | 1.3 | 0.7 | 0.9 | 1.5 | 1.5 | 0.5 | 0.8 | 1.1 | 0.8 | 0.22 |
| YNR051C | 0.7 | 0.5 | 1.1 | 0.6 | 1.3 | 1.8 | 1.3 | 0.7 | 2.4 | 1.4 | 1.5 | 0.9 | 2.1 | 1.0 | 1.2 | 0.6 | 0.7 | 0.8 | 1.58 |
| YOR022C | 1.3 | 1.1 | 1.2 | 1.1 | 1.2 | 1.4 | 1.2 | 1.6 | 2.0 | 1.4 | 1.7 | 0.9 | 1.7 | 1.0 | 0.8 | 1.8 | 1.1 | 1.1 | 0.36 |
| YOR087W | 0.7 | 0.9 | 1.8 | 1.3 | 0.8 | 0.3 | 0.9 | 0.8 | 2.8 | 1.3 | 1.3 | 0.8 | 1.2 | 0.9 | 0.8 | 1.2 | 0.8 | 1.1 | 0.61 |
| YOR138C | 0.8 | 1.5 | 0.7 | 0.8 | 0.8 | 1.0 | 1.1 | 0.8 | 2.1 | 3.7 | 0.7 | 1.0 | 1.8 | 0.9 | 1.0 | 1.1 | 1.1 | 1.1 | 0.47 |
| YOR267C | 0.8 | 0.7 | 1.0 | 0.9 | 1.2 | 1.6 | 0.9 | 0.7 | 2.4 | 2.2 | 0.4 | 0.9 | 1.4 | 0.9 | 1.3 | 0.8 | 1.3 | 1.0 | 0.58 |
| YPL005W | 1.0 | 1.0 | 1.4 | 1.0 | 1.0 | 1.4 | 2.0 | 1.0 | 2.6 | 2.8 | 1.1 | 0.7 | 1.2 | 1.0 | 1.2 | 1.6 | 1.2 | 1.1 | 0.32 |
| YPL150W | 0.7 | 0.9 | 1.6 | 0.9 | 1.0 | 0.6 | 1.2 | 1.1 | 3.1 | 2.0 | 1.1 | 1.0 | 2.1 | 1.0 | 1.2 | 1.2 | 1.4 | 1.1 | 0.47 |
| YPL152W | 1.4 | 1.1 | 1.4 | 1.8 | 1.4 | 1.2 | 1.3 | 1.1 | 3.6 | 2.7 | 1.4 | 0.9 | 1.4 | 1.2 | 2.3 | 1.4 | 1.2 | 1.9 | 0.42 |
| YPL168W | 1.1 | 1.5 | 0.5 | 1.4 | 1.0 | 0.8 | 1.2 | 1.2 | 2.1 | 1.6 | 0.7 | 0.7 | 1.0 | 1.0 | 0.8 | 1.3 | 1.1 | 1.2 | 0.41 |
| YPL180W | 0.9 | 2.0 | 0.7 | 0.6 | 1.2 | 1.5 | 1.0 | 1.0 | 1.9 | 1.8 | 1.0 | 0.8 | 1.5 | 1.0 | 0.7 | 1.0 | 1.0 | 0.9 | 0.30 |
| YPL188W | 1.3 | 1.2 | 2.9 | 1.0 | 0.9 | 0.6 | 1.3 | 1.6 | 2.5 | 2.6 | 1.0 | 0.6 | 0.9 | 1.4 | 0.8 | 1.7 | 0.7 | 0.9 | 0.55 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPR049C | 1.0 | 2.5 | 1.5 | 1.0 | 0.7 | 1.2 | 1.1 | 1.1 | 2.4 | 2.1 | 0.9 | 0.9 | 1.6 | 1.4 | 1.5 | 1.7 | 1.0 | 1.1 | 0.34 |
| YPR148C | 1.1 | 1.2 | 0.8 | 1.3 | 0.9 | 1.0 | 1.6 | 1.5 | 2.7 | 1.7 | 0.9 | 1.2 | 1.2 | 1.1 | 1.7 | 1.7 | 0.9 | 2.0 | 1.25 |
| YPR172W | 1.1 | 1.6 | 2.2 | 1.2 | 1.0 | 1.7 | 1.2 | 1.0 | 2.1 | 1.3 | 1.9 | 0.8 | 1.3 | 1.6 | 1.5 | 1.9 | 1.1 | 1.4 | 0.45 |
| YAL018C | 2.0 | 1.9 | 1.1 | 11.3 | 0.8 | 0.7 | 1.0 | 1.6 |  | 0.4 | 0.1 | 0.9 | 1.3 | 1.0 | 6.9 | 1.1 | 0.9 | 0.9 | 0.21 |
| YAR064W | 2.1 | 0.9 | 0.9 | 2.8 | 0.8 | 0.5 | 1.1 | 1.1 | 0.0 | 0.7 | 0.7 | 0.8 | 1.1 | 1.1 | 1.9 | 1.0 | 0.9 | 0.9 | 0.30 |
| YBR012C | 2.5 | 1.7 | 1.3 | 0.8 | 0.9 | 1.8 | 1.5 | 1.1 | 1.4 | 2.6 | 0.7 | 1.0 | 2.1 | 0.9 | 1.1 | 1.3 | 1.4 | 1.2 | 0.46 |
| YBR287W | 1.7 | 1.9 | 3.1 | 2.4 | 1.3 | 1.4 | 1.1 | 1.0 | 1.2 | 1.6 | 2.0 | 1.2 | 3.4 | 0.8 | 1.3 | 1.6 | 3.2 | 1.9 | 2.73 |
| YDR250C | 1.9 | 1.4 | 0.9 | 3.0 | 1.0 | 0.4 | 1.0 | 1.1 |  | 0.5 | 0.6 | 0.8 | 1.2 | 0.9 | 0.7 | 1.7 | 0.9 | 0.9 | 0.32 |
| YJL037W | 1.8 | 1.4 | 1.4 | 2.4 | 1.5 | 1.8 | 1.2 | 1.2 | 1.8 | 2.4 | 1.6 | 0.8 | 1.1 | 2.0 | 1.6 | 1.0 | 1.3 | 0.9 | 0.26 |
| YNL058C | 2.0 | 1.0 | 2.1 | 1.7 | 1.0 | 0.4 | 0.7 |  | 0.3 | 0.7 | 1.0 | 1.0 | 0.6 | 0.8 | 2.2 | 0.9 | 0.8 | 1.0 | 0.60 |
| YJR030C | 0.7 | 4.4 | 0.9 | 1.2 | 0.7 | 0.6 | 0.7 | 0.9 | 0.4 | 0.5 | 0.8 | 0.9 | 0.7 | 1.0 | 0.8 | 0.9 | 0.7 | 0.9 | 0.27 |
| YKR040C | 1.2 | 3.7 | 2.4 | 2.9 | 0.9 | 0.9 | 0.9 | 1.0 | 1.3 | 1.2 | 0.8 | 0.8 | 0.6 | 3.8 | 1.1 | 1.2 | 0.7 | 0.8 | 0.53 |
| YDR128W | 0.6 | 3.9 | 1.4 | 0.9 | 0.8 | 0.9 | 0.8 | 1.1 | 0.9 | 1.5 | 0.3 | 0.6 | 1.1 | 1.0 | 1.4 | 1.3 | 0.9 | 0.9 | 0.40 |
| YGR139W | 1.3 | 3.7 | 0.8 | 0.7 | 1.3 | 0.6 | 0.8 | 0.6 |  | 0.6 | 0.9 | 0.5 | 0.4 | 0.9 | 2.3 | 0.8 | 1.0 | 0.8 | 0.22 |
| YOR253W | 0.9 | 2.8 | 1.0 | 1.4 | 0.8 | 0.5 | 1.3 | 1.2 | 0.4 | 1.0 | 0.9 | 0.7 | 0.5 | 1.3 | 1.1 | 0.9 | 0.9 | 0.9 | 1.01 |
| YOL026C | 1.2 | 2.7 | 0.7 | 1.4 | 1.9 | 1.0 | 1.8 | 1.1 | 1.2 | 1.1 | 1.2 | 0.9 | 1.2 | 1.3 | 0.9 | 2.4 | 2.1 | 1.4 | 0.65 |
| YDR278C | 1.0 | 3.2 | 0.9 | 1.0 | 1.1 | 1.0 | 0.7 | 0.5 | 0.6 | 0.7 | 0.4 | 0.6 | 0.7 | 0.9 | 0.7 | 0.5 | 0.7 | 0.8 | 0.78 |
| YHR095W | 1.1 | 2.6 | 1.5 | 2.1 | 1.1 | 1.0 | 0.8 | 1.0 | 1.5 | 1.2 | 1.3 | 0.6 | 0.7 | 0.9 | 0.8 | 0.9 | 0.8 | 0.7 | 0.67 |
| YCL042W |  | 2.5 | 7.2 |  | 1.1 | 0.6 |  | 0.6 | 0.7 | 2.2 | 3.2 |  | 7.5 |  |  | 0.8 |  |  | 1.94 |
| YNL200C | 1.0 | 3.0 | 3.6 | 2.0 | 1.0 | 0.4 | 1.2 | 0.7 | 1.9 | 1.2 | 3.1 | 0.9 | 1.1 | 0.6 | 0.8 | 0.9 | 1.2 | 0.9 | 1.40 |
| YPL221W | 0.9 | 3.0 | 1.0 | 1.8 | 1.4 | 1.1 | 1.3 | 0.9 | 0.3 | 1.3 | 1.0 | 0.8 | 1.0 | 0.8 | 1.0 | 1.2 | 1.5 | 1.2 | 1.51 |
| YLR415C | 1.1 | 2.4 | 6.7 |  | 0.9 | 0.3 | 1.2 | 0.9 |  | 0.3 | 0.8 | 0.8 | 1.0 | 0.8 | 1.0 | 1.9 | 0.8 | 1.0 | 0.19 |
| YOR325W | 1.0 | 2.6 | 1.5 | 0.9 | 0.3 | 1.2 | 0.9 |  |  | 0.6 | 0.9 | 0.6 | 0.3 | 1.3 | 0.7 | 1.4 | 0.8 | 1.0 | 0.19 |
| YGL088W | 0.9 | 2.1 | 0.9 | 1.1 | 0.6 | 0.8 | 1.0 | 0.5 | 0.5 | 0.8 | 0.8 | 0.6 | 0.7 | 1.4 | 0.4 | 0.3 | 0.5 | 0.7 | 1.80 |
| YDR090C | 0.9 | 3.0 | 0.8 | 1.2 | 1.8 | 1.4 | 1.5 | 0.8 | 1.0 | 1.5 | 0.7 | 0.6 | 0.8 | 0.9 | 1.1 | 0.9 | 1.1 | 1.1 | 0.79 |
| YMR071C | 1.0 | 2.0 | 1.1 | 1.9 | 1.4 | 1.2 | 1.8 | 1.1 | 1.6 | 1.8 | 1.2 | 0.7 | 1.3 | 1.2 | 0.8 | 1.4 | 1.2 | 1.9 | 2.39 |
| YGR293C | 0.5 | 1.9 | 1.6 | 0.0 | 1.1 | 0.7 | 1.3 | 1.3 |  | 1.1 | 0.6 | 1.0 | 0.7 | 1.0 | 0.7 | 0.9 | 0.8 | 0.9 | 0.23 |
| YJL017W | 1.1 | 1.7 | 3.5 | 1.1 | 1.3 | 1.2 | 0.2 | 1.0 | 0.8 | 1.4 | 1.4 | 1.3 | 1.5 | 1.0 | 1.1 | 0.6 | 1.0 | 1.0 | 0.85 |
| YIL127C | 1.1 | 4.8 | 0.2 | 1.2 | 1.0 | 0.4 | 0.6 | 1.2 | 0.3 | 0.5 | 0.9 | 0.7 | 0.4 | 1.3 | 0.7 | 0.2 | 0.7 | 0.6 | 1.57 |
| YDR281C | 2.1 | 2.6 | 0.4 | 2.1 | 1.3 | 1.5 | 0.6 | 1.2 | 0.2 | 0.5 | 0.8 | 0.9 | 0.7 | 1.2 | 0.3 | 0.6 | 1.5 | 1.2 | 1.56 |
| YDR366C | 0.9 | 2.0 | 0.8 | 0.9 | 1.0 | 1.5 | 1.5 | 1.1 | 1.0 | 1.5 | 1.7 | 0.6 | 0.8 | 1.4 | 1.4 | 1.0 | 1.2 | 0.9 | 1.14 |
| YFR026C | 0.9 | 2.0 | 1.0 | 0.8 | 1.0 | 1.2 | 1.3 | 1.3 | 1.8 | 0.6 | 0.8 | 0.6 | 1.1 | 1.0 | 2.3 | 2.2 | 1.1 | 1.1 | 0.39 |
| YAR047C | 1.1 | 1.7 | 1.5 | 0.7 | 1.1 | 1.3 | 1.2 | 0.8 | 0.5 | 2.3 | 1.1 | 0.9 | 1.4 | 1.3 | 0.5 | 1.0 | 1.7 | 1.0 | 0.35 |
| YHL006C | 0.7 | 1.4 | 0.9 | 0.6 | 1.1 | 1.1 | 1.2 | 1.1 | 0.9 | 0.9 | 0.7 | 1.0 | 1.1 | 1.1 | 0.6 | 0.9 | 1.1 | 1.0 | 0.37 |
| YPL225W | 1.3 | 1.7 | 1.0 | 1.6 | 1.1 | 1.8 | 1.7 | 1.7 | 1.0 | 1.6 | 0.9 | 0.7 | 0.8 | 1.4 | 0.9 | 1.8 | 1.0 | 1.7 | 2.87 |
| YBR124W | 0.9 | 1.4 | 1.5 | 0.4 | 1.0 | 0.6 | 1.1 | 1.2 | 1.1 | 0.7 | 0.4 | 0.9 | 0.9 | 1.0 | 1.0 | 0.8 | 0.9 | 0.9 | 0.29 |
| YBL044W | 0.9 | 2.7 | 2.1 | 0.8 | 1.2 | 0.7 | 1.1 | 0.7 | 0.2 | 0.5 | 0.6 | 0.9 | 0.7 | 0.9 | 0.7 | 0.6 | 0.8 | 0.8 | 0.39 |
| YCL056C | 1.3 | 1.4 | 0.7 | 1.0 | 1.5 | 1.4 | 1.6 | 1.0 | 1.5 | 1.6 | 1.5 | 1.0 | 1.3 | 2.2 | 1.7 | 2.3 | 1.2 | 1.5 | 0.82 |
| YCR007C | 2.2 | 1.6 | 0.9 | 2.9 | 1.5 | 1.4 | 2.0 | 1.0 | 1.4 | 2.6 | 1.1 | 0.8 | 1.5 | 1.7 | 0.8 | 1.7 | 2.6 | 2.1 | 0.39 |
| YPR146C | 0.8 | 1.6 | 1.3 | 0.9 | 1.2 | 1.1 | 1.0 | 0.8 | 0.9 | 1.2 | 1.4 | 0.8 | 1.3 | 0.9 | 0.9 | 1.3 | 1.0 | 1.1 | 0.80 |
| YKL097C | 0.9 | 1.6 | 0.6 | 1.4 | 1.8 | 0.7 | 0.8 | 0.4 | 0.1 |  | 0.6 | 0.6 | 0.9 | 1.0 | 0.8 | 0.5 | 1.1 | 0.5 | 0.21 |
| YBR066C | 1.9 | 1.3 | 1.6 | 1.6 | 1.3 | 1.3 | 1.3 | 1.2 | 0.3 | 0.9 | 1.2 | 0.7 | 0.6 | 1.1 | 0.4 | 3.2 | 1.2 | 1.2 | 0.83 |
| YLR338W | 1.1 | 1.6 | 1.4 | 1.1 | 0.9 | 1.1 | 0.9 | 0.8 | 7.9 | 0.5 | 0.9 | 0.6 | 1.2 | 0.8 | 1.5 | 0.9 | 0.8 | 0.6 | 0.33 |
| YBR162C | 0.6 | 0.5 | 3.1 | 0.8 | 1.3 | 0.6 | 0.3 | 0.8 | 0.1 | 0.4 | 0.8 | 0.7 | 0.7 | 0.5 | 1.9 | 0.4 | 1.2 | 1.3 | 3.96 |
| YDL046W | 1.2 | 1.4 | 5.1 | 1.3 | 0.9 | 1.8 | 1.2 | 0.7 | 1.6 | 2.3 | 2.6 | 1.0 | 1.5 | 1.2 | 2.3 | 2.6 | 1.2 | 1.6 | 1.94 |
| YDR133C | 0.9 | 1.1 | 2.9 | 2.0 | 1.2 | 0.7 | 0.2 | 0.5 | 0.1 | 0.4 | 1.3 | 0.3 | 0.1 | 0.6 | 0.6 | 1.1 | 0.6 | 0.9 | 4.02 |
| YGR038W | 0.9 | 1.2 | 3.5 | 0.8 | 1.3 | 1.3 | 1.1 | 0.7 | 1.4 | 1.0 | 1.4 | 1.0 | 1.2 | 1.4 | 1.1 | 1.3 | 1.1 | 1.1 | 1.27 |
| YGR243W | 1.4 | 2.2 | 9.4 | 5.0 | 1.0 | 1.5 | 1.9 | 1.3 | 0.7 | 3.0 | 1.7 | 1.2 | 1.1 | 1.9 | 0.8 | 2.8 | 2.1 | 4.4 | 1.11 |
| YHR105W | 0.9 | 0.8 | 2.4 | 6.3 | 1.5 | 0.2 | 0.9 | 1.0 | 1.1 | 3.4 | 0.7 | 0.7 | 1.4 | 1.2 | 0.9 | 1.8 | 0.9 | 0.9 | 0.32 |
| YHR181W | 0.9 | 0.7 | 2.4 | 1.4 | 1.0 | 0.9 | 0.8 | 0.9 | 0.5 | 1.3 | 1.3 | 0.8 | 0.7 | 1.6 | 1.4 | 1.5 | 0.9 | 0.9 | 1.40 |
| YJL097W | 1.0 | 1.1 | 3.7 | 1.6 | 0.9 | 1.6 | 1.0 | 0.8 | 0.3 | 0.7 | 1.5 | 1.0 | 0.7 | 1.0 | 1.1 | 1.2 | 1.2 | 1.1 | 1.69 |
| YKL051W | 1.0 | 1.1 | 4.7 | 0.8 | 0.8 | 1.0 | 0.6 | 0.8 | 1.3 | 1.1 | 1.8 | 0.8 | 1.2 | 0.7 | 1.5 | 0.9 | 1.5 | 1.4 | 1.07 |
| YKL100C | 0.7 | 1.1 | 5.0 | 1.6 | 0.6 | 1.8 | 1.2 | 0.7 | 1.3 | 1.3 | 1.6 | 0.9 | 1.3 | 1.0 | 1.7 | 2.0 | 0.7 | 1.5 | 1.14 |
| YLR339C | 0.7 | 0.8 | 3.1 | 0.8 | 1.3 | 0.4 | 0.4 | 0.5 |  | 0.4 | 1.6 | 0.6 | 0.1 | 0.5 | 1.0 | 0.5 | 0.7 | 0.6 | 1.37 |
| YOL030W | 1.0 | 0.8 | 4.4 | 1.0 | 0.9 | 0.9 | 1.3 | 0.6 | 1.2 | 0.6 | 1.3 | 0.9 | 1.7 | 0.6 | 0.9 | 0.7 | 0.9 | 1.0 | 1.93 |
| YPR150W | 1.3 | 1.1 | 4.3 | 3.0 | 1.3 | 0.9 | 0.9 | 0.8 | 1.2 | 3.3 | 0.9 | 0.6 | 1.4 | 1.4 | 0.9 | 1.8 | 0.9 | 1.0 | 0.31 |
| YBL100C | 0.8 | 1.8 | 1.6 | 0.5 | 0.6 | 0.4 | 1.1 | 0.6 | 0.2 | 0.8 | 0.9 | 0.7 | 0.9 | 0.9 | 1.0 | 0.5 | 0.8 | 0.8 | 0.58 |
| YBR096W | 1.1 | 1.5 | 2.8 | 1.6 | 0.9 | 1.7 | 1.9 | 1.0 | 1.2 | 1.6 | 1.2 | 0.9 | 1.9 | 1.7 | 1.1 | 1.1 | 1.1 | 1.5 | 1.43 |
| YBR100W | 1.0 | 1.5 | 4.8 | 1.1 | 0.9 | 0.5 | 1.0 | 0.9 | 8.5 | 3.0 | 0.2 | 0.7 | 1.2 | 1.2 | 1.3 | 1.2 | 0.8 | 0.9 | 0.35 |
| YOL058W | 1.1 | 1.6 | 2.2 | 1.2 | 1.7 | 1.1 | 0.8 | 0.9 | 0.6 | 1.0 | 1.0 | 1.0 | 0.9 | 1.9 | 1.2 | 0.8 | 1.4 | 0.9 | 0.72 |
| YCR030C | 1.1 | 0.9 | 3.3 | 1.0 | 1.0 | 1.2 | 1.0 | 0.7 | 0.9 | 2.0 | 1.1 | 0.9 | 1.7 | 0.8 | 1.3 | 1.0 | 1.2 | 1.0 | 0.63 |
| YDL015C | 0.9 | 0.7 | 3.6 | 1.1 | 1.2 | 2.5 | 1.1 | 0.9 | 0.7 | 1.1 | 0.8 | 1.0 | 0.9 | 1.1 | 1.1 | 2.1 | 1.0 | 1.5 | 2.99 |
| YDL023C | 0.8 | 1.6 | 2.4 | 1.1 | 0.6 | 0.3 | 1.5 | 0.7 | 0.7 | 1.5 | 3.5 | 0.9 | 1.4 | 0.7 | 0.6 | 0.9 | 0.8 | 1.1 | 0.78 |
| YDL086W | 0.9 | 1.2 | 1.9 | 0.9 | 1.3 | 0.9 | 0.8 | 0.8 | 1.3 | 1.1 | 1.4 | 0.8 | 1.7 | 0.9 | 0.9 | 1.1 | 0.8 | 0.8 | 0.80 |
| YDR233C | 1.1 | 1.1 | 3.2 | 1.9 | 0.7 | 0.8 | 1.2 | 1.1 | 0.2 | 0.7 | 3.7 | 1.3 | 0.5 | 0.9 | 1.5 | 2.8 | 0.9 | 0.9 | 3.47 |
| YDR359C | 0.8 | 0.7 | 1.7 | 1.9 | 1.3 | 0.8 | 1.0 | 0.8 | 0.7 | 1.0 | 0.5 | 1.0 | 1.1 | 1.3 | 1.4 | 0.9 | 0.8 | 0.9 | 0.34 |
| YEL033W | 0.9 | 1.2 | 2.7 | 1.1 | 1.0 | 0.7 | 0.3 | 0.7 | 0.6 | 0.4 | 1.2 | 0.6 | 0.4 | 1.0 | 0.6 | 0.9 | 0.9 | 0.9 | 2.96 |
| YGR022C | 1.3 | 1.1 | 1.7 | 2.2 | 1.1 | 1.3 | 0.9 | 0.9 | 0.2 |  | 0.4 | 0.7 | 1.2 | 1.1 | 0.7 | 0.6 | 0.9 | 0.8 | 0.50 |
| YGR026W | 0.8 | 1.1 | 2.9 | 0.9 | 0.9 | 1.5 | 0.9 | 0.9 |  | 0.7 | 1.3 | 0.5 | 0.6 | 1.0 | 1.2 | 1.4 | 1.0 | 1.2 | 2.19 |
| YGR107W | 1.0 | 0.8 | 1.7 | 0.9 | 1.1 | 0.8 | 1.0 | 0.9 | 0.1 | 0.0 | 0.6 | 0.9 | 0.9 | 1.1 | 0.8 | 1.2 | 0.8 | 0.9 | 0.43 |
| YHL005C | 0.9 | 2.7 | 2.7 | 0.2 | 1.2 | 1.1 | 0.8 | 0.9 |  | 0.9 |  | 0.7 | 0.7 | 1.0 | 0.7 | 0.7 | 1.0 | 0.8 | 0.33 |
| YHR126C | 1.1 | 0.9 | 2.8 | 0.6 | 1.0 | 1.2 | 1.1 | 0.6 | 0.4 | 0.7 | 1.9 | 1.0 | 0.8 | 0.8 | 1.4 | 1.7 | 1.1 | 1.3 | 1.31 |
| YHR143W | 0.5 | 0.9 | 4.9 | 1.0 | 1.2 | 2.1 | 0.5 | 1.5 | 0.2 | 0.7 | 1.2 | 0.5 | 0.5 | 0.8 | 0.3 | 0.9 | 0.9 | 0.7 | 3.58 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YIL157C | 1.1 | 1.3 | 2.1 | 1.7 | 0.8 | 1.3 | 1.2 | 1.0 | 0.9 | 0.9 | 1.3 | 0.8 | 1.0 | 1.0 | 0.5 | 1.8 | 1.1 | 1.5 | 1.46 |
| YIR041W | 1.6 | 1.0 | 2.4 | 1.4 | 1.3 | 1.0 | 1.6 | 0.9 | 1.5 | 2.5 | 1.2 | 1.3 | 1.1 | 1.1 | 1.3 | 1.3 | 1.1 | 0.9 | 0.66 |
| YJL016W | 1.3 | 1.6 | 2.7 | 1.3 | 1.4 | 1.5 | 1.4 | 0.9 | 0.6 | 0.9 | 1.3 | 0.9 | 1.3 | 1.6 | 1.1 | 2.5 | 1.2 | 1.5 | 0.88 |
| YJR018W | 0.8 | 1.2 | 1.8 | 0.7 | 1.1 | 1.0 | 0.9 | 0.7 | 0.4 | 0.7 | 0.9 | 0.8 | 1.5 | 0.9 | 1.4 | 0.8 | 1.0 | 0.7 | 0.35 |
| YKL147C | 1.0 | 1.3 | 1.9 | 0.9 | 0.8 | 0.7 | 0.8 | 0.7 | 1.0 | 0.5 | 0.3 | 0.9 | 1.0 | 1.0 | 0.7 | 1.1 | 0.9 | 0.9 | 0.28 |
| YKL169C | 1.0 | 1.0 | 1.6 | 1.8 | 0.8 | 1.2 | 1.5 | 1.2 | 0.3 | 0.5 |  | 0.7 | 1.0 | 1.3 | 0.8 | 2.6 | 0.9 | 1.1 | 0.45 |
| YKR033C | 0.9 | 1.2 | 2.1 | 1.0 | 1.0 | 0.6 | 1.0 | 1.0 | 0.1 | 1.4 | 0.3 | 0.4 | 0.9 | 0.9 | 1.1 | 0.6 | 1.0 | 0.9 | 0.28 |
| YLL064C | 0.8 | 1.7 | 1.7 | 1.9 | 0.9 | 1.7 | 1.1 | 0.9 | 1.1 | 2.5 | 1.0 | 1.1 | 1.3 | 1.1 | 1.2 | 1.6 | 1.2 | 1.0 | 0.68 |
| YLR041W | 0.8 | 1.2 | 2.2 | 1.5 | 1.6 | 0.5 | 1.2 | 0.6 |  | 0.4 | 1.1 | 0.4 | 0.3 | 0.5 | 1.3 | 0.5 | 0.7 | 0.9 | 0.69 |
| YLR177W | 0.8 | 1.2 | 1.8 | 2.2 | 0.8 | 1.1 | 1.3 | 0.9 | 1.0 | 2.3 | 0.9 | 1.1 | 1.5 | 1.0 | 0.5 | 1.3 | 1.1 | 1.5 | 1.25 |
| YMR007W | 1.1 | 0.9 | 2.0 | 0.7 | 1.3 | 1.7 | 3.1 | 0.7 |  | 0.1 | 0.9 | 0.8 | 1.3 | 1.2 | 1.8 | 1.1 | 2.5 | 1.0 | 0.30 |
| YMR156C | 1.0 | 0.9 | 2.7 | 1.7 | 1.2 | 1.4 | 1.4 | 0.9 | 0.6 | 1.3 | 1.1 | 0.7 | 1.0 | 1.2 | 0.7 | 1.3 | 1.2 | 1.1 | 0.40 |
| YMR215W | 0.8 | 0.5 | 2.1 | 1.2 | 1.1 | 0.3 | 0.3 | 0.5 | 0.1 | 0.2 | 1.1 | 0.4 | 0.2 | 0.5 | 0.7 | 0.2 | 0.7 | 0.7 | 1.59 |
| YNL195C | 0.9 | 1.1 | 3.5 | 4.7 | 0.9 | 0.8 | 1.1 | 0.9 | 2.6 | 11.7 | 2.9 | 0.6 | 1.6 | 1.5 | 1.4 | 6.4 | 0.8 | 0.9 | 0.32 |
| YOL073C | 0.7 | 0.9 | 2.5 | 0.6 | 1.1 | 1.2 | 1.3 | 0.7 | 1.9 | 1.1 | 1.7 | 0.8 | 1.6 | 0.8 | 1.6 | 1.7 | 1.2 | 1.2 | 0.54 |
| YOR129C | 0.6 | 0.8 | 3.3 | 0.8 | 1.3 | 0.4 | 0.4 | 0.6 | 0.2 | 0.4 | 1.1 | 0.6 | 0.2 | 0.5 | 0.6 | 0.3 | 0.6 | 0.4 | 5.22 |
| YOR161C | 0.6 | 1.0 | 6.0 | 2.2 | 1.1 | 0.9 | 1.2 | 0.8 | 1.0 | 1.7 | 4.6 | 0.5 | 0.7 | 0.9 | 1.4 | 2.0 | 0.7 | 1.2 | 0.82 |
| YPL004C | 0.7 | 1.2 | 3.7 | 1.9 | 1.4 | 1.3 | 2.3 | 0.9 | 1.1 | 1.6 | 1.7 | 0.9 | 1.3 | 1.0 | 1.1 | 2.0 | 1.2 | 2.2 | 4.52 |
| YPL246C | 0.7 | 0.8 | 2.6 | 0.9 | 1.4 | 1.3 | 0.8 | 0.6 | 0.4 | 0.5 | 1.1 | 0.8 | 0.9 | 0.7 | 1.2 | 1.1 | 1.2 | 0.9 | 0.98 |
| YPL2720 | 1.1 | 0.9 | 2.2 | 0.6 | 1.3 | 1.1 | 0.7 | 0.8 | 1.2 | 2.5 | 1.1 | 0.7 | 1.1 | 1.1 | 0.6 | 2.5 | 0.9 | 1.2 | 0.25 |
| YPR063C | 1.0 | 0.8 | 2.6 | 0.8 | 1.2 | 1.0 | 0.6 | 0.7 | 0.5 | 0.6 | 1.0 | 0.7 | 0.8 | 1.0 | 1.0 | 1.2 | 1.0 | 0.9 | 1.41 |
| YDL129W | 1.0 | 0.7 | 1.0 | 2.3 | 1.3 | 0.9 | 0.9 | 1.0 | 0.5 | 0.9 | 0.6 | 0.9 | 0.5 | 0.8 | 0.5 | 1.4 | 0.6 | 0.8 | 0.69 |
| YDR066C | 1.3 | 1.5 | 0.9 | 2.2 | 1.0 | 1.4 | 1.1 | 1.3 | 1.5 | 1.1 | 0.6 | 0.8 | 1.4 | 1.3 | 0.9 | 1.4 | 1.1 | 1.1 | 0.57 |
| YGL059W | 1.3 | 1.5 | 0.9 | 3.1 | 0.7 | 0.7 | 1.0 | 1.4 | 1.6 | 1.7 | 1.4 | 1.0 | 2.0 | 1.2 | 1.6 | 1.7 | 1.4 | 1.4 | 0.49 |
| YNL144C | 1.8 | 0.8 | 1.2 | 4.5 | 0.9 | 1.1 | 1.1 | 1.1 | 0.7 | 1.9 | 1.7 | 1.4 | 1.0 | 1.1 | 0.1 | 1.7 | 2.4 | 2.8 | 0.51 |
| YAL037W | 1.6 | 0.9 | 1.1 | 3.5 | 1.2 | 1.1 | 1.0 | 1.3 | 0.6 | 1.9 | 0.5 | 0.8 | 1.1 | 1.2 | 0.8 | 0.6 | 0.9 | 0.9 | 0.55 |
| YAR023C | 1.4 | 1.0 | 1.7 | 2.1 | 1.3 | 1.0 | 1.1 | 0.8 | 0.9 | 1.4 | 1.0 | 1.2 | 1.1 | 1.0 | 3.1 | 1.6 | 0.9 | 1.1 | 0.62 |
| YCR015C | 1.1 | 0.9 | 0.5 | 2.1 | 1.7 | 1.0 | 1.5 | 1.2 | 0.5 | 1.0 | 1.1 | 0.9 | 0.6 | 1.2 | 0.9 | 1.1 | 1.1 | 1.2 | 0.58 |
| YCR043C | 1.4 | 0.5 | 0.8 | 2.3 | 0.9 | 0.8 | 0.7 | 1.2 | 0.3 | 0.7 | 1.0 | 0.6 | 0.8 | 1.6 | 1.2 | 0.8 | 1.0 | 1.1 | 1.25 |
| YDL146W | 1.0 | 1.2 | 1.2 | 2.0 | 0.7 | 0.7 | 1.4 | 0.9 | 0.8 | 2.3 | 1.4 | 1.0 | 1.4 | 1.0 | 1.7 | 1.8 | 1.0 | 1.2 | 0.62 |
| YDR057W | 0.9 | 1.4 | 1.6 | 2.6 | 0.8 | 0.7 | 1.4 | 1.2 | 1.5 | 1.1 | 1.0 | 0.7 | 0.9 | 1.2 | 1.1 | 1.7 | 0.7 | 1.1 | 0.70 |
| YDR222W | 1.0 | 1.1 | 1.7 | 1.7 | 1.4 | 1.3 | 0.5 | 1.0 | 0.6 | 1.0 | 1.0 | 0.5 | 0.8 | 1.3 | 0.5 | 0.6 | 0.7 | 0.8 | 0.52 |
| YDR286C | 1.6 | 0.9 | 1.1 | 2.1 | 1.0 | 1.7 | 1.3 | 1.9 | 0.8 | 1.2 | 1.1 | 0.9 | 1.4 | 1.3 | 0.8 | 2.1 | 1.1 | 1.4 | 0.90 |
| YDR438W | 1.2 | 1.8 | 0.8 | 2.1 | 1.6 | 1.3 | 1.4 | 1.0 | 1.1 | 0.8 | 1.1 | 0.8 | 1.2 | 1.3 | 1.0 | 1.2 | 1.6 | 1.2 | 0.48 |
| YDR479C | 1.1 | 1.8 | 1.0 | 2.3 | 0.9 | 1.6 | 1.2 | 0.9 | 1.2 | 1.6 | 1.0 | 1.0 | 1.2 | 1.4 | 1.6 | 2.1 | 1.1 | 1.5 | 0.51 |
| YEL057C | 1.1 | 0.6 | 1.3 | 2.4 | 1.0 | 0.9 | 1.1 | 1.2 | 1.2 | 1.9 | 0.7 | 0.8 | 1.5 | 1.5 | 1.0 | 1.8 | 0.9 | 0.7 | 0.44 |
| YEL073C | 1.6 | 0.8 | 1.0 | 2.8 | 1.2 | 1.5 | 0.8 | 0.9 | 0.7 | 1.2 | 1.1 | 0.5 | 1.0 | 1.1 | 2.8 | 1.0 | 1.3 | 0.8 | 0.38 |
| YER084W | 0.8 | 1.1 | 1.0 | 3.9 | 0.9 | 0.6 | 0.8 | 0.9 |  | 0.8 |  | 0.8 | 0.7 | 0.9 | 2.6 | 1.5 | 0.8 | 0.9 | 0.30 |
| YER121W | 1.1 | 1.2 | 0.7 | 7.7 | 1.3 | 2.5 | 1.3 | 1.3 | 0.6 | 0.5 | 1.2 | 0.7 | 0.6 | 1.3 | 0.9 | 4.6 | 1.2 | 1.8 | 0.73 |
| YER189W | 0.9 | 0.8 | 0.9 | 1.9 | 1.3 | 0.5 | 0.9 | 0.7 | 0.4 | 0.5 | 0.7 | 0.8 | 0.7 | 0.9 | 0.9 | 0.8 | 0.8 | 0.8 | 0.43 |
| YFL017C | 1.3 | 1.2 | 0.9 | 2.3 | 1.5 | 1.3 | 1.5 | 1.4 | 0.8 | 0.6 | 1.1 | 1.0 | 0.7 | 1.1 | 0.6 | 1.8 | 1.5 | 1.8 | 1.21 |
| YFL046W | 1.3 | 0.9 | 0.7 | 2.1 | 1.7 | 0.7 | 1.3 | 1.3 | 0.7 | 0.7 | 1.3 | 0.8 | 0.7 | 1.3 | 1.0 | 1.1 | 1.4 | 1.6 | 0.68 |
| YFR008W | 1.1 | 1.0 | 0.8 | 2.2 | 1.1 | 1.0 | 1.1 | 0.9 | 1.5 | 1.4 | 0.7 | 0.9 | 0.8 | 1.1 | 0.8 | 1.5 | 1.0 | 1.0 | 1.26 |
| YGL214W | 0.9 | 1.0 | 1.2 | 2.6 | 1.2 | 0.9 | 0.8 | 0.9 | 0.4 | 0.7 | 0.4 | 0.8 | 0.6 | 1.1 | 0.9 | 0.8 | 1.0 | 0.8 | 0.61 |
| YGL218W | 1.4 | 0.9 | 1.4 | 3.4 | 1.2 | 1.1 | 0.8 | 1.1 | 1.3 | 0.4 | 0.1 | 0.8 | 1.3 | 0.9 | 1.1 | 0.7 | 1.0 | 1.0 | 0.53 |
| YGR021W | 0.9 | 1.5 | 1.0 | 8.6 | 1.0 | 0.9 | 1.3 | 1.4 | 0.7 | 0.6 | 0.6 | 0.9 | 0.9 | 1.2 | 0.8 | 2.1 | 1.0 | 1.0 | 0.58 |
| YGR024C | 1.2 | 0.9 | 0.7 | 2.6 | 1.0 | 0.7 | 1.3 | 1.4 | 0.4 | 1.2 | 1.0 | 0.7 | 0.5 | 1.4 | 1.0 | 1.2 | 0.8 | 1.3 | 1.61 |
| YGR064W | 1.4 | 1.2 | 1.6 | 2.3 | 0.7 | 0.6 | 1.1 | 1.0 | 0.1 | 0.8 | 1.7 | 0.8 | 0.9 | 2.1 | 1.0 | 1.3 | 0.8 | 0.9 | 0.50 |
| YGR182C | 1.6 | 1.2 | 1.2 | 2.3 | 1.1 | 0.9 | 0.7 | 1.1 | 0.5 | 0.7 | 0.9 | 0.7 | 0.7 | 2.2 | 0.4 | 2.0 | 1.0 | 1.7 | 1.95 |
| YGR236C | 1.6 | 1.6 | 0.4 | 4.1 | 1.2 | 1.2 | 1.0 | 1.2 | 1.5 | 0.7 | 1.0 | 0.9 | 1.2 | 1.2 | 0.7 | 7.9 | 1.5 | 1.9 | 0.30 |
| YHL042W | 1.2 | 0.8 | 1.3 | 51.1 | 1.0 | 0.7 | 1.2 | 1.0 | 0.8 | 1.8 | 0.7 | 0.6 | 1.3 | 1.2 | 1.1 | 1.9 | 1.1 | 0.9 | 0.37 |
| YIL012W | 1.2 | 5.8 | 1.5 | 2.8 | 1.5 | 1.5 | 0.9 | 0.9 | 1.7 | 2.8 | 0.9 | 0.6 | 0.4 | 1.1 | 1.1 | 0.9 | 1.0 | 0.9 | 0.28 |
| YIL028W | 1.0 | 1.1 | 0.8 | 5.4 | 1.4 | 0.7 | 1.1 | 0.8 | 0.8 | 1.7 | 1.1 | 0.5 | 1.0 | 1.1 | 0.9 | 1.1 | 1.3 | 1.0 | 0.27 |
| YIL057C | 1.3 | 1.8 | 1.1 | 4.6 | 1.3 | 1.2 | 1.2 | 1.4 | 0.1 | 5.0 | 0.8 | 0.6 | 0.9 | 1.5 | 0.8 | 11.1 | 1.1 | 3.6 | 0.26 |
| YIL089W | 1.3 | 1.3 | 0.7 | 3.9 | 1.6 | 1.6 | 1.6 | 1.1 |  | 0.6 | 0.7 | 0.6 | 0.7 | 1.4 | 0.6 | 1.3 | 1.4 | 1.3 | 0.31 |
| YIL102C | 1.4 | 1.6 | 1.0 | 6.1 | 1.5 | 0.8 | 1.1 | 0.7 |  | 0.3 |  | 0.6 | 0.7 | 1.0 | 0.8 | 0.6 | 1.2 | 1.0 | 0.18 |
| YRL113W | 0.9 | 1.0 | 0.9 | 2.6 | 0.6 | 1.0 | 1.9 | 0.7 | 1.9 | 2.2 | 2.5 | 0.8 | 1.3 | 1.2 | 0.9 | 1.6 | 1.4 | 1.3 | 0.48 |
| YIL122W | 1.2 | 1.1 | 1.1 | 2.1 | 0.9 | 0.2 | 0.8 | 0.7 | 0.4 | 0.8 | 2.1 | 1.0 | 0.7 | 1.0 | 1.6 | 1.4 | 0.9 | 0.9 | 0.35 |
| YJL100W | 1.4 | 2.0 | 0.9 | 2.3 | 1.3 | 1.1 | 1.2 | 1.2 | 1.8 | 2.7 | 1.5 | 0.9 | 1.4 | 1.2 | 1.2 | 1.4 | 1.5 | 1.1 | 0.38 |
| YJL169W | 0.8 | 1.1 | 1.5 | 2.8 | 1.4 | 0.8 | 0.9 | 0.7 | 0.3 | 0.5 | 0.4 | 0.5 | 0.7 | 1.0 | 0.9 | 0.6 | 1.1 | 0.9 | 0.35 |
| YJL199C | 1.1 | 0.7 | 0.9 | 4.5 | 1.0 | 1.7 | 1.0 | 1.0 | 1.0 | 1.6 | 1.0 | 0.8 | 0.9 | 1.9 | 0.9 | 3.7 | 1.0 | 1.0 | 0.59 |
| YJR039W | 0.9 | 0.6 | 0.8 | 3.0 | 1.8 | 1.0 | 1.6 | 1.2 | 1.8 | 1.6 | 1.8 | 0.7 | 1.5 | 0.6 | 1.2 | 1.5 | 1.3 | 1.3 | 0.24 |
| YJR101W | 0.8 | 0.6 | 0.7 | 2.9 | 1.8 | 0.9 | 1.5 | 1.1 | 0.4 | 0.8 | 1.2 | 0.5 | 0.5 | 0.9 | 0.5 | 1.2 | 1.0 | 1.1 | 2.04 |
| YKL061W | 1.3 | 0.7 | 0.7 | 1.8 | 0.8 | 1.0 | 0.9 | 1.2 | 0.8 | 1.0 | 1.1 | 0.7 | 0.8 | 1.2 | 0.6 | 1.5 | 1.3 | 1.6 | 0.92 |
| YKL121W | 0.9 | 7.8 | 0.8 | 11.8 | 1.6 | 1.2 | 1.7 | 1.0 | 0.8 | 0.9 | 1.6 | 0.8 | 1.0 | 1.2 | 1.2 | 1.6 | 1.6 | 1.1 | 0.31 |
| YKL160W | 1.5 | 1.0 | 0.4 | 1.8 | 1.1 | 1.5 | 1.5 | 2.1 | 1.3 | 1.9 | 1.4 | 0.9 | 1.6 | 1.5 | 0.8 | 1.6 | 1.5 | 2.2 | 2.19 |
| YLR016C | 0.7 | 1.3 | 0.5 | 2.0 | 1.5 | 0.8 | 1.1 | 1.2 | 0.8 | 1.1 | 1.0 | 0.7 | 0.8 | 0.9 | 0.7 | 1.3 | 1.0 | 1.3 | 1.15 |
| YLR030W | 1.4 | 1.5 | 0.8 | 2.5 | 1.2 | 1.5 | 1.5 | 0.9 | 0.3 | 2.7 | 0.2 | 0.8 | 1.5 | 1.2 | 0.6 | 2.1 | 1.0 | 1.0 | 0.29 |
| YLR036C | 1.3 | 0.8 | 0.7 | 2.0 | 1.5 | 1.3 | 1.7 | 1.2 | 0.4 | 1.6 | 0.8 | 0.7 | 0.7 | 1.3 | 0.6 | 1.4 | 1.0 | 1.4 | 1.07 |
| YLR112W | 1.1 | 0.9 | 1.1 | 1.7 | 1.3 | 1.3 | 1.0 | 0.7 |  | 0.7 | 0.5 | 0.5 | 0.7 | 0.8 | 0.4 | 0.4 | 1.0 | 0.8 | 0.39 |
| YLR125W | 1.4 | 2.0 | 0.5 | 3.1 | 1.8 | 0.7 | 1.3 | 1.2 | 0.5 | 1.7 | 1.1 | 0.5 | 0.8 | 1.3 | 0.7 | 1.6 | 1.2 | 1.2 | 0.29 |
| YLR128W | 1.3 | 1.4 | 0.8 | 1.8 |  | 1.3 | 1.3 | 1.1 | 0.8 | 1.7 | 1.4 | 0.7 | 1.2 | 1.4 | 0.9 | 1.5 | 1.2 | 1.2 | 0.25 |
| YLR204W | 1.1 | 0.9 | 0.5 | 2.1 | 2.0 | 1.5 | 2.0 | 1.3 | 1.4 | 1.6 | 1.6 | 0.8 | 1.1 | 1.8 | 1.0 | 2.5 | 1.2 | 1.3 | 1.26 |

TABLE 1-continued

Unknown protein yeast genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YLR211C | 1.3 | 1.0 | 0.8 | 7.7 | 1.7 | 1.2 | 1.8 | 1.1 | 0.9 | 1.2 | 0.8 | 0.7 | 1.1 | 1.2 | 3.6 | 1.9 | 1.3 | 1.3 | 0.35 |
| YLR257W | 1.5 | 1.0 | 0.7 | 2.4 | 1.4 | 1.2 | 0.8 | 1.3 | 1.0 | 1.1 | 1.2 | 1.0 | 1.0 | 0.9 | 1.0 | 1.7 | 1.8 | 2.6 | 5.20 |
| YLR326W | 1.2 | 1.0 | 1.5 | 2.2 | 1.3 | 0.4 | 1.2 | 0.9 | 0.7 | 1.5 | 6.6 | 0.5 | 0.4 | 1.1 | 0.7 | 0.9 | 0.8 | 1.0 | 0.33 |
| YLR334C | 1.2 | 1.1 | 1.1 | 2.3 | 1.8 | 1.0 | 1.4 | 0.9 | 1.0 | 0.8 | 0.8 | 0.8 | 0.9 | 2.2 | 2.5 | 0.7 | 0.8 | 1.0 | 0.30 |
| YLR408C | 1.3 | 2.3 | 0.6 | 2.3 | 1.4 | 1.0 | 1.0 | 1.4 | 0.9 | 1.1 | 0.7 | 0.8 | 1.1 | 2.1 | 0.9 | 1.1 | 1.2 | 1.2 | 0.79 |
| YLR414C | 1.5 | 1.6 | 1.4 | 4.8 | 1.3 | 0.6 | 0.7 | 0.9 | 0.2 | 1.2 | 1.2 | 0.6 | 1.0 | 1.0 | 2.1 | 0.9 | 3.9 | 3.6 | 2.21 |
| YLR444C | 0.9 | 0.8 | 1.7 | 5.9 | 0.7 | 0.7 | 0.9 | 0.9 | 0.2 | 0.2 | 1.1 | 0.6 | 0.5 | 1.1 | 1.3 | 0.7 | 0.9 | 0.9 | 0.50 |
| YML055W | 1.5 | 1.2 | 1.3 | 2.1 | 0.8 | 0.5 | 0.9 | 1.1 | 1.3 | 1.6 | 1.2 | 0.8 | 0.9 | 1.9 | 1.0 | 1.5 | 0.8 | 1.1 | 0.42 |
| YML107C | 1.1 | 0.7 | 0.4 | 1.8 | 2.2 | 1.1 | 1.5 | 1.3 | 0.6 | 0.9 | 0.9 | 0.7 | 0.6 | 1.3 | 1.0 | 1.3 | 1.2 | 1.5 | 0.67 |
| YMR031C | 0.7 | 0.8 | 1.2 | 2.1 | 0.6 | 0.7 | 0.8 | 0.9 | 1.5 | 1.1 | 0.8 | 0.7 | 1.0 | 1.0 | 0.7 | 1.6 | 0.9 | 1.3 | 1.26 |
| YMR204C | 1.1 | 1.9 | 1.3 | 2.3 | 1.0 | 0.6 | 0.7 | 1.0 | 1.0 | 2.2 | 0.7 | 0.7 | 1.1 | 1.2 | 1.5 | 1.1 | 0.9 | 1.1 | 0.31 |
| YMR206W | 1.4 | 1.4 | 2.3 | 3.9 | 1.1 | 1.0 | 1.3 | 0.9 | 1.0 | 9.0 | 1.8 | 1.0 | 1.2 | 1.4 | 0.3 | 2.2 | 1.0 | 1.2 | 0.17 |
| YNL010W | 1.5 | 1.0 | 0.7 | 1.9 | 1.0 | 1.2 | 1.1 | 1.8 | 0.5 | 0.6 | 1.1 | 0.9 | 0.7 | 1.2 | 0.9 | 1.2 | 1.0 | 1.7 | 4.53 |
| YNL127W | 1.1 | 1.2 | 0.7 | 3.6 | 0.7 | 1.2 | 0.8 | 1.0 | 2.7 | 2.2 | 1.0 | 1.0 | 1.7 | 1.0 | 1.5 | 1.4 | 0.9 | 1.4 | 0.36 |
| YNL217W | 1.1 | 1.2 | 0.5 | 1.7 | 2.1 | 1.5 | 1.3 | 1.4 | 0.3 | 0.9 | 0.7 | 1.0 | 1.0 | 0.9 | 0.5 | 1.0 | 1.3 | 2.1 | 2.35 |
| YOL118C | 2.6 | 2.2 | 1.3 | 2.2 |  | 1.5 | 3.2 | 1.1 |  | 3.2 | 1.4 | 0.6 | 1.7 | 3.0 | 1.0 | 0.5 | 0.9 | 1.0 | 0.24 |
| YOR053W | 1.0 | 1.1 | 0.5 | 1.7 | 1.7 | 0.9 | 1.6 | 0.9 | 1.3 | 0.8 | 1.3 | 0.6 | 0.9 | 1.2 | 1.0 | 1.3 | 1.2 | 1.2 | 0.77 |
| YOR352W | 1.3 | 0.9 | 1.0 | 2.2 | 1.6 | 0.9 | 1.8 | 1.1 | 1.7 | 2.0 | 1.1 | 1.0 | 1.2 | 1.3 | 0.7 | 2.5 | 1.3 | 1.7 | 0.59 |
| YOR394W | 1.2 | 0.8 | 2.2 | 1.6 | 1.6 | 1.7 | 1.8 | 1.0 | 1.1 | 2.3 | 1.9 | 0.9 | 1.3 | 0.9 | 0.9 | 1.7 | 1.6 | 1.1 | 0.51 |
| YPL033C | 0.8 | 1.0 | 0.9 | 5.1 | 1.3 | 0.7 | 1.0 | 0.7 | 0.4 | 1.6 | 0.7 | 0.6 | 0.7 | 1.1 | 0.8 | 0.4 | 0.9 | 0.8 | 0.23 |
| YPL066W | 0.9 | 1.0 | 1.1 | 2.0 | 1.3 | 1.3 | 1.3 | 0.9 | 0.5 | 0.8 | 1.0 | 1.1 | 0.9 | 0.7 | 0.7 | 1.2 | 1.3 | 1.3 | 0.77 |
| YPR014C | 1.0 | 0.7 | 1.1 | 7.9 | 0.8 | 0.9 | 0.8 | 0.9 |  | 0.9 | 0.5 | 0.7 | 0.7 | 1.0 | 0.9 | 0.8 | 0.9 | 1.1 | 0.29 |
| YBR005W | 1.9 | 2.6 | 1.1 | 2.9 | 0.8 | 0.7 | 1.2 | 0.9 | 0.4 | 1.3 | 0.8 | 1.7 | 1.9 | 0.9 | 1.1 | 1.7 | 2.9 | 4.6 | 1.00 |
| YFL027C | 0.8 | 0.8 | 1.1 | 1.3 | 1.1 | 0.3 | 0.4 | 1.1 | 1.8 | 1.3 | 1.3 | 0.6 | 1.1 | 0.3 | 1.4 | 1.2 | 5.1 | 5.2 | 1.74 |
| YGL080W | 1.3 | 1.5 | 1.1 | 1.3 | 1.5 | 1.4 | 1.5 | 1.2 | 1.1 | 1.2 | 0.8 | 1.0 | 0.7 | 1.6 | 0.9 | 1.7 | 1.3 | 2.9 | 1.70 |
| YMR252C | 1.1 | 1.0 | 1.5 | 1.3 | 1.3 | 1.0 | 1.3 | 1.1 | 0.9 | 1.0 | 1.4 | 0.8 | 1.1 | 1.1 | 1.1 | 2.1 | 1.5 | 2.2 | 0.86 |
| YOR385W | 2.8 | 1.2 | 0.2 | 2.5 | 1.5 | 1.0 | 1.2 | 1.0 | 1.5 | 2.2 | 1.2 | 0.6 | 2.8 | 0.8 | 0.8 | 1.2 | 4.6 | 5.9 | 1.17 |
| YAR033W | 1.0 | 0.8 | 1.5 | 1.1 | 1.1 | 1.4 | 2.1 | 1.2 | 1.3 | 1.6 | 1.5 | 0.9 | 1.5 | 1.3 | 0.9 | 2.0 | 1.1 | 3.0 | 1.15 |
| YBR151W | 0.8 | 0.8 | 1.3 | 1.2 | 1.2 | 1.7 | 1.3 | 0.8 | 0.8 | 0.9 | 0.9 | 0.9 | 1.1 | 0.8 | 1.0 | 3.0 | 1.4 | 2.4 | 1.83 |
| YHR162W | 1.2 | 1.2 | 0.9 | 1.8 | 1.2 | 1.3 | 1.7 | 1.4 | 1.0 | 1.7 | 1.3 | 1.2 | 1.5 | 2.0 | 1.1 | 1.4 | 1.3 | 2.7 | 3.64 |
| YLR165C | 1.4 | 0.8 | 1.3 | 1.1 | 1.1 | 1.5 | 1.4 | 1.1 | 1.7 | 1.0 | 1.4 | 0.9 | 1.2 | 1.4 | 0.5 | 1.6 | 1.1 | 2.1 | 0.78 |
| YNL157W | 1.4 | 1.1 | 0.7 | 1.5 | 1.9 | 0.9 | 1.3 | 1.1 | 1.7 | 1.4 | 1.3 | 0.9 | 1.6 | 1.5 | 1.0 | 1.0 | 1.9 | 2.3 | 1.41 |
| YOL002C | 0.9 | 0.7 | 0.5 | 1.0 | 2.0 | 0.9 | 0.4 | 0.8 | 0.1 | 0.3 | 0.8 | 1.1 | 0.2 | 0.5 | 0.6 | 1.7 | 1.5 | 2.1 | 5.33 |
| YPL233W | 1.2 | 0.9 | 0.5 | 1.1 | 1.4 | 0.6 | 1.0 | 1.0 | 0.3 | 0.6 | 0.9 | 0.6 | 1.0 | 1.0 | 0.4 | 1.0 | 1.9 | 1.9 | 0.48 |
| YGR149W | 1.4 | 1.3 | 1.8 | 1.9 | 1.0 | 1.7 | 1.8 | 0.8 | 0.6 | 0.6 | 1.8 | 1.2 | 2.6 | 1.0 | 2.4 | 1.3 | 2.0 | 1.7 | 0.71 |
| YNL043C | 1.0 | 4.4 | 1.6 | 1.3 | 0.8 | 0.6 | 0.9 | 0.9 | 0.4 | 0.4 | 0.7 | 0.9 | 2.1 | 1.2 | 1.6 | 0.8 | 2.7 | 1.6 | 0.68 |
| YPL067C | 1.2 | 1.6 | 2.8 | 1.4 | 1.0 | 0.8 | 1.2 | 1.2 |  | 0.8 | 0.9 | 1.4 | 0.9 | 0.7 | 1.5 | 1.1 | 2.9 | 1.7 | 0.40 |
| YPL170W | 1.2 | 1.3 | 0.9 | 1.1 | 1.9 | 1.1 | 0.6 | 1.1 | 1.4 | 1.0 | 1.1 | 0.9 | 1.1 | 1.4 | 1.2 | 1.6 | 2.2 | 1.4 | 1.05 |
| YGL051W | 1.1 | 1.0 | 1.6 | 1.7 | 1.3 | 1.0 | 1.3 | 0.8 | 1.1 | 1.8 | 1.4 | 1.0 | 1.5 | 1.2 | 0.8 | 2.6 | 1.4 | 1.9 | 1.06 |
| YIL112W | 1.1 | 1.4 | 2.8 | 1.9 | 0.6 | 1.3 | 1.1 | 0.9 | 1.3 | 2.0 | 1.4 | 1.2 | 1.1 | 1.3 | 1.8 | 2.4 | 1.2 | 1.3 | 0.45 |
| YLR052W | 1.0 | 1.5 | 0.8 | 1.3 | 1.0 | 0.8 | 1.0 | 1.2 | 0.4 | 1.1 | 1.1 | 1.0 | 0.8 | 1.2 | 1.0 | 2.4 | 0.7 | 0.9 | 0.77 |
| YNL203C | 0.9 | 1.3 | 0.3 | 3.2 | 1.0 | 1.7 | 1.6 | 0.8 |  | 0.3 | 1.1 | 0.9 | 1.2 | 2.7 | 1.2 | 5.6 | 1.3 | 1.7 | 0.21 |
| YNR014W | 1.0 | 0.8 | 1.7 | 1.2 | 1.2 | 0.7 | 1.7 | 0.9 | 0.3 | 2.3 | 4.4 | 0.9 | 1.5 | 4.9 | 1.0 | 2.4 | 1.1 | 1.0 | 0.31 |
| YAL028W | 0.9 | 0.7 | 1.1 | 2.0 | 1.0 | 0.6 | 1.2 | 0.8 | 1.6 | 1.3 | 1.0 | 1.0 | 1.5 | 1.6 | 2.2 | 1.7 | 1.0 | 1.0 | 0.30 |
| YBL095W | 0.8 | 1.4 | 1.2 | 1.4 | 1.1 | 0.9 | 1.1 | 0.9 | 1.0 | 0.6 | 1.2 | 0.8 | 1.0 | 1.0 | 0.4 | 2.2 | 1.3 | 1.9 | 0.72 |
| YBR157C | 0.7 | 1.0 | 0.4 | 1.4 | 1.3 | 1.2 | 1.6 | 0.7 | 0.6 | 0.3 | 0.6 | 0.6 | 0.5 | 0.9 | 0.2 | 1.9 | 1.3 | 0.8 | 0.69 |
| YDL091C | 1.1 | 1.3 | 1.8 | 1.4 | 0.7 | 0.8 | 1.3 | 1.3 | 1.6 | 1.5 | 1.5 | 1.0 | 1.3 | 1.5 | 1.9 | 2.4 | 1.1 | 1.6 | 0.47 |
| YDL216C | 1.1 | 1.1 | 0.7 | 2.0 | 1.6 | 1.6 | 1.2 | 1.6 | 1.3 | 1.3 | 0.7 | 0.9 | 1.2 | 1.1 | 1.0 | 1.8 | 1.0 | 1.6 | 0.42 |
| YDR067C | 1.3 | 1.2 | 0.7 | 2.7 | 0.9 | 1.1 | 1.3 | 1.8 | 1.0 | 1.3 | 0.9 | 0.9 | 1.2 | 1.5 | 1.5 | 2.4 | 1.3 | 1.4 | 0.76 |
| YDR186C | 0.7 | 0.9 | 0.7 | 0.7 | 1.3 | 0.7 | 1.4 | 1.2 | 1.2 | 1.6 | 0.7 | 1.1 | 1.1 | 0.8 | 0.8 | 2.3 | 1.1 | 0.9 | 0.50 |
| YDR196C | 0.9 | 0.9 | 0.7 | 1.1 | 1.0 | 1.7 | 1.7 | 1.5 | 1.6 | 1.1 | 1.3 | 0.7 | 1.2 | 1.0 | 0.7 | 2.7 | 1.2 | 1.9 | 1.54 |
| YDR262W | 1.3 | 1.8 | 0.8 | 1.2 | 1.7 | 1.3 | 1.7 | 1.2 | 0.9 | 1.7 | 1.6 | 0.8 | 0.9 | 1.7 | 1.5 | 3.8 | 1.0 | 1.4 | 1.11 |
| YDR306C | 0.9 | 1.2 | 0.7 | 1.8 | 1.7 | 1.2 | 1.6 | 1.3 | 2.0 | 1.4 | 2.1 | 0.9 | 1.2 | 1.1 | 1.2 | 2.4 | 1.0 | 1.5 | 0.77 |
| YDR319C | 1.3 | 0.9 | 0.8 | 1.1 | 1.2 | 1.2 | 1.7 | 1.3 | 1.1 | 1.1 | 1.3 | 1.0 |  | 1.3 | 0.8 | 2.0 | 2.1 | 2.2 | 1.23 |
| YER188W | 1.3 | 0.9 | 1.2 | 1.9 | 0.9 | 1.5 | 1.2 | 0.7 | 0.4 | 0.9 | 1.2 | 0.9 | 1.1 | 1.1 | 0.3 | 2.5 | 1.0 | 1.1 | 0.61 |
| YGL004C | 0.8 | 1.4 | 1.3 | 1.0 | 1.0 | 1.4 | 2.9 | 1.4 | 1.8 | 2.2 | 1.0 | 0.8 | 1.3 | 0.9 | 0.6 | 2.2 | 1.1 | 1.4 | 0.48 |
| YGR141W | 0.8 | 1.6 | 1.6 | 1.7 | 1.1 | 1.5 | 1.5 | 0.9 | 0.3 | 1.0 | 0.6 | 0.6 | 1.0 | 0.7 | 2.6 | 2.1 | 1.1 | 1.3 | 0.65 |
| YHR080C | 0.6 | 1.8 | 1.9 | 0.7 | 0.8 | 1.8 | 1.1 | 1.1 | 1.9 | 1.2 | 0.7 | 1.2 | 2.0 | 0.9 | 0.9 | 2.3 | 1.1 | 1.3 | 0.49 |
| YHR097C | 1.6 | 0.7 | 0.7 | 0.9 |  | 0.8 | 0.8 | 0.7 | 0.4 | 0.6 | 0.7 | 0.8 | 1.3 | 0.9 | 2.7 | 2.0 | 1.7 | 1.4 | 0.24 |
| YIL077C | 0.9 | 0.8 | 1.2 | 1.2 | 1.3 | 1.8 | 1.2 | 0.9 | 1.5 | 1.4 | 1.3 | 1.6 | 1.3 | 1.3 | 0.9 | 2.4 | 1.3 | 1.1 | 0.75 |
| YJL046W | 0.9 | 0.9 | 0.6 | 1.8 | 1.0 | 0.7 | 1.5 | 1.1 | 1.8 | 2.7 | 4.2 | 0.9 | 1.3 | 1.3 | 1.0 | 2.5 | 1.0 | 1.3 | 0.68 |
| YLL005C | 1.0 | 1.1 | 1.1 | 1.2 | 1.6 | 1.9 | 1.3 | 1.0 | 0.4 | 1.0 | 0.9 | 0.8 | 1.1 | 1.7 | 1.0 | 2.1 | 1.1 | 1.2 | 0.44 |
| YLR151C | 1.4 | 2.0 | 1.4 | 1.0 | 1.0 |  | 1.4 | 1.4 | 1.5 | 0.9 | 1.1 | 0.5 | 0.7 | 1.3 | 0.7 | 2.4 | 1.0 | 1.4 | 0.30 |
| YLR271W | 1.6 | 1.2 | 0.8 | 1.8 | 1.4 | 1.4 | 1.7 | 1.5 | 1.0 | 1.0 | 1.3 | 0.8 | 1.2 | 1.2 | 1.0 | 3.0 | 1.5 | 1.8 | 0.78 |
| YMR025W | 1.2 | 1.2 | 0.7 | 1.5 | 1.3 | 1.3 | 1.4 | 1.2 | 1.0 | 1.6 | 1.2 | 0.9 | 1.2 | 1.8 | 1.1 | 2.4 | 1.0 | 1.5 | 0.42 |
| YMR135C | 1.0 | 1.0 | 1.1 | 1.9 | 1.8 | 1.0 | 1.0 | 1.0 | 1.1 | 1.4 | 1.1 | 1.0 | 1.3 | 1.0 | 1.4 | 2.3 | 1.5 | 1.3 | 1.06 |
| YMR210W | 1.0 | 1.1 | 1.8 | 1.9 | 0.6 | 0.8 | 1.1 | 1.1 | 1.5 | 2.2 | 0.8 | 0.9 | 1.0 | 1.0 | 1.0 | 2.2 | 0.8 | 1.5 | 0.56 |
| YNR040W | 0.8 | 4.9 | 0.5 | 0.9 | 0.9 | 1.6 | 2.1 | 1.3 | 1.1 | 0.8 | 1.2 | 0.6 | 0.8 | 1.5 | 0.7 | 2.1 | 1.1 | 1.0 | 0.30 |
| YPL039W | 1.2 | 0.9 | 0.6 | 1.3 | 1.4 | 1.5 | 1.5 | 1.4 | 1.1 | 1.0 | 0.9 | 0.9 | 1.1 | 1.1 | 0.6 | 2.4 | 1.1 | 1.1 | 0.52 |
| YPL099C | 1.1 | 1.9 | 0.7 | 2.0 | 0.9 | 1.2 | 1.4 | 1.4 | 2.4 | 1.7 | 0.8 | 0.9 | 1.1 | 1.3 | 0.5 | 2.1 | 1.0 | 1.7 | 0.92 |
| YPL107W | 1.2 | 0.8 | 1.1 | 1.3 | 1.0 | 1.1 | 1.2 | 1.5 | 1.4 | 1.3 | 1.1 | 0.7 | 0.8 | 1.7 | 0.7 | 1.8 | 1.0 | 1.1 | 0.59 |
| YPL138C | 1.1 | 1.7 | 1.1 | 1.8 | 0.7 | 0.5 | 1.1 | 1.3 | 1.1 | 1.5 | 0.5 | 0.9 | 0.6 | 1.3 | 2.7 | 2.6 | 0.8 | 1.1 | 0.38 |

TABLE 2

Mitochondria-located protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJR048W | 1.3 | 0.9 | 2.2 | 1.4 | 0.8 | 0.5 | 0.3 | 0.9 | 0.5 | 1.5 | 1.0 | 0.8 | 0.4 | 2.5 | 0.6 | 1.5 | 1.2 | 1.2 | 1.19 |
| YOR226C | 1.3 | 2.2 | 1.7 | 1.1 | 1.3 | 1.2 | 1.2 | 1.2 | 1.3 | 5.9 | 1.5 | 0.6 | 0.9 | 2.7 | 1.0 | 0.7 | 1.0 | 0.7 | 0.58 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YBL022C | 0.4 | 0.8 | 1.2 | 0.7 | 1.2 | 1.2 | 1.0 | 0.4 | 2.8 | 1.2 | 1.1 | 0.9 | 2.6 | 1.0 | 1.5 | 1.0 | 0.9 | 0.7 | 0.76 |
| YCL057W | 0.6 | 1.5 | 2.3 | 0.5 | 1.1 | 1.8 | 1.4 | 1.8 | 4.2 | 2.1 | 1.6 | 1.0 | 3.8 | 1.0 | 2.8 | 1.5 | 0.9 | 1.1 | 0.76 |
| YDR258C | 1.6 | 2.3 | 2.8 | 1.4 | 1.3 | 2.4 | 3.9 | 1.9 | 4.9 | 13.3 | 1.7 | 1.8 | 5.2 | 1.5 | 0.6 | 1.0 | 1.3 | 1.3 | 0.87 |
| YGR028W | 1.4 | 3.5 | 1.0 | 1.8 | 0.9 | 1.5 | 2.1 | 1.4 | 1.7 | 2.0 | 1.1 | 1.5 | 2.6 | 1.2 | 1.0 | 2.2 | 1.5 | 2.6 | 0.91 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YKL142W | 1.8 | 2.7 | 3.1 | 1.4 | 0.7 | 3.4 | 6.9 | 2.3 | 5.8 | 5.9 | 2.0 | 1.9 | 3.3 | 2.3 | 1.3 | 3.3 | 2.4 | 3.6 | 1.68 |
| YNL055C | 1.1 | 1.8 | 5.5 | 2.0 | 0.9 | 2.6 | 1.2 | 0.7 | 1.1 | 1.0 | 1.9 | 1.7 | 2.4 | 0.9 | 1.1 | 2.6 | 1.2 | 1.7 | 4.10 |
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |
| YOR020C | 1.4 | 2.1 | 1.7 | 1.7 | 1.5 | 2.3 | 1.7 | 1.7 | 5.8 | 2.6 | 2.5 | 0.8 | 3.0 | 1.6 | 1.5 | 1.4 | 1.4 | 1.7 | 1.66 |
| YOR037W | 1.0 | 1.5 | 0.6 | 1.4 | 1.5 | 1.6 | 2.5 | 1.5 | 1.3 | 1.0 | 1.2 | 1.2 | 2.1 | 1.0 | 0.9 | 1.4 | 1.2 | 1.6 | 0.61 |
| YDL198C | 1.4 | 1.0 | 2.1 | 1.4 | 0.7 | 0.8 | 1.0 | 1.1 | 1.9 | 2.7 | 2.5 | 1.2 | 2.0 | 1.7 | 1.2 | 1.4 | 1.5 | 1.1 | 1.19 |
| YDR231C | 1.1 | 1.6 | 1.0 | 1.5 | 1.1 | 2.2 | 1.7 | 1.3 | 1.5 | 1.4 | 1.3 | 1.1 | 2.4 | 1.5 | 1.0 | 3.0 | 1.2 | 1.3 | 0.92 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YFL016C | 0.8 | 1.0 | 1.6 | 0.9 | 1.3 | 1.3 | 1.4 | 0.7 | 6.4 | 2.9 | 1.2 | 1.0 | 2.8 | 0.8 | 0.8 | 0.6 | 1.2 | 0.9 | 1.25 |
| YGR008C | 2.1 | 3.0 | 1.7 | 3.2 | 0.9 | 2.9 | 3.7 | 1.9 | 3.1 | 2.4 | 2.6 | 2.0 | 3.4 | 1.3 | 1.5 | 2.3 | 1.7 | 4.2 | 3.03 |
| YIL155C | 1.0 | 0.7 | 1.4 | 3.7 | 1.3 | 1.4 | 2.2 | 1.0 | 2.5 | 2.9 | 1.3 | 1.4 | 2.0 | 1.3 | 1.4 | 3.8 | 1.1 | 1.4 | 0.51 |
| YJL102W | 1.1 | 0.7 | 0.4 | 0.8 | 1.3 | 1.6 | 0.6 | 0.9 | 3.1 | 2.2 | 0.7 | 0.8 | 2.6 | 1.5 | 1.5 | 0.6 | 1.0 | 1.1 | 0.22 |
| YJR045C | 0.5 | 1.9 | 3.9 |  | 0.5 | 1.2 | 1.0 | 0.8 | 3.2 | 3.0 | 1.4 | 1.0 | 2.3 | 0.5 | 2.3 | 0.8 | 0.7 | 0.9 | 3.78 |
| YLR259C | 0.7 | 1.0 | 3.1 | 1.6 | 1.1 | 0.9 | 1.8 | 0.8 | 1.8 | 2.6 | 3.0 | 0.7 | 2.5 | 0.8 | 2.1 | 1.3 | 0.8 | 1.0 | 2.09 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YMR089C | 0.8 | 1.1 | 0.9 | 0.9 | 0.8 | 1.2 | 1.2 | 1.3 | 5.6 | 2.5 | 1.3 | 0.8 | 2.3 | 0.9 | 1.8 | 1.1 | 0.9 | 1.1 | 0.69 |
| YMR152W | 0.9 | 1.1 | 1.8 | 0.9 | 0.8 | 7.5 | 0.8 | 0.8 | 2.7 | 1.3 | 1.2 | 1.3 | 1.9 | 1.1 | 0.6 | 1.0 | 1.5 | 0.9 | 0.71 |
| YNL104C | 1.1 | 1.3 | 3.0 | 0.9 | 0.8 | 0.8 | 0.6 | 0.9 | 1.1 | 2.0 | 2.1 | 1.1 | 2.1 | 0.9 | 2.5 | 1.5 | 0.9 | 0.9 | 1.69 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YPR024W | 0.7 | 1.0 | 1.3 | 1.0 | 1.3 | 1.0 | 1.4 | 0.7 | 3.0 | 1.7 | 0.9 | 0.8 | 2.5 | 0.7 | 1.0 | 1.6 | 1.1 | 0.8 | 0.84 |
| YPR067W | 1.6 | 1.2 | 1.7 | 0.9 | 1.3 | 1.3 | 1.5 | 1.4 | 3.5 | 3.4 | 1.2 | 1.0 | 3.0 | 1.6 | 1.3 | 0.8 | 1.0 | 1.0 | 0.66 |
| YBR029C | 0.7 | 0.2 | 1.8 | 1.0 | 1.4 | 0.8 | 0.4 | 0.7 | 2.0 | 1.1 | 0.7 | 1.3 | 1.7 | 0.9 | 3.5 | 0.9 | 0.6 | 0.8 | 1.56 |
| YCL009C | 0.6 | 0.9 | 2.0 | 0.5 | 0.7 | 1.8 | 1.3 | 1.1 | 0.9 | 1.6 | 1.5 | 1.7 | 1.6 | 0.7 | 6.5 | 0.9 | 1.1 | 0.8 | 0.68 |
| YER026C | 0.8 | 0.6 | 3.3 | 1.0 | 1.2 | 2.5 | 1.6 | 0.8 | 0.9 | 1.5 | 0.9 | 1.7 | 1.9 | 1.1 | 4.0 | 1.4 | 1.7 | 3.2 | 4.48 |
| YLR109W | 0.8 | 2.9 | 6.0 | 0.9 | 1.3 | 2.1 | 2.6 | 0.9 | 2.4 | 2.7 | 1.5 | 1.6 | 3.2 | 2.3 | 3.9 | 1.8 | 1.1 | 1.2 | 3.86 |
| YMR189W | 0.7 | 0.8 | 1.9 | 2.8 | 0.4 | 1.9 | 0.8 | 0.4 | 0.7 | 0.9 | 8.2 | 0.6 | 0.9 | 1.6 | 5.6 | 0.9 | 1.0 | 0.8 | 0.88 |
| YNL169C | 0.7 | 1.4 | 1.4 | 1.2 | 0.7 | 1.4 | 0.7 | 0.8 | 1.1 | 1.1 | 0.8 | 1.0 | 1.7 | 0.9 | 3.4 | 0.8 | 1.1 | 1.3 | 1.05 |
| YER069W | 1.3 | 0.8 | 3.3 | 1.4 | 1.5 | 1.3 | 1.0 | 1.5 | 0.8 | 10.4 | 1.5 | 0.8 | 1.4 | 1.3 | 2.4 | 1.1 | 1.1 | 0.9 | 0.25 |
| YIL022W | 0.8 | 0.7 | 1.1 | 1.6 | 0.8 | 1.2 | 0.7 | 0.8 | 1.1 | 1.3 | 1.0 | 0.9 | 1.2 | 0.6 | 2.9 | 1.1 | 0.8 | 0.7 | 0.52 |
| YBR146W | 0.9 | 0.8 | 0.7 | 1.5 | 1.3 | 2.6 | 1.5 | 1.0 | 0.9 | 1.1 | 1.2 | 1.0 | 1.7 | 1.2 | 1.0 | 2.9 | 1.0 | 1.2 | 1.61 |
| YDR019C | 1.4 | 0.5 | 1.7 | 4.0 | 0.9 | 4.8 | 1.4 | 0.7 | 0.4 | 0.7 | 1.8 | 0.7 | 1.0 | 1.6 | 1.8 | 1.8 | 1.2 | 1.6 | 2.48 |
| YGR207C | 1.5 | 1.1 | 1.0 | 1.1 | 1.5 | 2.8 | 1.7 | 1.9 | 2.1 | 2.6 | 1.4 | 1.1 | 1.0 | 2.2 | 0.6 | 1.8 | 1.2 | 1.8 | 1.49 |
| YMR072W | 1.1 | 1.0 | 1.4 | 1.0 | 1.7 | 2.4 | 1.4 | 1.0 | 3.0 | 1.2 | 1.9 | 0.8 | 2.1 | 1.2 | 0.8 | 1.7 | 0.9 | 1.9 | 2.06 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YAL044C | 1.5 | 1.1 | 1.0 | 3.0 | 0.8 | 2.2 | 1.0 | 0.8 | 0.4 | 0.6 | 1.4 | 0.6 | 1.1 | 1.4 | 0.7 | 1.0 | 1.4 | 1.8 | 4.07 |
| YAL054C | 1.2 | 1.1 | 1.4 | 1.6 | 1.1 | 2.2 | 1.1 | 1.1 | 8.9 | 4.1 | 1.3 | 1.8 | 1.3 | 0.9 | 2.5 | 1.5 | 1.4 |  | 0.24 |
| YBR024W | 1.0 | 1.0 | 1.1 | 2.4 | 1.0 | 2.2 | 1.9 | 1.4 | 1.3 | 1.4 | 1.3 | 1.1 | 1.7 | 1.9 | 0.8 | 2.3 | 1.0 | 1.2 | 1.14 |
| YDR405W | 0.9 | 1.1 | 4.7 | 1.0 | 1.1 | 2.4 | 1.2 | 0.9 | 0.6 | 1.0 | 1.0 | 1.2 | 1.3 | 1.1 | 2.5 | 1.3 | 1.3 | 0.9 | 0.44 |
| YGL068W | 1.0 | 0.6 | 1.1 | 1.4 | 0.9 | 2.6 | 1.5 | 0.9 | 0.7 | 0.8 | 1.0 | 1.1 | 1.0 | 0.9 | 0.6 | 1.8 | 1.8 | 1.0 | 3.35 |
| YGR220C | 1.1 | 0.6 | 0.9 | 1.1 | 1.3 | 2.1 | 1.4 | 1.5 | 0.8 | 1.5 | 1.1 | 0.9 | 1.1 | 1.5 | 1.1 | 2.3 | 0.9 | 1.1 | 1.42 |
| YHR037W | 0.7 | 0.9 | 1.3 | 1.6 | 0.9 | 1.8 | 1.2 | 1.0 | 0.9 | 2.2 | 1.7 | 1.1 | 1.1 | 1.1 | 1.1 | 2.0 | 1.0 | 1.4 | 1.15 |
| YIL070C | 1.2 | 1.0 | 0.8 | 1.4 | 1.3 | 2.3 | 1.6 | 1.1 | 0.3 | 0.6 | 1.0 | 0.8 | 0.7 | 1.3 | 1.0 | 2.4 | 0.7 | 1.1 | 1.69 |
| YIL111W | 1.6 | 1.0 | 1.8 | 2.7 |  | 2.6 | 3.2 | 1.2 | 1.6 | 1.1 | 2.1 | 0.9 | 1.7 | 1.5 | 1.1 | 2.5 | 1.9 | 3.9 | 1.52 |
| YKL138C | 1.2 | 0.9 | 0.6 | 0.9 | 1.3 | 2.3 | 1.9 | 1.7 | 1.1 | 2.1 | 1.2 | 0.8 | 0.8 | 1.6 | 0.6 | 2.5 | 1.0 | 1.3 | 1.29 |
| YKL150W | 1.1 | 2.0 | 3.0 | 1.4 | 1.4 | 2.3 | 2.4 | 1.3 | 1.1 | 1.3 | 1.9 | 1.2 | 1.8 | 1.4 | 0.9 | 6.1 | 1.2 | 2.7 | 2.20 |
| YKR006C | 1.0 | 0.7 | 1.2 | 1.2 | 1.4 | 2.4 | 1.6 | 1.2 | 1.0 | 1.5 | 1.2 | 0.8 | 0.9 | 1.6 | 0.9 | 2.3 | 0.8 | 1.1 | 1.39 |
| YLR142W | 4.4 | 2.7 | 1.1 | 6.1 | 1.3 | 3.1 | 1.2 | 2.1 | 3.1 | 4.4 | 3.8 | 0.8 | 1.2 | 2.1 | 1.6 | 3.4 | 1.9 | 3.2 | 0.28 |
| YML110C | 1.1 | 0.8 | 1.9 | 1.6 | 0.8 | 2.6 | 2.0 | 1.4 | 2.7 | 2.2 | 1.7 | 1.1 | 1.8 | 1.4 | 1.3 | 2.3 | 1.1 | 1.6 | 2.01 |
| YNL284C | 1.1 | 0.7 | 0.3 | 1.4 | 1.8 | 1.0 | 2.8 | 1.6 | 0.9 | 1.9 | 1.3 | 0.7 | 1.0 | 1.5 | 0.8 | 2.4 | 1.0 | 1.5 | 1.26 |
| YDR268W | 0.8 | 1.5 | 0.4 | 1.2 | 2.2 | 1.0 | 2.4 | 1.0 | 1.0 | 2.0 | 1.1 | 0.7 | 1.0 | 1.4 | 1.0 | 1.6 | 1.1 | 1.2 | 0.47 |
| YMR193W | 1.4 | 1.2 | 0.5 | 1.9 | 2.2 | 1.7 | 2.7 | 1.7 | 0.8 | 1.1 | 1.6 | 0.6 | 0.9 | 1.5 | 0.8 | 3.7 | 1.1 | 1.7 | 0.93 |
| YOR374W | 1.3 | 4.5 | 7.3 | 3.9 | 0.9 | 1.4 | 1.9 | 0.9 | 2.3 | 5.9 | 2.6 | 1.5 | 1.7 | 1.1 | 2.5 | 2.5 | 1.2 | 2.4 | 1.24 |
| YER061C | 0.9 | 0.9 | 1.2 | 2.5 | 0.8 | 0.4 | 0.9 | 0.7 | 0.3 | 0.7 | 2.2 | 0.7 | 0.9 | 1.0 | 0.8 | 1.8 | 1.2 | 1.2 | 0.84 |
| YIL136W | 1.1 | 1.0 | 1.2 | 2.5 | 1.0 | 1.0 | 1.8 | 1.1 | 3.4 | 1.7 | 4.8 | 0.9 | 1.7 | 1.7 | 1.5 | 4.5 | 1.3 | 3.2 | 0.95 |
| YLL009C | 1.0 | 1.2 | 0.6 | 1.9 | 1.5 | 1.2 | 1.7 | 1.0 | 1.3 | 1.7 | 3.5 | 0.7 | 0.9 | 1.4 | 1.1 | 2.8 | 0.9 | 1.2 | 1.66 |
| YLR163C | 1.0 | 0.9 | 0.7 | 1.4 | 1.6 | 1.3 | 1.7 | 1.4 | 2.6 | 2.9 | 2.2 | 0.7 | 1.4 | 1.3 | 1.2 | 1.4 | 0.9 | 1.1 | 0.55 |
| YBR291C | 2.0 | 0.9 | 1.0 | 1.5 | 0.9 | 1.1 | 0.9 | 2.2 | 0.9 | 1.0 | 1.1 | 0.9 | 1.0 | 1.7 | 0.5 | 1.5 | 0.9 | 1.1 | 1.19 |
| YIL094C | 1.5 | 0.4 | 0.8 | 0.7 | 1.4 | 1.2 | 1.3 | 3.6 | 0.3 | 0.4 | 1.8 | 1.0 | 0.7 | 1.0 | 0.5 | 0.9 | 0.9 | 1.0 | 2.26 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL085W | 1.4 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |

TABLE 2-continued

Mitochondria-located protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YMR177W | 1.4 | 0.8 | 1.1 | 1.0 | 1.6 | 0.8 | 1.0 | 1.2 | 2.4 | 3.8 | 1.4 | 0.6 | 0.5 | 1.2 | 0.8 | 0.5 | 0.9 | 0.9 | 0.55 |
| YPL224C | 1.0 | 2.2 | 1.3 | 2.5 | 0.6 | 1.3 | 2.2 | 1.3 | 3.2 | 4.2 | 0.8 | 1.1 | 1.3 | 1.4 | 1.0 | 2.5 | 1.3 | 1.9 | 0.64 |
| YER014W | 1.0 | 0.9 | 0.9 | 0.6 | 0.8 | 4.0 | | 1.2 | 3.5 | 1.1 | 0.9 | 1.1 | 1.5 | 1.2 | 2.3 | 0.8 | 1.0 | 0.9 | 0.43 |
| YFR049W | 1.5 | 1.5 | 1.8 | 1.2 | 1.3 | | | 1.3 | 2.6 | 1.5 | 1.7 | 1.2 | 1.4 | 1.2 | 0.7 | 0.9 | 1.3 | 1.0 | 0.83 |
| YGR112W | 1.0 | 2.9 | 1.1 | 1.3 | 0.9 | 1.1 | 1.3 | 1.3 | 2.6 | 1.3 | 1.3 | 0.7 | 1.1 | 1.1 | 1.2 | 2.8 | 0.9 | 1.2 | 0.31 |
| YLL001W | 0.9 | 0.7 | 1.2 | 1.2 | 0.6 | 1.0 | 0.8 | 1.0 | 3.5 | 2.4 | 0.9 | 0.7 | 1.7 | 1.2 | 0.9 | 1.3 | 0.9 | 1.3 | 0.70 |
| YML042W | 0.9 | 1.4 | 1.5 | 2.2 | 1.0 | 0.9 | 0.8 | 1.6 | 3.8 | 2.4 | 2.5 | 1.0 | 1.2 | 1.4 | 1.7 | 4.8 | 1.0 | 0.9 | 0.29 |
| YNL213C | 1.7 | 11.6 | 0.9 | 1.5 | 1.3 | 1.2 | 1.4 | 1.8 | 3.0 | 1.5 | 1.5 | 0.8 | 0.9 | 1.8 | 1.0 | 1.7 | 0.9 | 1.2 | 0.70 |
| YOR386W | 1.0 | 0.8 | 1.3 | 1.5 | 1.2 | 3.3 | 1.8 | 1.0 | 4.1 | 3.0 | 1.4 | 1.2 | 2.4 | 0.9 | 1.3 | 1.2 | 2.1 | 1.7 | 0.46 |
| YBR037C | 0.8 | 0.8 | 1.3 | 2.4 | 0.7 | 1.2 | 1.2 | 1.0 | 3.0 | 1.9 | 1.5 | 0.7 | 1.2 | 1.2 | 1.0 | 2.7 | 1.6 | 1.3 | 0.60 |
| YCR024C | 1.1 | 1.0 | 1.5 | 0.8 | 0.8 | 2.9 | 1.0 | 1.2 | 2.5 | 1.7 | 1.4 | 0.8 | 0.9 | 1.3 | 1.0 | 1.2 | 0.9 | 1.0 | 0.32 |
| YDR194C | 0.7 | 0.9 | 0.5 | 1.0 | 1.0 | 1.0 | 1.3 | 1.4 | 2.8 | 2.2 | 1.2 | 0.6 | 1.2 | 0.8 | 1.1 | 0.8 | 0.6 | 0.8 | 2.19 |
| YER017C | 0.8 | 1.1 | 1.4 | 1.3 | 1.0 | 0.5 | 1.1 | 0.5 | 2.7 | 1.8 | 0.9 | 1.0 | 1.5 | 1.1 | 2.1 | 1.0 | 0.9 | 1.0 | 0.43 |
| YGL125W | 1.0 | 3.2 | 4.3 | 0.7 | 0.9 | | 1.7 | 0.8 | 2.1 | 2.1 | 1.6 | 1.0 | 1.4 | 1.0 | 1.9 | 1.2 | 1.2 | 1.1 | 0.27 |
| YGR029W | 1.1 | 1.4 | 1.0 | 1.0 | 0.8 | 0.6 | 1.6 | 1.7 | 2.7 | 1.1 | 1.2 | 0.6 | 1.0 | 2.0 | 0.4 | 1.1 | 1.1 | 1.3 | 0.71 |
| YHL038C | 1.0 | 1.2 | 1.4 | 0.8 | 1.3 | 0.8 | 1.2 | 1.1 | 4.0 | 1.7 | 0.8 | 1.6 | 1.3 | 0.6 | 0.8 | 0.5 | 0.9 | 0.6 | 1.95 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YKR052C | 0.9 | 1.1 | 2.6 | 2.6 | 1.0 | 0.5 | 1.9 | 1.1 | 1.9 | 3.6 | 1.3 | 0.9 | 1.2 | 1.1 | 0.5 | 2.5 | 0.8 | 1.5 | 1.15 |
| YML078W | 1.2 | 1.9 | 2.5 | 1.5 | 0.7 | 1.4 | 1.3 | 1.4 | 2.6 | 2.2 | 2.4 | 1.2 | 1.7 | 1.7 | 1.0 | 1.8 | 1.3 | 1.6 | 1.98 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YNL005C | 1.1 | 1.0 | 0.6 | 1.2 | 1.2 | 1.7 | 1.3 | 1.5 | 2.0 | 2.0 | 1.2 | 0.9 | 1.5 | 1.3 | 1.0 | 1.6 | 0.9 | 1.5 | 1.52 |
| YPR047W | 1.0 | 1.0 | 0.9 | 1.5 | 0.9 | 1.0 | 1.8 | 1.2 | 2.1 | 1.9 | 1.1 | 0.9 | 1.3 | 1.0 | 0.8 | 2.8 | 1.0 | 1.5 | 0.39 |
| YPR134W | 1.1 | 1.1 | 0.8 | 1.7 | 1.5 | 0.6 | 1.5 | 1.4 | 1.8 | 2.3 | 1.3 | 0.9 | 1.1 | 1.5 | 0.7 | 2.4 | 1.0 | 1.2 | 0.65 |
| YGL191W | 1.7 | 1.6 | 1.4 | 1.8 | 0.9 | 1.6 | 1.0 | 1.6 | 1.1 | 1.3 | 1.6 | 0.9 | 1.1 | 1.6 | 0.7 | 1.8 | 1.2 | 1.7 | 2.35 |
| YLR038C | 2.3 | 1.1 | 0.6 | 2.1 | 1.8 | 1.2 | 1.0 | 1.4 | 0.4 | 0.9 | 1.4 | 0.6 | 0.5 | 1.6 | 0.7 | 2.1 | 1.2 | 2.1 | 1.52 |
| YHR008C | 1.3 | 5.4 | 4.8 | 1.8 | 0.6 | 1.0 | 0.7 | 0.9 | 1.7 | 2.4 | 2.1 | 0.7 | 1.2 | 1.6 | 1.7 | 2.2 | 0.9 | 1.0 | 1.04 |
| YPR037C | 1.2 | 2.3 | 1.6 | 1.3 | 0.8 | 0.9 | 1.2 | 1.1 | 1.5 | 1.3 | 0.9 | 0.9 | 1.0 | 1.6 | 4.1 | 1.8 | 1.2 | 1.7 | 0.80 |
| YAL039C | 1.1 | 2.2 | 1.7 | 1.0 | 1.1 | 0.8 | 1.0 | 1.2 | 1.6 | 2.2 | 1.1 | 1.4 | 1.6 | 1.2 | 3.3 | 2.2 | 1.4 | 1.1 | 0.39 |
| YDL181W | 1.3 | 1.8 | 1.9 | 1.8 | 1.7 | 1.2 | 1.1 | 0.6 | 0.7 | 0.8 | 0.8 | 0.9 | 0.9 | 1.1 | 0.4 | 1.1 | 1.5 | 1.4 | 0.85 |
| YPL215W | 1.1 | 1.9 | 1.0 | 1.5 | 0.8 | 0.7 | 0.7 | 1.1 | 1.7 | 1.2 | 1.1 | 0.7 | 0.7 | 1.2 | 0.6 | 1.4 | 1.0 | 1.1 | 1.10 |
| YPL262W | 1.0 | 1.7 | 3.8 | 1.2 | 0.6 | 1.6 | 1.3 | 1.0 | 1.4 | 5.8 | 1.4 | 1.1 | 1.5 | 1.2 | 0.6 | 1.4 | 1.1 | 1.2 | 0.79 |
| YNL256W | 0.7 | 1.6 | 0.6 | 0.6 | 1.0 | 0.5 | 0.6 | 0.9 | 0.8 | 0.6 | 0.6 | 0.6 | 1.3 | 0.7 | 0.9 | 0.4 | 0.6 | 0.6 | 1.09 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YKL141W | 1.6 | 1.1 | 4.7 | 1.7 | 1.5 | 1.2 | 0.5 | 0.8 | 0.8 | 0.5 | 1.2 | 0.8 | 0.8 | 1.4 | 0.6 | 2.8 | 0.9 | 1.8 | 2.84 |
| YKR066C | 0.9 | 1.4 | 5.5 | 0.7 | 1.0 | 0.9 | 0.5 | 0.7 | 0.7 | 2.4 | 1.3 | 0.9 | 0.6 | 1.5 | 0.6 | 1.3 | 0.9 | 1.1 | 1.25 |
| YMR083W | 1.4 | 1.7 | 2.6 | 1.1 | 1.5 | 1.8 | 1.7 | 1.1 | 0.4 | 1.1 | 1.6 | 0.7 | 0.9 | 0.8 | 1.3 | 1.3 | 0.9 | 1.1 | 2.52 |
| YMR203W | 0.8 | 0.7 | 3.0 | 1.4 | 0.6 | 1.1 | 0.8 | 0.7 | 0.7 | 1.2 | 2.3 | 0.7 | 1.1 | 0.7 | 1.2 | 0.9 | 0.8 | 0.7 | 1.62 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YEL024W | 1.3 | 0.9 | 3.8 | 1.1 | 1.3 | 1.1 | 0.7 | 1.0 | 0.7 | 0.6 | 0.9 | 0.8 | 0.6 | 1.1 | 0.6 | 2.1 | 1.1 | 1.5 | 1.59 |
| YGR082W | 1.0 | 0.9 | 2.2 | 1.0 | 0.9 | 1.1 | 0.9 | 0.8 | 0.6 | 0.9 | 1.3 | 0.8 | 0.5 | 0.9 | 1.2 | 1.3 | 0.9 | 0.8 | 1.47 |
| YJL133W | 1.0 | 1.0 | 2.0 | 0.9 | 0.9 | 0.5 | 0.5 | 0.9 | 0.6 | 1.4 | 1.2 | 0.8 | 0.8 | 0.7 | 0.9 | 0.6 | 0.8 | 0.7 | 0.91 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR121W | 0.9 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YLL041C | 1.1 | 0.5 | 4.6 | 1.0 | 1.6 | 1.2 | 0.3 | 0.8 | 0.7 | 0.8 | 1.3 | 0.8 | 1.0 | 1.2 | 0.4 | 3.1 | 1.1 | 1.7 | 1.75 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YOR142W | 1.0 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YOR176W | 0.7 | 2.6 | 2.7 | 0.9 | 1.0 | 0.9 | 0.5 | 1.0 | 1.0 | 0.5 | 1.4 | 1.3 | 1.5 | 0.8 | 1.4 | 0.8 | 1.4 | 2.1 | 1.23 |
| YPL135W | 0.9 | 1.2 | 2.5 | 1.2 | 1.6 | 1.3 | 1.2 | 1.0 | 0.5 | 2.8 | 1.3 | 1.1 | 1.2 | 1.1 | 1.5 | 1.2 | 1.5 | 1.7 | 1.50 |
| YOR529C | 1.8 | 1.0 | 0.9 | 3.2 | 1.2 | 0.8 | 0.5 | 1.3 | 0.5 | 0.6 | 0.8 | 0.6 | 0.7 | 1.5 | 0.5 | 1.8 | 1.0 | 2.3 | 3.11 |
| YGL018C | 1.1 | 1.0 | 1.8 | 3.0 | 1.1 | 0.4 | 1.1 | 0.8 | 0.5 | 1.4 | 1.1 | 1.0 | 1.3 | 1.2 | 1.1 | 1.5 | 0.8 | 1.0 | 0.36 |
| YBR003W | 0.9 | 0.8 | 1.0 | 1.9 | 0.7 | 1.2 | 1.1 | 0.9 | 1.0 | 1.3 | 1.3 | 0.8 | 1.2 | 0.8 | 0.7 | 2.0 | 1.1 | 1.3 | 1.06 |
| YBR044C | 0.8 | 1.4 | 0.7 | 1.9 | 1.4 | 1.0 | 1.5 | 1.1 | 0.8 | 1.2 | 1.1 | 0.8 | 1.2 | 0.9 | 0.9 | 1.4 | 0.9 | 1.3 | 0.57 |
| YBR091C | 1.1 | 1.0 | 0.6 | 3.0 | 1.1 | 0.7 | 1.0 | 1.5 | 0.7 | 1.6 | 0.7 | 0.8 | 1.2 | 1.7 | 0.9 | 0.9 | 1.0 | 1.0 | 0.87 |
| YBR185C | 1.2 | 1.0 | 1.3 | 2.0 | 0.8 | 1.2 | 1.2 | 1.1 | 0.9 | 1.6 | 1.2 | 0.7 | 1.0 | 1.7 | 1.0 | 1.7 | 0.8 | 1.3 | 0.89 |
| YBR282W | 1.0 | 1.0 | 0.5 | 2.3 | 1.0 | 1.4 | 1.2 | 1.4 | 1.0 | 0.9 | 0.9 | 0.8 | 1.3 | 1.4 | 1.1 | 1.5 | 0.9 | 1.2 | 1.36 |
| YDR347W | 1.1 | 0.8 | 0.9 | 3.5 | 0.8 | 1.2 | 1.2 | 1.2 | 0.8 | 1.6 | 0.8 | 0.8 | 1.3 | 1.5 | 1.0 | 1.7 | 0.9 | 1.2 | 1.33 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGR076C | 1.3 | 1.6 | 0.6 | 2.3 | 0.9 | 1.2 | 1.7 | 1.9 | 1.2 | 1.8 | 1.7 | 1.0 | 1.4 | 2.3 | 0.5 | 2.3 | 0.9 | 1.5 | 0.97 |
| YGR174C | 1.1 | 1.6 | 0.6 | 2.4 | 1.0 | 1.4 | 1.0 | 1.6 | 1.8 | 0.7 | 1.3 | 0.9 | 1.5 | 1.6 | 0.7 | 3.2 | 1.3 | 2.3 | 1.05 |
| YKL003C | 1.1 | 0.7 | 0.8 | 1.8 | 1.0 | 1.0 | 1.4 | 1.2 | 1.5 | 2.2 | 1.7 | 0.7 | 1.3 | 2.0 | 1.0 | 2.3 | 1.0 | 1.2 | 0.90 |
| YKL016C | 1.5 | 1.3 | 0.7 | 1.7 | 1.5 | 0.8 | 1.5 | 1.6 | 1.3 | 1.8 | 1.3 | 1.0 | 1.3 | 1.6 | 0.7 | 1.8 | 1.0 | 1.7 | 2.08 |
| YKL170W | 1.0 | 0.8 | 0.5 | 1.9 | 1.3 | 1.5 | 1.5 | 1.2 | 0.9 | 1.1 | 0.7 | 0.8 | 0.9 | 1.3 | 0.8 | 2.1 | 1.1 | 1.4 | 1.27 |
| YKL194C | 0.9 | 0.7 | 0.8 | 1.6 | 1.8 | 1.4 | 2.1 | 1.1 | 1.3 | 1.4 | 1.6 | 0.6 | 1.1 | 1.4 | 0.8 | 1.2 | 1.1 | 1.1 | 0.52 |
| YLR395C | 1.8 | 1.3 | 2.2 | 1.9 | 0.7 | 0.4 | | 1.0 | 1.0 | 0.9 | 1.5 | 0.6 | 0.5 | 1.7 | 0.4 | 1.2 | 1.2 | 2.3 | 1.76 |
| YML120C | 1.1 | 1.2 | 1.9 | 1.9 | 0.6 | 0.6 | 0.8 | 0.9 | 1.3 | 1.5 | 1.3 | 0.9 | 1.2 | 0.8 | 0.5 | 1.5 | 1.0 | 1.6 | 0.74 |
| YOR100C | 1.3 | 1.4 | 1.6 | 1.7 | 1.0 | 1.2 | 1.6 | 1.0 | 2.0 | 2.6 | 1.4 | 0.8 | 1.0 | 1.4 | 4.3 | 2.8 | 0.9 | 0.8 | 0.32 |
| YOR150W | 1.7 | 1.2 | 1.0 | 1.9 | 0.8 | 0.9 | 1.2 | 1.1 | 0.8 | 1.8 | 1.0 | 0.8 | 1.0 | 1.6 | 0.8 | 1.6 | 0.9 | 1.3 | 1.11 |
| YOR187W | 1.0 | 0.5 | 1.9 | 2.0 | 0.6 | 1.7 | 1.5 | 0.7 | 0.6 | 0.8 | 1.4 | 0.8 | 0.7 | 0.6 | 1.3 | 1.6 | 0.8 | 1.3 | 3.12 |

TABLE 2-continued

Mitochondria-located protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJL166W | 2.1 | 1.5 | 1.6 | 1.3 | 1.6 | 0.7 | 0.8 | 1.4 | 1.3 | 1.2 | 1.4 | 0.7 | 0.8 | 1.9 | 0.5 | 2.3 | 1.7 | 4.0 | 2.31 |
| YMR035W | 1.2 | 1.7 | 1.5 | 1.7 | 0.8 | 1.5 | 2.3 | 1.4 | 1.7 | 1.6 | 1.5 | 0.5 | 1.4 | 1.3 | 1.1 | 1.5 | 2.2 | 2.4 | 0.96 |
| YBL038W | 1.0 | 0.9 | 0.5 | 1.8 | 0.9 | 0.7 | 8.0 | 1.6 | 1.4 | 1.5 | 0.7 | 0.7 | 1.0 | 2.3 | 0.7 | 1.8 | 1.2 | 1.9 | 1.56 |
| YDR377W | 1.3 | 1.1 | 1.3 | 1.4 | 1.9 | 1.3 | 1.1 | 1.3 | 1.0 | 0.9 | 1.4 | 0.9 | 0.7 | 1.4 | 0.6 | 1.8 | 1.2 | 2.5 | 3.00 |
| YGL187C | 1.5 | 0.8 | 1.6 | 1.8 | 1.3 | 1.1 | 0.6 | 0.7 | 0.6 | 0.6 | 0.7 | 0.8 | 0.7 | 0.9 | 0.3 | 1.4 | 0.9 | 2.4 | 2.73 |
| YCR046C | 1.0 | 1.2 | 1.2 | 1.6 | 1.0 | 0.8 | 1.2 | 0.9 | 1.9 | 1.4 | 1.5 | 1.1 | 1.5 | 1.3 | 1.4 | 2.8 | 1.3 | 1.0 | 0.63 |
| YML129C | 1.1 | 0.9 | 0.9 | 1.2 | 1.7 | 1.7 | 1.8 | 1.2 | 1.4 | 2.2 | 1.2 | 0.8 | 1.0 | 1.4 | 1.1 | 2.9 | 1.3 | 1.3 | 1.04 |
| YOL096C | 1.1 | 1.0 | 1.2 | 1.6 | 1.2 | 1.3 | 1.7 | 1.0 | 1.3 | 1.4 | 1.2 | 1.2 | 1.4 | 1.4 | 1.0 | 2.3 | 1.2 | 1.2 | 0.64 |
| YBR122C | 0.9 | 0.9 | 0.3 | 1.1 | 1.5 | 1.1 | 2.0 | 1.3 | 1.1 | 1.4 | 1.4 | 0.7 | 0.8 | 1.2 | 0.7 | 1.9 | 0.9 | 1.5 | 1.53 |
| YBR251W | 1.0 | 0.9 | 1.0 | 1.2 | 1.3 | 2.0 | 1.4 | 1.3 | 0.5 | 1.1 | 1.5 | 1.1 | 1.0 | 1.6 | 0.8 | 3.0 | 0.9 | 1.4 | 1.13 |
| YCR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |
| YDL067C | 1.8 | 1.0 | 1.6 | 1.3 | 2.0 | 0.9 | 0.8 | 1.1 | 0.9 | 0.9 | 1.4 | 1.0 | 0.6 | 1.4 | 0.7 | 1.8 | 1.2 | 1.7 | 1.85 |
| YDR079W | 1.3 | 1.1 | 0.8 | 1.1 | 1.2 | 1.7 | 1.3 | 2.6 | 0.9 | 0.8 | 1.3 | 1.1 | 1.3 | 1.5 | 0.6 | 2.6 | 1.1 | 1.3 | 1.06 |
| YGR062C | 0.9 | 1.0 | 0.7 | 1.4 | 0.7 | 0.9 | 1.3 | 0.8 | 1.0 | 1.4 | 1.6 | 1.0 | 1.5 | 1.2 | 0.5 | 1.8 | 0.9 | 1.1 | 0.54 |
| YJL096W | 1.0 | 1.0 | 0.8 | 1.3 | 1.9 | 1.0 | 1.7 | 1.3 | 1.0 | 1.4 | 1.2 | 1.0 | 0.7 | 2.1 | 1.0 | 2.2 | 1.1 | 1.2 | 1.21 |
| YJL180C | 0.9 | 1.6 | 1.1 | 1.3 | 1.5 | 1.3 | 1.6 | 1.0 | 1.4 | 1.4 | 1.4 | 0.8 | 1.2 | 1.4 | 0.6 | 2.0 | 0.9 | 1.4 | 1.08 |
| YLR295C | 1.4 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YMR023C | 1.4 | 1.3 | 0.5 | 1.9 | 1.7 | 1.1 | 1.9 | 1.4 | 1.5 | 2.6 | 0.8 | 0.7 | 1.1 | 1.6 | 0.7 | 2.1 | 1.1 | 1.4 | 0.48 |
| YMR267W | 0.8 | 1.8 | 0.7 | 0.9 | 1.0 | 1.4 | 1.2 | 1.5 | 0.4 | 0.8 | 1.0 | 1.8 | 1.0 | 0.9 | 2.6 | 0.9 | 1.3 | 0.94 | |
| YNL073W | 0.8 | 1.4 | 0.9 | 1.7 | 0.6 | 0.5 | 1.1 | 1.0 | 0.9 | 1.8 | 1.1 | 0.7 | 1.2 | 0.7 | 0.7 | 1.8 | 0.8 | 1.0 | 0.52 |
| YOR316C | 0.7 | 2.5 | 1.5 | 1.5 | 1.0 | 0.9 | 1.4 | 0.8 | 1.6 | 2.0 | 2.4 | 1.1 | 1.6 | 1.0 | 1.5 | 2.2 | 0.8 | 1.0 | 0.93 |
| YPL040C | 1.1 | 1.0 | 0.8 | 1.7 | 0.8 | 1.1 | 0.8 | 1.1 | 0.2 | 1.2 | 0.9 | 0.9 | 1.0 | 1.1 | 1.1 | 2.7 | 0.8 | 1.1 | 0.33 |
| YPL134C | 1.5 | 1.0 | 1.6 | 1.6 | 1.4 | 1.2 | 1.2 | 1.3 | 0.6 | 0.8 | 1.7 | 0.8 | 1.0 | 1.4 | 1.1 | 3.3 | 1.3 | 1.3 | 0.70 |

TABLE 3

DNA repair protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YFL014W | 3.4 | 5.1 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YGL163C | 0.9 | 0.8 | 0.6 | 4.3 | 1.5 | 0.9 | 1.0 | 1.4 | 5.8 | 2.3 | 0.4 | 0.9 | 3.1 | 1.6 | 1.8 | 1.0 | 0.9 | 0.8 | 0.26 |
| YKL145W | 0.8 | 1.4 | 1.2 | 1.0 | 1.4 | 2.1 | 1.6 | 1.5 | 3.5 | 2.7 | 1.8 | 1.3 | 2.7 | 1.0 | 1.3 | 1.2 | 1.1 | 1.5 | 2.29 |
| YIL153W | 0.8 | 1.4 | 1.3 | 2.9 | 1.0 | 0.9 | 1.6 | 0.5 | 4.3 | 1.1 | 1.0 | 1.0 | 1.2 | 1.0 | 2.8 | 1.3 | 0.9 | 0.7 | 0.32 |
| YIR002C | 0.8 | 1.1 | 0.5 | 0.6 | 1.2 | 2.2 | 1.3 | 1.2 | 1.7 | 1.4 | 0.8 | 1.3 | 1.2 | 1.1 | 1.1 | 1.4 | 1.1 | 1.2 | 0.58 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YBR073W | 0.7 | 1.0 | 0.9 | 0.7 | 1.2 | 0.7 | 0.6 | 1.1 | 2.5 | 1.8 | 0.5 | 0.9 | 1.4 | 1.0 | 1.3 | 0.8 | 0.7 | 0.8 | 0.63 |
| YDL200C | 1.4 | 2.0 | 1.2 | 1.8 | 1.1 | 0.6 | 1.7 | 1.5 | 2.4 | 1.8 | 1.2 | 1.1 | 1.1 | 1.8 | 0.7 | 1.8 | 0.9 | 1.6 | 0.79 |
| YGL058W | 1.1 | 1.1 | 0.6 | 0.7 | 1.0 | 1.0 | 0.0 | 1.3 | 3.7 | 1.8 | 0.8 | 1.3 | 1.0 | 1.3 | 1.3 | 0.6 | 1.1 | 0.7 | 1.07 |
| YIL143C | 0.9 | 0.8 | 1.1 | 0.9 | 0.8 | 1.4 | 0.8 | 0.9 | 7.1 | 3.5 | 1.5 | 0.9 | 1.7 | 1.0 | 1.3 | 1.1 | 0.9 | 0.9 | 0.56 |
| YML032C | 0.8 | 0.9 | 1.1 | 0.7 | 1.0 | 0.9 | 0.8 | 0.9 | 3.0 | 1.1 | 1.0 | 0.9 | 1.8 | 1.0 | 1.7 | 1.2 | 1.0 | 1.0 | 0.66 |
| YNL250W | 0.9 | 2.2 | 0.8 | 1.2 | 0.8 | 0.8 | 1.2 | 1.3 | 4.2 | 2.3 | 1.0 | 1.4 | 1.3 | 1.6 | 1.3 | 1.4 | 1.0 | 1.0 | 0.31 |
| YOR386W | 1.0 | 0.8 | 1.3 | 1.5 | 1.2 | 3.3 | 1.8 | 1.0 | 4.1 | 3.0 | 1.4 | 1.2 | 2.4 | 0.9 | 1.3 | 1.2 | 2.1 | 1.7 | 0.46 |
| YBL019W | 0.9 | 9.1 | 0.7 | 1.2 | 1.0 | 0.0 | 1.2 | 1.2 | 2.6 | 1.4 | 1.0 | 0.8 | 0.9 | 1.1 | 0.6 | 1.9 | 0.8 | 1.1 | 0.38 |
| YDR369C | 1.1 | 1.1 | 2.4 | 1.1 | 1.0 | 0.6 | 0.4 | 1.0 | 2.4 | 1.8 | 1.1 | 0.9 | 0.1 | 0.7 | 1.2 | 0.6 | 0.8 | 0.7 | 1.88 |
| YEL037C | 0.9 | 2.0 | 1.0 | 1.0 | 0.5 | 0.6 | 0.8 | 0.8 | 2.6 | 1.2 | 1.0 | 1.1 | 2.0 | 1.0 | 1.6 | 0.5 | 1.0 | 0.8 | 0.82 |
| YER162C | 1.0 | 1.2 | 1.0 | 1.1 | 0.9 | 0.7 | 0.5 | 0.9 | 2.8 | 1.6 | 0.5 | 0.4 | 0.8 | 0.8 | 1.0 | 1.0 | 1.2 | 0.9 | 0.45 |
| YGR258C | 0.7 | 0.9 | 0.7 | 0.7 | 1.5 | 2.2 | 1.5 | 0.8 | 2.5 | 1.5 | 0.3 | 0.9 | 1.9 | 1.2 | 1.1 | 1.2 | 1.0 | 0.9 | 0.37 |
| YJR052W | 1.1 | 1.0 | 1.1 | 1.0 | 1.0 | 1.4 | 1.2 | 1.7 | 4.5 | 2.3 | 1.1 | 1.1 | 1.8 | 1.4 | 1.4 | 1.4 | 1.0 | 1.3 | 0.36 |
| YOR005C | 1.2 | 1.8 | 1.0 | 0.8 | 1.3 | 1.3 | 1.4 | 1.3 | 2.4 | 1.5 | 1.2 | 0.9 | 2.1 | 1.2 | 0.8 | 1.4 | 1.1 | 1.0 | 0.29 |
| YPL022W | 0.7 | 0.8 | 0.7 | 1.2 | 0.8 | 5.2 | 0.8 | 1.3 | 2.1 | 1.6 | 0.8 | 0.7 | 1.4 | 0.9 | 0.9 | 1.0 | 0.9 | 0.9 | 0.72 |
| YPL164C | 1.1 | 0.7 | 1.1 | 1.0 | 1.2 | 1.7 | 0.9 | 1.0 | 2.1 | 2.0 | 1.1 | 0.9 | 1.0 | 0.9 | 1.3 | 1.4 | 1.0 | 1.0 | 0.25 |
| YPL194W | 0.9 | 1.4 | 0.4 | 1.1 | 1.3 | 1.1 | 1.5 | 1.3 | 9.6 | 3.1 | 0.9 | 0.9 | 1.4 | 1.1 | 1.4 | 0.9 | 1.0 | 0.8 | 0.22 |
| YPR025C | 1.1 | 0.8 | 0.6 | 1.6 | 0.9 | 0.9 | 1.4 | 1.3 | 1.9 | 1.7 | 0.9 | 0.7 | 1.1 | 1.3 | 1.1 | 1.3 | 1.1 | 1.5 | 0.87 |
| YGR180C | 3.1 | 1.1 | 1.9 | 1.0 | 2.0 | 0.6 | 0.5 | 1.0 | 1.4 | 1.5 | 1.0 | 0.9 | 0.9 | 0.9 | 1.3 | 1.2 | 1.0 | 1.9 | 3.90 |
| YEL019C | 1.1 | 1.6 | 0.3 | 0.7 | 0.9 | 1.5 | 1.2 | 0.9 | 0.7 | 0.7 | 1.2 | 1.0 | 1.0 | 1.7 | 1.5 | 0.3 | 0.8 | 0.9 | 0.27 |
| YLR288C | 1.2 | 0.8 | 1.6 | 1.8 | 1.7 | 1.2 | 1.3 | 1.5 | 0.8 | 1.3 | 1.4 | 0.6 | 0.7 | 1.2 | 0.9 | 1.5 | 1.2 | 1.3 | 0.31 |
| YMR284W | 1.1 | 1.0 | 0.5 | 2.0 | 0.8 | 0.8 | 0.8 | 1.1 | 1.6 | 1.8 | 1.1 | 0.6 | 1.0 | 1.2 | 0.7 | 1.3 | 1.1 | 1.3 | 0.54 |
| YMR035W | 1.2 | 1.7 | 1.5 | 1.7 | 0.8 | 1.5 | 2.3 | 1.4 | 1.7 | 1.6 | 1.5 | 0.5 | 1.4 | 1.3 | 1.1 | 1.5 | 2.2 | 2.4 | 0.96 |
| YOL043C | 1.1 | 0.9 | 0.8 | 1.7 | 1.2 | 0.8 | 1.0 | 0.9 | 1.0 | 1.8 | 1.2 | 0.8 | 0.9 | 1.5 | 0.6 | 2.5 | 1.0 | 1.0 | 0.38 |
| YGR231C | 1.0 | 1.2 | 0.7 | 1.0 | 1.3 | 1.9 | 2.1 | 1.1 | 3.2 | 2.3 | 1.6 | 1.3 | 3.9 | 2.2 | 1.3 | 2.5 | 1.0 | 1.5 | 1.74 |
| YHR164C | 0.9 | 1.3 | 0.9 | 0.7 | 0.9 | 1.4 | 0.8 | 1.1 | 1.3 | 3.1 | 0.6 | 1.2 | 2.0 | 1.3 | 2.2 | 1.1 | 1.8 | 1.0 | 0.44 |
| YJR046W | 1.0 | 1.2 | 1.2 | 1.5 | 0.8 | 2.0 | 0.9 | 0.9 | 6.0 | 2.4 | 0.6 | 0.9 | 3.0 | 1.0 | 1.1 | 0.8 | 0.7 | 0.7 | 0.45 |
| YLR103C | 0.8 | 1.5 | 1.1 | 0.4 | 1.0 | 1.1 | 1.3 | 1.4 | 0.8 | 0.5 | 0.9 | 1.6 | 3.0 | 1.0 | 0.8 | 1.5 | 1.1 | 1.4 | 1.32 |
| YMR072W | 1.1 | 1.0 | 1.4 | 1.0 | 1.7 | 1.6 | 1.4 | 1.0 | 3.0 | 1.2 | 1.9 | 0.8 | 2.1 | 1.2 | 0.8 | 1.7 | 0.9 | 1.9 | 2.06 |
| YDR054C | 1.3 | 1.0 | 0.7 | 1.4 | 0.7 | 1.9 | 1.1 | 1.5 | 2.9 | 3.2 | 1.9 | 1.0 | 2.5 | 1.1 | 1.6 | 1.4 | 0.8 | 1.4 | 1.18 |
| YAR007C | 0.7 | 1.9 | 0.8 | 0.5 | 1.5 | 1.6 | 0.8 | 1.1 | 4.1 | 1.7 | 0.9 | 0.9 | 1.7 | 1.4 | 1.2 | 0.9 | 0.8 | 1.0 | 1.03 |

TABLE 3-continued

DNA repair protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGL058W | 1.1 | 1.1 | 0.6 | 0.7 | 1.0 | 1.5 | 0.0 | 1.3 | 3.7 | 1.8 | 0.8 | 1.3 | 1.0 | 1.3 | 1.3 | 0.6 | 1.1 | 0.7 | 1.07 |
| YIL036W | 0.9 | 1.3 | 1.3 | 1.8 | 0.9 | 1.8 | 1.4 | 1.1 | 3.6 | 2.7 | 1.2 | 1.2 | 1.9 | 1.1 | 0.8 | 1.3 | 1.1 | 1.3 | 0.66 |
| YNL213C | 1.7 | 11.6 | 0.9 | 1.5 | 1.3 | 1.7 | 1.4 | 1.8 | 3.0 | 1.5 | 1.5 | 0.8 | 0.9 | 1.8 | 1.0 | 1.7 | 0.9 | 1.2 | 0.70 |
| YNL312W | 0.9 | 1.0 | 1.6 | 0.7 | 1.4 | 1.7 | 0.5 | 1.2 | 3.7 | 2.5 | 1.4 | 0.9 | 0.7 | 1.1 | 0.8 | 0.8 | 1.2 | 1.1 | 2.05 |
| YNL261W | 1.0 | 1.3 | 0.6 | 1.3 | 0.7 | 1.3 | 1.0 | 1.1 | 2.3 | 1.5 | 0.8 | 0.8 | 0.8 | 1.4 | 0.7 | 1.1 | 0.8 | 1.0 | 0.91 |
| YGR180C | 3.1 | 1.1 | 1.9 | 1.0 | 2.0 | 1.0 | 0.5 | 1.0 | 1.4 | 1.5 | 1.0 | 0.9 | 0.9 | 0.9 | 1.3 | 1.2 | 1.0 | 1.9 | 3.90 |
| YJL026W | 2.5 | 2.4 | 2.9 | 1.0 | 1.7 | 1.0 | 0.5 | 1.2 | 1.0 | 1.1 | 1.3 | 1.0 | 1.2 | 1.0 | 1.1 | 1.6 | 1.4 | 2.1 | 3.74 |
| YDL017W | 0.8 | 2.3 | 1.2 | 1.3 | 1.2 | 1.1 | 1.1 | 1.2 | 0.8 | 1.8 | 0.8 | 0.8 | 0.9 | 1.3 | 1.3 | 1.0 | 0.8 | 1.0 | 0.38 |
| YML058W | 1.9 | 1.2 | 5.8 | 1.9 | 0.6 | 1.3 | 0.6 | 0.7 | 1.1 | 1.2 | 3.3 | 0.9 | 1.4 | 1.1 | 2.5 | 1.3 | 1.3 | 1.5 | 2.14 |
| YLR233C | 1.1 | 0.9 | 2.0 | 2.0 | 1.2 | 0.8 | 0.8 | 1.1 | 0.6 | 0.5 | 0.8 | 0.9 | 1.0 | 1.1 | 1.1 | 1.1 | 1.0 | 1.2 | 0.43 |
| YMR284W | 1.1 | 1.0 | 0.5 | 2.0 | 0.8 | 1.2 | 0.8 | 1.1 | 1.6 | 1.8 | 1.1 | 0.6 | 1.0 | 1.2 | 0.7 | 1.3 | 1.1 | 1.3 | 0.54 |
| YGL163C | 0.9 | 0.8 | 0.6 | 4.3 | 1.5 | 0.9 | 1.0 | 1.4 | 5.8 | 2.3 | 0.4 | 0.9 | 3.1 | 1.6 | 1.8 | 1.0 | 0.9 | 0.8 | 0.26 |
| YGL127C | 1.0 | 1.9 | 1.3 | 1.7 | 1.3 | 0.6 | 1.0 | 0.9 | 1.2 | 1.5 | 1.0 | 1.4 | 1.7 | 1.0 | 1.5 | 1.3 | 1.0 | 1.2 | 0.54 |
| YMR072W | 1.1 | 1.0 | 1.4 | 1.0 | 1.7 | 2.4 | 1.4 | 1.0 | 3.0 | 1.2 | 1.9 | 0.8 | 2.1 | 1.2 | 0.8 | 1.7 | 0.9 | 1.9 | 2.06 |
| YGL249W | 1.4 | 0.8 | 0.5 | 0.8 | 1.1 | 2.5 | 1.2 | 0.9 | 0.3 | 2.4 | 0.6 | 0.8 | 0.8 | 1.9 | 0.7 | 1.4 | 1.0 | 1.0 | 0.20 |
| YBR272C | 0.8 | 1.8 | 1.3 | 1.0 | 1.1 |  | 1.9 | 1.1 | 1.7 | 2.7 | 1.1 | 0.5 | 1.3 | 1.0 | 0.5 | 1.7 | 1.1 | 1.2 | 0.52 |
| YDL059C | 2.6 | 5.1 | 1.4 | 1.7 | 1.2 | 1.2 | 1.1 | 1.2 | 10.5 | 7.8 | 2.0 | 1.3 | 1.7 | 4.7 | 0.7 | 1.5 | 0.8 | 0.9 | 0.63 |
| YAR007C | 0.7 | 1.9 | 0.8 | 0.5 | 1.5 | 0.6 | 0.8 | 1.1 | 4.1 | 1.7 | 0.9 | 0.9 | 1.7 | 1.4 | 1.2 | 0.9 | 0.8 | 1.0 | 1.03 |
| YBR073W | 0.7 | 1.0 | 0.9 | 0.7 | 1.2 | 0.7 | 0.6 | 1.1 | 2.5 | 1.8 | 0.5 | 0.9 | 1.4 | 1.0 | 1.3 | 0.8 | 0.7 | 0.8 | 0.63 |
| YML032C | 0.8 | 0.9 | 1.1 | 0.7 | 1.0 | 0.9 | 0.8 | 0.9 | 3.0 | 1.1 | 1.0 | 0.9 | 1.8 | 1.0 | 1.7 | 1.2 | 1.0 | 1.0 | 0.66 |
| YNL250W | 0.9 | 2.2 | 0.8 | 1.2 | 0.8 | 0.8 | 1.2 | 1.3 | 4.2 | 2.3 | 1.0 | 1.4 | 1.3 | 1.6 | 1.3 | 1.4 | 1.0 | 1.0 | 0.31 |
| YCR014C | 0.8 | 1.0 | 0.8 | 0.6 | 1.2 | 1.1 | 1.1 | 1.0 | 2.4 | 1.0 | 0.8 | 0.7 | 1.2 | 1.0 | 0.7 | 1.5 | 1.0 | 0.9 | 0.34 |
| YDR369C | 1.1 | 1.1 | 2.4 | 1.1 | 1.0 | 0.6 | 0.4 | 1.0 | 2.4 | 1.8 | 1.1 | 0.9 | 0.1 | 0.7 | 1.2 | 0.6 | 0.8 | 0.7 | 1.88 |
| YIL072W | 0.8 | 3.1 | 1.1 | 2.6 | 1.5 | 1.2 | 1.7 | 1.4 | 2.9 | 2.1 | 1.8 | 1.1 | 1.4 | 2.0 | 1.4 | 1.4 | 1.0 | 1.1 | 0.23 |
| YOR005C | 1.2 | 1.8 | 1.0 | 0.8 | 1.3 | 1.3 | 1.4 | 1.3 | 2.4 | 1.5 | 1.2 | 0.9 | 2.1 | 1.2 | 0.8 | 1.4 | 1.1 | 1.0 | 0.29 |
| YPL164C | 1.1 | 0.7 | 1.1 | 1.0 | 1.2 | 1.7 | 0.9 | 1.0 | 2.1 | 2.0 | 1.1 | 0.9 | 1.0 | 0.9 | 1.3 | 1.4 | 1.0 | 1.0 | 0.25 |
| YPL194W | 0.9 | 1.4 | 0.4 | 1.1 | 1.3 | 1.1 | 1.5 | 1.3 | 9.6 | 3.1 | 0.9 | 0.9 | 1.4 | 1.1 | 1.4 | 0.9 | 1.0 | 0.8 | 0.22 |
| YGR180C | 3.1 | 1.1 | 1.9 | 1.0 | 2.0 | 0.6 | 0.5 | 1.0 | 1.4 | 1.5 | 1.0 | 0.9 | 0.9 | 0.9 | 1.3 | 1.2 | 1.0 | 1.9 | 3.90 |
| YEL019C | 1.1 | 1.6 | 0.3 | 0.7 | 0.9 | 1.5 | 1.2 | 0.9 | 0.7 | 0.7 | 1.2 | 1.0 | 1.0 | 1.7 | 1.5 | 0.3 | 0.8 | 0.9 | 0.27 |
| YML058W | 1.9 | 1.2 | 5.8 | 1.9 | 0.6 | 0.6 | 0.6 | 0.7 | 1.1 | 1.2 | 3.3 | 0.9 | 1.4 | 1.1 | 2.5 | 1.3 | 1.3 | 1.5 | 2.14 |
| YLR288C | 1.2 | 0.8 | 1.6 | 1.8 | 1.7 | 1.2 | 1.3 | 1.5 | 0.8 | 1.3 | 1.4 | 0.6 | 0.7 | 1.2 | 0.9 | 1.5 | 1.2 | 1.3 | 0.31 |
| YMR284W | 1.1 | 1.0 | 0.5 | 2.0 | 0.8 | 0.8 | 0.8 | 1.1 | 1.6 | 1.8 | 1.1 | 0.6 | 1.0 | 1.2 | 0.7 | 1.3 | 1.1 | 1.3 | 0.54 |
| YMR096W | 1.7 | 1.7 | 1.1 | 0.8 | 1.0 | 2.2 | 1.9 | 2.0 | 3.3 | 3.7 | 1.5 | 1.4 | 8.4 | 4.7 | 28.9 | 2.2 | 2.2 | 1.0 | 0.62 |
| YGL091C | 2.0 | 1.8 | 1.0 | 1.7 | 0.8 | 1.6 | 1.3 | 1.8 | 10.8 | 6.0 | 2.1 | 1.2 | 2.5 | 3.1 | 0.7 | 1.0 | 1.4 | 1.8 | 0.96 |

TABLE 4

Energy system protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR107W | 12.1 | 2.6 | 1.8 | 1.6 | 0.7 | 1.5 | 1.5 | 15.6 | 196.6 | 34.0 | 23.0 | 0.9 | 4.0 | 8.3 | 4.8 | 3.1 | 1.3 | 1.1 | 0.59 |
| YDL243C | 14.5 | 2.7 | 2.4 | 1.0 | 1.1 | 2.2 | 1.6 | 11.8 | 64.2 | 29.6 | 19.6 | 1.1 | 4.1 | 12.0 | 4.2 | 3.0 | 1.8 | 1.5 | 0.76 |
| YFL056C | 19.0 | 2.3 | 2.3 | 1.5 | 0.9 | 0.6 | 1.4 | 18.5 | 162.3 | 31.3 | 68.3 | 1.0 | 4.7 | 7.8 | 5.0 | 3.4 | 1.0 | 1.1 | 0.55 |
| YFL057C | 20.9 | 5.9 | 1.5 | 1.8 | 0.9 | 1.2 | 1.8 | 18.0 | 51.8 | 46.1 | 27.7 | 1.0 | 4.1 | 23.4 | 3.1 | 3.9 | 1.6 | 1.3 | 0.71 |
| YJR155W | 7.6 | 3.7 | 1.4 | 2.5 | 0.7 | 1.4 | 1.7 | 10.6 | 38.2 | 18.8 | 15.4 | 1.0 | 5.7 | 9.4 | 2.6 | 5.6 | 1.3 | 1.4 | 0.64 |
| YNL331C | 8.6 | 3.6 | 1.3 | 1.0 | 1.6 | 1.8 | 1.9 | 13.3 | 42.6 | 36.3 | 21.8 | 0.9 | 3.1 | 7.5 | 2.3 | 4.0 | 1.7 | 1.3 | 0.58 |
| YOL165C | 10.1 | 4.5 | 1.8 | 0.9 | 0.9 | 1.7 | 1.4 | 17.8 | 46.9 | 23.3 | 17.6 | 0.8 | 3.7 | 9.1 | 3.0 | 1.8 | 1.6 | 1.0 | 0.69 |
| YPL171C | 15.2 | 4.1 | 3.5 | 2.2 | 1.1 | 1.3 | 1.7 | 20.5 | 60.0 | 50.6 | 37.0 | 1.4 | 2.4 | 9.3 | 1.4 | 1.2 | 2.4 | 1.5 | 0.47 |
| YDL021W | 5.1 | 1.7 | 2.4 | 3.7 | 1.7 | 6.5 | 5.9 | 2.7 | 2.5 | 7.4 | 4.7 | 2.4 | 5.3 | 3.7 | 0.7 | 7.3 | 1.9 | 3.2 | 0.47 |
| YGR043C | 2.6 | 3.7 | 3.2 | 7.9 | 0.9 | 16.3 | 6.5 | 2.6 | 10.9 | 8.4 | 3.6 | 3.3 | 6.9 | 4.1 | 3.0 | 13.7 | 1.6 | 4.8 | 0.66 |
| YHR179W | 3.3 | 2.3 | 2.6 | 0.7 | 1.2 | 3.7 | 1.9 | 3.3 | 3.6 | 5.8 | 2.0 | 2.2 | 2.6 | 5.8 | 2.7 | 1.0 | 1.9 | 1.6 | 2.69 |
| YJR048W | 1.3 | 0.9 | 2.2 | 1.4 | 0.8 | 0.5 | 0.3 | 0.9 | 0.5 | 1.5 | 1.0 | 0.8 | 0.4 | 2.5 | 0.6 | 1.5 | 1.2 | 1.2 | 1.19 |
| YKR097W | 1.6 | 2.4 | 1.3 | 3.3 | 1.1 | 1.7 | 3.7 | 2.5 | 1.9 | 3.3 | 0.8 | 1.8 | 17.5 | 2.1 | 2.5 | 2.2 | 1.1 | 1.5 | 0.16 |
| YML087C | 1.8 | 1.6 | 0.8 | 2.5 | 0.9 | 0.9 | 1.1 | 1.3 | 1.9 | 4.9 | 1.6 | 0.8 | 1.5 | 2.1 | 0.3 | 2.0 | 0.7 | 0.8 | 0.52 |
| YPL088W | 3.3 | 1.3 | 0.6 | 2.5 | 1.5 | 7.1 | 3.7 | 1.9 | 0.6 | 2.8 | 1.1 | 3.6 | 4.8 | 1.6 | 3.2 | 4.3 | 9.1 | 8.3 | 0.69 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YCR012W | 1.2 | 1.5 | 5.1 | 1.2 | 1.1 | 2.5 | 1.4 | 0.8 | 1.4 | 1.5 | 1.8 | 1.2 | 4.1 | 0.9 | 1.4 | 1.4 | 0.8 | 1.3 | 4.48 |
| YFR053C | 1.8 | 1.4 | 3.0 | 2.2 | 0.9 | 3.2 | 2.1 | 2.8 | 0.6 | 1.1 | 1.5 | 1.7 | 3.0 | 0.6 | 0.6 | 3.0 | 1.4 | 2.2 | 4.17 |
| YGL062W | 0.6 | 1.3 | 1.1 | 0.6 | 0.9 | 1.0 | 1.3 | 0.8 | 1.6 | 2.5 | 0.7 | 1.6 | 4.5 | 1.2 | 2.7 | 1.5 | 1.1 | 0.9 | 0.77 |
| YGR192C | 1.4 | 1.0 | 3.8 | 1.0 | 1.1 | 1.7 | 1.7 | 1.1 | 0.9 | 1.3 | 2.3 | 2.2 | 3.4 | 1.0 | 1.9 | 1.1 | 1.1 | 1.3 | 7.49 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YGR254W | 1.2 | 1.3 | 3.8 | 1.3 | 1.2 | 1.9 | 1.5 | 1.4 | 0.8 | 1.2 | 1.3 | 1.7 | 3.1 | 0.6 | 2.4 | 1.4 | 1.3 | 1.2 | 7.01 |
| YIL160C | 0.8 | 2.4 | 2.3 | 3.5 | 1.0 | 1.6 | 1.1 | 1.2 | 3.2 | 3.8 | 2.4 | 1.0 | 2.3 | 1.5 | 5.6 | 8.8 | 2.4 | 3.0 | 0.27 |
| YJL052W | 1.6 | 0.9 | 4.0 | 1.8 | 0.7 | 2.4 | 2.1 | 1.5 | 1.6 | 2.0 | 4.3 | 2.4 | 5.6 | 1.3 | 2.3 | 2.3 | 1.2 | 1.9 | 6.19 |
| YJR009C | 1.1 | 1.7 | 5.6 | 1.0 | 1.2 | 1.6 | 1.6 | 1.1 | 1.1 | 1.3 | 1.1 | 1.5 | 2.7 | 1.0 | 2.1 | 1.5 | 1.1 | 1.3 | 5.86 |
| YLR345W | 1.4 | 1.4 | 1.4 | 1.2 | 1.2 | 1.6 | 1.2 | 1.4 | 4.5 | 4.0 | 2.5 | 1.6 | 3.5 | 1.5 | 1.0 | 1.2 | 1.2 | 1.4 | 2.65 |
| YMR118C | 1.3 | 2.9 | 1.4 | 1.6 | 1.2 | 2.0 | 1.0 | 1.0 | 9.3 | 1.4 | 0.7 | 0.8 | 4.2 | 0.9 | 0.9 | 8.1 | 0.8 | 1.0 | 0.38 |

TABLE 4-continued

Energy system protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YPL240C | 0.7 | 1.4 | 2.4 | 0.9 | 1.3 | 1.2 | 1.4 | 1.2 | 3.5 | 2.6 | 1.0 | 0.8 | 2.9 | 0.7 | 1.2 | 0.7 | 0.8 | 1.0 | 4.83 |
| YAL060W | 1.1 | 1.8 | 3.2 | 2.7 | 1.2 | 4.2 | 3.3 | 0.9 | 0.6 | 2.5 | 2.4 | 0.8 | 2.2 | 0.9 | 0.9 | 3.2 | 1.1 | 1.8 | 2.39 |
| YCL040W | 0.9 | 5.6 | 10.1 | 2.0 | 0.5 | 3.5 | 2.9 | 0.7 | 0.9 | 3.0 | 8.2 | 2.3 | 5.6 | 0.7 | 3.4 | 3.1 | 1.4 | 1.7 | 1.98 |
| YDR001C | 1.0 | 2.2 | 2.6 | 1.0 | 1.1 | 2.2 | 1.5 | 0.9 | 2.2 | 3.0 | 0.7 | 1.1 | 2.8 | 1.0 | 4.4 | 1.9 | 1.1 | 1.6 | 0.75 |
| YDR231C | 1.1 | 1.6 | 1.0 | 1.5 | 1.1 | 2.2 | 1.7 | 1.3 | 1.5 | 1.4 | 1.3 | 1.1 | 2.4 | 1.5 | 1.0 | 3.0 | 1.2 | 1.3 | 0.92 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YGR008C | 2.4 | 3.0 | 1.7 | 3.2 | 0.9 | 2.9 | 3.7 | 1.9 | 3.1 | 2.4 | 2.6 | 2.0 | 3.4 | 1.3 | 1.5 | 2.3 | 1.7 | 4.2 | 3.03 |
| YGR256W | 1.2 | 1.5 | 2.3 | 0.8 | 0.9 | 6.2 | 1.4 | 2.2 | 3.4 | 2.5 | 2.7 | 1.5 | 3.9 | 1.1 | 2.7 | 5.3 | 1.1 | 0.8 | 0.94 |
| YHL008C | 0.9 | 0.5 | 1.0 | 1.6 | 0.8 | 0.8 | 0.7 | 0.9 | 1.6 | 1.7 | 1.4 | 0.8 | 1.8 | 1.0 | 1.8 | 0.9 | 0.8 | 0.9 | 0.40 |
| YHR174W | 1.1 | 1.4 | 3.3 | 1.2 | 1.3 | 1.5 | 1.6 | 1.2 | 1.0 | 1.5 | 1.4 | 1.5 | 3.6 | 0.6 | 2.0 | 1.1 | 1.0 | 1.2 | 7.34 |
| YIL045W | 1.7 | 1.4 | 1.9 | 2.2 | 1.3 | 1.7 | 1.6 | 1.1 | 2.1 | 3.2 | 1.2 | 1.5 | 2.0 | 1.6 | 0.6 | 2.9 | 1.1 | 1.8 | 0.37 |
| YKL035W | 1.0 | 0.9 | 4.8 | 1.2 | 0.8 | 1.2 | 0.6 | 1.0 | 0.8 | 1.2 | 2.1 | 1.0 | 2.0 | 0.6 | 1.0 | 1.5 | 1.0 | 1.9 | 2.54 |
| YKL152C | 1.4 | 1.3 | 1.9 | 0.9 | 1.3 | 1.6 | 1.5 | 1.0 | 0.9 | 1.5 | 1.7 | 1.5 | 2.7 | 1.0 | 1.8 | 2.0 | 1.1 | 1.7 | 3.28 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YML100W | 0.8 | 2.7 | 10.6 | 1.4 | 0.9 | 2.8 | 2.2 | 0.7 | 1.7 | 1.4 | 3.2 | 1.2 | 3.8 | 1.2 | 1.8 | 2.2 | 1.0 | 1.5 | 0.88 |
| YML125C | 0.8 | 0.9 | 0.7 | 0.7 | 0.9 | 1.3 | 1.0 | 1.3 | 2.6 | 1.6 | 1.0 | 1.0 | 2.2 | 1.6 | 1.9 | 0.7 | 1.2 | 0.9 | 2.21 |
| YMR089C | 1.0 | 1.1 | 0.9 | 0.9 | 0.8 | 1.2 | 1.2 | 1.3 | 5.6 | 2.5 | 1.3 | 0.8 | 2.3 | 0.9 | 1.8 | 1.1 | 0.9 | 1.1 | 0.69 |
| YMR105C | 2.0 | 3.0 | 5.0 | 4.2 | 0.9 | 2.8 | 2.8 | 1.1 | 0.6 | 2.9 | 3.0 | 1.7 | 3.3 | 1.0 | 0.9 | 2.0 | 1.6 | 2.6 | 1.21 |
| YNL237W | 1.3 | 1.3 | 1.5 | 1.0 | 1.5 | 4.6 | 4.9 | 1.1 | 0.9 | 2.1 | 1.5 | 1.8 | 3.2 | 1.3 | 1.6 | 4.4 | 1.3 | 1.1 | 0.21 |
| YOL126C | 1.1 | 0.8 | 1.0 | 1.6 | 0.7 | 1.5 | 1.4 | 0.9 | 0.8 | 2.4 | 1.8 | 1.1 | 2.6 | 1.2 | 1.4 | 2.5 | 1.6 | 2.4 | 0.59 |
| YOR347C | 0.9 | 0.9 | 2.1 | 2.2 | 0.7 | 0.9 | 0.9 | 0.8 | 0.5 | 0.9 | 1.4 | 1.2 | 1.8 | 0.9 | 2.0 | 1.4 | 1.7 | 1.3 | 1.31 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YAL038W | 1.0 | 1.0 | 3.0 | 1.4 | 1.4 | 1.3 | 0.9 | 1.1 | 0.1 | 1.1 | 1.0 | 1.2 | 1.8 | 0.5 | 3.1 | 0.9 | 1.0 | 1.0 | 7.02 |
| YDR380W | 0.8 | 0.8 | 0.8 | 1.7 | 1.1 | 0.4 | 0.5 | 0.2 | 0.2 | 0.3 | 0.4 | 0.4 | 0.4 | 0.6 | 2.4 | 0.2 | 0.8 | 0.8 | 1.04 |
| YLR273C | 1.5 | 1.0 | 1.3 | 2.4 |  | 1.2 | 1.2 | 1.3 | 2.8 | 2.4 | 1.4 | 0.9 | 1.7 | 1.3 | 2.6 | 1.5 | 1.0 | 1.0 | 0.20 |
| YGR207C | 1.5 | 1.1 | 1.0 | 1.1 | 1.5 | 2.8 | 1.7 | 1.9 | 2.1 | 2.6 | 1.4 | 1.1 | 1.0 | 2.2 | 0.6 | 1.8 | 1.2 | 1.8 | 1.49 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YAL054C | 1.2 | 1.1 | 1.4 | 1.6 | 1.1 | 2.2 | 1.1 | 1.1 | 8.9 | 4.1 | 1.3 | 1.0 | 1.8 | 1.3 | 0.9 | 2.5 | 1.5 | 1.4 | 0.24 |
| YEL011W | 2.0 | 1.6 | 1.7 | 6.3 | 1.1 | 2.8 | 2.7 | 0.9 | 2.5 | 1.6 | 3.7 | 1.5 | 1.5 | 1.5 | 0.4 | 2.4 | 1.4 | 2.5 | 0.89 |
| YFR015C | 1.2 | 0.8 | 3.2 | 2.1 | 1.2 | 3.0 | 7.3 | 0.7 | 0.3 | 1.8 | 3.9 | 0.4 | 2.5 | 3.1 | 0.4 | 2.4 | 1.3 | 1.2 | 0.66 |
| YGL253W | 0.8 | 1.0 | 3.2 | 0.7 | 1.3 | 2.4 | 1.7 | 1.1 | 0.3 | 1.4 | 1.0 | 1.2 | 1.5 | 0.5 | 0.8 | 0.4 | 0.7 | 0.8 | 4.63 |
| YIL111W | 1.9 | 1.0 | 1.8 | 2.7 |  | 2.6 | 3.2 | 1.2 | 1.6 | 1.1 | 2.1 | 0.9 | 1.7 | 1.5 | 1.1 | 2.5 | 1.9 | 3.9 | 1.52 |
| YKL150W | 1.1 | 2.0 | 3.0 | 1.4 | 1.4 | 2.3 | 2.4 | 1.3 | 1.1 | 1.3 | 1.9 | 1.2 | 1.8 | 1.4 | 0.9 | 6.1 | 1.2 | 2.7 | 2.20 |
| YPR006C | 1.9 | 1.5 | 0.5 | 1.9 | 2.0 | 2.4 | 2.8 | 1.5 | 1.5 | 3.9 | 2.4 | 1.1 | 1.8 | 1.2 | 0.7 | 1.6 | 1.8 | 2.1 | 0.46 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YBR299W | 2.0 | 0.9 | 1.1 | 3.5 | 1.6 | 0.8 | 3.6 | 2.2 | 1.1 | 5.3 | 2.4 | 1.2 | 0.7 | 1.4 | 0.6 | 3.9 | 1.0 | 1.1 | 0.32 |
| YEL020C | 1.0 | 1.5 | 0.8 | 2.9 | 1.5 | 1.3 | 2.4 | 1.2 | 1.4 | 1.1 | 1.3 | 0.8 | 1.2 | 1.0 | 1.4 | 2.1 | 1.2 | 1.3 | 0.31 |
| YGL134W | 1.2 | 1.3 | 0.5 | 0.8 | 1.4 | 1.2 | 2.3 | 1.4 | 1.1 | 1.4 | 1.1 | 0.9 | 0.7 | 1.1 | 0.5 | 1.7 | 0.9 | 1.3 | 0.53 |
| YOL157C | 1.0 | 1.1 | 1.3 | 2.5 | 1.4 | 0.9 | 2.7 | 1.4 | 2.3 | 4.8 | 1.2 | 1.2 | 1.4 | 1.2 | 1.1 | 3.5 | 1.4 | 1.3 | 0.41 |
| YBR126C | 0.8 | 1.9 | 5.6 | 1.2 | 0.7 | 2.9 | 2.3 | 0.6 |  | 1.7 |  | 1.1 | 1.3 | 2.1 | 0.7 | 1.0 | 1.7 | 1.5 | 1.3 | 1.96 |
| YCR005C | 1.2 | 1.9 | 2.0 | 1.2 | 0.9 | 1.6 | 4.4 | 1.2 | 1.5 | 1.5 | 2.1 | 0.5 | 0.7 | 0.8 | 0.7 | 0.7 | 1.6 | 1.7 | 2.38 |
| YIL172C | 1.1 | 1.1 | 1.6 | 1.7 |  | 1.3 | 2.5 | 1.6 | 2.8 | 7.1 | 1.0 | 1.4 | 2.0 | 1.3 | 1.4 | 2.8 | 1.1 | 1.2 | 0.42 |
| YOR221C | 0.8 | 1.0 | 0.9 | 1.1 | 1.7 | 0.8 | 2.1 | 0.9 | 1.4 | 1.7 | 1.1 | 0.8 | 1.0 | 1.1 | 1.0 | 1.4 | 0.9 | 1.2 | 0.39 |
| YBR196C | 0.8 | 0.6 | 3.9 | 1.4 | 0.8 | 0.8 | 1.4 | 1.1 | 0.3 | 0.9 | 2.3 | 1.0 | 1.4 | 0.5 | 1.9 | 1.1 | 0.8 | 1.0 | 6.60 |
| YEL047C | 1.3 | 1.9 | 3.2 | 1.2 | 0.8 | 0.6 | 1.3 | 1.0 | 2.7 | 2.3 | 4.2 | 1.2 | 1.6 | 1.1 | 1.0 | 1.3 | 0.9 | 1.0 | 1.02 |
| YMR318C | 1.8 | 2.4 | 2.2 | 0.7 | 1.2 | 2.1 | 0.8 | 3.6 | 2.3 | 4.8 | 3.6 | 0.8 | 1.8 | 1.7 | 1.5 | 1.1 | 1.1 | 1.1 | 3.17 |
| YER061C | 0.9 | 0.9 | 1.2 | 2.5 | 0.8 | 0.4 | 0.9 | 0.7 | 0.3 | 0.7 | 2.2 | 0.7 | 0.9 | 1.0 | 0.8 | 1.8 | 1.2 | 1.2 | 0.84 |
| YJL045W | 1.8 | 2.2 | 1.6 | 5.3 | 0.7 | 0.6 | 0.7 | 0.9 | 9.7 | 1.6 | 2.3 | 1.1 | 1.6 | 1.2 | 3.4 | 2.4 | 0.9 | 0.9 | 0.42 |
| YLL009C | 1.0 | 1.2 | 0.6 | 1.9 | 1.5 | 1.2 | 1.7 | 1.0 | 1.3 | 1.7 | 3.5 | 0.7 | 0.9 | 1.4 | 1.1 | 2.8 | 0.9 | 1.2 | 1.66 |
| YPR160W | 1.4 | 3.8 | 3.6 | 3.3 | 0.7 | 4.5 | 1.8 | 0.9 | 0.9 | 1.3 | 4.4 | 2.1 | 2.2 | 1.1 | 1.4 | 5.3 | 1.0 | 2.9 | 1.42 |
| YDL085W | 1.2 | 1.9 | 1.2 | 2.0 | 1.2 | 1.2 | 1.4 | 1.0 | 7.8 | 3.4 | 2.7 | 0.8 | 1.7 | 1.2 | 0.7 | 4.5 | 0.9 | 0.9 | 0.23 |
| YJL221C | 1.1 | 1.0 | 1.1 | 1.3 | 0.9 | 6.6 | 2.5 | 1.8 | 2.7 | 4.4 | 0.8 | 1.1 | 1.4 | 1.1 | 1.1 | 3.3 | 1.1 | 1.4 | 0.41 |
| YKL085W | 1.5 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |
| YLR174W | 1.2 | 1.5 | 1.7 | 2.1 | 0.9 | 0.9 | 1.6 | 1.1 | 2.5 | 8.3 | 1.3 | 1.3 | 1.8 | 1.7 | 0.8 | 4.6 | 0.9 | 1.2 | 0.41 |
| YNL009W | 1.1 | 1.9 | 2.0 | 1.4 | 1.4 | 1.1 | 1.2 | 1.1 | 1.4 | 3.3 | 1.3 | 0.9 | 1.3 | 1.3 | 2.7 | 3.3 | 1.2 | 2.3 | 0.45 |
| YNL117W | 0.9 | 4.7 | 1.7 | 0.8 | 0.9 |  | 1.1 | 1.7 | 12.8 | 4.4 | 1.4 | 0.7 | 1.3 | 2.0 | 2.6 | 1.6 | 1.1 | 0.9 | 0.24 |
| YAL061W | 1.7 | 2.4 | 3.3 | 3.8 | 1.0 | 1.0 | 2.0 | 0.8 | 5.5 | 1.4 | 4.1 | 1.1 | 1.4 | 0.7 | 0.6 | 1.1 | 1.4 | 1.2 | 0.88 |
| YBR117C | 0.8 | 1.6 | 1.5 | 1.4 | 0.9 | 2.3 | 1.0 | 0.7 | 5.9 | 1.5 | 0.4 | 0.8 | 2.1 | 0.9 | 1.0 | 12.0 | 0.7 | 0.7 | 0.49 |
| YEL071W | 1.1 | 1.6 | 2.6 | 0.4 | 1.3 | 1.9 | 2.0 | 1.2 | 3.6 | 2.8 | 2.1 | 0.9 | 1.6 | 1.2 | 1.6 | 1.2 | 1.1 | 1.2 | 1.13 |
| YGR112W | 1.0 | 2.9 | 1.1 | 1.3 | 0.9 | 1.1 | 1.3 | 1.3 | 2.6 | 1.3 | 1.3 | 0.7 | 1.1 | 1.1 | 1.2 | 2.8 | 0.9 | 1.2 | 0.31 |
| YLR164W | 1.0 | 2.4 | 0.3 | 1.0 | 1.2 | 1.2 | 1.1 | 1.2 | 5.3 | 2.0 | 3.2 | 0.7 | 1.0 | 1.5 | 0.7 | 11.0 | 1.5 | 1.2 | 0.31 |
| YNR032W | 1.0 | 1.5 | 1.0 | 2.1 | 1.5 | 1.0 | 1.1 | 1.0 | 6.2 | 2.4 | 1.4 | 0.6 | 1.3 | 1.4 | 0.9 | 1.0 | 1.2 | 1.3 | 0.71 |
| YPL031C | 0.9 | 2.0 | 1.4 | 0.8 | 1.5 | 1.8 | 1.6 | 1.0 | 5.7 | 1.4 | 1.4 | 0.8 | 1.6 | 0.9 | 0.7 | 2.0 | 1.4 | 1.2 | 0.49 |
| YPR048W | 1.3 | 2.0 | 0.9 | 1.1 | 0.9 | 0.6 | 0.9 | 1.5 | 4.0 | 2.1 | 1.0 | 0.8 | 0.6 | 1.2 | 0.6 | 0.8 | 0.7 | 0.8 | 0.75 |
| YBL058W | 0.9 | 1.9 | 0.5 | 1.1 | 1.6 | 0.9 | 1.5 | 1.2 | 2.6 | 2.1 | 1.0 | 1.3 | 1.6 | 1.3 | 1.8 | 1.8 | 1.0 | 1.4 | 1.42 |
| YBR001C | 0.9 | 1.4 | 1.1 | 1.4 | 0.9 | 1.1 | 0.9 | 1.3 | 2.3 | 2.1 | 1.0 | 1.0 | 2.0 | 1.2 | 1.8 | 1.4 | 1.0 | 1.6 | 0.61 |
| YCR105W | 2.2 | 1.2 | 1.2 | 3.0 | 0.9 | 1.0 | 1.0 | 1.4 | 2.0 | 3.9 | 2.3 | 0.9 | 1.9 | 1.9 | 3.1 | 1.3 | 1.3 | 1.1 | 0.36 |
| YIR031C | 0.9 | 1.6 | 0.6 | 0.6 | 1.6 | 1.7 | 1.4 | 1.0 | 2.6 | 1.0 | 1.2 | 0.8 | 1.0 | 1.2 | 0.8 | 0.7 | 0.9 | 0.8 | 0.44 |
| YGL191W | 2.3 | 1.6 | 1.4 | 1.8 | 0.9 | 1.6 | 1.0 | 1.6 | 1.1 | 1.3 | 1.6 | 0.9 | 1.1 | 1.6 | 0.7 | 1.8 | 1.2 | 1.7 | 2.35 |

TABLE 4-continued

Energy system protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YLR038C | 2.6 | 1.1 | 0.6 | 2.1 | 1.8 | 1.2 | 1.0 | 1.4 | 0.4 | 0.9 | 1.4 | 0.6 | 0.5 | 1.6 | 0.7 | 2.1 | 1.2 | 2.1 | 1.52 |
| YGR087C | 1.0 | 15.0 | 1.7 | 0.6 | 1.0 | 1.1 | 1.0 | 0.8 | 0.2 | 0.9 | 0.8 | 1.2 | 1.2 | 0.7 | 3.5 | 0.6 | 1.0 | 0.6 | 1.88 |
| YGL256W | 0.9 | 5.3 | 1.1 | 1.3 | 0.7 | 0.7 | 0.5 | 1.0 | 0.4 | 1.2 | 1.0 | 0.9 | 0.8 | 0.9 | 1.0 | 0.7 | 0.7 | 0.8 | 0.90 |
| YDL181W | 1.4 | 1.8 | 1.9 | 1.8 | 1.7 | 1.2 | 1.1 | 0.6 | 0.7 | 0.8 | 0.8 | 0.9 | 0.9 | 1.1 | 0.4 | 1.1 | 1.5 | 1.4 | 0.85 |
| YPL262W | 1.1 | 1.7 | 3.8 | 1.2 | 0.6 | 1.6 | 1.3 | 1.0 | 1.4 | 5.8 | 1.4 | 1.1 | 1.5 | 1.2 | 0.6 | 1.4 | 1.1 | 1.2 | 0.79 |
| YLR377C | 1.1 | 2.6 | 1.8 | 1.2 | 1.0 | 0.7 | 0.9 | 0.7 | 1.8 | 1.6 | 0.6 | 0.6 | 1.2 | 2.9 | 0.8 | 2.7 | 0.9 | 1.4 | 0.14 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YKL141W | 1.6 | 1.1 | 4.7 | 1.7 | 1.5 | 1.2 | 0.5 | 0.8 | 0.8 | 0.5 | 1.2 | 0.8 | 0.8 | 1.4 | 0.6 | 2.8 | 0.9 | 1.8 | 2.84 |
| YLR134W | 0.9 | 0.6 | 2.3 | 0.8 | 1.3 | 2.5 | 1.1 | 0.8 | 0.1 | 0.7 | 1.1 | 1.2 | 1.5 | 0.6 | 1.7 | 0.5 | 0.6 | 0.8 | 3.47 |
| YLR258W | 1.7 | 1.0 | 4.2 | 3.5 | 0.9 | 1.8 | 1.8 | 0.9 | 0.8 | 1.3 | 1.2 | 0.9 | 1.4 | 1.2 | 0.6 | 1.7 | 1.0 | 2.0 | 1.36 |
| YOR178C | 1.4 | 1.3 | 4.8 | 2.3 | 1.0 | 2.7 | 0.9 | 0.9 | 0.2 | 1.7 | 4.1 | 1.7 | 1.0 | 1.0 | 1.1 | 1.7 | 1.0 | 1.5 | 0.56 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YDR050C | 1.9 | 1.3 | 2.3 | 1.8 | 0.9 | 1.7 | 1.5 | 1.3 | 0.4 | 1.3 | 2.0 | 1.4 | 2.0 | 1.2 | 1.9 | 1.3 | 1.1 | 2.3 | 6.26 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YEL024W | 1.5 | 0.9 | 3.8 | 1.1 | 1.3 | 1.1 | 0.7 | 1.0 | 0.7 | 0.6 | 0.9 | 0.8 | 0.6 | 1.1 | 0.6 | 2.1 | 1.1 | 1.5 | 1.59 |
| YJL121C | 1.0 | 0.5 | 1.9 | 0.8 | 1.0 | 1.1 | 0.7 | 1.0 | 0.1 | 0.4 | 1.1 | 0.6 | 0.7 | 0.9 | 1.0 | 0.6 | 1.1 | 1.0 | 1.00 |
| YJR121W | 1.2 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YKL060C | 1.7 | 0.8 | 2.5 | 1.0 | 1.6 | 1.3 | 1.2 | 1.1 | 0.3 | 0.8 | 2.1 | 1.3 | 1.2 | 0.8 | 1.6 | 1.5 | 1.2 | 1.7 | 6.01 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YLL041C | 1.5 | 0.5 | 4.6 | 1.0 | 1.6 | 1.2 | 0.3 | 0.8 | 0.7 | 0.8 | 1.3 | 0.8 | 1.0 | 1.2 | 0.4 | 3.1 | 1.1 | 1.7 | 1.75 |
| YLR044C | 0.8 | 0.6 | 2.2 | 0.9 | 1.7 | 1.5 | 1.3 | 0.7 | 1.0 | 1.2 | 1.1 | 1.4 | 1.7 | 0.5 | 2.2 | 0.6 | 0.9 | 0.9 | 5.16 |
| YLR284C | 0.9 | 1.0 | 3.8 | 1.9 | 1.6 | 0.9 | 0.8 | 1.2 | 0.9 | 0.9 | 1.5 | 0.6 | 0.8 | 1.3 | 1.0 | 4.5 | 2.9 | 8.1 | 0.84 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YLR354C | 1.2 | 2.5 | 2.3 | 1.5 | 1.6 | 1.5 | 1.1 | 1.4 | 0.4 | 0.9 | 1.7 | 1.2 | 1.0 | 0.9 | 2.4 | 1.3 | 1.0 | 1.5 | 4.53 |
| YMR205C | 0.5 | 0.7 | 2.3 | 0.8 | 1.2 | 1.2 | 0.9 | 0.7 | 0.3 | 0.8 | 1.0 | 1.1 | 1.3 | 0.5 | 0.9 | 0.9 | 0.6 | 0.5 | 4.75 |
| YMR261C | 0.8 | 1.6 | 3.6 | 0.8 | 0.9 | 0.6 | 1.3 | 0.7 | 1.6 | 1.3 | 0.8 | 0.9 | 1.6 | 0.6 | 0.8 | 1.6 | 0.7 | 1.1 | 0.78 |
| YMR323W | 0.8 | 1.1 | 2.9 | 1.1 | 0.7 | 0.4 | 1.1 | 0.8 | 0.5 | 1.3 | 2.5 | 1.2 | 1.8 | 1.2 | 37.3 | 0.6 | 1.1 | 0.6 | 1.04 |
| YOL086C | 1.1 | 0.5 | 2.2 | 1.1 | 1.9 | 1.7 | 1.9 | 0.8 | 0.1 | 1.2 | 2.6 | 1.3 | 1.7 | 0.6 | 1.6 | 1.4 | 1.1 | 1.3 | 4.19 |
| YOR142W | 1.3 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YPL061W | 0.4 | 1.4 | 5.0 | 1.3 | 1.6 | 1.7 | 0.5 | 0.8 | 1.3 | 0.7 | 1.1 | 1.0 | 1.1 | 0.6 | 1.7 | 1.0 | 1.6 | 2.6 | 3.23 |
| YDL107W | 1.3 | 1.3 | 1.0 | 2.2 | 1.0 | 1.3 | 1.8 | 1.8 | 1.2 | 1.8 | 1.0 | 1.0 | 1.2 | 1.5 | 1.0 | 2.0 | 1.1 | 1.5 | 0.51 |
| YDR529C | 1.8 | 1.0 | 0.9 | 3.2 | 1.2 | 0.8 | 0.5 | 1.3 | 0.5 | 0.6 | 0.8 | 0.6 | 0.7 | 1.5 | 0.5 | 1.8 | 1.0 | 2.3 | 3.11 |
| YGL018C | 1.5 | 1.0 | 1.8 | 3.0 | 1.1 | 0.4 | 1.1 | 0.8 | 0.5 | 1.4 | 1.1 | 1.0 | 1.3 | 1.2 | 1.1 | 1.5 | 0.8 | 1.0 | 0.36 |
| YBR185C | 1.5 | 1.0 | 1.3 | 2.0 | 0.8 | 1.2 | 1.2 | 1.1 | 0.9 | 1.6 | 1.2 | 0.7 | 1.0 | 1.7 | 1.0 | 1.7 | 0.8 | 1.3 | 0.89 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGR174C | 1.1 | 1.6 | 0.6 | 2.4 | 1.0 | 1.4 | 1.0 | 1.6 | 1.8 | 0.7 | 1.3 | 0.9 | 1.5 | 1.6 | 0.7 | 3.2 | 1.3 | 2.3 | 1.05 |
| YKL016C | 1.5 | 1.3 | 0.7 | 1.7 | 1.5 | 0.8 | 1.5 | 1.6 | 1.3 | 1.8 | 1.3 | 1.0 | 1.3 | 1.6 | 0.7 | 1.8 | 1.0 | 1.7 | 2.08 |
| YLR395C | 1.8 | 1.3 | 2.2 | 1.9 | 0.7 | 0.4 |  | 1.0 | 1.0 | 0.9 | 1.5 | 0.6 | 0.5 | 1.7 | 0.4 | 1.2 | 1.2 | 2.3 | 1.76 |
| YML1200 | 1.1 | 1.2 | 1.9 | 1.9 | 0.6 | 0.6 | 0.8 | 0.9 | 1.3 | 1.5 | 1.3 | 0.9 | 1.2 | 0.8 | 0.5 | 1.5 | 1.0 | 1.6 | 0.74 |
| YMR073C | 1.1 | 1.1 | 1.2 | 1.5 | 0.8 | 0.9 | 1.0 | 1.1 | 1.2 | 1.2 | 0.9 | 0.8 | 1.2 | 2.0 | 0.9 | 1.5 | 0.8 | 1.2 | 0.69 |
| YOR388C | 1.0 | 1.6 | 1.3 | 4.7 | 1.3 | 1.4 | 1.0 | 0.7 | 0.1 | 1.4 | 1.3 | 0.7 | 1.1 | 1.3 | 4.0 | 0.8 | 1.0 | 0.9 | 0.21 |
| YPL275W | 0.6 | 1.5 | 1.3 | 5.1 | 1.2 | 1.0 | 1.1 | 1.0 | 0.2 | 1.2 | 0.9 | 0.6 | 1.0 | 1.0 | 1.4 | 0.9 | 1.0 | 1.0 | 0.28 |
| YPL276W | 1.2 | 1.5 | 1.6 | 3.0 | 1.5 | 1.1 | 1.2 | 0.9 | −0.2 | 1.8 | −0.4 | 0.6 | 0.9 | 0.9 | 1.0 | 0.6 | 1.1 | 0.8 | 0.22 |
| YGL205W | 1.0 | 0.9 | 0.7 | 0.8 | 1.1 | 1.6 | 0.8 | 1.2 | 0.5 | 0.6 | 0.4 | 1.1 | 1.0 | 1.0 | 2.0 | 4.1 | 3.9 | 9.1 | 0.24 |
| YJL166W | 2.1 | 1.5 | 1.6 | 1.3 | 1.6 | 0.7 | 0.8 | 1.4 | 1.3 | 1.2 | 1.4 | 0.7 | 0.8 | 1.9 | 0.5 | 2.3 | 1.7 | 4.0 | 2.31 |
| YNL202W | 0.7 | 1.3 | 1.2 | 1.7 | 0.9 | 2.0 | 0.9 | 1.2 | 1.3 | 1.1 | 1.2 | 0.9 | 1.8 | 1.0 | 1.4 | 4.2 | 2.4 | 3.3 | 0.47 |
| YDR377W | 1.3 | 1.1 | 1.3 | 1.4 | 1.9 | 1.3 | 1.1 | 1.3 | 1.0 | 0.9 | 1.4 | 0.9 | 0.7 | 1.4 | 0.6 | 1.8 | 1.2 | 2.5 | 3.00 |
| YGL187C | 1.5 | 0.8 | 1.6 | 1.8 | 1.3 | 1.1 | 0.6 | 0.7 | 0.6 | 0.6 | 0.7 | 0.8 | 0.7 | 0.9 | 0.3 | 1.4 | 0.9 | 2.4 | 2.73 |
| YJL216C | 1.1 | 4.7 | 2.2 | 0.9 | 0.8 |  | 1.5 | 1.9 | 1.5 | 1.3 | 1.1 | 1.0 | 1.1 | 1.1 | 1.2 | 1.5 | 1.2 | 2.0 | 0.25 |
| YKR009C | 1.0 | 1.2 | 1.5 | 0.9 | 1.0 | 1.8 | 1.0 | 0.9 | 2.4 | 2.1 | 1.2 | 1.0 | 1.8 | 1.0 | 1.0 | 4.6 | 1.9 | 2.5 | 0.27 |
| YCR046C | 1.0 | 1.2 | 1.2 | 1.6 | 1.0 | 0.8 | 1.2 | 0.9 | 1.9 | 1.4 | 1.5 | 1.1 | 1.5 | 1.3 | 1.4 | 2.8 | 1.3 | 1.0 | 0.63 |
| YML129C | 1.1 | 0.9 | 0.9 | 1.2 | 1.7 | 1.7 | 1.8 | 1.2 | 1.4 | 2.2 | 1.2 | 0.8 | 1.0 | 1.4 | 1.1 | 2.9 | 1.3 | 1.3 | 1.04 |
| YPR184W | 1.2 | 1.4 | 5.7 | 2.2 | 0.9 | 1.5 | 1.3 | 0.7 | 1.9 | 3.2 | 3.6 | 1.4 | 2.5 | 1.3 | 1.5 | 3.1 | 1.0 | 1.7 | 0.37 |
| YDL067C | 1.8 | 1.0 | 1.6 | 1.3 | 2.0 | 0.9 | 0.8 | 1.1 | 0.9 | 0.9 | 1.4 | 1.0 | 0.6 | 1.4 | 0.7 | 1.8 | 1.2 | 1.7 | 1.85 |
| YDL078C | 0.7 | 1.1 | 1.2 | 0.8 | 1.3 | 1.1 | 1.7 | 1.0 | 1.1 | 1.0 | 1.7 | 0.8 | 1.0 | 0.8 | 0.5 | 2.2 | 1.1 | 2.0 | 1.65 |
| YDR079W | 1.3 | 1.1 | 0.8 | 1.1 | 1.2 | 1.7 | 1.3 | 2.6 | 0.9 | 0.8 | 1.3 | 1.1 | 1.3 | 1.5 | 0.6 | 2.6 | 1.1 | 1.3 | 1.06 |
| YGR062C | 0.9 | 1.0 | 0.7 | 1.4 | 0.7 | 0.9 | 1.3 | 0.8 | 1.0 | 1.4 | 1.6 | 1.0 | 1.5 | 1.2 | 0.5 | 1.8 | 0.9 | 1.1 | 0.54 |
| YKR058W | 1.3 | 0.9 | 1.4 | 1.9 | 0.8 | 1.4 | 1.4 | 1.5 | 1.3 | 1.2 | 1.5 | 0.9 | 0.7 | 1.3 | 0.5 | 2.6 | 0.8 | 1.6 | 0.73 |
| YLR295C | 1.5 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YMR267W | 0.8 | 1.8 | 0.7 | 0.9 | 1.0 | 1.4 | 1.2 | 1.5 | 0.4 | 0.8 | 1.0 | 0.8 | 0.7 | 1.0 | 0.9 | 2.6 | 0.9 | 1.3 | 0.94 |

TABLE 5

Transport facilitation protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR008C | 3.0 | 2.4 | 4.9 | 0.7 | 0.9 | 1.0 | 0.9 | 2.8 | 54.6 | 21.1 | 9.4 | 0.8 | 2.0 | 4.1 | 0.8 | 3.1 | 2.0 | 1.2 | 0.37 |
| YBR296C | 7.0 | 4.3 | 2.2 | 2.5 | 1.4 | 1.4 | 0.2 | 1.1 | 0.4 | 1.8 | 1.5 | 1.6 | 2.0 | 2.3 | 1.7 | 0.3 | 3.8 | 4.0 | 0.54 |
| YDR406W | 0.8 | 1.2 | 3.1 | 1.1 | 1.0 | 5.9 | 1.8 | 0.6 | 1.1 | 1.7 | 1.4 | 3.9 | 7.7 | 0.5 | 0.8 | 5.5 | 2.7 | 5.6 | 0.53 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YGR281W | 1.2 | 1.0 | 1.3 | 2.2 | 0.6 | 1.9 | 0.9 | 0.7 | 2.7 | 1.4 | 0.7 | 2.4 | 12.9 | 0.9 | 2.1 | 1.1 | 2.8 | 3.1 | 1.04 |
| YHL047C | 0.6 | 4.4 | 1.0 | 1.0 | 1.2 | 8.4 | 16.8 | 1.5 | 1.2 | 11.9 | 1.0 | 2.6 | 3.8 | 0.5 | 1.1 | 2.3 | 1.2 | 1.2 | 0.74 |
| YBR294W | 6.3 | 14.4 | 0.9 | 2.6 | 1.4 | 1.2 | 1.1 | 1.0 | 5.2 | 5.2 | 1.2 | 1.0 | 3.1 | 1.3 | 1.0 | 0.9 | 1.0 | 0.9 | 0.18 |
| YGL006W | 2.5 | 1.3 | 1.3 | 2.6 | 1.0 | 1.0 | 1.3 | 0.9 | 3.0 | 1.2 | 0.8 | 0.9 | 4.5 | 0.9 | 1.1 | 1.7 | 2.4 | 4.1 | 1.37 |
| YGR197C | 1.1 | 2.4 | 2.5 | 1.0 | 0.7 | 0.5 | 1.3 | 0.8 | 16.7 | 3.2 | 1.1 | 1.2 | 2.4 | 1.5 | 1.0 | 1.5 | 1.7 | 1.9 | 0.37 |
| YJL034W | 0.7 | 1.7 | 3.0 | 0.8 | 1.2 | 1.1 | 1.3 | 1.5 | 2.8 | 1.1 | 1.3 | 1.6 | 6.1 | 0.6 | 7.9 | 0.6 | 1.1 | 1.0 | 4.58 |
| YNL055C | 1.1 | 1.8 | 5.5 | 2.0 | 0.9 | 2.6 | 1.2 | 0.7 | 1.1 | 1.0 | 1.9 | 1.7 | 2.4 | 0.9 | 1.1 | 2.6 | 1.2 | 1.7 | 4.10 |
| YBR052C | 1.6 | 1.6 | 1.5 | 2.6 | 1.4 | 2.1 | 3.0 | 1.3 | 2.3 | 2.5 | 1.7 | 1.3 | 2.1 | 1.5 | 0.7 | 3.1 | 1.8 | 3.1 | 2.77 |
| YBR207W | 0.8 | 1.7 | 0.8 | 2.0 | 1.7 | 1.6 | 4.3 | 0.9 | 1.7 | 2.2 | 1.1 | 0.9 | 2.2 | 0.9 | 1.4 | 1.4 | 1.2 | 1.4 | 1.39 |
| YBR293W | 1.9 | 3.1 | 1.0 | 1.8 | 0.8 | 0.9 | 0.9 | 0.9 | 5.5 | 2.4 | 1.1 | 1.0 | 3.0 | 1.4 | 3.1 | 1.6 | 1.0 | 0.9 | 0.94 |
| YDL198C | 1.4 | 1.0 | 2.1 | 1.4 | 0.7 | 0.8 | 1.0 | 1.1 | 1.9 | 2.7 | 2.5 | 1.2 | 2.0 | 1.7 | 1.2 | 1.4 | 1.5 | 1.1 | 1.19 |
| YDL245C | 1.0 | 2.4 | 1.6 | 2.2 | 1.3 | 1.1 | 1.2 | 1.2 | 0.4 | 2.8 | 1.5 | 1.0 | 2.0 | 1.2 | 1.8 | 1.5 | 1.0 | 1.1 | 0.28 |
| YDR497C | 0.7 | 0.5 | 0.6 | 1.3 | 0.7 | 0.6 | 0.5 | 0.6 | 0.4 | 0.8 | 0.7 | 0.9 | 2.7 | 0.6 | 10.1 |  | 1.6 | 1.8 | 1.45 |
| YER053C | 1.6 | 1.8 | 1.9 | 1.7 | 0.6 | 2.8 | 2.8 | 1.3 | 1.3 | 3.9 | 2.4 | 1.7 | 4.1 | 1.3 | 1.1 | 2.8 | 1.2 | 2.3 | 1.83 |
| YFL041W | 0.7 | 1.6 | 1.4 | 1.2 | 1.2 | 2.0 | 3.4 | 1.0 | 0.8 | 5.1 | 0.9 | 1.1 | 1.8 | 1.0 | 0.9 | 1.4 | 1.1 | 0.9 | 0.89 |
| YGR055W | 2.5 | 5.7 | 12.0 | 0.7 | 1.3 | 1.1 | 0.6 | 1.1 | 5.0 | 2.4 | 1.5 | 0.9 | 1.9 | 1.2 | 2.1 | 0.6 | 0.7 | 0.7 | 1.42 |
| YJL219W | 1.2 | 2.5 | 3.1 | 1.6 | 1.2 | 1.5 | 0.9 | 1.5 | 4.0 | 2.3 | 2.3 | 1.1 | 4.0 | 1.1 | 2.6 | 1.4 | 1.6 | 1.2 | 0.91 |
| YJR106W | 0.9 | 3.8 | 1.5 | 1.1 | 0.9 | 1.2 | 1.0 | 0.9 | 2.0 | 1.6 | 1.6 | 0.9 | 3.5 | 0.9 | 1.2 | 1.9 | 1.2 | 1.3 | 0.29 |
| YKL146W | 0.8 | 1.3 | 1.3 | 0.9 | 1.0 | 1.3 | 0.9 | 0.8 | 4.6 | 2.8 | 0.9 | 1.1 | 2.7 | 1.0 | 1.5 | 1.3 | 1.0 | 0.9 | 0.42 |
| YLL028W | 0.6 | 0.9 | 4.6 | 0.5 | 0.9 | 1.7 | 1.0 | 0.7 | 1.2 | 2.3 | 0.7 | 1.3 | 4.1 | 0.7 | 3.1 | 0.6 | 1.2 | 1.2 | 1.02 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YOL119C | 2.6 | 4.8 | 1.5 | 2.3 | 1.5 | 0.9 | 2.2 | 2.0 | 5.0 | 7.4 | 3.4 | 0.9 | 1.6 | 2.4 | 4.7 | 2.8 | 1.4 | 1.0 | 0.37 |
| YOL163W | 1.5 | 3.2 | 2.1 | 3.3 | 0.9 | 0.5 | 0.9 | 1.1 | 7.5 | 6.2 | 1.6 | 1.0 | 2.4 | 1.2 | 1.0 | 1.4 | 0.8 | 0.3 | 0.30 |
| YOR035C | 1.2 | 1.2 | 0.3 | 1.2 | 1.0 | 1.9 | 1.3 | 1.0 | 1.3 | 1.7 | 1.0 | 1.1 | 2.5 | 0.9 | 3.8 | 1.8 | 1.6 | 2.1 | 0.52 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YOR273C | 0.7 | 1.0 | 1.7 | 1.0 | 1.1 | 0.4 | 0.4 | 0.6 | 0.6 | 0.5 | 1.5 | 0.8 | 2.6 | 0.5 | 0.8 | 0.6 | 3.2 | 3.1 | 1.20 |
| YOR332W | 1.1 | 1.0 | 1.0 | 1.0 | 0.9 | 1.8 | 0.9 | 1.5 | 1.8 | 1.1 | 1.5 | 1.0 | 2.2 | 1.1 | 1.2 | 1.2 | 1.3 | 1.7 | 3.58 |
| YCR098C | 1.6 | 3.0 | 1.7 | 2.0 | 1.4 | 1.6 | 1.2 | 1.0 | 1.4 | 2.4 | 1.3 | 1.3 | 1.4 | 1.1 | 11.0 | 0.8 | 1.7 | 1.6 | 0.22 |
| YGR138C | 1.1 | 1.6 | 1.0 | 1.2 | 0.8 | 0.8 | 0.7 | 1.0 | 0.5 | 1.0 | 0.7 | 0.6 | 0.6 | 0.9 | 4.5 | 0.7 | 0.7 | 0.7 | 1.24 |
| YBR295W | 1.4 | 1.5 | 3.3 | 1.1 | 0.8 |  | 1.6 | 0.9 | 1.2 | 3.3 | 1.1 | 0.9 | 1.8 | 1.1 | 4.8 | 1.4 | 1.3 | 1.2 | 0.27 |
| YGL255W | 0.7 | 0.9 | 0.9 | 0.8 | 1.4 | 1.1 | 1.0 | 0.7 | 0.3 | 5.0 | 0.5 | 0.7 | 0.2 | 1.0 | 2.6 | 0.5 | 0.6 | 0.5 | 1.36 |
| YHL035C | 0.7 | 1.3 | 0.9 | 1.9 | 0.9 | 4.1 | 1.7 | 1.1 | 0.6 | 4.6 | 0.9 | 1.4 | 1.1 | 0.8 | 3.1 | 2.4 | 1.1 | 1.2 | 0.77 |
| YIL022W | 0.8 | 0.7 | 1.1 | 1.6 | 0.8 | 1.2 | 0.7 | 0.8 | 1.1 | 1.3 | 1.0 | 0.9 | 1.2 | 0.6 | 2.9 | 1.1 | 0.8 | 0.7 | 0.52 |
| YLR378C | 0.7 | 0.9 | 2.6 | 0.5 | 1.0 | 1.2 | 0.7 | 0.5 | 1.1 | 0.7 | 1.0 | 1.2 | 1.6 | 0.4 | 5.9 | 0.4 | 0.9 | 0.7 | 1.23 |
| YCL038C | 1.6 | 1.6 | 1.4 | 1.6 | 1.2 | 3.2 | 1.5 | 1.2 | 1.1 | 0.9 | 2.0 | 1.3 | 1.9 | 1.3 | 2.0 | 1.8 | 1.4 | 1.5 | 1.04 |
| YFL054C | 1.6 | 1.1 | 1.4 | 2.2 | 1.3 | 2.4 | 1.1 | 1.5 | 2.0 | 2.3 | 1.7 | 1.2 | 2.3 | 0.9 | 1.4 | 1.3 | 1.7 | 1.4 | 1.06 |
| YHL040C | 1.6 | 4.9 | 1.5 | 0.4 | 1.1 | 7.3 | 4.0 | 1.5 | 1.1 | 11.3 | 1.7 | 2.0 | 2.0 | 1.1 | 3.4 | 1.0 | 1.4 | 1.0 | 0.69 |
| YKR039W | 1.4 | 3.5 | 1.3 | 1.7 | 1.0 | 2.8 | 1.0 | 1.0 | 1.9 | 2.0 | 1.9 | 1.5 | 1.3 | 1.2 | 1.7 | 1.9 | 0.9 | 1.1 | 0.40 |
| YPL271W | 1.2 | 3.2 | 4.1 | 1.2 | 1.4 | 3.3 | 1.2 | 0.9 | 0.6 | 1.2 | 1.7 | 0.8 | 1.2 | 1.3 | 0.8 | 1.4 | 1.2 | 1.3 | 1.34 |
| YBR068C | 1.1 | 1.0 | 1.9 | 2.5 | 1.4 | 1.9 |  | 1.0 | 0.8 | 2.5 | 0.8 | 0.8 | 2.2 | 1.8 | 1.6 | 5.5 | 1.1 | 1.3 | 1.99 |
| YCR037C | 0.7 | 1.0 | 0.8 | 0.8 | 1.3 | 1.8 | 1.0 | 0.7 | 0.6 | 0.6 | 0.8 | 0.7 | 1.3 | 0.8 | 1.0 | 1.1 | 1.4 | 0.9 | 0.74 |
| YDL128W | 0.8 | 1.1 | 2.1 | 1.0 | 1.0 | 2.3 | 0.9 | 0.8 | 0.5 | 0.7 | 1.2 | 0.9 | 1.6 | 0.7 | 1.1 | 1.0 | 0.9 | 1.0 | 2.80 |
| YDR270W | 0.7 | 1.5 | 1.4 | 1.3 | 1.0 | 2.2 | 1.7 | 1.2 | 2.9 | 3.6 | 1.0 | 1.0 | 1.8 | 1.0 | 1.4 | 1.1 | 0.9 | 0.7 | 0.38 |
| YEL065W | 0.3 | 3.8 | 1.2 | 0.4 | 1.4 | 2.3 | 4.3 | 0.9 | 0.1 | 4.9 | 0.6 | 1.7 | 0.8 | 0.4 | 2.2 | 2.6 | 0.7 | 0.6 | 2.10 |
| YGL008C | 0.6 | 0.7 | 3.1 | 0.9 | 0.8 | 1.9 | 1.4 | 0.7 | 0.0 | 0.4 | 0.7 | 2.4 | 1.9 | 1.2 | 1.0 | 2.1 | 1.1 | 1.0 | 4.08 |
| YGL104C | 0.8 | 2.0 | 2.1 | 1.8 | 1.0 | 2.1 | 1.2 | 0.8 | 4.6 | 2.1 | 1.8 | 1.1 | 2.0 | 1.0 | 0.9 | 1.7 | 1.3 | 1.3 | 0.58 |
| YGL167C | 0.9 | 0.7 | 1.6 | 1.3 | 1.2 | 2.0 | 1.2 | 0.8 | 1.3 | 1.1 | 0.8 | 1.1 | 1.5 | 0.8 | 1.3 | 1.3 | 1.4 | 1.4 | 1.41 |
| YGR065C | 0.8 | 1.5 | 2.6 | 1.1 | 1.2 | 2.4 | 1.0 | 1.0 | 1.2 | 2.6 | 1.1 | 0.5 | 0.8 | 1.3 | 1.2 | 1.1 | 0.7 | 0.7 | 0.68 |
| YHR092C | 2.3 | 1.0 | 7.5 | 2.5 | 1.4 | 1.7 | 0.5 | 1.5 | 0.2 | 0.9 | 1.5 | 1.0 | 0.5 | 1.6 | 0.2 | 1.2 | 0.9 | 1.3 | 6.09 |
| YIL088C | 0.9 | 2.1 | 2.1 | 1.3 | 1.6 | 2.2 | 1.7 | 0.8 | 1.0 | 1.7 | 1.8 | 0.9 | 1.5 | 1.2 | 1.2 | 1.8 | 1.2 | 1.4 | 1.89 |
| YNL259C | 1.6 | 3.5 | 1.1 | 1.2 | 1.1 | 3.9 | 3.8 | 1.5 | 1.6 | 2.1 | 1.6 | 0.7 | 1.1 | 1.4 | 0.7 | 1.7 | 2.6 | 2.4 | 1.22 |
| YOR270C | 0.7 | 0.5 | 2.0 | 0.8 | 0.8 | 1.8 | 1.0 | 0.6 | 0.4 | 0.9 | 1.5 | 0.7 | 1.3 | 0.7 | 1.1 | 0.8 | 0.9 | 0.9 | 3.49 |
| YPL265W | 0.7 | 0.4 | 2.3 | 1.1 | 1.0 | 2.3 | 8.9 | 2.3 | 0.2 | 1.2 | 1.8 | 0.9 | 1.1 | 1.1 | 1.2 | 2.0 | 0.5 | 0.4 | 1.42 |
| YPR124W | 0.2 | 0.4 | 0.3 | 1.4 | 2.0 | 2.0 | 2.9 | 2.7 | 0.2 | 1.5 | 2.0 | 0.8 | 0.6 | 0.4 | 1.1 | 2.4 | 1.0 | 1.3 | 2.57 |
| YER119C | 0.7 | 2.1 | 1.8 | 0.7 | 0.8 | 1.3 | 0.8 | 0.6 | 5.8 | 1.2 | 2.2 | 0.7 | 1.6 | 1.0 | 2.3 | 0.8 | 1.0 | 0.9 | 0.32 |
| YFL055W | 2.0 | 6.7 | 1.3 | 2.5 | 1.5 | 1.1 | 1.4 | 1.3 | 23.9 | 6.5 | 2.7 | 0.9 | 1.3 | 1.5 | 0.7 | 1.4 | 1.4 | 1.0 | 0.23 |
| YLL055W | 2.6 | 19.0 | 4.8 | 1.7 | 1.0 | 1.4 | 1.7 | 1.4 | 19.1 | 14.0 | 3.6 | 0.7 | 1.5 | 1.3 | 0.7 | 2.8 | 1.1 | 1.3 | 0.47 |
| YHL036W | 2.2 | 4.8 | 3.4 | 2.0 | 1.3 | 1.3 | 1.0 | 1.2 | 9.0 | 4.4 | 2.3 | 1.2 | 1.5 | 1.2 | 0.9 | 1.1 | 1.0 | 1.0 | 0.60 |
| YHR048W | 2.5 | 1.4 | 1.4 | 1.7 | 1.0 | 0.8 | 0.8 | 1.9 | 4.5 | 2.7 | 2.0 | 0.9 | 1.1 | 1.7 | 0.9 | 1.4 | 0.7 | 0.9 | 0.26 |
| YKL221W | 1.3 | 0.7 | 1.2 | 1.0 | 1.0 | 0.9 | 1.3 | 1.2 | 7.3 | 2.7 | 1.9 | 0.7 | 1.6 | 1.4 | 1.1 | 1.3 | 0.8 | 0.9 | 0.27 |
| YLR092W | 5.0 | 5.6 | 1.4 | 0.6 | 1.3 | 1.0 | 1.3 | 1.5 | 12.7 | 5.8 | 3.1 | 1.0 | 1.8 | 1.4 | 0.9 | 1.2 | 1.0 | 1.1 | 0.24 |
| YML116W | 4.1 | 1.3 | 1.5 | 1.4 | 1.2 | 0.9 | 1.4 | 2.2 | 1.4 | 3.1 | 4.3 | 0.5 | 0.8 | 2.0 | 1.9 | 1.0 | 1.0 | 1.0 | 0.94 |
| YBR291C | 2.0 | 0.9 | 1.0 | 1.5 | 0.9 | 1.1 | 0.9 | 2.2 | 0.9 | 1.0 | 1.1 | 0.9 | 1.0 | 1.7 | 0.5 | 1.5 | 0.9 | 1.3 | 1.19 |
| YCL069W | 0.9 | 4.5 | 0.9 | 0.8 | 0.9 |  | 1.4 | 1.3 | 1.2 | 6.9 | 1.0 | 0.9 | 0.8 | 1.3 | 1.4 | 0.9 | 1.0 | 1.0 | 0.25 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL188C | 1.3 | 0.7 | 1.9 | 2.4 | 1.0 | 0.8 | 1.1 | 0.7 | 2.5 | 2.8 | 1.1 | 1.2 | 1.2 | 2.1 | 1.4 | 2.7 | 1.1 | 1.5 | 0.27 |
| YKL217W | 1.8 | 2.4 | 1.0 | 2.1 | 1.1 | 1.2 | 1.6 | 1.1 | 0.9 | 4.1 | 1.6 | 0.8 | 1.2 | 1.2 | 2.2 | 3.0 | 1.7 | 3.3 | 0.29 |
| YKR105C | 0.8 | 0.9 | 0.9 | 1.5 | 1.0 | 1.2 | 1.0 | 1.3 | 1.0 | 5.2 | 0.0 | 0.8 | 2.5 | 1.2 | 1.5 | 0.7 | 0.8 | 1.0 | 0.26 |
| YOL158C | 0.7 | 4.0 | 2.4 | 0.9 | 1.2 | 2.0 | 1.6 | 0.7 | 1.7 | 6.1 | 0.7 | 0.9 | 1.4 | 1.0 | 0.9 | 1.2 | 1.4 | 1.7 | 1.30 |

TABLE 5-continued

Transport facilitation protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPL224C | 1.0 | 2.2 | 1.3 | 2.5 | 0.6 | 1.3 | 2.2 | 1.3 | 3.2 | 4.2 | 0.8 | 1.1 | 1.3 | 1.4 | 1.0 | 2.5 | 1.3 | 1.9 | 0.64 |
| YPR201W | 33.2 | 0.9 | 1.1 | 1.0 | 1.2 | 1.9 | 0.8 | 0.9 | 8.3 | 5.6 | 2.2 | 0.7 | 1.1 | 1.8 | 0.8 | 0.9 | 0.8 | 0.9 | 0.29 |
| YAL067C | 2.7 | 12.1 | 1.5 | 1.4 | 0.7 | 1.2 | 0.8 | 1.1 | 7.6 | 2.9 | 1.2 | 1.0 | 1.1 | 1.3 | 2.4 | 1.6 | 1.0 | 1.0 | 0.33 |
| YDL149W | 0.8 | 2.0 | 1.2 | 1.6 | 1.5 | 1.0 | 0.7 | 1.2 | 3.2 | 2.0 | 1.2 | 0.7 | 1.5 | 1.2 | 1.8 | 1.4 | 0.8 | 1.0 | 0.33 |
| YJL094C | 1.0 | 1.7 | 1.3 | 2.0 | 1.4 | 1.3 | 1.7 | 0.8 | 5.4 | 2.9 | 1.1 | 1.2 | 2.6 | 1.0 | 1.0 | 1.8 | 2.1 | 2.0 | 0.84 |
| YLL061W | 3.6 | 2.8 | 9.2 | 0.4 | 0.8 | 0.8 | 0.9 | 1.4 | 3.7 | 5.5 | 1.7 | 0.7 | 0.9 | 1.3 | 1.4 | 1.0 | 0.6 | 0.7 | 0.33 |
| YPL274W | 0.8 | 4.2 | 3.8 | 0.8 | 0.6 | 1.1 | 0.7 | 0.9 | 4.1 | 3.6 | 2.0 | 0.5 | 0.6 | 0.9 | 1.5 | 1.1 | 0.7 | 0.6 | 0.41 |
| YBR241C | 0.9 | 9.3 | 2.6 | 0.9 | 0.9 | 1.5 | 1.4 | 0.7 | 29.8 | 2.2 | 1.4 | 1.4 | 1.4 | 0.9 | 1.6 | 0.7 | 1.0 | 1.2 | 1.25 |
| YDL206W | 0.9 | 1.7 | 1.8 | 1.4 | 1.1 | 5.7 | 2.0 | 1.1 | 1.6 | 1.5 | 0.6 | 1.0 | 1.3 | 1.0 | 1.1 | 3.1 | 1.0 | 1.1 | 0.35 |
| YDR040C | 0.7 | 1.4 | 3.7 | 0.8 | 1.0 | 1.7 | 0.7 | 0.8 | 2.0 | 1.2 | 0.8 | 0.9 | 1.8 | 0.9 | 0.8 | 1.4 | 1.4 | 1.6 | 1.25 |
| YFR045W | 1.1 | 1.6 | 1.1 | 1.1 | 1.0 | 1.0 | 0.6 | 1.0 | 2.2 | 1.0 | 1.4 | 1.0 | 1.1 | 1.0 | 1.1 | 0.6 | 0.9 | 0.8 | 0.84 |
| YIL170W | 1.1 | 1.0 | 2.5 | 2.2 | 0.9 | 8.8 | 0.5 | 1.2 | 5.7 | 3.2 | 1.7 | 0.7 | 1.9 | 1.1 | 2.3 | 1.8 | 1.6 | 1.5 | 0.48 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YKL209C | 1.0 | 1.0 | 1.3 | 0.8 | 1.2 | 3.3 | 0.9 | 1.4 | 2.4 | 1.6 | 0.8 | 0.9 | 1.4 | 1.1 | 1.0 | 1.1 | 1.1 | 1.0 | 0.30 |
| YKR106W | 1.3 | 0.8 | 2.1 | 1.4 | 1.2 | 1.6 | 0.9 | 1.3 | 10.5 | 7.4 | 1.8 | 0.8 | 1.4 | 1.7 |  | 2.8 | 0.9 | 0.8 | 0.16 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YPL147W | 1.0 | 0.8 | 2.3 | 1.2 | 1.2 | 1.1 | 1.0 | 0.9 | 2.4 | 2.4 | 1.3 | 0.9 | 1.5 | 1.0 | 2.4 | 2.5 | 1.5 | 3.6 | 0.33 |
| YIL166C | 1.9 | 12.5 | 2.1 | 1.2 | 1.0 | 1.9 |  | 1.3 | 2.5 | 2.9 | 1.8 | 0.9 | 1.5 | 1.1 | 1.3 | 0.7 | 1.2 | 0.9 | 0.28 |
| YMR058W | 0.3 | 5.1 | 2.1 | 0.3 | 0.8 | 2.6 | 1.8 | 0.8 | 0.2 | 1.4 | 0.8 | 0.8 | 0.4 | 0.3 | 0.5 | 0.4 | 0.6 | 0.5 | 1.66 |
| YNL142W | 0.7 | 2.4 | 2.5 | 0.8 | 1.3 | 0.9 | 1.1 | 0.8 | 0.9 | 0.6 | 0.9 | 1.2 | 0.9 | 0.8 | 0.3 | 1.0 | 1.0 | 0.9 | 0.44 |
| YDL210W | 1.2 | 2.2 | 2.7 | 1.1 | 0.9 | 1.3 | 0.8 | 1.1 | 1.2 | 1.4 | 0.6 | 0.8 | 1.2 | 1.1 | 1.9 | 0.9 | 1.1 | 0.9 | 0.20 |
| YCL025C | 1.1 | 4.6 | 2.5 | 1.7 | 0.9 | 0.9 | 0.7 | 0.7 | 0.3 | 0.3 | 1.0 | 1.1 | 0.5 | 0.7 | 0.8 | 0.6 | 0.6 | 0.6 | 1.98 |
| YJL212C | 0.8 | 3.2 | 3.1 | 0.5 | 1.2 | 1.1 | 0.7 | 0.7 | 1.1 | 1.3 | 0.9 | 0.4 | 1.0 | 0.8 | 0.3 | 0.5 | 0.6 | 0.5 | 0.59 |
| YBR132C | 0.9 | 1.9 | 2.4 | 1.8 | 0.8 | 1.2 | 1.1 | 0.8 | 0.8 | 1.1 | 1.9 | 1.0 | 1.4 | 1.1 | 1.5 | 1.3 | 1.1 | 1.3 | 0.43 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YCR024C-A | 0.8 | 0.9 | 3.2 |  | 0.9 | 1.2 | 0.8 | 0.8 | 0.2 | 0.7 | 1.5 | 1.0 | 0.5 | 0.8 | 1.3 | 1.5 | 0.9 | 1.4 | 4.02 |
| YDR342C | 2.8 | 1.1 | 12.2 | 5.7 | 1.6 | 1.1 | 0.8 | 1.2 | 0.2 | 2.2 | 2.9 | 1.0 | 0.6 | 0.9 | 0.5 | 2.4 | 1.0 | 2.2 | 5.23 |
| YDR343C | 1.2 | 1.0 | 20.6 | 4.6 | 1.3 | 1.3 | 0.7 | 1.2 | 0.3 | 2.1 | 2.3 | 1.0 | 0.8 | 0.8 | 0.5 | 2.8 | 1.1 | 2.3 | 5.81 |
| YEL027W | 1.2 | 0.6 | 3.4 | 1.1 | 1.0 | 1.1 | 0.8 | 0.9 | 0.9 | 1.1 | 0.9 | 0.9 | 0.7 | 1.4 | 1.5 | 1.6 | 1.0 | 1.4 | 4.75 |
| YHR094C | 0.7 | 1.2 | 5.3 | 1.6 | 1.1 | 1.6 | 0.8 | 1.2 | 0.3 | 1.2 | 0.6 | 0.9 | 0.7 | 0.6 | 2.7 | 0.9 | 1.4 | 1.4 | 4.82 |
| YHR175W | 0.8 | 2.0 | 2.4 | 1.5 | 0.9 | 1.0 | 1.6 | 0.9 | 0.6 | 2.0 | 1.1 | 1.4 | 1.2 | 0.7 | 1.3 | 2.3 | 1.3 | 1.2 | 1.01 |
| YIL056W | 1.1 | 0.9 | 6.2 | 1.4 | 1.2 | 1.0 | 0.6 | 0.7 | 1.2 | 1.6 | 0.7 | 1.0 | 1.5 | 1.0 | 0.5 | 0.9 | 1.5 | 1.2 | 0.71 |
| YMR203W | 0.8 | 0.7 | 3.0 | 1.4 | 0.6 | 1.1 | 0.8 | 0.7 | 0.7 | 1.2 | 2.3 | 0.7 | 1.1 | 0.7 | 1.2 | 0.9 | 0.8 | 0.7 | 1.62 |
| YBL099W | 0.8 | 0.9 | 3.1 | 1.4 | 1.0 | 0.9 | 0.9 | 0.8 | 0.9 | 0.7 | 2.1 | 1.0 | 0.9 | 0.6 | 1.0 | 0.9 | 0.7 | 1.2 | 3.49 |
| YBR127C | 0.8 | 0.7 | 2.2 | 1.1 | 1.4 | 1.1 | 0.9 | 1.1 | 0.6 | 1.3 | 1.1 | 0.9 | 0.9 | 0.6 | 1.3 | 1.4 | 0.8 | 1.0 | 4.59 |
| YDR038C | 0.6 | 1.3 | 3.1 | 0.9 | 0.9 | 1.8 | 0.7 | 0.9 | 1.4 | 0.9 | 0.9 | 0.7 | 2.0 | 0.8 | 0.8 | 1.4 | 1.3 | 1.5 | 1.32 |
| YDR039C | 0.6 | 1.6 | 3.2 | 0.9 | 1.3 | 1.1 | 0.8 | 0.6 | 1.8 | 1.0 | 0.9 | 0.8 | 1.8 | 0.9 | 1.2 | 1.4 | 1.1 | 1.6 | 1.39 |
| YDR298C | 1.3 | 1.2 | 2.6 | 1.3 | 1.3 | 1.2 | 1.0 | 1.2 | 1.0 | 1.6 | 1.2 | 1.1 | 1.2 | 1.5 | 0.8 | 2.0 | 1.1 | 1.6 | 2.69 |
| YDR345C | 0.8 | 0.9 | 5.6 | 2.6 | 1.3 | 1.2 | 1.1 | 1.2 | 0.2 | 1.1 | 1.5 | 1.4 | 1.2 | 0.8 | 0.8 | 1.0 | 1.3 | 1.8 | 5.65 |
| YEL063C | 0.7 | 0.8 | 2.4 | 1.3 | 1.2 | 1.3 | 0.7 | 0.6 | 0.8 | 1.7 | 0.8 | 1.1 | 1.1 | 0.8 | 1.3 | 1.0 | 0.7 | 0.7 | 1.12 |
| YFL011W | 1.2 | 0.7 | 3.7 | 3.3 | 1.3 | 1.0 | 0.8 | 0.8 | 0.3 | 1.6 | 2.1 | 0.9 | 0.8 | 0.8 | 1.7 | 1.2 | 0.8 | 1.0 | 1.25 |
| YGR082W | 1.0 | 0.9 | 2.2 | 1.0 | 0.9 | 1.1 | 0.9 | 0.8 | 0.6 | 0.9 | 1.3 | 0.8 | 0.5 | 0.9 | 1.2 | 1.3 | 0.9 | 0.8 | 1.47 |
| YGR191W | 0.8 | 0.7 | 1.6 | 1.5 | 0.8 | 1.1 | 0.7 | 0.7 | 0.1 | 0.7 | 1.6 | 0.7 | 1.0 | 0.7 | 1.5 | 0.7 | 0.8 | 0.8 | 1.58 |
| YGR260W | 0.6 | 0.7 | 3.4 | 0.8 | 0.8 | 0.9 | 0.9 | 0.5 | 0.3 | 0.4 | 1.3 | 0.6 | 0.5 | 0.7 | 1.8 | 1.0 | 0.9 | 0.9 | 1.71 |
| YHR026W | 0.9 | 1.0 | 1.9 | 1.0 | 1.1 | 1.3 | 0.9 | 1.6 | 1.1 | 0.9 | 1.4 | 0.7 | 0.7 | 1.3 | 2.4 | 1.2 | 0.9 | 1.1 | 3.40 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR121W | 0.9 | 1.1 | 3.3 | 1.0 | 0.8 | 1.5 | 1.0 | 0.7 | 0.8 | 1.3 | 0.9 | 0.8 | 1.0 | 0.7 | 0.9 | 1.2 | 1.1 | 1.4 | 3.99 |
| YLR081W | 1.3 | 0.8 | 2.8 | 3.6 | 1.0 | 0.9 | 0.7 | 0.9 | 0.1 | 2.2 | 2.6 | 1.0 | 0.6 | 1.0 | 0.7 | 1.2 | 0.7 | 0.9 | 1.46 |
| YMR011W | 1.3 | 1.0 | 9.4 | 5.5 | 0.9 | 0.6 | 0.8 | 1.1 | 0.0 | 0.7 | 1.5 | 0.8 | 0.4 | 0.6 | 0.6 | 1.2 | 1.3 | 1.6 | 4.95 |
| YOL156W | 1.1 | 0.7 | 2.5 | 1.1 | 1.2 | 1.2 | 1.0 | 1.0 | 2.3 | 2.1 | 1.1 | 0.9 | 1.7 | 0.9 | 1.9 | 0.9 | 0.9 | 0.9 | 0.53 |
| YPL036W | 0.5 | 0.8 | 2.8 | 0.9 | 1.3 | 0.7 | 0.3 | 0.5 | 0.1 | 0.3 | 0.8 | 0.5 | 0.3 | 0.6 | 1.0 | 0.7 | 0.4 | 0.5 | 3.66 |
| YGR096W | 1.5 | 1.0 | 1.1 | 4.6 | 1.2 | 1.7 | 0.9 | 1.0 | 0.8 | 0.8 | 0.8 | 0.8 | 1.1 | 1.2 | 0.9 | 0.8 | 0.8 | 1.0 | 0.49 |
| YIL006W | 1.0 | 1.1 | 1.4 | 2.9 | 0.8 | 0.3 | 0.8 | 0.6 | 0.9 | 1.1 | 1.0 | 0.9 | 0.8 | 1.0 | 1.5 | 1.7 | 0.8 | 0.9 | 0.28 |
| YKL016C | 1.5 | 1.3 | 0.7 | 1.7 | 1.5 | 0.8 | 1.5 | 1.6 | 1.3 | 1.8 | 1.3 | 1.0 | 1.3 | 1.6 | 0.7 | 1.8 | 1.0 | 1.7 | 2.08 |
| YKR067W | 0.8 | 2.6 | 1.5 | 2.5 | 1.3 | 1.8 | 2.0 | 0.8 | 1.6 | 2.3 | 1.3 | 1.0 | 1.3 | 1.3 | 1.3 | 2.0 | 0.8 | 1.5 | 0.58 |
| YMR162C | 0.8 | 1.1 | 1.1 | 2.0 | 0.9 | 1.0 | 0.8 | 0.8 | 0.7 | 1.0 | 1.7 | 0.7 | 0.9 | 1.0 | 1.0 | 0.8 | 0.8 | 1.1 | 0.32 |
| YOR348C | 1.1 | 0.7 | 1.2 | 2.0 | 0.9 | 0.7 | 0.8 | 0.8 | 0.5 | 0.4 | 1.1 | 0.7 | 1.1 | 1.2 | 1.6 | 1.7 | 0.9 | 0.9 | 0.18 |
| YPR192W | 0.9 | 1.1 | 0.9 | 5.0 | 1.2 | 0.9 | 0.9 | 0.6 | 0.7 | 1.3 | 0.7 | 0.5 | 1.1 | 0.7 | 1.7 | 2.6 | 1.6 | 0.9 | 0.28 |
| YPR194C | 2.2 | 1.4 | 0.5 | 2.9 | 1.3 | 1.5 | 0.7 | 1.0 | 0.5 | 0.6 | 0.7 | 0.7 | 1.0 | 1.0 | 0.4 | 0.8 | 1.0 | 0.9 | 0.27 |
| YDR086C | 1.3 | 1.0 | 1.2 | 1.4 | 1.0 | 0.8 | 2.0 | 1.9 | 0.6 | 0.8 | 1.1 | 0.7 | 0.7 | 1.5 | 2.1 | 1.3 | 1.4 | 1.9 | 2.60 |
| YGR224W | 0.9 | 1.2 | 1.2 | 1.2 | 1.4 | 0.8 | 0.4 | 0.6 | 0.9 | 0.9 | 0.8 | 0.6 | 0.8 | 0.9 | 1.1 | 1.0 | 2.8 | 1.3 | 0.27 |
| YDR387C | 0.8 | 0.9 | 1.2 | 2.2 | 0.9 | 1.2 | 1.3 | 0.7 | 1.4 | 2.0 | 2.0 | 1.0 | 1.3 | 0.9 | 1.4 | 2.7 | 1.2 | 1.1 | 0.86 |
| YFL050C | 0.7 | 1.0 | 1.1 | 2.2 | 1.0 | 0.9 | 0.8 | 0.9 | 0.5 | 1.6 | 1.2 | 0.9 | 1.2 | 1.0 | 1.4 | 2.3 | 0.8 | 1.0 | 0.36 |
| YBR298C | 1.1 | 1.1 | 1.6 | 2.3 | 1.4 | 0.4 | 1.7 | 0.5 | 0.3 | 1.1 | 1.5 | 1.1 | 0.8 | 0.9 | 0.2 | 2.1 | 0.9 | 0.8 | 0.88 |
| YLR295C | 1.4 | 1.1 | 1.1 | 1.7 | 2.2 | 1.1 | 1.1 | 1.2 | 1.4 | 1.2 | 1.3 | 0.5 | 0.8 | 1.2 | 0.5 | 2.4 | 0.9 | 1.5 | 1.07 |
| YNR072W | 1.1 | 1.5 | 0.5 | 0.7 | 1.0 | 0.9 | 1.5 | 0.9 | 0.7 | 1.8 | 1.4 | 1.0 | 1.5 | 1.0 | 1.8 | 2.1 | 1.3 | 1.0 | 0.26 |
| YOR316C | 0.7 | 2.5 | 1.5 | 1.5 | 1.0 | 0.9 | 1.4 | 0.8 | 1.6 | 2.0 | 2.4 | 1.1 | 1.6 | 1.0 | 1.5 | 2.2 | 0.8 | 1.0 | 0.93 |
| YOR328W | 1.0 | 1.0 |  | 1.0 | 1.0 | 2.9 |  |  |  | 1.1 | 1.8 |  |  | 0.8 | 3.3 | 2.1 |  |  | 0.19 |
| YPL134C | 1.5 | 1.0 | 1.6 | 1.6 | 1.4 | 1.2 | 1.2 | 1.3 | 0.6 | 0.8 | 1.7 | 0.8 | 1.0 | 1.4 | 1.1 | 3.3 | 1.3 | 1.3 | 0.70 |

TABLE 6

Stress protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR072W | 18.5 | 17.4 | 18.4 | 10.5 | 1.2 | 32.2 | 6.6 | 2.1 | 29.4 | 43.4 | 6.3 | 16.3 | 38.5 | 5.8 | 4.9 | 23.1 | 1.8 | 2.2 | 0.59 |
| YFL014W | 3.4 | 5.1 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YLL060C | 12.5 | 4.2 | 2.3 | 2.6 | 0.9 | 1.4 | 2.0 | 5.8 | 13.0 | 23.2 | 14.1 | 1.1 | 1.8 | 10.6 | 1.5 | 3.6 | 1.9 | 2.3 | 0.57 |
| YAL005C | 0.6 | 1.6 | 7.0 | 0.9 | 1.2 | 1.6 | 1.2 | 0.9 | 3.9 | 1.8 | 1.0 | 1.2 | 5.0 | 0.4 | 1.6 | 0.7 | 0.8 | 0.5 | 5.23 |
| YBL075C | 1.3 | 4.3 | 3.1 | 1.6 | 1.1 | 0.8 | 1.3 | 0.8 | 60.3 | 6.7 | 1.6 | 1.1 | 8.0 | 1.1 | 2.6 | 2.2 | 1.2 | 0.7 | 1.17 |
| YBR169C | 1.0 | 2.1 | 3.9 | 1.9 | 0.8 | 4.9 | 2.5 | 0.9 | 7.0 | 4.3 | 2.2 | 1.7 | 7.2 | 1.1 | 1.6 | 2.4 | 1.3 | 1.6 | 1.10 |
| YCL035C | 2.0 | 2.3 | 1.5 | 1.7 | 1.5 | 5.1 | 2.7 | 1.4 | 1.9 | 2.3 | 2.1 | 1.5 | 2.8 | 2.5 | 1.9 | 5.5 | 2.6 | 4.2 | 1.74 |
| YCR060W |  | 0.7 | 0.9 |  | 0.8 | 3.3 | 2.4 | 1.2 | 0.7 | 1.1 | 1.2 | 1.7 | 8.6 | 1.7 |  | 3.3 | 1.2 | 1.7 | 1.04 |
| YDR155C | 1.1 | 1.5 | 3.2 | 1.8 | 0.8 | 1.5 | 1.2 | 1.4 | 1.3 | 1.3 | 3.8 | 1.4 | 3.3 | 1.0 | 2.5 | 1.6 | 1.2 | 2.5 | 4.99 |
| YDR258C | 1.6 | 2.3 | 2.8 | 1.4 | 1.3 | 2.4 | 3.9 | 1.9 | 4.9 | 13.3 | 1.7 | 1.8 | 5.2 | 1.5 | 0.6 | 1.0 | 1.3 | 1.3 | 0.87 |
| YER103W | 0.7 | 2.1 | 5.2 | 2.1 | 1.1 | 1.7 | 1.0 | 0.9 | 20.3 | 9.0 | 1.8 | 1.9 | 9.0 | 0.9 | 3.2 | 1.2 | 1.4 | 0.6 | 2.10 |
| YKL210W | 0.5 | 1.7 | 2.7 | 0.7 | 0.8 | 1.4 | 1.0 | 0.9 | 3.5 | 2.9 | 1.4 | 1.3 | 2.9 | 0.8 | 1.0 | 0.9 | 0.7 | 1.1 | 2.29 |
| YLL024C | 0.5 | 1.6 | 5.3 | 0.8 | 0.7 | 1.0 | 1.1 | 0.7 | 2.8 | 2.4 | 1.6 | 1.0 | 4.8 | 0.4 | 1.3 | 0.5 | 0.5 | 0.6 | 5.12 |
| YLL026W | 1.8 | 2.9 | 7.7 | 1.7 | 0.9 | 1.9 | 2.9 | 1.4 | 11.4 | 6.6 | 1.7 | 1.9 | 8.1 | 0.8 | 0.9 | 1.6 | 1.7 | 2.5 | 2.56 |
| YNL160W | 2.1 | 3.7 | 10.6 | 2.0 | 1.3 | 5.8 | 2.4 | 1.2 | 3.5 | 2.7 | 5.4 | 1.4 | 6.0 | 1.3 | 0.7 | 4.0 | 1.0 | 1.0 | 1.77 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YOR027W | 0.7 | 2.4 | 4.4 | 0.8 | 1.0 | 1.6 | 1.3 | 0.9 | 3.5 | 4.0 | 1.3 | 1.3 | 5.1 | 0.8 | 1.4 | 0.6 | 0.9 | 0.8 | 1.52 |
| YPL240C | 0.7 | 1.4 | 2.4 | 0.9 | 1.3 | 1.2 | 1.4 | 1.2 | 3.5 | 2.6 | 1.0 | 0.8 | 2.9 | 0.7 | 1.2 | 0.7 | 0.8 | 1.0 | 4.83 |
| YDR293C | 0.9 | 0.9 | 1.2 | 1.4 | 0.6 | 0.9 | 0.9 | 0.6 | 1.2 | 1.2 | 1.1 | 0.9 | 2.3 | 0.8 | 1.7 | 1.6 | 1.4 | 1.3 | 1.12 |
| YDR436W | 0.9 | 0.9 | 1.1 | 1.4 | 0.7 | 1.1 | 1.2 | 0.9 | 3.5 | 1.1 | 2.0 | 0.9 | 2.7 | 1.2 | 0.8 | 1.4 | 0.9 | 1.2 | 0.53 |
| YDR519W | 1.3 | 3.2 | 1.7 | 1.6 | 0.7 | 1.3 | 1.9 | 1.4 | 0.5 | 1.2 | 1.2 | 1.7 | 2.5 | 1.3 | 2.0 | 1.5 | 1.8 | 2.4 | 2.01 |
| YEL030W | 0.7 | 0.9 | 1.9 | 1.1 | 0.4 | 0.6 | 0.9 | 0.7 | 2.3 | 2.5 | 1.7 | 0.9 | 2.7 | 0.7 | 0.8 | 0.8 | 0.9 | 0.6 | 1.28 |
| YER125W | 0.6 | 1.1 | 1.5 | 0.9 | 1.4 | 0.7 | 0.8 | 0.7 | 0.6 | 1.2 | 1.0 | 0.7 | 1.9 | 0.7 | 0.8 | 1.0 | 1.0 | 1.0 | 1.48 |
| YFL016C | 0.8 | 1.0 | 1.6 | 0.9 | 1.3 | 1.3 | 1.4 | 0.7 | 6.4 | 2.9 | 1.2 | 1.0 | 2.8 | 0.8 | 0.8 | 0.6 | 1.2 | 0.9 | 1.25 |
| YFR052W | 1.1 | 1.6 | 1.3 | 1.5 | 1.4 | 3.2 | 2.2 | 1.5 | 3.7 | 3.0 | 0.9 | 1.8 | 3.8 | 3.3 | 1.4 | 2.7 | 1.2 | 1.9 | 1.62 |
| YHR057C | 1.1 | 1.2 | 0.7 | 0.9 | 1.3 | 1.3 | 1.3 | 1.0 | 2.6 | 1.2 | 1.6 | 1.1 | 1.9 | 1.9 | 1.2 | 2.2 | 1.6 | 1.3 | 1.07 |
| YIR037W | 1.4 | 2.2 | 2.0 | 2.3 | 0.6 | 2.7 | 1.8 | 1.3 | 6.2 | 3.8 | 3.0 | 1.3 | 2.4 | 2.3 | 1.0 | 4.0 | 1.7 | 2.9 | 1.97 |
| YIR038C | 1.3 | 3.5 | 4.6 | 2.0 | 0.7 | 2.5 | 2.0 | 1.3 | 4.6 | 4.5 | 3.4 | 1.1 | 2.5 | 2.5 | 1.2 | 6.0 | 2.8 | 2.0 | 1.11 |
| YJR045C | 0.5 | 1.9 | 3.9 |  | 0.5 | 1.2 | 1.0 | 0.8 | 3.2 | 3.0 | 1.4 | 1.0 | 2.3 | 0.5 | 2.3 | 0.8 | 0.7 | 0.9 | 3.78 |
| YLL039C | 1.1 | 1.0 | 1.7 | 1.2 | 0.9 | 1.5 | 1.1 | 1.1 | 3.4 | 1.5 | 1.1 | 1.0 | 2.2 | 1.4 | 3.0 | 1.1 | 1.6 | 2.1 | 3.60 |
| YLR259C | 0.7 | 1.0 | 3.1 | 1.6 | 1.1 | 0.9 | 1.8 | 0.8 | 1.8 | 2.6 | 3.0 | 0.7 | 2.5 | 0.8 | 2.1 | 1.3 | 0.8 | 1.0 | 2.09 |
| YML070W | 0.9 | 1.7 | 2.5 | 1.9 | 1.4 | 2.2 | 3.1 | 1.3 | 4.5 | 3.9 | 1.5 | 1.3 | 3.3 | 1.3 | 0.9 | 2.6 | 1.2 | 1.3 | 1.03 |
| YPL106C | 0.6 | 1.7 | 2.4 | 1.1 | 1.2 | 1.6 | 1.1 | 1.2 | 4.9 | 1.8 | 1.3 | 1.1 | 3.1 | 0.9 | 1.1 | 0.5 | 0.5 | 0.5 | 3.34 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YDR077W | 1.2 | 1.0 | 3.5 | 2.1 | 0.8 | 1.0 | 0.7 | 0.8 | 0.7 | 0.7 | 6.8 | 0.8 | 1.0 | 0.3 | 6.1 | 1.0 | 1.4 | 1.1 | 4.77 |
| YKL163W | 1.1 | 1.4 | 3.4 | 1.9 | 0.6 | 1.1 | 0.9 | 0.8 | 0.7 | 1.6 | 1.3 | 0.9 | 1.5 | 0.5 | 16.8 | 3.0 | 0.8 | 1.0 | 2.01 |
| YLR109W | 0.8 | 2.9 | 6.0 | 0.9 | 1.3 | 2.1 | 2.6 | 0.9 | 2.4 | 2.7 | 1.5 | 1.6 | 3.2 | 2.3 | 3.9 | 1.8 | 1.1 | 1.2 | 3.86 |
| YOR208W | 1.3 | 1.0 | 1.2 | 2.9 | 1.4 | 1.8 | 1.1 | 1.0 | 1.5 | 2.0 | 1.2 | 1.2 | 1.5 | 1.3 | 4.4 | 1.9 | 1.6 | 1.6 | 0.56 |
| YDR098C | 0.8 | 1.4 | 1.0 | 0.8 | 1.5 | 1.1 | 1.5 | 1.2 | 3.7 | 1.5 | 1.4 | 1.3 | 1.2 | 1.5 | 2.2 | 0.8 | 1.0 | 1.2 | 1.59 |
| YHR030C | 2.1 | 0.8 | 0.6 | 2.9 | 1.8 | 0.9 | 1.8 | 1.5 | 0.6 | 2.5 | 1.5 | 0.7 | 1.0 | 1.1 | 3.4 | 1.4 | 2.0 | 1.8 | 1.05 |
| YJL159W | 1.0 | 1.3 | 2.8 | 1.1 | 1.0 | 1.8 | 0.9 | 0.8 | 0.5 | 1.2 | 1.2 | 1.0 | 1.7 | 0.6 | 5.3 | 1.0 | 1.4 | 0.9 | 2.45 |
| YMR173W | 1.5 | 3.6 | 3.0 | 0.9 | 1.1 | 5.0 | 2.4 | 2.3 | 2.7 | 8.2 | 3.2 | 1.4 | 2.0 | 2.3 | 2.5 | 1.2 | 1.9 | 1.8 | 1.37 |
| YCR021C | 5.2 | 1.4 | 4.2 | 8.6 | 0.9 | 2.2 | 0.9 | 0.8 | 2.2 | 1.0 | 0.6 | 0.5 | 0.9 | 1.6 | 0.5 | 0.6 | 0.7 | 0.8 | 1.36 |
| YDL022W | 0.9 | 2.6 | 6.9 | 1.5 | 0.7 | 2.1 | 1.5 | 0.8 | 1.2 | 1.8 | 2.8 | 1.2 | 1.5 | 0.8 | 0.9 | 1.1 | 1.0 | 1.4 | 1.79 |
| YDR033W | 1.1 | 1.3 | 4.6 | 1.5 | 1.1 | 6.7 | 0.8 | 1.0 | 0.3 | 1.0 | 0.7 | 1.0 | 0.7 | 1.0 | 0.8 | 1.0 | 0.7 | 1.0 | 5.78 |
| YFL020C | 1.0 | 1.1 | 1.9 | 1.2 | 1.1 | 2.0 | 1.4 | 0.7 | 1.3 | 1.4 | 1.2 | 1.3 | 1.4 | 1.0 | 1.4 | 0.9 | 1.5 | 0.9 | 0.70 |
| YGL073W | 1.0 | 2.1 | 0.9 | 1.0 | 1.7 | 1.9 | 1.3 | 0.8 | 1.9 | 2.4 | 0.8 | 0.8 | 1.5 | 1.2 | 0.9 | 1.1 | 2.5 | 1.2 | 0.66 |
| YIL033C | 0.8 | 1.3 | 3.3 | 1.3 | 0.7 | 2.0 | 1.1 | 0.7 | 2.4 | 1.3 | 1.8 | 1.1 | 2.5 | 0.7 | 1.0 | 2.0 | 1.0 | 1.2 | 1.18 |
| YMR021C | 1.0 | 0.7 | 0.9 | 1.1 | 1.6 | 2.2 | 2.5 | 1.3 | 0.6 | 1.3 | 0.9 | 0.8 | 1.4 | 1.3 | 1.0 | 2.0 | 3.3 | 3.4 | 1.14 |
| YBR126C | 0.8 | 1.9 | 5.6 | 1.2 | 0.7 | 2.9 | 2.3 | 0.6 | 1.7 |  | 1.1 | 1.3 | 2.1 | 0.7 | 1.0 | 1.7 | 1.5 | 1.3 | 1.96 |
| YBR067C | 1.6 | 2.5 | 2.8 | 0.9 | 1.1 | 1.1 | 1.1 | 1.1 | 1.7 | 1.0 | 3.1 | 1.0 | 0.9 | 0.7 | 3.3 | 2.5 | 0.5 | 0.4 | 1.76 |
| YDR513W | 2.2 | 2.5 | 2.3 | 2.6 | 0.9 | 2.1 | 1.4 | 4.6 | 3.1 | 2.0 | 0.9 | 1.8 | 2.0 | 1.3 | 3.8 | 1.3 | 3.2 | 3.10 |  |
| YGR088W | 1.3 | 1.2 | 7.7 | 2.4 | 1.0 | 1.3 | 0.8 | 0.8 | 1.5 | 3.2 | 3.9 | 1.1 | 1.2 | 1.3 | 0.7 | 5.6 | 0.9 | 2.0 | 0.75 |
| YHR104W | 1.0 | 4.1 | 15.7 | 1.9 | 1.1 | 1.2 | 1.5 | 1.1 | 4.8 | 2.3 | 2.6 | 1.0 | 1.2 | 1.5 | 1.6 | 1.3 | 1.9 | 1.9 | 1.57 |
| YKL161C | 4.2 | 0.8 | 0.9 | 2.2 | 1.4 | 2.0 | 2.0 | 1.9 | 1.4 | 1.7 | 3.1 | 0.9 | 1.3 | 1.4 | 1.3 | 1.1 | 1.4 | 1.9 | 0.45 |
| YPL223C | 4.8 | 20.0 | 1.2 | 5.1 | 0.9 | 1.5 | 1.1 | 1.2 | 29.4 | 16.5 | 1.8 | 0.9 | 2.3 | 2.5 | 1.5 | 19.0 | 1.0 | 1.3 | 0.31 |
| YBR054W | 1.9 | 1.8 | 5.4 | 1.7 | 0.8 | 1.1 | 0.6 | 2.1 | 0.4 | 1.2 | 1.8 | 0.7 | 1.5 | 1.0 | 0.6 | 0.4 | 0.7 | 0.7 | 3.02 |
| YAL015C | 1.2 | 1.1 | 1.7 | 1.9 | 1.1 | 0.7 | 1.2 | 1.1 | 4.0 | 2.7 | 1.4 | 1.0 | 1.2 | 1.6 | 0.7 | 2.0 | 1.1 | 1.2 | 0.61 |
| YDL025C | 1.7 | 5.0 | 3.5 | 1.5 | 0.6 | 0.6 | 1.0 | 1.1 | 3.6 | 4.5 | 1.5 | 0.9 | 1.2 | 1.7 | 1.0 | 1.7 | 1.0 | 1.4 | 0.56 |
| YML007W | 0.9 | 0.8 | 0.9 | 1.3 | 1.0 | 0.5 | 1.1 | 1.9 | 2.1 | 2.5 | 1.3 | 1.1 | 1.7 | 1.2 | 1.0 | 1.4 | 1.0 | 1.4 | 1.54 |
| YER042W | 3.0 | 2.2 | 3.1 | 1.0 | 1.1 | 1.6 | 1.1 | 1.7 | 6.8 | 2.1 | 1.8 | 1.1 | 1.4 | 5.2 | 1.0 | 1.9 | 0.7 | 1.1 | 1.80 |
| YOL064C | 1.4 | 2.1 | 1.1 | 0.6 | 0.9 | 1.4 | 1.2 | 1.0 | 8.7 | 2.7 | 1.0 | 0.9 | 2.0 | 0.9 | 1.0 | 1.7 | 1.2 | 1.3 | 1.32 |
| YGL181W | 0.9 | 0.9 | 1.2 | 1.1 | 1.1 | 1.9 | 1.3 | 1.2 | 2.7 | 2.3 | 1.2 | 1.0 | 2.8 | 1.0 | 1.5 | 1.3 | 1.0 | 1.3 | 0.98 |
| YJL128C | 0.8 | 1.4 | 0.4 | 0.8 | 1.2 | 1.3 | 1.8 | 0.9 | 2.0 | 1.7 | 0.6 | 1.0 | 1.7 | 0.8 | 1.2 | 0.9 | 1.0 | 1.0 | 0.42 |
| YJL165C | 1.0 | 0.8 | 1.3 | 1.6 | 1.1 | 0.5 | 0.8 | 0.7 | 2.8 | 1.0 | 1.7 | 0.9 | 1.5 | 0.9 | 1.0 | 1.5 | 1.3 | 1.8 | 0.87 |
| YJR090C | 0.8 | 1.0 | 0.6 | 0.8 | 1.2 | 1.2 | 0.8 | 0.8 | 1.9 | 1.2 | 0.4 | 0.8 | 2.2 | 1.0 | 1.6 | 0.8 | 1.1 | 1.0 | 0.60 |
| YMR186W | 0.6 | 1.4 | 2.0 | 0.9 | 1.3 | 1.3 | 1.2 | 0.8 | 2.6 | 1.3 | 1.1 | 1.0 | 2.4 | 0.6 | 1.3 | 0.6 | 0.7 | 1.1 | 6.64 |
| YNL064C | 0.9 | 1.8 | 1.8 | 1.1 | 0.9 | 0.8 | 0.6 | 1.4 | 2.4 | 1.8 | 0.9 | 0.8 | 1.1 | 0.8 | 0.7 | 0.3 | 0.7 | 0.7 | 3.79 |
| YOR008C | 0.7 | 0.8 | 1.4 | 1.1 | 1.4 | 1.1 | 0.8 | 0.8 | 1.9 | 1.0 | 1.0 | 0.7 | 0.9 | 0.9 | 0.9 | 1.2 | 0.8 | 1.3 | 1.75 |
| YPL194W | 0.9 | 1.4 | 0.4 | 1.1 | 1.3 | 1.1 | 1.5 | 1.3 | 9.6 | 3.1 | 0.9 | 0.9 | 1.4 | 1.1 | 1.4 | 0.9 | 1.0 | 0.8 | 0.22 |
| YBL093C | 1.0 | 2.0 | 0.4 | 1.4 | 1.0 | 0.8 | 1.3 | 1.6 | 0.7 | 1.1 | 1.3 | 1.1 | 2.1 | 1.0 | 0.5 | 0.9 | 1.4 | 1.3 | 1.47 |
| YKR053C | 0.9 | 2.0 | 1.0 | 1.2 | 1.0 | 1.1 | 1.7 | 0.9 | 0.8 | 1.8 | 0.5 | 0.7 | 0.7 | 1.3 | 0.3 | 0.9 | 2.8 | 2.4 | 0.35 |
| YJL158C | 0.9 | 0.6 | 2.8 | 1.5 | 1.4 | 0.5 | 0.4 | 0.7 | 0.2 | 0.5 | 1.9 | 1.1 | 0.4 | 0.5 | 1.7 | 0.6 | 1.4 | 1.4 | 3.48 |

TABLE 6-continued

Stress protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YER057C | 1.2 | 2.0 | 3.0 | 1.8 | 0.8 | 1.6 | 1.4 | 1.0 | 0.6 | 1.4 | 1.8 | 1.5 | 1.0 | 1.4 | 1.7 | 2.8 | 1.1 | 1.8 | 2.03 |
| YHL046C | 1.1 | 1.7 | 2.1 | 1.3 | 0.9 | 0.8 | 1.3 | 1.0 | 1.0 | 2.1 | 0.4 | 1.1 | 1.4 | 1.4 | 1.0 | 1.4 | 0.9 | 0.9 | 0.55 |
| YIL011W | 0.7 | 0.5 | 3.9 | 0.6 | 1.1 | 0.7 | 0.6 | 0.7 | 0.0 | 0.5 | 2.5 | 0.6 | 0.5 | 0.5 | 0.9 | 1.0 | 0.8 | 0.8 | 0.57 |
| YKL164C | 0.6 | 1.1 | 2.5 | 0.9 | 1.1 | 1.4 | 0.8 | 0.8 | 0.4 | 0.7 | 1.0 | 0.8 | 0.9 | 0.3 | 1.2 | 1.1 | 0.8 | 0.8 | 2.75 |
| YNR076W | 1.3 | 1.3 | 2.5 | 1.0 | 1.2 | 1.2 | 1.2 | 1.0 | 1.3 | 2.5 | 1.4 | 0.7 | 0.9 | 0.8 | 1.1 | 0.8 | 1.5 | 0.8 | 0.42 |
| YOL161C | 1.2 | 1.1 | 2.4 | 1.4 | 0.9 | 1.0 | 0.9 | 0.8 | 0.7 | 2.0 | 1.5 | 1.3 | 1.2 | 0.9 | 1.1 | 1.6 | 1.1 | 1.0 | 0.89 |
| YOR009W | 0.9 | 0.8 | 3.2 | 0.7 | 0.8 | 0.9 | 0.6 | 0.7 | 0.4 | 0.5 | 1.4 | 0.4 | 0.4 | 0.7 | 0.6 | 0.8 | 0.9 | 0.8 | 0.36 |
| YOR010C | 0.7 | 0.7 | 3.2 | 0.6 | 1.2 | 0.5 | 0.4 | 0.5 | 0.6 | 0.7 | 1.2 | 0.5 | 0.5 | 0.4 | 0.6 | 1.1 | 1.4 | 0.6 | 0.61 |
| YPL059W | 1.2 | 0.9 | 2.6 | 1.3 | 1.2 | 1.3 | 0.7 | 1.4 | 2.0 | 1.3 | 1.6 | 0.8 | 0.7 | 1.3 | 1.0 | 2.1 | 1.8 | 1.3 | 1.35 |
| YBR044C | 0.8 | 1.4 | 0.7 | 1.9 | 1.4 | 1.0 | 1.5 | 1.1 | 0.8 | 1.2 | 1.1 | 0.8 | 1.2 | 0.9 | 0.9 | 1.4 | 0.9 | 1.3 | 0.57 |
| YEL039C | 1.1 | 0.7 | 1.3 | 5.1 | 0.9 | 1.5 | 0.6 | 1.1 | 1.2 | 1.2 | 1.7 | 0.6 | 0.5 | 1.4 | 0.4 | 3.5 | 0.7 | 1.1 | 1.59 |
| YGL115W | 0.9 | 0.6 | 1.2 | 2.0 | 1.2 | 1.2 | 1.4 | 1.0 | 1.2 | 1.2 | 1.0 | 0.9 | 0.7 | 1.2 | 0.7 | 1.7 | 0.8 | 1.2 | 2.46 |
| YLR006C | 0.7 | 0.7 | 0.9 | 6.2 | 1.6 | 0.9 | 1.1 | 0.9 | 1.1 | 1.1 | 1.5 | 0.7 | 0.8 | 1.0 | 0.9 | 0.8 | 1.6 | 1.0 | 0.40 |
| YPR005C | 1.3 | 0.8 | 1.5 | 3.8 | 1.0 | 0.8 | 1.2 | 1.2 | 2.8 | 2.0 | 0.4 | 0.6 | 0.7 | 1.3 | 2.7 | 0.8 | 1.0 | 1.1 | 0.24 |
| YHL028W | 0.7 | 0.8 | 1.4 | 0.5 | 1.1 | 1.8 | 2.1 | 0.4 | 0.2 | 0.4 | 0.7 | 1.5 | 2.1 | 1.3 | 0.6 | 2.6 | 1.6 | 2.5 | 0.62 |
| YOR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |
| YPL140C | 0.9 | 1.3 | 0.9 | 1.0 | 0.8 | 0.3 | 1.4 | 1.1 | 0.9 | 0.9 | 0.8 | 0.8 | 0.9 | 1.1 | 0.7 | 1.8 | 0.9 | 1.4 | 0.46 |

TABLE 7

Metabolism protein genes

| yeast genes | The level of expressed mRNA in the presence of chemical substance/The level of expressed mRNA in the absence of chemical substance | | | | | | | | | | | | | | | | | | |
|---|---|---|---|---|---|---|---|---|---|---|---|---|---|---|---|---|---|---|---|
| | (1) | (2) | (3) | (4) | (5) | (6) | (7) | (8) | (9) | (10) | (11) | (12) | (13) | (14) | (15) | (16) | (17) | (18) | Intensity |
| YCR107W | 12.0 | 2.6 | 1.8 | 1.6 | 0.7 | 1.5 | 1.5 | 15.6 | 196.6 | 34.0 | 23.0 | 0.9 | 4.0 | 8.3 | 4.8 | 3.1 | 1.3 | 1.1 | 0.59 |
| YDL243C | 14.4 | 2.7 | 2.4 | 1.0 | 1.1 | 2.2 | 1.6 | 11.8 | 64.2 | 29.6 | 19.6 | 1.1 | 4.1 | 12.0 | 4.2 | 3.0 | 1.8 | 1.5 | 0.76 |
| YFL014W | 3.4 | 7.2 | 5.7 | 11.0 | 1.0 | 9.3 | 5.5 | 3.4 | 13.1 | 5.8 | 5.0 | 4.3 | 15.2 | 7.3 | 6.3 | 14.2 | 1.5 | 8.8 | 2.14 |
| YFL056C | 19.0 | 2.3 | 2.3 | 1.5 | 0.9 | 0.6 | 1.4 | 18.5 | 162.3 | 31.3 | 68.3 | 1.0 | 4.7 | 7.8 | 5.0 | 3.4 | 1.0 | 1.1 | 0.55 |
| YFL057C | 20.9 | 5.8 | 1.5 | 1.8 | 0.9 | 1.2 | 1.8 | 18.0 | 51.8 | 46.1 | 27.7 | 1.0 | 4.1 | 23.4 | 3.1 | 3.9 | 1.6 | 1.3 | 0.71 |
| YJR155W | 10.6 | 3.7 | 1.4 | 2.5 | 0.7 | 1.4 | 1.7 | 10.6 | 38.2 | 18.8 | 15.4 | 1.0 | 5.7 | 9.4 | 2.6 | 5.6 | 1.3 | 1.4 | 0.64 |
| YNL331C | 8.6 | 3.6 | 1.3 | 1.0 | 1.6 | 1.8 | 1.9 | 13.1 | 42.6 | 36.3 | 21.8 | 0.9 | 3.1 | 7.5 | 2.3 | 4.0 | 1.7 | 1.3 | 0.58 |
| YNL332W | 1.1 | 1.5 | 1.1 | 2.0 | 1.6 | 1.1 | 2.1 | 1.5 | 3.3 | 2.1 | 2.6 | 1.2 | 2.1 | 3.0 | 5.4 | 2.2 | 1.0 | 1.0 | 0.24 |
| YOL165C | 10.1 | 4.5 | 1.8 | 0.9 | 0.9 | 1.7 | 1.4 | 17.8 | 46.9 | 23.3 | 17.6 | 0.8 | 3.7 | 9.1 | 3.0 | 1.8 | 1.6 | 1.0 | 0.69 |
| YPR167C | 5.3 | 5.8 | 1.9 | 0.8 | 1.4 | 2.6 | 1.2 | 5.5 | 76.6 | 9.0 | 1.9 | 1.3 | 1.9 | 4.2 | 0.9 | 0.9 | 1.7 | 1.4 | 0.54 |
| YBR256C | 3.0 | 1.4 | 0.6 | 1.3 | 1.6 | 2.0 | 2.1 | 2.3 | 18.1 | 6.8 | 3.2 | 1.7 | 3.5 | 5.6 | 1.6 | 3.0 | 2.6 | 3.3 | 1.97 |
| YBR296C | 7.0 | 11.2 | 2.2 | 2.5 | 1.4 | 1.4 | 0.2 | 1.1 | 0.4 | 1.8 | 1.5 | 1.6 | 2.0 | 2.3 | 1.7 | 0.3 | 3.8 | 4.0 | 0.54 |
| YDL021W | 4.8 | 1.7 | 2.4 | 3.7 | 1.7 | 6.5 | 5.9 | 2.7 | 2.5 | 7.4 | 4.7 | 2.4 | 5.3 | 3.7 | 0.7 | 7.3 | 1.9 | 3.2 | 0.47 |
| YFL061W | 1.5 | 1.4 | 2.1 | 3.0 | 1.0 | 0.5 | 1.2 | 1.2 | 3.2 | 9.9 | 1.1 | 0.9 | 1.2 | 6.0 | 2.1 | 1.0 | 1.2 | 0.9 | 0.31 |
| YGR043C | 2.5 | 4.7 | 3.2 | 7.9 | 0.9 | 16.3 | 6.5 | 2.6 | 10.9 | 8.4 | 3.6 | 3.3 | 6.9 | 4.1 | 3.0 | 13.7 | 1.6 | 4.8 | 0.66 |
| YHR112C | 1.8 | 3.1 | 0.7 | 1.4 | 1.3 | 2.9 | 3.4 | 1.7 | 10.5 | 4.4 | 1.5 | 1.9 | 3.9 | 2.4 | 2.0 | 2.7 | 1.6 | 1.8 | 0.55 |
| YIR030C | 1.4 | 1.0 | 0.9 | 1.3 | 0.9 | 0.5 | 1.2 | 1.4 | 5.4 | 2.1 | 1.4 | 0.9 | 1.3 | 2.9 | 0.7 | 0.8 | 0.9 | 1.0 | 0.42 |
| YJR010W | 9.1 | 7.3 | 4.9 | 0.8 | 1.1 | 2.5 | 1.4 | 3.1 | 30.0 | 11.1 | 2.9 | 1.4 | 3.2 | 5.4 | 1.7 | 1.7 | 1.2 | 1.0 | 0.56 |
| YKL001C | 6.8 | 21.4 | 5.6 | 1.8 | 0.8 | 0.9 | 1.1 | 3.4 | 10.3 | 3.4 | 2.6 | 2.1 | 1.6 | 6.2 | 1.1 | 1.8 | 2.7 | 1.7 | 0.91 |
| YKR097W | 1.3 | 2.4 | 1.3 | 3.3 | 1.1 | 1.7 | 3.7 | 2.5 | 1.9 | 3.3 | 0.8 | 1.8 | 17.5 | 2.1 | 2.5 | 2.2 | 1.1 | 1.5 | 0.16 |
| YLR303W | 7.3 | 9.8 | 12.1 | 1.1 | 1.1 | 3.0 | 3.6 | 5.3 | 18.6 | 5.6 | 9.8 | 4.3 | 9.9 | 3.8 | 5.8 | 3.4 | 1.5 | 1.4 | 1.42 |
| YNL274C | 1.4 | 18.7 | 2.6 | 1.9 | 0.7 | 4.2 | 2.0 | 2.3 | 6.3 | 5.3 | 4.0 | 1.1 | 2.3 | 3.3 | 2.5 | 6.4 | 1.4 | 2.6 | 0.85 |
| YOL151W | 6.7 | 3.8 | 9.1 | 1.3 | 1.3 | 8.4 | 4.4 | 6.7 | 22.8 | 17.0 | 9.0 | 4.6 | 16.9 | 4.0 | 2.8 | 3.7 | 4.0 | 5.6 | 1.12 |
| YOR226C | 1.3 | 2.2 | 1.7 | 1.1 | 1.3 | 1.2 | 1.2 | 1.2 | 1.3 | 5.9 | 1.5 | 0.6 | 0.9 | 2.7 | 1.0 | 0.7 | 1.0 | 0.7 | 0.58 |
| YJL153C | 1.3 | 1.7 | 1.7 | 17.6 | 0.7 | 0.8 | 2.3 | 1.3 | 3.9 | 2.5 | 0.7 | 10.2 | 38.0 | 1.4 | 37.0 | 1.0 | 6.5 | 1.8 | 0.27 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YPL088W | 3.3 | 1.3 | 0.6 | 2.5 | 1.5 | 7.1 | 3.7 | 1.9 | 0.6 | 2.8 | 1.1 | 3.6 | 4.8 | 1.6 | 3.2 | 4.3 | 9.1 | 8.3 | 0.69 |
| YDL124W | 2.1 | 8.5 | 5.7 | 1.7 | 0.7 | 3.4 | 2.9 | 2.1 | 3.3 | 5.3 | 3.4 | 2.4 | 6.0 | 1.6 | 3.4 | 3.6 | 2.2 | 2.6 | 2.43 |
| YDL174C | 0.9 | 1.8 | 0.9 | 1.3 | 0.5 | 1.7 | 3.6 | 0.8 | 0.5 | 1.7 | 0.9 | 2.8 | 5.9 | 1.1 | 0.6 | 5.1 | 2.2 | 4.0 | 0.63 |
| YGL156W | 1.3 | 2.5 | 1.8 | 2.2 | 1.4 | 2.1 | 2.1 | 1.4 | 5.6 | 2.4 | 2.1 | 2.6 | 6.0 | 1.6 | 3.0 | 4.1 | 1.4 | 1.9 | 0.29 |
| YGR157W | 1.0 | 0.9 | 5.2 | 0.8 | 1.2 | 1.0 | 0.8 | 0.7 | 3.3 | 2.0 | 1.0 | 1.8 | 4.8 | 0.7 | 4.6 | 1.0 | 0.8 | 1.3 | 2.10 |
| YHR043C | 1.3 | 1.8 | 1.2 | 1.7 | 0.9 | 2.2 | 2.9 | 3.0 | 1.2 | 1.0 | 1.6 | 2.2 | 2.7 | 1.3 | 2.1 | 2.2 | 1.4 | 1.7 | 1.38 |
| YHR044C | 1.3 | 1.3 | 1.7 | 1.5 | 1.2 | 3.3 | 2.6 | 2.0 | 1.1 | 1.1 | 1.7 | 2.3 | 4.3 | 1.3 | 1.5 | 2.4 | 1.3 | 1.4 | 1.12 |
| YJR073C | 1.1 | 2.4 | 2.7 | 2.7 | 0.6 | 2.2 | 2.9 | 1.0 | 6.8 | 2.8 | 2.8 | 4.1 | 10.0 | 2.3 | 28.9 | 3.7 | 2.9 | 2.6 | 0.99 |
| YOR303W | 1.1 | 2.2 | 0.5 | 1.0 | 1.2 | 1.8 | 1.2 | 1.6 | 0.9 | 5.2 | 0.9 | 1.9 | 3.3 | 1.6 | 4.1 | 1.2 | 1.2 | 0.8 | 1.47 |
| YBR294W | 6.3 | 12.0 | 0.9 | 2.6 | 1.4 | 1.2 | 1.1 | 1.0 | 5.2 | 5.2 | 1.2 | 1.0 | 3.1 | 1.3 | 1.0 | 0.9 | 0.9 | 1.1 | 0.18 |
| YCL043C | 0.6 | 3.7 | 2.5 | 0.7 | 0.9 | 1.3 | 1.0 | 0.8 | 1.6 | 1.2 | 1.7 | 1.5 | 4.1 | 0.6 | 5.7 | 0.8 | 0.9 | 1.2 | 2.37 |
| YCL050C | 1.0 | 1.1 | 1.9 | 0.7 | 1.4 | 1.2 | 1.2 | 1.2 | 3.0 | 2.9 | 1.3 | 1.2 | 2.8 | 1.2 | 0.8 | 0.7 | 1.0 | 1.0 | 2.20 |
| YCR012W | 1.1 | 1.5 | 5.1 | 1.2 | 1.1 | 2.5 | 1.4 | 0.8 | 1.4 | 1.5 | 1.8 | 1.2 | 4.1 | 0.9 | 1.4 | 1.4 | 0.8 | 1.3 | 4.48 |
| YDR158W | 1.1 | 0.5 | 1.3 | 0.8 | 1.3 | 1.0 | 0.8 | 1.2 | 1.1 | 1.7 | 1.6 | 1.0 | 2.6 | 0.9 | 1.0 | 0.6 | 1.0 | 0.9 | 3.54 |
| YDR204W | 0.9 | 2.3 | 3.0 | 1.4 | 1.0 | 2.2 | 2.2 | 1.1 | 5.7 | 3.7 | 2.2 | 1.2 | 2.9 | 1.1 | 0.6 | 2.8 | 1.1 | 1.7 | 0.62 |
| YDR313C | 1.2 | 1.2 | 1.2 | 1.4 | 1.3 | 1.4 | 1.5 | 1.2 | 4.7 | 2.6 | 1.5 | 1.2 | 2.3 | 1.3 | 0.8 | 2.9 | 1.1 | 1.3 | 0.84 |
| YDR368W | 2.0 | 2.2 | 2.2 | 1.8 | 1.0 | 3.0 | 2.1 | 1.7 | 3.8 | 3.8 | 1.8 | 1.4 | 2.6 | 2.0 | 1.2 | 2.3 | 1.1 | 2.0 | 1.70 |
| YER091C | 3.6 | 3.9 | 30.7 | 1.3 | 0.9 | 2.3 | 2.1 | 0.9 | 5.8 | 1.4 | 3.2 | 2.0 | 5.4 | 1.2 | 10.2 | 2.7 | 1.2 | 1.0 | 1.23 |

TABLE 7-continued

Metabolism protein genes yeast | The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YFR053C | 1.7 | 1.4 | 3.0 | 2.2 | 0.9 | 3.2 | 2.1 | 2.8 | 0.6 | 1.1 | 1.5 | 1.7 | 3.0 | 0.6 | 0.6 | 3.0 | 1.4 | 2.2 | 4.17 |
| YGL062W | 0.6 | 1.3 | 1.1 | 0.6 | 0.9 | 1.0 | 1.3 | 0.8 | 1.6 | 2.5 | 0.7 | 1.6 | 4.5 | 1.2 | 2.7 | 1.5 | 1.1 | 0.9 | 0.77 |
| YGL157W | 0.7 | 0.9 | 1.8 | 0.9 | 1.5 | 5.4 | 3.3 | 1.4 | 0.6 | 1.8 | 1.4 | 1.5 | 4.8 | 1.2 | 5.1 | 1.7 | 1.8 | 2.3 | 1.69 |
| YGL184C | 4.6 | 15.9 | 57.4 | 1.3 | 1.1 | 1.0 | 1.2 | 1.9 | 37.9 | 66.8 | 1.7 | 2.6 | 7.4 | 1.4 | 0.4 | 1.5 | 1.0 | 0.9 | 0.16 |
| YGR032W | 1.0 | 1.4 | 1.0 | 1.3 | 0.7 | 1.9 | 0.8 | 0.6 | 0.5 | 0.7 | 1.5 | 1.5 | 3.9 | 1.1 | 5.4 | 1.5 | 3.2 | 2.8 | 1.18 |
| YGR124W | 0.5 | 0.6 | 1.7 | 0.7 | 1.2 | 1.1 | 0.7 | 1.0 | 2.2 | 1.3 | 1.1 | 1.1 | 2.3 | 0.5 | 1.5 | 0.3 | 0.7 | 0.6 | 3.56 |
| YGR192C | 1.4 | 1.0 | 3.8 | 1.0 | 1.1 | 1.7 | 1.7 | 1.1 | 0.9 | 1.3 | 2.3 | 2.2 | 3.4 | 1.0 | 1.9 | 1.1 | 1.1 | 1.3 | 7.49 |
| YGR244C | 1.0 | 1.2 | 1.6 | 1.6 | 0.8 | 2.6 | 3.9 | 1.8 | 1.4 | 1.1 | 1.8 | 1.9 | 2.6 | 1.2 | 2.0 | 2.6 | 1.9 | 3.1 | 1.12 |
| YGR254W | 1.2 | 1.3 | 3.8 | 1.3 | 1.2 | 1.9 | 1.5 | 1.4 | 0.8 | 1.2 | 1.3 | 1.7 | 3.1 | 0.6 | 2.4 | 1.4 | 1.3 | 1.2 | 7.01 |
| YHR018C | 1.0 | 1.0 | 1.5 | 1.4 | 1.7 | 1.1 | 0.8 | 1.0 | 1.4 | 4.4 | 1.4 | 1.4 | 3.3 | 1.0 | 4.4 | 1.0 | 1.9 | 1.2 | 1.21 |
| YIL160C | 0.8 | 2.4 | 2.3 | 3.5 | 1.0 | 1.6 | 1.1 | 1.2 | 3.2 | 3.8 | 2.4 | 1.0 | 2.3 | 1.5 | 5.6 | 8.8 | 2.4 | 3.0 | 0.27 |
| YIR017C | 3.5 | 8.6 | 2.5 | 1.9 | 0.8 | 1.9 | 1.5 | 1.2 | 5.2 | 3.4 | 4.2 | 1.2 | 3.4 | 1.9 | 2.3 | 3.0 | 1.5 | 1.3 | 0.36 |
| YJL052W | 1.5 | 0.9 | 4.0 | 1.8 | 0.7 | 2.4 | 2.1 | 1.5 | 1.6 | 2.0 | 4.3 | 2.4 | 5.6 | 1.3 | 2.3 | 2.3 | 1.2 | 1.9 | 6.19 |
| YJR009C | 1.1 | 1.7 | 5.6 | 1.0 | 1.2 | 1.6 | 1.6 | 1.1 | 1.1 | 1.3 | 1.1 | 1.5 | 2.7 | 1.0 | 2.1 | 1.5 | 1.1 | 1.3 | 5.86 |
| YJR130C | 1.1 | 0.6 | 0.8 | 0.9 | 1.4 | 2.0 | 1.3 | 1.3 | 5.2 | 3.8 | 1.7 | 1.0 | 2.9 | 1.1 | 0.9 | 1.5 | 1.1 | 1.3 | 0.62 |
| YJR149W | 1.0 | 1.8 | 1.4 | 2.3 | 0.8 | 1.0 | 1.7 | 1.0 | 1.4 | 1.0 | 0.7 | 1.0 | 3.5 | 1.4 | 1.4 | 2.4 | 1.1 | 1.2 | 0.34 |
| YKL218C | 2.1 | 1.0 | 2.2 | 1.8 | 1.2 | 3.6 | 1.6 | 1.7 | 3.4 | 2.7 | 1.7 | 1.2 | 5.1 | 1.4 | 0.8 | 3.1 | 2.5 | 2.6 | 0.60 |
| YLR027C | 1.0 | 1.5 | 2.3 | 0.8 | 0.9 | 2.0 | 1.4 | 0.7 | 1.6 | 2.7 | 1.6 | 1.3 | 2.5 | 1.0 | 1.4 | 0.9 | 1.3 | 1.3 | 1.39 |
| YLR133W | 0.9 | 1.6 | 1.4 | 0.7 | 1.0 | 2.2 | 1.3 | 0.7 | 6.1 | 2.3 | 0.6 | 1.5 | 3.3 | 1.1 | 1.9 | 1.0 | 1.1 | 1.3 | 0.36 |
| YLR155C | 1.4 | 1.1 | 2.4 | 1.8 | 1.7 | 1.6 | 2.0 | 1.0 | 3.0 | 1.8 | 2.0 | 1.1 | 3.3 | 1.1 | 1.2 | 2.2 | 1.4 | 2.2 | 1.63 |
| YLR158C | 1.4 | 1.2 | 2.1 | 1.7 | 1.7 | 1.5 | 2.0 | 1.1 | 2.7 | s | 2.4 | 1.1 | 3.2 | 1.2 | 1.1 | 2.1 | 1.4 | 2.0 | 1.57 |
| YLR195C | 0.8 | 0.9 | 1.0 | 0.8 | 1.0 | 0.8 | 1.1 | 1.0 | 0.6 | 0.7 | 0.8 | 1.3 | 2.3 | 0.7 | 0.9 | 0.8 | 0.9 | 1.0 | 1.55 |
| YLR345W | 1.4 | 1.4 | 1.4 | 1.2 | 1.2 | 1.6 | 1.2 | 1.4 | 4.5 | 4.0 | 2.5 | 1.6 | 3.5 | 1.5 | 1.0 | 1.2 | 1.2 | 1.4 | 2.65 |
| YML004C | 0.8 | 1.6 | 2.5 | 1.0 | 0.7 | 1.7 | 2.1 | 1.9 | 3.9 | 2.2 | 2.2 | 1.1 | 2.4 | 1.4 | 2.1 | 4.5 | 1.5 | 2.4 | 2.41 |
| YML131W | 11.2 | 4.3 | 7.7 | 1.9 | 0.7 | 2.0 | 3.0 | 6.1 | 11.1 | 17.7 | 14.4 | 1.1 | 2.4 | 2.7 | 2.2 | 1.6 | 2.5 | 3.0 | 1.15 |
| YNL071W | 0.9 | 0.9 | 1.7 | 1.5 | 0.6 | 1.3 | 1.4 | 0.9 | 1.1 | 1.2 | 1.6 | 1.3 | 2.5 | 0.8 | 1.1 | 1.1 | 1.0 | 1.2 | 1.61 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YOR120W | 1.8 | 5.4 | 2.8 | 3.2 | 1.4 | 3.4 | 2.7 | 2.0 | 3.3 | 3.0 | 3.0 | 1.2 | 3.6 | 2.4 | 1.5 | 3.9 | 1.3 | 2.6 | 1.06 |
| YAL023C | 0.4 | 1.5 | 1.0 | 0.7 | 1.0 | 0.6 | 0.8 | 0.6 | 0.3 | 0.4 | 1.7 | 1.2 | 2.3 | 0.4 | 2.5 | 0.4 | 1.0 | 0.7 | 1.49 |
| YAL060W | 1.1 | 1.8 | 3.2 | 2.7 | 1.2 | 4.2 | 3.3 | 0.9 | 0.6 | 2.5 | 2.4 | 0.8 | 2.2 | 0.9 | 0.9 | 3.2 | 1.1 | 1.8 | 2.39 |
| YAL062W | 0.8 | 1.5 | 1.4 | 1.1 | 1.0 | 1.2 | 1.1 | 0.8 | 1.4 | 0.7 | 1.2 | 1.0 | 2.1 | 0.8 | 1.1 | 1.3 | 1.0 | 0.8 | 0.86 |
| YBR006W | 1.3 | 1.6 | 2.6 | 1.5 | 1.3 | 3.1 | 3.3 | 1.0 | 4.5 | 2.7 | 1.9 | 1.1 | 2.2 | 1.1 | 1.1 | 3.0 | 1.2 | 1.8 | 0.62 |
| YBR056W | 1.4 | 1.7 | 1.4 | 2.3 | 1.4 | 2.3 | 5.5 | 1.4 | 3.0 | 3.3 | 1.8 | 1.4 | 3.0 | 1.0 | 0.7 | 2.8 | 2.4 | 3.4 | 1.13 |
| YBR149W | 1.1 | 2.0 | 2.7 | 1.7 | 1.4 | 2.8 | 3.1 | 1.5 | 1.7 | 1.9 | 1.9 | 1.4 | 2.2 | 1.2 | 0.7 | 2.7 | 2.1 | 3.4 | 2.72 |
| YBR284W | 0.9 | 1.5 | 2.8 | 4.8 | 1.3 | 1.9 | 1.0 | 0.9 | 6.5 | 3.2 | 1.4 | 1.2 | 2.8 | 1.6 | 0.8 | 0.8 | 1.1 | 1.0 | 0.25 |
| YCL018W | 1.2 | 2.7 | 2.4 | 1.4 | 0.8 | 2.3 | 2.3 | 1.3 | 2.1 | 4.3 | 3.7 | 1.6 | 3.2 | 1.0 | 0.6 | 2.3 | 1.3 | 1.0 | 0.99 |
| YCL040W | 0.9 | 7.1 | 10.1 | 2.0 | 0.5 | 3.5 | 2.9 | 0.7 | 0.9 | 3.0 | 8.2 | 2.3 | 5.6 | 0.7 | 3.4 | 3.1 | 1.4 | 1.7 | 1.98 |
| YDL010W | 1.7 | 0.8 | 0.6 | 0.7 | 1.2 | 1.1 | 1.9 | 1.1 | 2.2 | 1.3 | 1.3 | 0.9 | 2.0 | 2.2 | 1.4 | 1.4 | 1.5 | 2.4 | 0.93 |
| YDL024C | 1.6 | 1.5 | 1.2 | 2.2 | 1.0 | 1.7 | 0.9 | 1.7 | 4.2 | 3.4 | 1.2 | 1.7 | 2.6 | 1.9 | 2.1 | 2.8 | 0.9 | 1.1 | 0.40 |
| YDL095W | 0.5 | 1.3 | 1.0 | 0.8 | 0.8 | 1.0 | 0.8 | 0.7 | 1.2 | 0.7 | 1.0 | 1.1 | 2.2 | 0.5 | 2.0 | 0.5 | 0.7 | 0.9 | 1.57 |
| YDL245C | 1.0 | 2.4 | 1.6 | 2.2 | 1.3 | 1.1 | 1.2 | 1.2 | 0.4 | 2.8 | 1.5 | 1.0 | 2.0 | 1.2 | 1.8 | 1.5 | 1.0 | 1.1 | 0.28 |
| YDL246C | 1.2 | 1.5 | 1.3 | 1.1 | 1.1 | 1.4 | 2.1 | 2.4 | 4.4 | 3.6 | 2.6 | 1.2 | 2.9 | 1.7 | 2.6 | 1.7 | 1.8 | 1.8 | 0.43 |
| YDR001C | 0.8 | 2.2 | 2.6 | 1.0 | 1.1 | 2.2 | 1.5 | 0.9 | 2.2 | 3.0 | 0.7 | 1.1 | 2.8 | 1.0 | 4.4 | 1.9 | 1.1 | 1.6 | 0.75 |
| YDR058C | 1.2 | 2.2 | 0.8 | 2.7 | 0.7 | 1.0 | 1.4 | 1.9 | 2.4 | 1.7 | 1.7 | 1.2 | 2.5 | 1.8 | 1.2 | 1.9 | 1.1 | 1.6 | 0.56 |
| YDR072C | 1.3 | 1.3 | 1.7 | 1.2 | 0.9 | 1.5 | 0.9 | 0.7 | 0.6 | 0.7 | 0.7 | 0.9 | 1.9 | 0.6 | 0.4 | 0.7 | 1.9 | 1.9 | 2.81 |
| YDR127W | 0.8 | 0.9 | 1.5 | 0.7 | 1.2 | 0.8 | 0.9 | 0.7 | 0.6 | 1.3 | 1.3 | 0.8 | 1.7 | 1.0 | 1.3 | 0.6 | 0.9 | 0.7 | 0.78 |
| YDR261C | 1.2 | 1.2 | 1.9 | 0.7 | 1.3 | 1.4 | 0.8 | 0.9 | 1.7 | 1.0 | 1.2 | 1.0 | 1.9 | 0.9 | 2.3 | 0.6 | 0.9 | 0.8 | 0.68 |
| YDR272W | 1.0 | 4.0 | 0.8 | 1.8 | 0.7 | 2.3 | 1.7 | 2.1 | 2.5 | 1.9 | 2.1 | 1.2 | 2.4 | 1.4 | 2.1 | 1.4 | 2.3 | | 1.51 |
| YDR497C | 0.7 | 0.5 | 0.6 | 1.3 | 0.7 | 0.6 | 0.5 | 0.6 | 0.4 | 0.8 | 0.7 | 0.9 | 2.7 | 0.6 | 10.1 | | 1.6 | 1.8 | 1.45 |
| YDR516C | 1.2 | 1.5 | 7.8 | 2.1 | 1.3 | 1.8 | 3.9 | 1.3 | 1.8 | 5.2 | 2.8 | 1.1 | 2.5 | 0.7 | 0.4 | 1.7 | 1.1 | 1.2 | 1.66 |
| YER053C | 1.6 | 1.8 | 1.9 | 1.7 | 0.6 | 2.8 | 2.8 | 1.3 | 1.3 | 3.9 | 2.4 | 1.7 | 4.1 | 1.3 | 1.1 | 2.8 | 1.2 | 2.3 | 1.83 |
| YER096W | 1.1 | 2.3 | 2.0 | 2.0 | 1.3 | 1.2 | 0.9 | 1.0 | 7.5 | 3.5 | 1.1 | 0.9 | 2.3 | 3.1 | 1.4 | 2.0 | 1.0 | 1.2 | 0.22 |
| YER178W | 0.8 | 0.9 | 3.6 | 1.0 | 0.7 | 2.5 | 1.6 | 0.8 | 1.7 | 1.3 | 2.5 | 1.3 | 2.4 | 0.9 | 1.8 | 1.0 | 1.1 | 0.9 | 2.18 |
| YFL030W | 1.6 | 6.0 | 3.1 | 2.0 | 1.1 | 1.3 | 0.6 | 1.6 | 24.5 | 4.9 | 5.4 | 1.2 | 2.2 | 0.8 | 1.1 | 0.6 | 1.0 | 0.8 | 0.50 |
| YFL031W | 0.5 | 1.3 | 2.1 | 0.7 | 1.0 | 0.3 | 0.9 | 0.7 | 1.0 | 0.7 | 1.2 | 1.0 | 2.6 | 0.4 | 2.7 | 0.9 | 1.2 | 1.1 | 3.16 |
| YFR047C | 1.3 | 4.0 | 2.7 | 2.6 | 1.2 | 2.0 | 2.0 | 1.0 | 3.0 | 1.5 | 2.3 | 1.7 | 2.7 | 1.9 | 0.6 | 3.6 | 1.5 | 1.6 | 1.57 |
| YGL248W | 1.3 | 1.3 | 0.9 | 0.7 | 1.3 | 2.7 | 1.6 | 0.8 | 0.2 | 2.9 | 1.0 | 0.8 | 2.0 | 1.3 | 1.8 | 2.9 | 1.1 | 1.2 | 0.22 |
| YGR037C | 1.0 | 1.2 | 2.2 | 0.8 | 1.0 | 1.1 | 1.4 | 1.4 | 1.7 | 1.4 | 1.4 | 1.5 | 2.7 | 1.5 | 1.5 | 2.6 | 1.4 | 2.0 | 3.40 |
| YGR055W | 2.5 | 5.7 | 12.0 | 0.7 | 1.3 | 1.1 | 0.6 | 1.1 | 5.0 | 2.4 | 1.5 | 0.9 | 1.9 | 1.2 | 2.1 | 0.6 | 0.7 | 0.7 | 1.42 |
| YGR194C | 0.9 | 1.0 | 1.3 | 2.1 | 0.8 | 1.9 | 2.2 | 1.2 | 2.4 | 2.1 | 0.7 | 0.8 | 2.2 | 1.0 | 0.6 | 2.6 | 1.1 | 2.0 | 0.63 |
| YGR256W | 1.2 | 1.5 | 2.3 | 0.8 | 0.9 | 6.2 | 1.4 | 2.2 | 3.4 | 2.5 | 2.7 | 1.5 | 3.9 | 1.1 | 2.7 | 5.3 | 1.1 | 0.8 | 0.94 |
| YHR111W | 1.4 | 1.3 | 0.8 | 1.9 | 1.5 | 1.3 | 1.6 | 1.3 | 4.5 | 4.2 | 1.9 | 0.9 | 2.2 | 1.7 | 1.1 | 1.3 | 1.1 | 1.2 | 0.44 |
| YHR174W | 1.1 | 1.4 | 3.3 | 1.2 | 1.3 | 1.5 | 1.6 | 1.2 | 1.0 | 1.5 | 1.4 | 1.5 | 3.6 | 0.6 | 2.0 | 1.1 | 1.0 | 1.2 | 7.34 |
| YHR176W | 1.8 | 2.0 | 1.1 | 1.4 | 1.0 | 2.3 | 1.4 | 1.3 | 6.3 | 6.4 | 1.2 | 1.2 | 1.9 | 1.3 | 1.5 | 1.8 | 1.4 | 1.6 | 0.27 |
| YIL045W | 1.7 | 1.4 | 1.9 | 2.2 | 1.3 | 1.7 | 1.6 | 1.1 | 2.1 | 3.2 | 1.2 | 1.5 | 2.0 | 1.6 | 0.6 | 2.9 | 1.1 | 1.8 | 0.37 |
| YIL107C | 1.5 | 0.8 | 1.1 | 1.5 | 0.8 | 1.0 | 1.6 | 1.3 | 3.5 | 3.5 | 0.9 | 1.1 | 1.9 | 1.6 | 1.0 | 2.7 | 1.2 | 2.0 | 0.58 |
| YIL155C | 1.0 | 0.7 | 1.4 | 3.7 | 1.3 | 1.4 | 2.2 | 1.0 | 2.5 | 2.9 | 1.3 | 1.4 | 2.0 | 1.3 | 1.4 | 3.8 | 1.1 | 1.4 | 0.51 |
| YRR034C | 1.2 | 1.1 | 2.5 | 0.6 | 1.1 | 1.3 | 0.8 | 1.7 | 3.2 | 3.5 | 3.0 | 1.4 | 2.6 | 1.2 | 1.9 | 1.3 | 1.0 | 1.0 | 0.92 |
| YIR036C | 1.0 | 1.7 | 2.6 | 1.8 | 0.9 | 0.7 | 1.0 | 1.0 | 3.3 | 1.9 | 2.8 | 1.2 | 1.9 | 1.2 | 1.1 | 4.0 | 1.5 | 1.3 | 0.64 |
| YJL031C | 1.6 | 1.2 | 0.5 | 1.3 | 1.7 | 1.6 | 2.3 | 1.8 | 4.7 | 3.6 | 1.9 | 1.3 | 2.6 | 3.0 | 2.0 | 1.9 | 1.2 | 1.9 | 1.02 |
| YJL068C | 1.2 | 2.7 | 3.4 | 1.6 | 0.7 | 1.1 | 1.2 | 1.1 | 6.5 | 3.1 | 3.2 | 1.7 | 2.7 | 1.5 | 0.5 | 2.6 | 1.4 | 1.5 | 0.95 |
| YJL099W | 1.2 | 1.2 | 0.3 | 1.3 | 1.9 | 2.0 | 1.8 | 1.0 | 3.1 | 3.1 | 0.9 | 1.0 | 2.4 | 1.8 | 1.4 | 1.7 | 1.2 | 1.6 | 0.55 |
| YJL172W | 0.8 | 2.1 | 1.8 | 1.5 | 0.9 | 3.8 | 1.0 | 0.7 | 0.7 | 1.9 | 1.4 | 1.1 | 3.1 | 0.9 | 1.2 | 0.5 | 1.8 | 1.8 | 0.62 |

TABLE 7-continued

Metabolism protein genes yeast | The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YJL219W | 1.2 | 2.5 | 3.1 | 1.6 | 1.2 | 1.5 | 0.9 | 1.5 | 4.0 | 2.3 | 2.3 | 1.1 | 4.0 | 1.1 | 2.6 | 1.4 | 1.6 | 1.2 | 0.91 |
| YJR137C | 2.7 | 2.9 | 4.6 | 0.8 | 0.6 | 1.5 | 0.8 | 1.6 | 9.0 | 4.8 | 2.0 | 1.4 | 2.1 | 1.2 | 1.0 | 1.3 | 0.9 | 0.8 | 0.46 |
| YKL035W | 1.0 | 0.9 | 4.8 | 1.2 | 0.8 | 1.2 | 0.6 | 1.0 | 0.8 | 1.2 | 2.1 | 1.0 | 2.0 | 0.6 | 1.0 | 1.5 | 1.0 | 1.9 | 2.54 |
| YKL091C | 1.2 | 1.3 | 1.4 | 2.6 | 1.0 | 2.2 | 1.9 | 1.3 | 2.3 | 3.2 | 1.7 | 1.3 | 2.0 | 1.5 | 1.1 | 4.6 | 1.4 | 2.0 | 0.83 |
| YKL104C | 1.0 | 1.0 | 1.6 | 1.2 | 1.4 | 0.9 | 2.3 | 1.1 | 1.4 | 1.8 | 2.2 | 1.6 | 2.2 | 0.8 | 3.3 | 0.6 | 1.0 | 1.1 | 1.25 |
| YKL152C | 1.3 | 1.3 | 1.9 | 0.9 | 1.3 | 1.6 | 1.5 | 1.0 | 0.9 | 1.5 | 1.7 | 1.5 | 2.7 | 1.0 | 1.8 | 2.0 | 1.1 | 1.7 | 3.28 |
| YKL213C | 0.9 | 0.8 | 1.0 | 1.3 | 0.7 | 1.0 | 1.0 | 1.1 | 4.8 | 2.1 | 1.3 | 0.9 | 2.1 | 0.9 | 1.1 | 1.5 | 1.4 | 1.6 | 0.77 |
| YKL215C | 0.6 | 1.1 | 1.3 | 0.8 | 1.0 | 2.1 | 1.1 | 1.1 | 1.3 | 1.9 | 0.5 | 1.0 | 2.6 | 1.0 | 0.9 | 0.8 | 0.8 | 0.9 | 0.38 |
| YLL058W | 1.0 | 3.8 | 1.4 | 0.9 | 0.8 | 1.4 | 1.5 | 0.9 | 3.5 | 3.6 | 2.0 | 1.0 | 2.3 | 0.8 | 1.9 | 1.1 | 1.4 | 1.3 | 0.39 |
| YLR299W | 1.2 | 1.9 | 1.5 | 1.3 | 0.6 | 0.9 | 0.8 | 1.0 | 4.9 | 2.3 | 1.7 | 1.0 | 2.9 | 1.3 | 1.5 | 0.9 | 1.3 | 1.4 | 0.57 |
| YLR348C | 1.1 | 4.5 | 1.2 | 1.2 | 0.9 | 1.9 | 0.9 | 0.9 | 2.1 | 1.3 | 1.3 | 0.9 | 1.9 | 1.0 | 2.4 | 1.1 | 1.1 | 1.0 | 0.64 |
| YML054C | 1.5 | 1.8 | 1.3 | 3.4 | 1.3 | 1.8 | 1.2 | 1.5 | 4.1 | 1.8 | 1.4 | 1.8 | 2.8 | 2.1 | 1.1 | 7.8 | 1.1 | 1.6 | 0.25 |
| YML070W | 0.9 | 1.7 | 2.5 | 1.9 | 1.4 | 2.2 | 3.1 | 1.3 | 4.5 | 3.9 | 1.5 | 1.3 | 3.3 | 1.3 | 0.9 | 2.6 | 1.2 | 1.3 | 1.03 |
| YML100W | 0.8 | 2.7 | 10.6 | 1.4 | 0.9 | 2.8 | 2.2 | 0.7 | 1.7 | 1.4 | 3.2 | 1.2 | 3.8 | 1.2 | 1.8 | 2.2 | 1.0 | 1.5 | 0.88 |
| YMR008C | 0.7 | 0.9 | 1.4 | 1.0 | 1.1 | 1.7 | 0.9 | 0.5 | 0.3 | 0.6 | 1.3 | 1.1 | 3.7 | 0.7 | 2.0 | 1.2 | 3.0 | 1.9 | 1.59 |
| YMR020W | 1.3 | 1.0 | 0.9 | 1.7 | 1.4 | 1.6 | 2.7 | 1.2 | 2.3 | 2.9 | 1.5 | 1.1 | 3.0 | 1.1 | 1.8 | 2.8 | 2.3 | 2.2 | 0.81 |
| YMR105C | 1.9 | 3.0 | 5.0 | 4.2 | 0.9 | 2.8 | 2.8 | 1.1 | 0.6 | 2.9 | 3.0 | 1.7 | 3.3 | 1.0 | 0.9 | 2.0 | 1.6 | 2.6 | 1.21 |
| YMR271C | 1.6 | 1.6 | 1.3 | 2.0 | 1.1 | 4.2 | 3.4 | 1.8 | 8.0 | 4.4 | 1.7 | 1.3 | 3.6 | 1.8 | 0.6 | 5.7 | 1.3 | 2.2 | 0.70 |
| YNL012W | 1.3 | 1.3 | 1.8 | 0.8 | 1.3 | 1.7 | 2.0 | 1.8 | 3.3 | 3.2 | 1.6 | 1.3 | 2.9 | 1.0 | 1.6 | 1.2 | 1.3 | 1.5 | 0.24 |
| YNL045W | 0.8 | 1.3 | 2.0 | 1.3 | 1.1 | 2.2 | 1.8 | 0.7 | 1.3 | 1.1 | 2.1 | 0.9 | 2.6 | 0.8 | 0.8 | 2.4 | 1.1 | 1.1 | 0.80 |
| YNL104C | 1.1 | 1.3 | 3.0 | 0.9 | 0.8 | 0.8 | 0.6 | 0.9 | 1.1 | 2.0 | 2.1 | 1.1 | 2.1 | 0.9 | 2.5 | 1.5 | 0.9 | 0.9 | 1.69 |
| YNL231C | 1.5 | 0.8 | 0.8 | 0.5 | 2.1 | 1.8 | 2.5 | 1.5 | 2.2 | 1.3 | 1.3 | 1.8 | 2.9 | 0.9 | 0.9 | 0.7 | 3.1 | 4.0 | 2.13 |
| YNR019W | 1.0 | 1.3 | 1.6 | 1.2 | 0.8 | 1.3 | 0.8 | 0.7 | 1.8 | 1.9 | 0.7 | 1.0 | 2.1 | 1.0 | 1.6 | 0.8 | 2.4 | 2.0 | 0.37 |
| YNR033W | 0.6 | 0.8 | 0.8 | 1.0 | 1.3 | 1.6 | 1.2 | 1.1 | 3.6 | 4.2 | 0.4 | 1.1 | 3.8 | 0.9 | 1.3 | 2.2 | 0.9 | 1.1 | 0.72 |
| YNR059W | 1.1 | 0.9 | 0.2 | 1.4 | 1.4 | 0.8 | 1.6 | 1.3 | 1.8 | 1.4 | 1.0 | 0.8 | 2.4 | 1.0 | 1.0 | 2.0 | 2.6 | 2.2 | 0.45 |
| YOL126C | 1.0 | 0.8 | 1.0 | 1.6 | 0.7 | 1.5 | 1.4 | 0.9 | 0.8 | 2.4 | 1.8 | 1.1 | 2.6 | 1.2 | 1.4 | 2.5 | 1.6 | 2.4 | 0.59 |
| YOL153C | 1.0 | 1.2 | 2.1 | 3.9 | 1.2 | 1.9 | 3.3 | 1.0 | 2.5 | 3.2 | 2.4 | 1.9 | 2.9 | 1.5 | 1.2 | 5.4 | 1.1 | 1.7 | 0.37 |
| YOR099W | 0.8 | 1.3 | 2.1 | 1.3 | 1.5 | 0.9 | 1.0 | 0.9 | 0.6 | 0.7 | 1.2 | 1.1 | 1.6 | 0.7 | 1.5 | 1.1 | 1.2 | 2.3 | 3.94 |
| YOR130C | 0.8 | 1.7 | 1.4 | 1.0 | 1.8 | 1.6 | 1.3 | 0.8 | 2.0 | 1.7 | 0.6 | 0.9 | 2.1 | 1.3 | 1.0 | 0.8 | 1.5 | 1.1 | 0.51 |
| YOR336W | 0.7 | 1.4 | 0.7 | 1.0 | 1.3 | 1.7 | 1.2 | 0.8 | 1.7 | 1.5 | 1.4 | 1.0 | 2.1 | 1.1 | 0.6 | 0.9 | 1.0 | 1.0 | 0.44 |
| YOR347C | 0.9 | 0.9 | 2.1 | 2.2 | 0.7 | 0.9 | 0.9 | 0.8 | 0.5 | 0.9 | 1.4 | 1.2 | 1.8 | 0.9 | 2.0 | 1.4 | 1.7 | 1.3 | 1.31 |
| YPL017C | 1.0 | 2.5 | 0.8 | 1.0 | 1.3 | 1.5 | 1.4 | 1.3 | 3.0 | 6.7 | 0.4 | 1.0 | 1.9 | 1.6 | 1.0 | 1.3 | 1.3 | 0.8 | 0.19 |
| YPR026W | 0.9 | 1.2 | 5.0 | 1.3 | 0.8 |  | 1.3 | 1.0 | 0.9 | 3.1 | 1.6 | 1.2 | 2.3 | 1.5 | 3.1 | 2.5 | 0.9 | 1.3 | 0.26 |
| YAL012W | 1.1 | 6.5 | 10.4 | 0.8 | 0.6 | 1.6 | 0.6 | 0.7 | 4.7 | 3.9 | 4.0 | 1.1 | 1.1 | 0.9 | 3.1 | 1.0 | 0.9 | 0.8 | 0.96 |
| YBR029C | 0.7 | 0.2 | 1.8 | 1.0 | 1.4 | 0.8 | 0.4 | 0.7 | 2.0 | 1.1 | 0.7 | 1.3 | 1.7 | 0.9 | 3.5 | 0.9 | 0.6 | 0.8 | 1.56 |
| YBR222C | 0.6 | 1.2 | 1.3 | 0.8 | 0.7 | 1.3 | 1.0 | 0.6 | 0.7 | 1.0 | 1.3 | 0.9 | 1.6 | 0.5 | 4.3 | 2.1 | 0.8 | 0.9 | 0.52 |
| YCL009C | 0.6 | 0.9 | 2.0 | 0.5 | 0.7 | 1.8 | 1.3 | 1.1 | 0.9 | 1.6 | 1.5 | 1.7 | 1.6 | 0.7 | 6.5 | 0.9 | 1.1 | 0.8 | 0.68 |
| YCL064C | 0.6 | 0.6 | 0.8 | 0.8 | 1.4 | 3.3 | 13.4 | 2.4 | 1.7 | 5.2 | 1.8 | 0.7 | 1.6 | 0.8 | 21.4 | 1.0 | 0.3 | 0.3 | 1.42 |
| YDR098C | 1.6 | 3.0 | 1.7 | 2.0 | 1.4 | 1.6 | 1.2 | 1.0 | 1.4 | 2.4 | 1.3 | 1.3 | 1.4 | 1.1 | 11.0 | 0.8 | 1.7 | 1.6 | 0.22 |
| YDR502C | 1.2 | 2.8 | 2.4 | 1.2 | 1.5 | 1.5 | 0.9 | 0.9 | 1.6 | 0.9 | 1.3 | 1.3 | 1.2 | 0.8 | 8.2 | 1.0 | 0.9 | 0.9 | 2.75 |
| YER026C | 0.8 | 0.6 | 3.3 | 1.0 | 1.2 | 2.5 | 1.6 | 0.8 | 0.9 | 1.5 | 0.9 | 1.7 | 1.9 | 1.1 | 4.0 | 1.4 | 1.7 | 3.2 | 4.48 |
| YHR137W | 0.7 | 1.0 | 2.4 | 1.7 | 1.0 | 0.7 | 0.4 | 0.4 | 0.2 | 0.9 | 0.6 | 0.6 | 0.6 | 0.8 | 2.8 | 0.4 | 0.8 | 1.3 | 1.40 |
| YMR189W | 0.7 | 0.8 | 1.9 | 2.8 | 0.4 | 1.9 | 0.8 | 0.4 | 0.7 | 0.9 | 8.2 | 0.6 | 0.9 | 1.6 | 5.6 | 0.9 | 1.0 | 0.8 | 0.88 |
| YNL106C | 1.0 | 1.4 | 0.8 | 1.5 | 0.8 | 1.0 | 0.9 | 0.8 | 0.7 | 1.4 | 0.9 | 0.8 | 0.9 | 1.1 | 3.3 | 1.2 | 1.1 | 0.9 | 0.37 |
| YNL169C | 0.7 | 1.4 | 1.4 | 1.2 | 0.7 | 1.4 | 0.7 | 0.8 | 1.1 | 1.1 | 0.8 | 1.0 | 1.7 | 0.9 | 3.4 | 0.8 | 1.1 | 1.3 | 1.05 |
| YNL322C | 0.8 | 0.9 | 1.9 | 0.8 | 1.4 | 1.1 | 0.9 | 0.7 | 0.7 | 0.8 | 0.6 | 0.7 | 0.8 | 1.2 | 3.7 | 0.9 | 0.9 | 1.0 | 0.75 |
| YAL038W | 1.0 | 1.0 | 3.0 | 1.4 | 1.4 | 1.3 | 0.9 | 1.1 | 0.1 | 1.1 | 1.0 | 1.2 | 1.8 | 0.5 | 3.1 | 0.9 | 1.0 | 1.0 | 7.02 |
| YBR023C | 0.5 | 0.8 | 1.1 | 0.8 | 1.8 | 0.5 | 0.7 | 0.5 | 0.3 | 0.4 | 0.9 | 0.8 | 0.5 | 0.8 | 2.8 | 0.7 | 0.7 | 0.9 | 0.93 |
| YCR048W | 0.5 | 1.1 | 1.0 | 0.6 | 0.9 | 0.2 | 0.9 | 0.8 | 0.8 | 0.5 | 1.2 | 0.9 | 1.3 | 0.9 | 3.1 | 1.1 | 1.2 | 0.8 | 0.29 |
| YDR380W | 0.8 | 0.8 | 0.8 | 1.7 | 1.1 | 0.4 | 0.5 | 0.2 | 0.2 | 0.3 | 0.4 | 0.4 | 0.4 | 0.6 | 2.4 | 0.2 | 0.8 | 0.8 | 1.04 |
| YER069W | 1.3 | 0.8 | 3.3 | 1.4 | 1.5 | 1.3 | 1.0 | 1.5 | 0.8 | 10.4 | 1.5 | 0.8 | 1.4 | 1.3 | 2.4 | 1.1 | 1.1 | 0.9 | 0.25 |
| YGL022W | 0.5 | 0.8 | 1.4 | 0.3 | 1.0 | 0.9 | 0.7 | 0.4 | 0.9 | 0.4 | 0.8 | 0.7 | 1.0 | 0.5 | 4.0 | 0.3 | 0.9 | 0.7 | 0.91 |
| YGL126W | 0.6 | 1.3 | 1.4 | 0.8 | 1.1 | 1.6 |  | 0.7 | 1.6 | 0.7 | 1.0 | 0.6 |  |  | 2.8 |  | 0.9 | 0.9 | 0.34 |
| YGL209W | 1.2 | 1.6 | 1.1 | 2.6 | 0.7 | 1.0 | 1.0 | 1.1 | 0.6 | 0.4 | 0.8 | 1.3 | 1.9 | 1.6 | 3.2 | 2.8 | 1.1 | 1.5 | 0.63 |
| YGR282C | 1.3 | 0.7 | 4.6 | 1.9 | 1.0 | 2.2 | 1.1 | 1.0 | 0.8 | 0.8 | 1.5 | 1.3 | 1.2 | 1.0 | 2.9 | 1.4 | 1.1 | 1.5 | 5.04 |
| YIL154C | 0.8 | 1.3 | 1.9 | 0.8 | 0.9 | 1.1 | 1.3 | 0.6 | 2.4 | 1.0 | 1.2 | 1.1 | 1.7 | 0.9 | 4.3 | 1.2 | 1.2 | 1.0 | 0.39 |
| YJL088W | 0.9 | 0.8 | 2.2 | 0.5 | 0.9 | 2.8 |  | 1.3 | 3.2 | 4.1 | 0.9 | 0.7 | 1.0 | 2.0 | 5.7 | 0.7 | 1.4 | 0.9 | 0.27 |
| YJR148W | 0.7 | 1.4 | 2.0 | 3.5 | 0.6 | 2.0 | 2.1 | 0.6 | 0.7 | 3.0 | 0.6 | 0.8 | 1.1 | 1.3 | 3.2 | 1.3 | 1.3 | 1.7 | 1.50 |
| YLR180W | 1.3 | 1.4 | 2.4 | 1.0 | 0.8 | 1.2 | 0.6 | 0.9 | 0.8 | 0.9 | 1.7 | 0.6 | 0.6 | 0.6 | 2.5 | 0.5 | 0.8 | 0.7 | 3.23 |
| YLR273C | 1.4 | 1.4 | 2.4 |  |  | 1.2 | 1.2 | 1.3 | 2.8 | 2.4 | 1.4 | 0.9 | 1.7 | 1.3 | 2.6 | 1.5 | 1.0 | 1.0 | 0.20 |
| YLR300W | 0.9 | 0.8 | 0.8 | 1.0 | 0.8 | 1.1 | 0.5 | 0.8 | 0.0 | 0.5 | 1.0 | 0.5 | 0.2 | 0.6 | 2.7 | 0.3 | 0.7 | 0.5 | 5.14 |
| YLR307W | 0.9 | 0.4 | 0.7 | 3.3 | 1.4 | 1.2 | 1.5 | 1.2 | 0.6 | 0.7 | 0.8 | 0.7 | 1.0 | 1.9 | 3.9 | 0.9 | 1.1 | 1.0 | 0.16 |
| YMR296C | 0.6 | 0.7 | 1.2 | 2.6 | 0.4 | 0.4 | 0.6 | 0.5 | 0.4 | 0.6 | 0.8 | 0.8 | 0.9 | 0.7 | 6.7 | 0.5 | 0.8 | 0.7 | 0.52 |
| YOL058W | 0.8 | 0.5 | 1.7 | 0.9 | 1.2 | 0.8 | 0.4 | 1.6 | 0.1 | 15.7 | 2.3 | 1.3 | 1.2 | 1.5 | 2.7 | 0.9 | 1.2 | 0.8 | 0.82 |
| YBR183W | 1.8 | 1.5 | 2.0 | 2.9 | 0.9 | 2.5 | 1.7 | 1.0 | 0.4 | 2.0 | 1.9 | 1.2 | 1.4 | 1.3 | 1.1 | 2.1 | 1.4 | 2.4 | 1.47 |
| YDR019C | 1.4 | 0.5 | 1.7 | 4.0 | 0.9 | 4.8 | 1.4 | 0.7 | 0.4 | 0.7 | 1.8 | 0.7 | 1.0 | 1.6 | 1.8 | 1.8 | 1.2 | 1.6 | 2.48 |
| YIL167W | 3.3 | 1.6 | 2.0 | 1.0 | 1.0 | 7.7 | 1.2 | 1.9 | 6.9 | 12.7 | 1.9 | 0.7 | 1.2 | 1.4 | 0.6 | 2.3 | 0.7 | 0.8 | 2.11 |
| YKR039W | 1.4 | 3.5 | 1.3 | 1.7 | 1.0 | 2.8 | 1.0 | 1.0 | 1.9 | 2.0 | 1.9 | 1.5 | 1.3 | 1.2 | 1.7 | 1.9 | 0.9 | 1.1 | 0.40 |
| YNL037C | 1.4 | 1.8 | 1.7 | 1.1 | 1.7 | 2.8 | 2.8 | 1.0 | 0.6 | 3.2 | 1.4 | 1.3 | 1.9 | 1.3 | 0.9 | 1.4 | 0.9 | 1.3 | 2.05 |
| YNR002C | 1.3 | 1.6 | 1.0 | 2.0 | 1.2 | 2.3 | 1.2 | 1.0 | 3.9 | 1.6 | 1.6 | 1.2 | 2.1 | 1.2 | 1.0 | 2.4 | 1.5 | 2.1 | 0.29 |
| YOL143C | 1.0 | 1.4 | 1.2 | 1.2 | 0.9 | 3.5 | 1.3 | 1.2 | 0.8 | 1.0 | 2.0 | 1.2 | 1.2 | 0.7 | 1.0 | 2.2 | 1.8 | 1.4 | 2.30 |
| YOR136W | 1.0 | 0.9 | 3.5 | 1.0 | 1.5 | 3.9 | 3.2 | 1.1 | 0.3 | 3.4 | 1.4 | 1.2 | 1.5 | 0.9 | 1.2 | 1.3 | 0.8 | 1.3 | 3.20 |
| YAL044C | 1.5 | 1.1 | 1.0 | 3.0 | 0.8 | 2.2 | 1.0 | 0.8 | 0.4 | 0.6 | 1.4 | 0.6 | 1.1 | 1.4 | 0.7 | 1.0 | 1.4 | 1.8 | 4.07 |

TABLE 7-continued

Metabolism protein genes

| yeast genes | The level of expressed mRNA in the presence of chemical substance/The level of expressed mRNA in the absence of chemical substance | | | | | | | | | | | | | | | | | | |
|---|---|---|---|---|---|---|---|---|---|---|---|---|---|---|---|---|---|---|---|
| | (1) | (2) | (3) | (4) | (5) | (6) | (7) | (8) | (9) | (10) | (11) | (12) | (13) | (14) | (15) | (16) | (17) | (18) | Intensity |
| YAL054C | 1.2 | 1.1 | 1.4 | 1.6 | 1.1 | 2.2 | 1.1 | 1.1 | 8.9 | 4.1 | 1.3 | 1.0 | 1.8 | 1.3 | 0.9 | 2.5 | 1.5 | 1.4 | 0.24 |
| YAR071W | 1.6 | 0.8 | 1.0 | 0.7 | 1.6 | 2.0 | 0.3 | 1.4 | 0.3 | 0.3 | 1.1 | 2.0 | 0.3 | 1.1 | 1.1 | 0.3 | 0.7 | 1.6 | 3.21 |
| YBL001C | 1.1 | 1.5 | 1.0 | 1.6 | 1.0 | 2.4 | 1.3 | 1.0 | 1.5 | 0.9 | 2.3 | 0.7 | 1.0 | 1.5 | 1.0 | 1.7 | 1.6 | 1.8 | 2.38 |
| YBR014C | 1.1 | 1.2 | 0.8 | 0.9 | 1.4 | 2.0 | 1.4 | 1.2 | 1.3 | 0.8 | 1.8 | 0.6 | 0.9 | 1.2 | 1.2 | 1.5 | 1.0 | 1.6 | 1.29 |
| YBR035C | 1.1 | 1.0 | 1.7 | 1.1 | 1.3 | 2.3 | 1.5 | 1.5 | 2.2 | 1.5 | 2.0 | 1.2 | 1.8 | 1.3 | 0.7 | 2.1 | 1.5 | 1.9 | 1.89 |
| YBR068C | 1.1 | 1.0 | 1.9 | 2.5 | 1.4 | 1.9 | | 1.0 | 0.8 | 2.5 | 0.8 | 0.8 | 2.2 | 1.8 | 1.6 | 5.5 | 1.1 | 1.3 | 1.99 |
| YBR111C | 1.0 | 0.9 | 1.0 | 1.7 | 1.3 | 3.0 | 2.2 | 1.7 | 1.9 | 1.9 | 1.5 | 1.2 | 1.6 | 1.6 | 0.7 | 3.5 | 1.4 | 2.4 | 3.20 |
| YCR037C | 0.7 | 1.0 | 0.8 | 0.8 | 1.3 | 1.8 | 1.0 | 0.7 | 0.6 | 0.6 | 0.8 | 0.7 | 1.3 | 0.8 | 1.0 | 1.1 | 1.4 | 0.9 | 0.74 |
| YDL022W | 0.9 | 2.6 | 6.9 | 1.5 | 0.7 | 2.1 | 1.5 | 0.8 | 1.2 | 1.8 | 2.8 | 1.2 | 1.5 | 0.8 | 0.9 | 1.1 | 1.0 | 1.4 | 1.79 |
| YDR009W | 1.4 | 0.8 | 1.5 | 1.0 | 1.2 | 2.4 | 1.4 | 1.2 | 1.3 | 2.0 | 0.1 | 1.0 | 1.2 | 1.5 | 3.2 | 1.0 | 1.2 | 1.0 | 0.21 |
| YDR410C | 0.8 | 2.0 | 1.3 | 0.9 | 1.1 | 2.5 | 1.4 | 0.9 | 1.2 | 1.5 | 1.6 | 0.9 | 1.2 | 1.3 | 1.2 | 0.8 | 1.0 | 1.0 | 1.33 |
| YDR487C | 2.2 | 0.9 | 1.3 | 1.1 | 1.3 | 2.3 | 1.3 | 1.8 | 2.7 | 2.3 | 2.1 | 1.3 | 1.5 | 2.5 | 1.0 | 1.5 | 1.5 | 1.9 | 2.61 |
| YEL011W | 2.0 | 1.6 | 1.7 | 6.3 | 1.1 | 2.8 | 2.7 | 0.9 | 2.5 | 1.6 | 3.7 | 1.5 | 1.5 | 1.5 | 0.4 | 2.4 | 1.4 | 2.5 | 0.89 |
| YFR015C | 1.2 | 0.8 | 3.2 | 2.1 | 1.2 | 3.0 | 7.3 | 0.7 | 0.3 | 1.8 | 3.9 | 0.4 | 2.5 | 3.1 | 0.4 | 2.4 | 1.3 | 1.2 | 0.66 |
| YGL001C | 1.0 | 1.0 | 1.4 | 1.1 | 1.5 | 2.8 | 1.4 | 1.1 | 0.8 | 0.8 | 1.6 | 0.9 | 1.0 | 1.1 | 0.9 | 2.2 | 1.9 | 2.1 | 2.53 |
| YGL104C | 0.8 | 2.0 | 2.1 | 1.8 | 1.0 | 2.1 | 1.2 | 0.8 | 4.6 | 2.1 | 1.8 | 1.1 | 2.0 | 1.0 | 0.9 | 1.7 | 1.3 | 1.3 | 0.58 |
| YGL154C | 1.3 | 1.4 | 1.5 | 0.9 | 1.0 | 1.7 | 0.7 | 1.2 | 2.0 | 1.4 | 0.9 | 0.9 | 2.0 | 1.1 | 0.8 | 0.7 | 1.0 | 1.1 | 0.57 |
| YGL253W | 0.8 | 1.0 | 3.2 | 0.7 | 1.3 | 2.4 | 1.7 | 1.0 | 0.3 | 1.4 | 1.0 | 1.2 | 1.5 | 0.5 | 0.8 | 0.4 | 0.7 | 0.8 | 4.63 |
| YGR060W | 0.7 | 0.6 | 0.9 | 0.7 | 1.9 | 2.5 | 0.5 | 1.0 | 0.5 | 0.4 | 0.8 | 1.0 | 0.6 | 0.8 | 1.4 | 2.1 | 1.3 | 1.6 | 4.19 |
| YHR037W | 0.7 | 0.9 | 1.3 | 1.6 | 0.9 | 1.8 | 1.2 | 1.0 | 0.9 | 2.2 | 1.7 | 1.1 | 1.1 | 1.1 | 1.1 | 2.0 | 1.0 | 1.4 | 1.15 |
| YHR092C | 2.3 | 1.0 | 7.5 | 2.5 | 1.4 | 1.7 | 0.5 | 1.5 | 0.2 | 0.9 | 1.5 | 1.0 | 0.5 | 1.6 | 0.2 | 1.2 | 0.9 | 1.3 | 6.09 |
| YHR190W | 0.8 | 3.9 | 1.2 | 1.2 | 1.8 | 1.7 | 1.9 | 1.2 | 2.4 | 1.9 | 1.3 | 1.1 | 1.7 | 1.3 | 1.3 | 1.8 | 1.3 | 1.8 | 2.15 |
| YIL033C | 0.8 | 1.3 | 3.3 | 1.3 | 0.7 | 2.0 | 1.1 | 0.7 | 2.4 | 1.3 | 1.8 | 1.1 | 2.5 | 0.7 | 1.0 | 2.0 | 1.0 | 1.2 | 1.18 |
| YIR035C | 1.4 | 1.8 | 0.9 | 1.6 | 0.7 | 2.1 | 1.3 | 1.3 | 0.7 | 1.2 | 1.3 | 0.9 | 1.1 | 1.1 | 1.4 | 1.0 | 1.1 | 0.9 | 1.51 |
| YJL132W | 1.0 | 0.7 | 0.8 | 1.6 | 1.3 | 2.0 | 1.7 | 1.0 | 1.6 | 1.4 | 1.4 | 1.0 | 1.3 | 1.4 | 1.1 | 2.1 | 1.3 | 1.5 | 0.37 |
| YJL196C | 0.9 | 0.9 | 2.5 | 1.3 | 1.1 | 2.0 | 0.7 | 0.7 | 1.1 | 0.9 | 2.3 | 1.1 | 0.6 | 0.8 | 0.6 | 1.7 | 0.9 | 1.9 | 2.85 |
| YJR142W | 1.2 | 0.6 | 1.1 | 1.1 | 1.3 | 2.4 | 1.7 | 1.0 | 0.6 | 0.8 | 0.9 | 0.8 | 1.6 | 1.3 | 0.6 | 2.0 | 1.2 | 1.4 | 0.94 |
| YKL067W | 1.1 | 1.9 | 2.1 | 1.4 | 1.9 | 2.2 | 2.6 | 1.2 | 0.9 | 1.6 | 1.8 | 0.9 | 1.7 | 1.2 | 1.1 | 2.4 | 1.4 | 3.2 | 3.29 |
| YLR142W | 4.4 | 2.7 | 1.1 | 6.1 | 1.3 | 3.1 | 1.2 | 2.1 | 3.1 | 4.4 | 3.8 | 0.8 | 1.2 | 2.1 | 1.6 | 3.4 | 1.9 | 3.2 | 0.28 |
| YML110C | 1.1 | 0.8 | 1.9 | 1.6 | 0.8 | 2.6 | 2.0 | 1.4 | 2.7 | 2.2 | 1.7 | 1.1 | 1.8 | 1.4 | 1.3 | 2.3 | 1.1 | 1.6 | 2.01 |
| YMR272C | 0.7 | 1.0 | 1.6 | 0.7 | 1.1 | 2.6 | 1.0 | 0.8 | 0.4 | 0.6 | 0.8 | 1.2 | 1.2 | 0.8 | 1.1 | 1.5 | 1.3 | 1.4 | 1.66 |
| YNL130C | 0.6 | 0.7 | 2.4 | 0.7 | 0.8 | 2.4 | 1.3 | 0.8 | 1.7 | 2.4 | 1.5 | 0.9 | 1.9 | 1.0 | 2.5 | 0.7 | 0.7 | 1.2 | 1.18 |
| YPR006C | 1.9 | 1.5 | 0.5 | 1.9 | 2.0 | 2.4 | 2.8 | 1.5 | 1.5 | 3.9 | 2.4 | 1.1 | 1.8 | 1.2 | 0.7 | 1.6 | 1.8 | 2.1 | 0.46 |
| YBR050C | 2.4 | 1.9 | 1.9 | 3.1 | 1.0 | 4.1 | 2.6 | 1.7 | 5.8 | 3.2 | 1.1 | 1.0 | 1.3 | 1.3 | 0.5 | 1.7 | 1.5 | 1.8 | 0.41 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YBR299W | 1.8 | 0.9 | 1.1 | 3.5 | 1.6 | 0.8 | 3.6 | 2.2 | 1.1 | 5.3 | 2.4 | 1.2 | 0.7 | 1.4 | 0.6 | 3.9 | 1.0 | 1.1 | 0.32 |
| YEL020C | 1.0 | 1.5 | 0.8 | 2.9 | 1.5 | 1.3 | 2.4 | 1.2 | 1.4 | 1.1 | 1.3 | 0.8 | 1.2 | 1.0 | 1.4 | 2.1 | 1.2 | 1.3 | 0.31 |
| YGL039W | 0.8 | 1.4 | 2.1 | 1.3 | 1.3 | 1.7 | 4.2 | 1.3 | 0.7 | 2.8 | 1.1 | 1.3 | 1.5 | 0.9 | 1.5 | 1.5 | 0.6 | 1.0 | 1.09 |
| YGL134W | 0.9 | 1.3 | 0.5 | 0.8 | 1.4 | 1.2 | 2.3 | 1.4 | 1.1 | 1.4 | 1.1 | 0.9 | 0.7 | 1.1 | 0.5 | 1.7 | 0.9 | 1.3 | 0.53 |
| YJR159W | 1.4 | 2.3 | 1.3 | 1.7 | 0.9 | 1.4 | 2.3 | 2.7 | 5.2 | 2.8 | 2.2 | 1.5 | 2.1 | 2.0 | 2.3 | 5.2 | 1.7 | 2.3 | 0.30 |
| YOL157C | 1.0 | 1.1 | 1.3 | 2.5 | 1.4 | 0.9 | 2.7 | 1.4 | 2.3 | 4.8 | 1.2 | 1.2 | 1.4 | 1.2 | 1.1 | 3.5 | 1.4 | 1.3 | 0.41 |
| YOR344C | 1.1 | 1.1 | 0.4 | 0.7 | 1.9 | 2.0 | 2.4 | 1.4 | 0.3 | 0.9 | 0.6 | 1.3 | 1.8 | 0.6 | 0.7 | 0.6 | 1.3 | 1.3 | 2.11 |
| YPL265W | 0.7 | 0.4 | 2.3 | 1.1 | 1.0 | 2.3 | 8.9 | 2.3 | 0.2 | 1.2 | 1.8 | 0.9 | 1.1 | 1.1 | 1.2 | 2.0 | 0.5 | 0.4 | 1.42 |
| YBR126C | 0.8 | 1.9 | 5.6 | 1.2 | 0.7 | 2.9 | 2.3 | 0.6 | 1.7 | | 1.1 | 1.3 | 2.1 | 0.7 | 1.0 | 1.7 | 1.5 | 1.3 | 1.96 |
| YCR005C | 1.1 | 1.9 | 2.0 | 1.2 | 0.9 | 1.6 | 4.4 | 1.2 | 1.5 | 1.5 | 2.1 | 0.5 | 0.7 | 0.8 | 0.7 | 0.7 | 1.6 | 1.7 | 2.38 |
| YDR452W | 1.1 | 1.1 | 1.3 | 0.8 | 1.2 | 2.0 | 1.9 | 1.0 | 1.4 | 1.3 | 1.5 | 0.9 | 1.4 | 1.2 | 1.3 | 1.3 | 1.9 | 2.2 | 1.54 |
| YGR019W | 1.2 | 0.8 | 1.4 | 1.7 | 0.8 | 2.4 | 2.4 | 1.2 | 2.9 | | 1.1 | 1.2 | 2.1 | 1.3 | 2.2 | 2.4 | 1.3 | 2.0 | 0.79 |
| YGR255C | 0.9 | 1.4 | 1.4 | 1.5 | 1.3 | 3.2 | 1.8 | 1.0 | 2.5 | 1.8 | 2.0 | 1.3 | 2.5 | 0.9 | 1.0 | 1.1 | 1.1 | 1.1 | 0.81 |
| YIL098C | 1.4 | 1.6 | 0.5 | 2.0 | 1.7 | 1.7 | 2.2 | 1.6 | 1.9 | 1.9 | 1.4 | 0.8 | 1.3 | 1.9 | 0.7 | 2.0 | 1.2 | 1.6 | 0.75 |
| YIL172C | 1.1 | 1.1 | 1.6 | 1.7 | | 1.3 | 2.5 | 1.6 | 2.8 | 7.1 | 1.0 | 1.4 | 2.0 | 1.3 | 1.4 | 2.8 | 1.1 | 1.2 | 0.42 |
| YLR100W | 0.8 | 1.4 | 1.3 | 1.9 | 1.8 | 1.8 | 2.3 | 1.0 | 0.9 | 1.0 | 0.9 | 1.1 | 1.6 | 1.1 | 0.6 | 1.9 | 1.5 | 2.1 | 1.88 |
| YOR221C | 0.8 | 1.0 | 0.9 | 1.1 | 1.7 | 0.8 | 2.1 | 0.9 | 1.4 | 1.7 | 1.1 | 0.8 | 1.0 | 1.1 | 1.0 | 1.4 | 0.9 | 1.2 | 0.39 |
| YPL123C | 1.2 | 0.8 | 1.8 | 3.0 | 0.8 | 1.9 | 2.7 | 1.2 | 4.2 | 2.3 | 1.9 | 1.0 | 2.2 | 1.6 | 1.4 | 2.6 | 1.6 | 3.2 | 0.71 |
| YBR093C | 2.9 | 1.2 | 1.7 | 1.3 | 1.1 | 0.6 | 0.3 | 1.7 | 0.1 | 0.5 | 3.1 | 2.0 | 0.2 | 1.3 | 2.7 | 0.4 | 0.8 | 1.9 | 3.33 |
| YBR196C | 0.8 | 0.6 | 3.9 | 1.4 | 0.8 | 0.8 | 1.4 | 1.1 | 0.3 | 0.9 | 2.3 | 1.0 | 1.4 | 0.5 | 1.9 | 1.1 | 0.8 | 1.0 | 6.60 |
| YER023W | 0.8 | 0.6 | 1.2 | 1.2 | 0.8 | 1.3 | 0.7 | 0.9 | 1.1 | 0.6 | 2.1 | 0.8 | 1.2 | 0.7 | 1.2 | 1.6 | 1.5 | 1.4 | 1.77 |
| YFL055W | 2.0 | 6.7 | 1.3 | 2.5 | 1.5 | 1.1 | 1.4 | 1.3 | 23.9 | 6.5 | 2.7 | 0.9 | 1.3 | 1.5 | 0.7 | 1.4 | 1.4 | 1.0 | 0.23 |
| YIL124W | 0.9 | 0.8 | 2.8 | 1.6 | 0.9 | 1.2 | 1.3 | 0.9 | 1.0 | 0.7 | 2.8 | 1.1 | 0.9 | 1.1 | 0.6 | 3.1 | 1.2 | 2.1 | 2.39 |
| YMR318C | 1.4 | 2.4 | 2.2 | 0.7 | 1.2 | 2.1 | 0.8 | 3.6 | 2.3 | 4.8 | 3.6 | 0.8 | 1.8 | 1.7 | 1.5 | 1.1 | 1.1 | 1.1 | 3.17 |
| YBR067C | 1.6 | 2.5 | 2.8 | 0.9 | 1.1 | 1.1 | 1.1 | 1.1 | 1.7 | 1.0 | 3.1 | 1.0 | 0.9 | 0.7 | 3.3 | 2.5 | 0.5 | 0.4 | 1.76 |
| YBR115C | 0.6 | 0.7 | 1.4 | 0.4 | 0.7 | 0.9 | 1.1 | 1.3 | 0.8 | 1.6 | 1.8 | 0.9 | 2.3 | 0.7 | 1.1 | 0.5 | 0.6 | 0.6 | 0.64 |
| YDL131W | 1.1 | 0.9 | 1.8 | 1.0 | 1.0 | 0.9 | 0.7 | 2.2 | 0.8 | 2.7 | 2.2 | 1.2 | 1.0 | 0.9 | 1.1 | 0.9 | 0.7 | 0.6 | 1.81 |
| YDL168W | 2.3 | 2.0 | 2.1 | 0.9 | 1.2 | 1.4 | 1.1 | 1.7 | 8.2 | 4.7 | 1.9 | 0.6 | 1.3 | 1.6 | 1.2 | 1.1 | 0.9 | 0.8 | 1.08 |
| YDR216W | 1.3 | 1.1 | 2.0 | 0.8 | 1.3 | 1.0 | 1.0 | 2.5 | 2.7 | 2.1 | 1.0 | 2.4 | 0.9 | 2.5 | 1.6 | 1.0 | 1.8 | | 0.44 |
| YDR253C | 5.7 | 6.4 | 1.4 | 3.2 | 0.9 | 0.8 | 1.0 | 1.7 | 14.8 | 6.3 | 2.3 | 1.0 | 2.2 | 3.6 | 1.2 | 1.6 | 1.0 | 1.0 | 0.38 |
| YDR513W | 2.2 | 2.5 | 2.3 | 2.6 | 0.9 | 2.1 | 1.6 | 1.6 | 4.6 | 3.1 | 2.0 | 0.9 | 1.8 | 2.0 | 1.3 | 3.8 | 1.3 | 3.2 | 3.10 |
| YER061C | 0.9 | 0.9 | 1.2 | 2.5 | 0.8 | 0.4 | 0.9 | 0.7 | 0.3 | 0.7 | 2.2 | 0.7 | 0.9 | 1.0 | 0.8 | 1.8 | 1.2 | 1.2 | 0.84 |
| YFL052W | 1.3 | 0.8 | 0.7 | 2.3 | 1.5 | 2.1 | 1.4 | 1.3 | 0.6 | 1.2 | 2.3 | 0.8 | 1.0 | 1.6 | 0.4 | 1.0 | 1.1 | 0.9 | 0.32 |
| YFL058W | 1.2 | 1.7 | 1.1 | 1.4 | 1.1 | 2.0 | 0.9 | 1.7 | 3.2 | 2.4 | 2.4 | 1.2 | 1.2 | 1.0 | 1.7 | 0.7 | 1.1 | 0.9 | 0.40 |
| YFR030W | 3.1 | 5.5 | 8.5 | 0.5 | 0.8 | 1.8 | 1.1 | 1.7 | 24.1 | 9.0 | 2.4 | 2.4 | 4.1 | 1.3 | 1.7 | 1.6 | 1.3 | 0.9 | 0.30 |
| YGL202W | 0.8 | 0.7 | 2.2 | 0.7 | 0.7 | 0.7 | 0.6 | 1.0 | 1.3 | 1.7 | 2.4 | 0.9 | 1.1 | 0.8 | 2.2 | 0.6 | 1.3 | 0.9 | 1.70 |
| YGR070W | 1.1 | 1.0 | 2.0 | 1.5 | 1.4 | | 1.4 | 1.8 | 1.1 | 1.5 | 1.8 | 0.6 | 1.4 | 1.0 | 2.6 | 2.3 | 1.2 | 1.3 | 0.40 |
| YHL036W | 2.2 | 4.8 | 3.4 | 2.0 | 1.3 | 1.3 | 1.0 | 1.2 | 9.0 | 4.4 | 2.3 | 1.2 | 1.5 | 1.2 | 0.9 | 1.1 | 1.0 | 1.0 | 0.60 |

TABLE 7-continued

Metabolism protein genes

| yeast genes | The level of expressed mRNA in the presence of chemical substance/The level of expressed mRNA in the absence of chemical substance | | | | | | | | | | | | | | | | | | Intensity |
|---|---|---|---|---|---|---|---|---|---|---|---|---|---|---|---|---|---|---|---|
| | (1) | (2) | (3) | (4) | (5) | (6) | (7) | (8) | (9) | (10) | (11) | (12) | (13) | (14) | (15) | (16) | (17) | (18) | |
| YHR104W | 1.0 | 4.1 | 15.7 | 1.9 | 1.1 | 1.2 | 1.5 | 1.1 | 4.8 | 2.3 | 2.6 | 1.0 | 1.2 | 1.5 | 1.6 | 1.3 | 1.9 | 1.9 | 1.57 |
| YJL045W | 1.8 | 2.2 | 1.6 | 5.3 | 0.7 | 0.6 | 0.7 | 0.9 | 9.7 | 1.6 | 2.3 | 1.1 | 1.6 | 1.2 | 3.4 | 2.4 | 0.9 | 0.9 | 0.42 |
| YJL060W | 1.8 | 2.6 | 9.6 | 1.0 | 1.4 | 1.3 | 1.3 | 0.8 | 5.3 | 2.8 | 1.6 | 1.5 | 2.1 | 1.7 | 1.4 | 1.5 | 1.2 | 1.1 | 0.95 |
| YJL155C | 2.1 | 5.0 | 0.8 | 2.4 | 0.8 | 0.8 | 2.0 | 1.5 | 3.8 | 2.8 | 2.4 | 1.0 | 6.6 | 1.2 | 1.2 | 2.3 | 1.8 | 3.1 | 0.60 |
| YJR109C | 0.8 | 0.7 | 1.4 | 0.9 | 0.7 | 0.9 | 0.8 | 1.0 | 1.8 | 4.3 | 1.5 | 1.4 | 3.1 | 0.9 | 1.3 | 0.5 | 1.1 | 0.6 | 0.84 |
| YJR156C | 1.6 | 3.2 | 2.4 | 1.8 | 0.9 | 0.9 | 1.3 | 1.5 | 3.4 | 2.8 | 3.0 | 1.1 | 1.6 | 2.4 | 3.0 | 2.3 | 0.8 | 1.1 | 0.24 |
| YLR092W | 5.0 | 7.5 | 1.4 | 0.6 | 1.3 | 1.0 | 1.3 | 1.5 | 12.7 | 5.8 | 3.1 | 1.0 | 1.8 | 1.4 | 0.9 | 1.2 | 1.0 | 1.1 | 0.24 |
| YMR081C | 3.5 | 1.4 | 2.0 | 5.8 | 1.7 | 1.1 | 0.9 | 1.7 | 0.3 | 2.2 | 2.5 | 1.1 | 0.7 | 1.8 | 0.2 | 3.0 | 1.9 | 3.0 | 0.62 |
| YMR250W | 0.9 | 5.1 | 5.6 | 1.3 | 0.6 | 4.5 | 3.0 | 0.9 | 6.1 | 2.4 | 4.3 | 1.2 | 2.6 | 1.1 | 2.0 | 5.0 | 1.2 | 3.0 | 0.84 |
| YNL277W | 5.7 | 10.3 | 5.3 | 0.6 | 1.1 | 1.7 | 1.4 | 2.2 | 55.0 | 10.9 | 3.2 | 1.3 | 1.8 | 1.5 | 0.6 | 1.3 | 0.9 | 0.7 | 0.27 |
| YOR184W | 1.1 | 0.9 | 2.1 | 2.1 | 1.0 | 0.6 | 1.2 | 0.7 | 0.9 | 0.7 | 2.7 | 0.7 | 0.6 | 0.7 | 1.0 | 0.9 | 1.2 | 1.2 | 3.19 |
| YPR160W | 1.4 | 3.8 | 3.6 | 3.3 | 0.7 | 4.5 | 1.8 | 0.9 | 0.9 | 1.3 | 4.4 | 2.1 | 2.2 | 1.1 | 1.4 | 5.3 | 1.0 | 2.9 | 1.42 |
| YDL182W | 0.8 | 0.7 | 1.3 | 0.8 | 1.3 | 1.0 | 1.0 | 2.9 | 0.8 | 2.4 | 2.0 | 1.4 | 1.5 | 0.8 | 0.7 | 1.1 | 0.6 | 0.6 | 2.31 |
| YBR291C | 2.0 | 0.9 | 1.0 | 1.5 | 0.9 | 1.1 | 0.9 | 2.2 | 0.9 | 1.0 | 1.1 | 0.9 | 1.0 | 1.7 | 0.5 | 1.5 | 0.9 | 1.3 | 1.19 |
| YIL094C | 1.5 | 0.4 | 0.8 | 0.7 | 1.4 | 1.2 | 1.3 | 3.6 | 0.3 | 0.4 | 1.8 | 1.0 | 0.7 | 1.0 | 0.5 | 0.9 | 0.9 | 1.0 | 2.26 |
| YNR050C | 1.7 | 0.5 | 1.2 | 0.6 | 1.3 | 0.9 | 1.0 | 2.2 | 0.4 | 0.7 | 1.5 | 1.0 | 1.1 | 0.6 | 0.3 | 1.4 | 0.6 | 0.7 | 2.13 |
| YDL244W | 1.1 | 3.5 | 1.8 | 1.6 | 0.9 | 1.3 | 1.7 | 1.8 | 2.5 | 3.7 | 1.2 | 1.2 | 2.0 | 2.0 | 2.9 | 1.5 | 1.1 | 1.0 | 0.25 |
| YDR054C | 1.3 | 1.0 | 0.7 | 1.4 | 0.7 | 1.0 | 1.1 | 1.5 | 2.9 | 3.2 | 1.9 | 1.0 | 2.5 | 1.1 | 1.6 | 1.4 | 0.8 | 1.4 | 1.18 |
| YDR353W | 0.9 | 1.6 | 3.4 | 1.6 | 0.6 | 0.9 | 1.0 | 1.1 | 2.0 | 5.1 | 1.4 | 0.8 | 0.7 | 1.6 | 1.3 | 1.0 | 0.9 | 1.3 | 3.20 |
| YEL070W | 1.4 | 0.9 | 1.6 | 3.4 | 1.3 | 1.2 | 1.3 | 1.2 | 1.9 | 13.0 | 1.1 | 1.1 | 1.1 | 2.1 | 3.2 | 1.9 | 0.9 | 1.0 | 0.27 |
| YJL168W | 2.8 | 1.4 | 1.0 | 1.2 | 1.4 | 0.7 | 1.3 | 1.6 | 7.8 | 19.3 | 1.9 | 0.8 | 0.9 | 1.5 | 1.2 | 1.2 | 1.0 | 1.1 | 0.39 |
| YJL221C | 1.1 | 1.0 | 1.1 | 1.3 | 0.9 | 6.6 | 2.5 | 1.8 | 2.7 | 4.4 | 0.8 | 1.1 | 1.4 | 1.1 | 1.1 | 3.3 | 1.1 | 1.4 | 0.41 |
| YJR095W | 1.2 | 20.5 | 1.9 | 6.7 | 1.2 | 1.5 | 2.0 | 0.9 | 0.5 | 6.3 | 0.6 | 0.7 | 0.8 | 1.3 | 0.8 | 0.8 | 1.3 | 0.9 | 0.23 |
| YKL085W | 1.4 | 2.3 | 1.6 | 1.2 | 1.2 | 1.9 | 1.5 | 1.2 | 1.9 | 3.0 | 1.8 | 0.8 | 1.5 | 1.0 | 0.5 | 1.7 | 0.9 | 1.3 | 2.16 |
| YKL188C | 1.3 | 0.7 | 1.9 | 2.4 | 1.0 | 0.8 | 1.1 | 0.7 | 2.5 | 2.8 | 1.1 | 1.2 | 1.2 | 2.1 | 1.4 | 2.7 | 1.1 | 1.5 | 0.27 |
| YKL217W | 1.8 | 2.4 | 1.0 | 2.1 | 1.1 | 1.2 | 1.6 | 1.1 | 0.9 | 4.1 | 1.6 | 0.8 | 1.2 | 1.2 | 2.2 | 3.0 | 1.7 | 3.3 | 0.29 |
| YKR061W | 2.0 | 0.9 | 0.5 | 1.9 | 1.2 | 1.2 | 1.4 | 1.5 | 1.5 | 2.6 | 1.1 | 0.9 | 0.9 | 1.6 | 0.9 | 0.8 | 1.5 | 1.6 | 0.70 |
| YLR174W | 1.2 | 1.5 | 1.7 | 2.1 | 0.9 | 0.9 | 1.6 | 1.1 | 2.5 | 8.3 | 1.3 | 1.3 | 1.8 | 1.7 | 0.8 | 4.6 | 0.9 | 1.2 | 0.41 |
| YLR260W | 1.1 | 1.5 | 1.5 | 2.4 | 1.2 | 1.0 | 1.2 | 1.2 | 2.6 | 3.2 | 0.6 | 0.8 | 1.9 | 1.2 | 1.0 | 1.0 | 1.1 | 1.2 | 0.44 |
| YNL009W | 1.1 | 1.9 | 2.0 | 1.4 | 1.4 | 1.1 | 1.2 | 1.1 | 1.4 | 3.3 | 1.3 | 0.9 | 1.3 | 1.3 | 2.7 | 3.3 | 1.2 | 2.3 | 0.45 |
| YNL117W | 0.9 | 4.7 | 1.7 | 0.8 | 0.8 | | 1.1 | 1.7 | 12.8 | 4.4 | 1.4 | 0.7 | 1.3 | 2.0 | 2.6 | 1.6 | 1.1 | 0.9 | 0.24 |
| YNL183C | 0.9 | 3.5 | 6.4 | 1.3 | 0.7 | 1.2 | 1.3 | 0.9 | 4.8 | 4.3 | 1.3 | 1.1 | 2.3 | 1.1 | 1.1 | 1.2 | 0.8 | 1.0 | 0.47 |
| YNR073C | 1.1 | 1.4 | 0.8 | 2.7 | 1.4 | 1.7 | 2.2 | 1.5 | 2.5 | 16.8 | 2.2 | 1.1 | 1.2 | 2.3 | 1.7 | 1.6 | 1.0 | 0.9 | 0.18 |
| YPL161C | 1.0 | 1.7 | 1.1 | 1.1 | 0.8 | 0.7 | 1.3 | 1.8 | 1.2 | 2.7 | 1.0 | 1.0 | 1.2 | 1.1 | 0.8 | 1.4 | 1.3 | 1.3 | 0.41 |
| YAL061W | 1.7 | 2.4 | 3.3 | 3.8 | 1.0 | 1.0 | 2.0 | 0.8 | 5.5 | 1.4 | 4.1 | 1.1 | 1.4 | 0.7 | 0.6 | 1.1 | 1.4 | 1.2 | 0.88 |
| YAL067C | 2.7 | 7.5 | 1.5 | 1.4 | 0.7 | 1.2 | 0.8 | 1.1 | 7.6 | 2.9 | 1.2 | 1.0 | 1.1 | 1.3 | 2.4 | 1.6 | 1.0 | 1.0 | 0.33 |
| YBL033C | 1.3 | 1.9 | 2.4 | 1.0 | 1.1 | 0.4 | 0.9 | 1.4 | 6.6 | 4.2 | 1.1 | 0.9 | 1.8 | 1.4 | 1.0 | 1.2 | 1.2 | 1.0 | 0.53 |
| YBL086C | 0.8 | 0.5 | 1.0 | 0.6 | 1.3 | 0.7 | 1.0 | 1.1 | 3.3 | 1.4 | 1.3 | 0.5 | 0.9 | 0.8 | 0.5 | 1.4 | 0.9 | 1.0 | 0.43 |
| YBR117C | 0.8 | 1.6 | 1.5 | 1.4 | 0.9 | 2.3 | 1.0 | 0.7 | 5.9 | 1.5 | 0.4 | 0.8 | 2.1 | 0.9 | 1.0 | 12.0 | 0.7 | 0.7 | 0.49 |
| YBR213W | 1.0 | 1.6 | 1.6 | 0.5 | 1.1 | 2.4 | 1.3 | 1.3 | 11.4 | 2.3 | 0.5 | 1.2 | 1.4 | 1.3 | 1.7 | 0.8 | 0.9 | 0.9 | 0.23 |
| YCR036W | 1.3 | 1.2 | 1.3 | 1.3 | 1.5 | 1.4 | 1.5 | 1.1 | 2.6 | 1.5 | 1.0 | 1.3 | 1.8 | 1.5 | 1.7 | 1.6 | 1.6 | 1.7 | 1.35 |
| YDL132W | 0.8 | 1.2 | 1.1 | 0.7 | 1.3 | 0.9 | 1.4 | 1.0 | 3.8 | 2.4 | 1.3 | 0.7 | 2.0 | 0.9 | 1.7 | 1.0 | 0.9 | 1.1 | 0.74 |
| YER014W | 1.0 | 0.9 | 0.9 | 0.6 | 0.8 | 4.0 | | 1.2 | 3.5 | 1.1 | 0.9 | 1.1 | 1.5 | 1.2 | 2.3 | 0.8 | 1.0 | 0.9 | 0.43 |
| YER042W | 3.0 | 2.2 | 3.1 | 1.0 | 1.1 | 1.6 | 1.1 | 1.7 | 6.8 | 2.1 | 1.8 | 1.1 | 1.4 | 5.2 | 1.0 | 1.9 | 0.7 | 1.1 | 1.80 |
| YER090W | 1.0 | 1.1 | 2.0 | 0.7 | 1.3 | 0.7 | 0.9 | 1.4 | 3.7 | 2.5 | 1.8 | 1.3 | 1.2 | 1.2 | 1.5 | 0.8 | 1.1 | 0.9 | 0.97 |
| YGL026C | 0.7 | 9.3 | 1.9 | 0.6 | 1.2 | 1.7 | 0.9 | 0.8 | 3.7 | 1.5 | 3.4 | 1.3 | 1.8 | 0.9 | 2.4 | 0.7 | 1.5 | 0.8 | 0.87 |
| YGL252C | 1.1 | 2.4 | 1.4 | 0.7 | 1.3 | 0.8 | 1.4 | 1.2 | 2.7 | 1.7 | 0.9 | 0.9 | 1.2 | 1.0 | 1.3 | 1.2 | 1.0 | 1.3 | 0.91 |
| YGL254W | 1.2 | 1.1 | 0.8 | 0.6 | 1.1 | 0.7 | 1.3 | 1.4 | 3.1 | 1.8 | 1.1 | 1.2 | 2.4 | 1.3 | 1.1 | 1.4 | 0.8 | 1.2 | 0.53 |
| YGR276C | 0.9 | 0.8 | 0.3 | 1.3 | 1.5 | 0.7 | 1.9 | 1.5 | 4.5 | 2.2 | 0.9 | 1.0 | 1.8 | 1.0 | 0.8 | 1.3 | 0.9 | 1.1 | 0.97 |
| YHR106W | 0.9 | 1.7 | 1.7 | 1.5 | 1.7 | 1.3 | 1.2 | 1.0 | 2.8 | 2.5 | 1.4 | 0.7 | 1.0 | 1.2 | 0.9 | 2.4 | 1.3 | 1.1 | 1.73 |
| YIL046W | 1.5 | 2.7 | 1.6 | 0.7 | 1.4 | 0.9 | 1.0 | 1.0 | 10.7 | 2.5 | 1.2 | 1.0 | 1.7 | 1.1 | 1.3 | 1.8 | 9.0 | 5.8 | 0.68 |
| YJL071W | 1.0 | 1.5 | 1.3 | 1.6 | 1.4 | 1.0 | 1.3 | 1.1 | 2.8 | 2.2 | 1.3 | 1.1 | 1.0 | 1.0 | 1.5 | 1.2 | 0.9 | 0.9 | 0.41 |
| YJR139C | 1.4 | 2.6 | 2.9 | 1.1 | 1.2 | 1.8 | 1.3 | 1.1 | 4.1 | 1.9 | 1.5 | 1.0 | 1.5 | 1.4 | 0.7 | 1.2 | 1.0 | 1.3 | 4.47 |
| YKR069W | 3.4 | 6.3 | 5.0 | 3.1 | 0.7 | 0.5 | 1.0 | 1.2 | 10.9 | 9.0 | 2.0 | 1.4 | 1.4 | 1.7 | 1.1 | 1.8 | 1.0 | 1.0 | 0.25 |
| YLL061W | 3.6 | 2.8 | 9.2 | 0.4 | 0.8 | 0.8 | 0.9 | 1.4 | 3.7 | 5.5 | 1.7 | 0.7 | 0.9 | 1.3 | 1.4 | 1.0 | 0.6 | 0.7 | 0.33 |
| YLR070C | 1.0 | 1.3 | 1.4 | 1.1 | 0.7 | 1.1 | 1.3 | 1.0 | 3.5 | 1.6 | 0.4 | 0.7 | 2.0 | 1.3 | 0.5 | 2.1 | 1.0 | 0.9 | 0.31 |
| YLR099C | 2.0 | 2.2 | 1.4 | 0.8 | 0.9 | 0.4 | 0.2 | 1.2 | 3.6 | 1.1 | 1.2 | 0.9 | 0.8 | 0.7 | 0.9 | 0.7 | 0.7 | 0.5 | 0.92 |
| YLR157C | 1.1 | 1.1 | 3.4 | 1.1 | 1.3 | 1.9 | 1.9 | 1.5 | 5.1 | 1.8 | 1.9 | 1.2 | 1.8 | 1.1 | 1.1 | 2.1 | 1.6 | 2.1 | 1.70 |
| YLR160C | 1.2 | 1.4 | 3.9 | 1.1 | 1.3 | 1.8 | 1.9 | 2.0 | 4.8 | 1.8 | 1.6 | 1.2 | 2.0 | 1.2 | 1.0 | 2.0 | 1.6 | 2.2 | 1.59 |
| YLR164W | 1.0 | 2.4 | 0.3 | 1.2 | 1.2 | 1.2 | 1.1 | 1.2 | 5.3 | 2.0 | 3.2 | 0.7 | 1.0 | 1.5 | 0.7 | 11.0 | 1.5 | 1.2 | 0.31 |
| YML042W | 0.9 | 1.4 | 1.5 | 2.2 | 1.0 | 0.9 | 0.8 | 1.6 | 3.8 | 2.4 | 2.5 | 1.0 | 1.2 | 1.4 | 1.7 | 4.8 | 1.0 | 0.9 | 0.29 |
| YOL049W | 0.9 | 1.1 | 1.3 | 0.9 | 1.4 | 0.6 | 1.1 | 1.7 | 3.0 | 1.9 | 1.8 | 0.8 | 0.9 | 0.9 | 0.7 | 1.3 | 1.0 | 1.3 | 1.61 |
| YOL064C | 1.4 | 2.1 | 1.1 | 0.6 | 0.9 | 1.4 | 1.2 | 1.0 | 8.7 | 2.7 | 1.0 | 0.9 | 2.0 | 0.9 | 1.0 | 1.7 | 1.2 | 1.3 | 1.32 |
| YOR377W | 0.6 | 0.6 | 0.6 | 1.0 | 1.4 | 1.6 | 1.6 | 1.0 | 3.8 | 1.1 | 1.2 | 0.9 | 1.3 | 0.9 | 1.2 | 1.3 | 1.1 | 1.1 | 0.46 |
| YPL031C | 0.9 | 2.0 | 1.4 | 0.8 | 1.5 | 1.8 | 1.6 | 1.0 | 5.7 | 1.4 | 1.4 | 0.8 | 1.6 | 0.9 | 0.7 | 2.0 | 1.4 | 1.2 | 0.49 |
| YPL113C | 1.4 | 1.7 | 0.4 | 2.4 | 1.3 | 1.0 | 1.9 | 1.4 | 5.5 | 2.0 | 1.5 | 1.1 | 1.7 | 1.6 | 0.9 | 2.5 | 1.2 | 1.7 | 0.28 |
| YPL274W | 0.8 | 4.2 | 3.8 | 0.8 | 0.6 | 1.1 | 0.7 | 0.9 | 4.1 | 3.6 | 2.0 | 0.5 | 0.6 | 0.9 | 1.5 | 1.1 | 0.7 | 0.6 | 0.41 |
| YPR048W | 1.3 | 2.0 | 0.9 | 1.1 | 0.9 | 0.6 | 0.9 | 1.5 | 4.0 | 2.1 | 1.0 | 0.8 | 0.6 | 1.2 | 0.6 | 0.8 | 0.7 | 0.8 | 0.75 |
| YBR001C | 0.9 | 1.4 | 1.0 | 1.4 | 0.9 | 1.1 | 0.9 | 1.3 | 2.3 | 2.1 | 1.0 | 1.0 | 2.0 | 1.2 | 1.8 | 1.4 | 1.0 | 1.6 | 0.61 |
| YBR018C | 0.9 | 1.1 | 1.9 | 2.9 | 0.9 | 0.7 | 1.4 | 0.6 | 1.3 | 1.7 | 5.8 | 1.0 | 1.0 | 2.4 | 1.3 | 6.2 | 0.8 | 0.9 | 0.20 |
| YBR204C | 1.0 | 1.0 | 1.5 | 1.8 | 1.1 | 0.9 | 1.7 | 1.1 | 1.8 | 1.9 | 2.2 | 1.0 | 1.7 | 1.4 | 1.2 | 2.3 | 1.1 | 1.5 | 0.84 |
| YBR241C | 0.9 | 9.3 | 2.6 | 0.9 | 0.9 | 1.5 | 1.4 | 0.7 | 29.8 | 2.2 | 1.4 | 1.4 | 1.4 | 0.9 | 1.6 | 0.7 | 1.0 | 1.2 | 1.25 |
| YCR105W | 2.2 | 1.2 | 1.2 | 3.0 | 0.9 | 1.0 | 1.0 | 1.4 | 2.0 | 3.9 | 2.3 | 0.9 | 1.9 | 1.9 | 3.1 | 1.3 | 1.3 | 1.1 | 0.36 |

TABLE 7-continued

Metabolism protein genes

| yeast genes | The level of expressed mRNA in the presence of chemical substance/The level of expressed mRNA in the absence of chemical substance | | | | | | | | | | | | | | | | | | Intensity |
|---|---|---|---|---|---|---|---|---|---|---|---|---|---|---|---|---|---|---|---|
| | (1) | (2) | (3) | (4) | (5) | (6) | (7) | (8) | (9) | (10) | (11) | (12) | (13) | (14) | (15) | (16) | (17) | (18) | |
| YDR287W | 1.1 | 8.4 | 1.9 | 1.2 | 1.2 | 1.6 | 1.2 | 1.2 | 2.5 | 1.8 | 1.5 | 1.1 | 1.5 | 1.2 | 1.6 | 2.7 | 1.5 | 1.3 | 0.52 |
| YDR294C | 0.7 | 1.1 | 1.9 | 1.2 | 0.9 | 0.7 | 1.0 | 1.0 | 2.0 | 2.9 | 1.2 | 1.1 | 1.6 | 1.0 | 2.0 | 1.7 | 0.9 | 1.1 | 1.02 |
| YER052C | 1.1 | 1.0 | 3.6 | 1.1 | 0.6 | 0.6 | 0.5 | 1.0 | 2.7 | 2.4 | 1.1 | 0.9 | 2.1 | 0.7 | 1.2 | 0.2 | 0.8 | 0.4 | 1.54 |
| YFL021W | 0.8 | 1.4 | 2.4 | 1.7 | 1.1 | 0.8 | 0.8 | 0.6 | 2.7 | 1.2 | 1.3 | 0.9 | 1.5 | 1.1 | 1.3 | 1.0 | 0.8 | 0.5 | 0.40 |
| YGL040C | 0.7 | 1.2 | 1.4 | 0.9 | 1.3 | 2.0 | 1.1 | 1.0 | 2.1 | 1.9 | 0.9 | 0.6 | 1.6 | 1.3 | 0.7 | 1.5 | 0.7 | 1.0 | 1.77 |
| YGL125W | 1.0 | 3.2 | 4.3 | 0.7 | 0.9 | | 1.7 | 0.8 | 2.1 | 2.1 | 1.6 | 1.0 | 1.4 | 1.0 | 1.9 | 1.2 | 1.2 | 1.1 | 0.27 |
| YGR007W | 1.3 | 1.7 | 0.7 | 1.6 | 0.6 | 0.8 | 1.2 | 1.1 | 2.2 | 2.3 | 0.9 | 0.8 | 1.4 | 1.8 | 1.9 | 1.3 | 1.1 | 1.4 | 0.74 |
| YGR155W | 1.3 | 4.4 | 1.2 | 0.6 | 1.3 | 1.6 | 1.1 | 1.4 | 2.4 | 1.7 | 1.3 | 1.0 | 1.4 | 0.7 | 0.5 | 1.0 | 0.5 | 0.6 | 4.15 |
| YIL099W | 0.9 | 1.6 | 1.5 | 0.4 | 0.8 | | 101.4 | 1.0 | 2.2 | 1.8 | 0.9 | 0.9 | 1.4 | 1.6 | 5.5 | 1.2 | 1.0 | 1.1 | 0.18 |
| YIL170W | 1.1 | 1.0 | 2.5 | 2.2 | 0.9 | 8.8 | 0.5 | 1.2 | 5.7 | 3.2 | 1.7 | 0.7 | 1.9 | 1.1 | 2.3 | 1.8 | 1.6 | 1.5 | 0.48 |
| YIR031C | 0.8 | 1.6 | 0.6 | 0.6 | 1.6 | 1.7 | 1.4 | 1.0 | 2.6 | 1.0 | 1.2 | 0.8 | 1.0 | 1.2 | 0.8 | 0.7 | 0.9 | 0.8 | 0.44 |
| YIR032C | 1.1 | 1.9 | 1.3 | 2.6 | 1.0 | 0.6 | 1.0 | 1.2 | 2.6 | 2.3 | 1.4 | 1.0 | 1.4 | 1.6 | 0.6 | 1.6 | 0.9 | 1.1 | 0.40 |
| YJL128C | 0.8 | 1.4 | 0.4 | 0.8 | 1.2 | 1.3 | 1.8 | 0.9 | 2.0 | 1.7 | 0.6 | 1.0 | 1.7 | 0.8 | 1.2 | 0.9 | 1.0 | 1.0 | 0.42 |
| YJR090C | 0.8 | 1.0 | 0.6 | 0.8 | 1.2 | 1.2 | 0.8 | 0.8 | 1.9 | 1.2 | 0.4 | 0.8 | 2.2 | 1.0 | 1.6 | 0.8 | 1.1 | 1.0 | 0.60 |
| YJR103W | 1.1 | 3.8 | 1.2 | 1.6 | 0.7 | 0.6 | 0.6 | 0.8 | 1.8 | 3.0 | 1.1 | 0.6 | 0.7 | 0.7 | 3.2 | 2.3 | 0.9 | 1.0 | 0.74 |
| YJR153W | 1.1 | 1.7 | 1.1 | 0.8 | 0.9 | 0.4 | 1.3 | 0.9 | 2.4 | 1.6 | 2.0 | 0.7 | 1.3 | 1.7 | 2.9 | 1.6 | 0.8 | 1.0 | 0.18 |
| YKL192C | 1.1 | 1.0 | 3.7 | 1.1 | 1.1 | 1.8 | 1.1 | 0.9 | 3.5 | 1.6 | 1.1 | 1.2 | 1.7 | 1.5 | 1.2 | 2.1 | 1.0 | 0.8 | 1.57 |
| YLR025W | 1.2 | 5.1 | 0.7 | 1.1 | 1.9 | 1.5 | 1.7 | 1.5 | 2.4 | 1.5 | 1.1 | 0.9 | 1.0 | 1.7 | 1.5 | 2.2 | 1.2 | 1.3 | 1.15 |
| YML051W | 1.0 | 1.4 | 1.8 | 0.9 | 1.0 | 0.7 | 0.9 | 0.9 | 2.0 | 1.5 | 1.4 | 0.7 | 1.2 | 1.1 | 1.4 | 1.1 | 0.7 | 1.0 | 0.57 |
| YML099C | 0.6 | 1.0 | 1.1 | 1.3 | 1.0 | 0.5 | 1.0 | 0.7 | 2.2 | 1.7 | 1.6 | 1.1 | 1.3 | 0.9 | 1.0 | 1.6 | 0.7 | 0.8 | 0.48 |
| YMR056C | 1.1 | 1.3 | 1.7 | 1.0 | 1.1 | 0.9 | 1.4 | 1.2 | 1.8 | 1.1 | 1.6 | 0.9 | 0.9 | 1.1 | 0.7 | 2.4 | 1.0 | 1.1 | 0.72 |
| YNL257C | 0.7 | 1.0 | 0.9 | 0.8 | 0.9 | 2.0 | 1.1 | 1.1 | 2.1 | 1.4 | 1.0 | 1.1 | 1.7 | 0.8 | 1.0 | 1.4 | 0.9 | 1.3 | 0.63 |
| YNL264C | 1.0 | 2.4 | 1.3 | 1.0 | 0.8 | 1.4 | 1.5 | 1.1 | 3.3 | 1.3 | 1.0 | 1.1 | 1.5 | 1.2 | 1.1 | 1.3 | 0.7 | 1.1 | 0.48 |
| YNR071C | 1.4 | 1.0 | 0.9 | 3.2 | 1.1 | 0.9 | 1.4 | 1.2 | 3.1 | 7.0 | 1.3 | 0.6 | 1.7 | 1.1 | 1.8 | 1.0 | 1.0 | 0.9 | 0.16 |
| YOL065C | 1.0 | 1.7 | 1.6 | 1.3 | 0.8 | 1.3 | 1.9 | 1.0 | 2.1 | 1.8 | 1.0 | 0.8 | 1.3 | 1.1 | 0.7 | 2.6 | 1.1 | 1.5 | 0.43 |
| YOL067C | 0.8 | 0.9 | 0.9 | 1.4 | 0.7 | 0.3 | 0.7 | 1.0 | 2.1 | 1.3 | 1.3 | 0.7 | 1.7 | 0.7 | 1.2 | 1.1 | 1.4 | 0.9 | 0.55 |
| YPL147W | 1.0 | 0.8 | 2.3 | 1.2 | 1.2 | 1.1 | 1.0 | 0.9 | 2.4 | 2.4 | 1.3 | 0.9 | 1.5 | 1.0 | 2.4 | 2.5 | 1.5 | 3.6 | 0.33 |
| YDR043C | 2.8 | 1.1 | 1.2 | 6.9 | 1.7 | 1.4 | 1.3 | 1.2 | 1.0 | 2.7 | 1.3 | 0.9 | 0.7 | 1.8 | 1.2 | 1.4 | 1.9 | 1.2 | 0.66 |
| YGR180C | 3.1 | 1.1 | 1.9 | 1.0 | 2.0 | 0.6 | 0.5 | 1.0 | 1.4 | 1.5 | 1.0 | 0.9 | 0.9 | 0.9 | 1.3 | 1.2 | 1.0 | 1.9 | 3.90 |
| YJL026W | 2.5 | 2.4 | 2.9 | 1.0 | 1.7 | 1.4 | 0.5 | 1.2 | 1.0 | 1.1 | 1.3 | 1.0 | 1.2 | 1.0 | 1.1 | 1.6 | 1.4 | 2.1 | 3.74 |
| YGR087C | 1.0 | 15.0 | 1.7 | 0.6 | 1.0 | 1.1 | 1.0 | 0.8 | 0.2 | 0.9 | 0.8 | 1.2 | 1.2 | 0.7 | 3.5 | 0.6 | 1.0 | 0.6 | 1.88 |
| YGL256W | 0.9 | 5.3 | 1.1 | 1.3 | 0.7 | 0.7 | 0.5 | 1.0 | 0.4 | 1.2 | 1.0 | 0.9 | 0.8 | 0.9 | 1.0 | 0.7 | 0.7 | 0.8 | 0.90 |
| YAL039C | 1.1 | 2.2 | 1.7 | 1.0 | 1.1 | 0.8 | 1.0 | 1.2 | 1.6 | 2.2 | 1.1 | 1.4 | 1.6 | 1.2 | 3.3 | 2.2 | 1.4 | 1.1 | 0.39 |
| YJR107W | 1.0 | 3.1 | 1.5 | 1.8 | 0.7 | 1.5 | 1.3 | 1.3 | 1.4 | 0.9 | 1.3 | 1.1 | 1.7 | 1.4 | 1.1 | 1.1 | 1.4 | 1.3 | 0.41 |
| YNL142W | 0.7 | 2.4 | 2.5 | 0.8 | 1.3 | 0.9 | 1.1 | 0.8 | 0.9 | 0.6 | 0.9 | 1.2 | 0.9 | 0.8 | 0.3 | 1.0 | 1.0 | 0.9 | 0.44 |
| YDL210W | 1.2 | 2.2 | 2.7 | 1.1 | 0.9 | 1.3 | 0.8 | 1.1 | 1.2 | 1.4 | 0.6 | 0.8 | 1.2 | 1.1 | 1.9 | 0.9 | 1.1 | 0.9 | 0.20 |
| YGL055W | 1.1 | 1.8 | 0.3 | 2.5 | 1.5 | 1.6 | 0.6 | 1.4 | 0.2 | 0.7 | 0.9 | 1.3 | 0.2 | 0.7 | 0.5 | 3.0 | 1.0 | 1.5 | 5.60 |
| YCL025C | 1.1 | 4.6 | 2.5 | 1.7 | 0.9 | 0.9 | 0.7 | 0.7 | 0.3 | 0.3 | 1.0 | 1.1 | 0.5 | 0.7 | 0.8 | 0.6 | 0.6 | 0.6 | 1.98 |
| YBR132C | 0.9 | 1.9 | 2.4 | 1.8 | 0.8 | 1.2 | 1.1 | 0.8 | 0.8 | 1.1 | 1.9 | 1.0 | 1.4 | 1.1 | 1.5 | 1.3 | 1.1 | 1.3 | 0.43 |
| YHL018W | 0.8 | 1.5 | 0.5 | 0.5 | 0.9 | 0.4 | 1.2 | 0.8 | 0.8 | 0.6 | 1.2 | 0.7 | 0.8 | 1.0 | 0.9 | 0.9 | 1.1 | 0.9 | 0.37 |
| YPL038W | 0.8 | 1.5 | 0.2 | 1.1 | 1.4 | 0.5 | 1.0 | 1.2 | 0.9 | 0.7 | 1.1 | 0.6 | 0.6 | 0.9 | 0.6 | 0.8 | 0.9 | 0.9 | 0.64 |
| YKR053C | 0.9 | 2.0 | 1.0 | 1.2 | 1.0 | 1.1 | 1.7 | 0.9 | 0.8 | 1.8 | 0.5 | 0.7 | 0.7 | 1.3 | 0.3 | 0.9 | 2.8 | 2.4 | 0.35 |
| YNL256W | 0.7 | 1.6 | 0.6 | 0.6 | 1.0 | 0.5 | 0.6 | 0.9 | 0.8 | 0.6 | 0.6 | 0.6 | 1.3 | 0.7 | 0.9 | 0.4 | 0.6 | 0.6 | 1.09 |
| YLR377C | 1.1 | 2.6 | 1.8 | 1.2 | 1.0 | 0.7 | 0.9 | 0.7 | 1.8 | 1.6 | 0.6 | 0.6 | 1.2 | 2.9 | 1.3 | 2.7 | 0.9 | 1.4 | 0.14 |
| YBR253W | 1.3 | 4.4 | 0.4 | 1.1 | 1.4 | 1.3 | 1.4 | 1.8 | 1.8 | 1.5 | 1.1 | 1.0 | 0.8 | 1.2 | 0.9 | 1.3 | 1.3 | 1.1 | 0.96 |
| YBL030C | 1.0 | 0.9 | 4.5 | 0.9 | 0.7 | 1.1 | 0.9 | 0.8 | 0.4 | 0.9 | 1.1 | 0.9 | 0.5 | 0.8 | 1.8 | 1.0 | 1.0 | 1.1 | 3.12 |
| YBR221C | 0.8 | 0.7 | 3.2 | 1.5 | 1.3 | 1.7 | 1.5 | 0.8 | 1.0 | 1.3 | 1.2 | 1.3 | 1.7 | 0.8 | 1.1 | 1.5 | 0.9 | 1.0 | 3.62 |
| YDR342C | 2.8 | 1.1 | 12.2 | 1.6 | 1.1 | 1.1 | 0.8 | 1.2 | 0.2 | 2.2 | 2.9 | 1.0 | 0.6 | 0.9 | 0.5 | 2.4 | 1.0 | 2.2 | 5.23 |
| YDR343C | 1.2 | 1.0 | 20.6 | 4.6 | 1.3 | 1.3 | 0.7 | 1.2 | 0.3 | 2.1 | 2.3 | 1.0 | 0.8 | 0.8 | 0.5 | 2.8 | 1.1 | 2.3 | 5.81 |
| YEL034W | 0.9 | 0.6 | 3.3 | 0.9 | 1.4 | 0.9 | 0.4 | 0.8 | 0.4 | 1.0 | 1.1 | 0.9 | 0.8 | 0.9 | 0.8 | 0.9 | 0.9 | 0.9 | 5.44 |
| YHR094C | 0.7 | 1.2 | 5.3 | 1.6 | 1.1 | 1.6 | 0.8 | 1.2 | 0.3 | 1.2 | 0.6 | 0.9 | 0.7 | 0.6 | 2.7 | 0.9 | 1.4 | 1.4 | 4.82 |
| YIL162W | 1.3 | 1.5 | 6.8 | 2.4 | 1.2 | 1.0 | 1.2 | 1.6 | 0.8 | 3.7 | 2.8 | 2.0 | 1.0 | 1.0 | 1.5 | 1.7 | 0.9 | 1.4 | 1.22 |
| YJR105W | 0.6 | 0.7 | 3.0 | 0.8 | 0.7 | 0.3 | 0.5 | 0.8 | 0.9 | 0.5 | 1.0 | 0.8 | 0.8 | 0.5 | 1.2 | 0.7 | 1.1 | 0.9 | 3.75 |
| YLR134W | 0.8 | 0.6 | 2.3 | 0.8 | 1.3 | 2.5 | 1.1 | 0.8 | 0.1 | 0.7 | 1.1 | 1.2 | 1.5 | 0.6 | 1.7 | 0.5 | 0.6 | 0.8 | 3.47 |
| YLR258W | 1.5 | 1.0 | 4.2 | 3.5 | 0.9 | 1.8 | 1.8 | 0.9 | 0.8 | 1.3 | 1.2 | 0.9 | 1.4 | 1.2 | 0.6 | 1.7 | 1.0 | 2.0 | 1.36 |
| YML058W | 1.9 | 1.2 | 5.8 | 0.9 | 0.6 | 0.6 | 0.6 | 0.7 | 1.1 | 1.2 | 3.3 | 0.9 | 1.4 | 1.1 | 2.5 | 1.3 | 1.3 | 1.5 | 2.14 |
| YMR083W | 1.4 | 1.7 | 2.6 | 1.1 | 1.5 | 1.8 | 1.7 | 1.1 | 0.4 | 1.1 | 1.6 | 0.7 | 0.9 | 0.8 | 1.3 | 1.3 | 0.9 | 1.1 | 2.52 |
| YOR178C | 1.4 | 1.3 | 4.8 | 2.3 | 1.0 | 2.7 | 0.9 | 0.9 | 0.2 | 1.7 | 4.1 | 1.7 | 1.0 | 1.0 | 1.1 | 1.7 | 1.0 | 1.5 | 0.56 |
| YPL028W | 0.7 | 0.9 | 2.6 | 0.9 | 1.0 | 1.2 | 1.3 | 0.9 | 1.2 | 0.8 | 1.2 | 1.4 | 0.9 | 0.8 | 0.6 | 2.2 | 1.4 | 1.8 | 4.35 |
| YPR113W | 1.1 | 0.8 | 3.7 | 1.3 | 2.0 | 1.1 | 1.2 | 0.9 | 0.4 | 0.8 | 2.0 | 0.7 | 0.7 | 1.3 | 1.0 | 2.3 | 1.2 | 1.9 | 2.85 |
| YPR183W | 0.9 | 1.5 | 3.5 | 0.8 | 0.9 | 1.2 | 1.2 | 1.0 | 0.9 | 0.6 | 2.5 | 1.2 | 1.6 | 0.7 | 0.9 | 0.8 | 1.2 | 1.0 | 1.17 |
| YBR011C | 1.3 | 1.8 | 2.5 | 1.1 | 0.9 | 2.0 | 1.1 | 1.3 | 2.2 | 1.0 | 1.7 | 1.1 | 1.5 | 0.9 | 2.1 | 1.7 | 0.8 | 1.1 | 3.68 |
| YCR034W | 0.8 | 0.4 | 2.5 | 0.9 | 0.9 | 0.3 | 0.3 | 0.9 | 0.1 | 0.2 | 0.8 | 0.5 | 0.2 | 0.6 | 0.9 | 0.3 | 0.9 | 0.7 | 3.77 |
| YDR050C | 1.6 | 1.3 | 2.3 | 1.8 | 0.9 | 1.7 | 1.5 | 1.3 | 0.4 | 1.3 | 2.0 | 1.4 | 2.0 | 1.2 | 1.9 | 1.3 | 1.1 | 2.3 | 6.26 |
| YDR178W | 2.0 | 2.0 | 3.4 | 2.2 | 0.9 | 2.1 | 0.6 | 0.9 | 0.9 | 0.8 | 2.0 | 1.3 | 1.5 | 1.5 | 0.7 | 3.0 | 1.2 | 2.3 | 2.27 |
| YDR284C | 0.8 | 1.5 | 3.0 | 2.9 | 0.8 | 1.8 | 1.4 | 0.9 | 0.9 | 1.0 | 1.3 | 0.9 | 1.2 | 1.3 | 0.9 | 1.7 | 1.5 | 1.5 | 1.44 |
| YDR345C | 0.8 | 0.9 | 5.6 | 2.6 | 1.3 | 1.2 | 1.1 | 1.2 | 0.2 | 1.1 | 1.5 | 1.4 | 1.2 | 0.8 | 0.8 | 1.0 | 1.3 | 1.8 | 5.65 |
| YDR400W | 1.0 | 2.0 | 2.2 | 0.7 | 1.0 | 1.1 | 0.6 | 1.4 | 1.1 | 1.4 | 1.3 | 0.4 | 0.7 | 0.9 | 0.8 | 1.1 | 1.1 | 0.8 | 0.56 |
| YEL063C | 0.7 | 0.8 | 2.4 | 1.3 | 1.2 | 1.3 | 0.7 | 0.6 | 0.8 | 1.7 | 0.8 | 1.1 | 1.1 | 1.3 | 1.0 | 0.7 | 0.7 | 0.7 | 1.12 |
| YER081W | 1.6 | 1.9 | 2.7 | 1.4 | 1.1 | 1.1 | 0.5 | 0.6 | 1.8 | 1.1 | 1.1 | 1.0 | 0.6 | 1.6 | 0.5 | 0.8 | 1.1 | 1.7 | 2.31 |
| YER120W | 0.9 | 1.1 | 2.5 | 0.8 | 0.8 | 1.5 | 0.9 | 0.6 | 0.8 | 0.9 | 1.1 | 1.3 | 1.0 | 0.9 | 1.5 | 1.0 | 1.2 | 1.0 | 1.52 |
| YFL011W | 1.2 | 0.7 | 3.7 | 3.3 | 1.3 | 1.0 | 0.8 | 0.8 | 0.3 | 1.6 | 2.1 | 0.9 | 0.8 | 0.8 | 1.7 | 1.2 | 0.8 | 1.0 | 1.25 |
| YGL012W | 1.0 | 0.8 | 3.0 | 1.2 | 1.5 | 1.6 | 0.9 | 0.8 | 0.3 | 0.9 | 0.6 | 0.6 | 0.3 | 0.8 | 0.6 | 1.2 | 0.9 | 1.1 | 4.88 |

TABLE 7-continued

Metabolism protein genes

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGR191W | 0.8 | 0.7 | 1.6 | 1.5 | 0.8 | 1.1 | 0.7 | 0.7 | 0.1 | 0.7 | 1.6 | 0.7 | 1.0 | 0.7 | 1.5 | 0.7 | 0.8 | 0.8 | 1.58 |
| YGR204W | 0.5 | 1.1 | 2.7 | 1.3 | 0.6 | 0.6 | 0.8 | 0.4 | 0.9 | 2.3 | 2.1 | 1.0 | 1.3 | 0.5 | 1.6 | 0.6 | 1.0 | 0.7 | 1.49 |
| YHR025W | 0.6 | 0.8 | 2.4 | 0.6 | 0.9 | 0.8 | 0.8 | 0.8 | 0.2 | 0.4 | 2.1 | 0.9 | 0.7 | 0.6 | 2.1 | 0.5 | 1.0 | 0.6 | 0.68 |
| YHR123W | 0.7 | 1.2 | 1.8 | 1.0 |  | 1.0 | 0.9 | 0.8 | 0.8 | 1.1 | 1.2 | 0.7 | 1.5 | 0.8 | 2.3 | 0.5 | 1.1 | 1.0 | 0.85 |
| YJL121C | 1.0 | 0.5 | 1.9 | 0.8 | 1.0 | 1.1 | 0.7 | 1.0 | 0.1 | 0.4 | 1.1 | 0.6 | 0.7 | 0.9 | 1.0 | 0.6 | 1.1 | 1.0 | 1.00 |
| YJR077C | 1.1 | 1.1 | 2.0 | 1.6 | 0.9 | 0.9 | 0.7 | 0.8 | 0.4 | 0.7 | 1.6 | 1.0 | 0.9 | 0.7 | 1.5 | 0.7 | 1.0 | 0.8 | 1.79 |
| YJR143C | 0.6 | 0.6 | 2.1 | 0.8 | 1.6 | 0.6 | 0.5 | 0.7 | 0.1 | 0.3 | 1.3 | 0.6 | 0.3 | 0.6 | 1.1 | 0.5 | 0.7 | 0.8 | 3.24 |
| YKL060C | 1.6 | 0.8 | 2.5 | 1.0 | 1.6 | 1.3 | 1.2 | 1.1 | 0.3 | 0.8 | 2.1 | 1.3 | 1.2 | 0.8 | 1.6 | 1.5 | 1.2 | 1.7 | 6.01 |
| YKL148C | 0.9 | 0.8 | 3.7 | 0.7 | 0.8 | 0.5 | 0.6 | 0.8 | 1.7 | 1.7 | 1.5 | 0.8 | 0.8 | 0.8 | 0.6 | 1.1 | 0.8 | 1.0 | 0.54 |
| YKL157W | 0.7 | 1.0 | 2.3 | 1.3 | 1.5 | 1.5 | 1.9 | 1.1 | 1.7 | 1.9 | 1.5 | 1.0 | 2.3 | 0.8 | 1.2 | 1.7 | 1.2 | 1.5 | 1.22 |
| YLR044C | 0.8 | 0.6 | 2.2 | 0.9 | 1.7 | 1.5 | 1.3 | 0.7 | 0.0 | 1.2 | 1.1 | 1.4 | 1.7 | 0.5 | 2.2 | 0.6 | 0.9 | 0.9 | 5.16 |
| YLR056W | 1.0 | 0.6 | 2.5 | 0.8 | 1.6 | 1.2 | 0.8 | 0.9 | 0.0 | 0.5 | 0.8 | 0.9 | 0.2 | 0.7 | 0.9 | 2.1 | 1.1 | 1.1 | 3.61 |
| YLR058C | 0.9 | 0.8 | 5.5 | 2.6 | 0.7 | 0.9 | 0.5 | 0.3 | 0.2 | 0.1 | 2.6 | 0.4 | 0.3 | 0.7 | 1.5 | 0.4 | 0.8 | 0.8 | 2.71 |
| YLR081W | 1.3 | 0.8 | 2.8 | 3.6 | 1.0 | 0.9 | 0.7 | 0.9 | 0.1 | 2.2 | 2.6 | 1.0 | 0.6 | 1.0 | 0.7 | 1.2 | 0.7 | 0.9 | 1.46 |
| YLR089C | 0.9 | 1.2 | 2.1 | 0.9 | 0.8 | 1.5 | 1.6 | 0.7 | 0.5 | 0.8 | 1.7 | 0.6 | 1.0 | 0.7 | 1.7 | 1.4 | 1.2 | 1.3 | 1.27 |
| YLR284C | 0.9 | 1.0 | 3.8 | 1.9 | 1.6 | 0.9 | 0.8 | 1.2 | 0.9 | 0.9 | 1.5 | 0.6 | 0.8 | 1.3 | 1.0 | 4.5 | 2.9 | 8.1 | 0.84 |
| YLR304C | 0.7 | 0.6 | 5.0 | 0.7 | 0.6 | 1.9 | 0.6 | 0.6 | 0.1 | 2.2 | 1.6 | 1.0 | 0.5 | 0.7 | 1.6 | 1.8 | 0.5 | 0.7 | 2.39 |
| YLR354C | 1.1 | 2.5 | 2.3 | 1.5 | 1.6 | 1.5 | 1.1 | 1.4 | 0.4 | 0.9 | 1.7 | 1.2 | 1.0 | 0.9 | 2.4 | 1.3 | 1.0 | 1.5 | 4.53 |
| YLR372W | 0.7 | 0.3 | 1.7 | 0.8 | 1.4 | 0.5 | 0.2 | 0.9 | 0.0 | 0.1 | 0.9 | 0.6 | 0.1 | 0.6 | 0.7 | 0.2 | 0.5 | 0.6 | 4.46 |
| YML022W | 0.9 | 0.6 | 2.0 | 1.1 | 1.3 | 0.8 | 0.6 | 1.1 | 0.3 | 0.6 | 1.2 | 0.6 | 0.2 | 0.9 | 0.6 | 0.6 | 0.5 | 0.7 | 4.93 |
| YMR011W | 1.3 | 1.0 | 9.4 | 5.5 | 0.9 | 0.6 | 0.8 | 1.1 | 0.0 | 0.7 | 1.5 | 0.8 | 0.4 | 0.6 | 0.6 | 1.2 | 1.3 | 1.6 | 4.95 |
| YMR015C | 0.7 | 0.7 | 1.9 | 0.9 | 1.7 | 1.3 | 0.4 | 0.7 | 0.1 | 0.3 | 1.0 | 0.9 | 0.4 | 0.8 | 1.2 | 1.5 | 1.0 | 1.0 | 2.51 |
| YMR205C | 0.5 | 0.7 | 2.3 | 0.8 | 1.2 | 1.2 | 0.9 | 0.7 | 0.3 | 0.8 | 1.0 | 1.1 | 1.3 | 0.5 | 0.9 | 0.9 | 0.6 | 0.5 | 4.75 |
| YMR261C | 0.7 | 1.6 | 3.6 | 0.8 | 0.9 | 0.6 | 1.3 | 0.7 | 1.6 | 1.3 | 0.8 | 0.9 | 1.6 | 0.6 | 0.8 | 1.6 | 0.7 | 1.1 | 0.78 |
| YMR323W | 0.8 | 1.1 | 2.9 | 1.1 | 0.7 | 0.4 | 1.1 | 0.8 | 0.5 | 1.3 | 2.5 | 1.2 | 1.8 | 1.2 | 37.3 | 0.6 | 1.1 | 0.6 | 1.04 |
| YOL086C | 1.1 | 0.5 | 2.2 | 1.1 | 1.9 | 1.7 | 1.9 | 0.8 | 0.1 | 1.2 | 2.6 | 1.3 | 1.7 | 0.6 | 1.6 | 1.4 | 1.1 | 1.3 | 4.19 |
| YOL156W | 1.1 | 0.7 | 2.5 | 1.1 | 1.2 | 1.2 | 1.0 | 1.0 | 2.3 | 2.1 | 1.1 | 0.9 | 1.7 | 0.9 | 1.9 | 0.9 | 0.9 | 0.9 | 0.53 |
| YOR002W | 0.8 | 1.1 | 1.9 | 0.9 | 1.1 | 1.1 | 1.0 | 0.9 | 0.8 | 0.9 | 1.2 | 0.5 | 0.6 | 0.9 | 1.5 | 0.8 | 0.9 | 1.1 | 1.49 |
| YOR085W | 0.7 | 0.8 | 1.9 | 1.0 | 1.0 | 0.6 | 0.6 | 0.7 | 0.5 | 0.6 | 1.1 | 0.8 | 1.0 | 0.7 | 1.8 | 0.8 | 0.9 | 0.9 | 1.86 |
| YOR108W | 0.8 | 0.9 | 2.3 | 0.6 | 1.1 | 1.6 | 1.2 | 0.9 | 0.4 | 1.1 | 1.4 | 0.7 | 1.3 | 0.9 | 0.7 | 1.0 | 1.1 | 1.1 | 1.07 |
| YOR128C | 0.9 | 0.7 | 2.1 | 1.1 | 1.1 | 1.0 | 0.7 | 0.6 | 0.3 | 0.4 | 0.8 | 0.5 | 0.4 | 0.7 | 1.6 | 0.5 | 1.2 | 1.2 | 2.14 |
| YOR142W | 1.0 | 1.2 | 3.4 | 1.0 | 1.4 | 1.6 | 1.0 | 0.8 | 1.1 | 1.5 | 1.5 | 0.8 | 1.4 | 0.8 | 1.1 | 0.8 | 0.9 | 1.0 | 1.31 |
| YOR176W | 0.7 | 2.6 | 2.7 | 0.9 | 1.0 | 0.9 | 0.5 | 1.0 | 1.0 | 0.5 | 1.4 | 1.3 | 1.5 | 0.8 | 0.8 | 1.4 | 1.2 | 2.1 | 1.23 |
| YPL057C | 1.9 | 1.1 | 3.2 | 3.1 | 1.9 | 0.6 | 0.6 | 1.0 | 0.4 | 1.4 | 1.6 | 1.0 | 1.3 | 0.7 | 1.1 | 2.5 | 2.2 | 2.0 | 2.08 |
| YPL135W | 0.9 | 1.2 | 2.5 | 1.2 | 1.6 | 1.3 | 1.2 | 1.0 | 0.5 | 2.8 | 1.3 | 1.1 | 1.2 | 1.1 | 1.5 | 1.2 | 1.5 | 1.7 | 1.50 |
| YCR010C | 1.6 | 1.6 | 1.6 | 4.2 | 1.7 | 1.3 | 1.3 | 0.8 | 0.9 | 4.7 | 1.1 | 0.8 | 1.0 | 1.2 | 1.2 | 2.8 | 1.9 | 1.5 | 0.26 |
| YBR003W | 0.9 | 0.8 | 1.0 | 1.9 | 0.7 | 1.2 | 1.1 | 0.9 | 1.0 | 1.3 | 1.3 | 0.8 | 1.2 | 0.8 | 0.7 | 2.0 | 1.1 | 1.3 | 1.06 |
| YBR020W | 1.0 | 0.5 | 1.9 | 1.9 | 1.0 | 0.8 | 0.7 | 1.0 | -0.4 | 1.1 | 1.0 | 0.8 | 1.1 | 1.0 | 1.3 | 0.7 | 0.8 | 0.9 | 0.27 |
| YDR123C | 1.2 | 0.8 | 0.4 | 2.1 | 1.6 | 0.7 | 0.9 | 1.3 | 0.5 | 0.6 | 0.6 | 0.5 | 0.9 | 0.7 | 1.2 | 0.8 | 1.3 | 1.0 | 0.30 |
| YDR277C | 1.6 | 1.2 | 1.0 | 3.0 | 0.8 | 1.1 | 1.2 | 1.7 | 0.2 | 0.9 | 1.2 | 0.9 | 1.2 | 1.3 | 0.4 | 2.3 | 1.2 | 1.7 | 0.89 |
| YDR408C | 1.0 | 1.0 | 1.4 | 4.1 | 0.9 | 0.9 | 0.8 | 0.7 | 0.3 | 0.5 | 1.7 | 0.6 | 0.5 | 0.9 | 1.0 | 1.0 | 1.1 | 1.1 | 2.16 |
| YDR483W | 1.1 | 1.0 | 1.3 | 2.0 | 0.7 | 1.5 | 0.8 | 1.0 | 0.4 | 1.1 | 1.4 | 0.8 | 1.3 | 0.8 | 1.5 | 1.2 | 1.2 | 1.4 | 3.24 |
| YGL115W | 0.9 | 0.6 | 1.2 | 2.0 | 1.2 | 1.2 | 1.4 | 1.0 | 1.2 | 1.2 | 1.0 | 0.9 | 0.7 | 1.2 | 0.7 | 1.7 | 0.8 | 1.2 | 2.46 |
| YGR096W | 1.5 | 1.0 | 1.1 | 4.6 | 1.2 | 1.7 | 0.9 | 1.0 | 0.8 | 0.8 | 0.8 | 0.8 | 1.1 | 1.2 | 0.9 | 0.8 | 0.8 | 1.0 | 0.49 |
| YGR288W | 0.9 | 0.5 | 1.0 | 2.6 | 0.8 |  | 1.4 | 1.0 | 1.6 | 2.6 | 1.3 | 0.9 | 1.3 | 1.1 | 0.8 | 1.7 | 1.2 | 1.3 | 0.41 |
| YHR210C | 1.3 | 1.0 | 0.6 | 5.2 | 1.8 | 0.7 | 1.9 | 1.3 | -0.1 | 0.9 | 1.5 | 0.5 | 0.4 | 1.0 | 0.5 | 1.5 | 1.4 | 1.2 | 0.33 |
| YIL006W | 1.0 | 1.1 | 1.4 | 2.9 | 0.8 | 0.3 | 0.8 | 0.6 | 0.9 | 1.1 | 1.0 | 0.9 | 0.8 | 1.0 | 1.5 | 1.7 | 0.8 | 0.9 | 0.28 |
| YKR034W | 0.9 | 1.5 | 1.1 | 4.7 | 0.9 | 0.9 | 0.7 | 1.5 | 0.5 | 0.6 | 0.0 | 0.7 | 1.2 | 1.1 | 1.7 | 0.6 | 0.8 | 1.0 | 0.26 |
| YLR006C | 0.7 | 0.7 | 0.9 | 6.2 | 1.6 | 0.9 | 1.1 | 0.9 | 1.1 | 1.1 | 1.5 | 0.7 | 0.8 | 1.0 | 0.9 | 0.8 | 1.6 | 1.0 | 0.40 |
| YNL025C | 0.9 | 1.4 | 1.4 | 12.8 | 0.7 | 0.5 | 1.2 | 1.0 | 1.1 | 1.8 | 1.1 | 0.8 | 1.3 | 1.2 | 1.4 | 2.9 | 0.7 | 1.3 | 0.37 |
| YOL116W | 1.1 | 1.0 | 0.9 | 2.8 | 1.7 | 0.7 | 1.5 | 1.3 | 0.6 | 1.8 | 1.0 | 0.6 | 0.8 | 0.9 | 0.7 | 1.9 | 1.1 | 1.4 | 0.47 |
| YOR103C | 1.1 | 0.8 | 1.3 | 1.8 | 1.5 | 1.0 | 1.2 | 1.0 | 0.8 | 0.9 | 1.0 | 1.2 | 0.8 | 1.2 | 1.4 | 1.3 | 1.1 | 1.5 | 2.84 |
| YOR251C | 1.1 | 1.0 | 1.3 | 1.8 | 0.8 | 0.9 | 1.0 | 1.1 | 0.8 | 0.8 | 1.0 | 0.9 | 1.0 | 1.1 | 0.6 | 1.2 | 0.9 | 1.3 | 1.34 |
| YOR348C | 1.1 | 0.7 | 1.2 | 2.0 | 0.9 | 0.7 | 0.8 | 0.8 | 0.5 | 0.4 | 1.1 | 0.7 | 1.1 | 1.2 | 1.6 | 1.7 | 0.9 | 0.9 | 0.18 |
| YPL148C | 1.2 | 0.8 | 0.9 | 2.3 | 1.1 | 0.6 | 1.0 | 0.9 | 0.7 | 1.5 | 3.5 | 0.7 | 0.6 | 1.6 | 0.6 | 1.6 | 1.0 | 1.1 | 0.48 |
| YGL205W | 0.9 | 0.9 | 0.7 | 0.8 | 1.1 | 1.6 | 0.8 | 1.2 | 0.5 | 0.6 | 0.4 | 1.1 | 1.0 | 1.0 | 2.0 | 4.1 | 3.9 | 9.1 | 0.24 |
| YNL192W | 1.1 | 1.2 | 1.5 | 1.6 | 0.9 | 0.6 | 1.0 | 0.8 | 0.6 | 1.8 | 1.1 | 1.1 | 2.7 | 0.7 | 2.1 | 0.8 | 2.3 | 2.8 | 1.31 |
| YOL108C | 1.4 | 1.5 | 0.4 | 1.9 | 2.1 | 0.9 | 1.1 | 1.3 | 1.6 | 0.9 | 1.1 | 1.0 | 1.3 | 0.9 | 1.5 | 1.8 | 1.5 | 2.7 | 0.87 |
| YPR165W | 1.3 | 0.7 | 1.6 | 1.0 | 1.5 | 1.8 | 1.0 | 1.0 | 0.9 | 0.7 | 1.0 | 0.8 | 1.0 | 1.0 | 0.9 | 1.0 | 2.3 | 2.7 | 3.64 |
| YDR073W | 1.7 | 0.9 | 0.7 | 1.4 | 1.2 | 1.3 | 1.2 | 1.3 | 0.5 | 1.2 | 1.0 | 0.8 | 0.6 | 1.2 | 0.8 | 1.6 | 1.8 | 2.3 | 1.27 |
| YER015W | 0.7 | 0.9 | 1.1 | 1.5 | 1.3 | 0.9 | 1.2 | 1.1 | 0.4 | 0.9 | 1.0 | 0.9 | 0.8 | 1.1 | 0.8 | 3.0 | 1.6 | 2.6 | 0.41 |
| YJL167W | 0.9 | 1.4 | 1.4 | 1.1 | 0.7 | 1.3 | 1.5 | 1.5 | 0.9 | 0.9 | 1.2 | 1.3 | 0.9 | 0.9 | 1.6 | 1.4 | 1.4 | 2.1 | 2.94 |
| YJL216C | 0.8 | 4.7 | 2.2 | 0.9 | 0.8 |  | 1.5 | 1.9 | 1.5 | 1.3 | 1.1 | 1.0 | 1.1 | 1.1 | 1.2 | 1.5 | 1.2 | 2.0 | 0.25 |
| YKR009C | 1.0 | 1.2 | 1.5 | 0.9 | 1.0 | 1.8 | 1.0 | 0.9 | 2.4 | 2.1 | 1.2 | 1.0 | 1.8 | 1.0 | 1.0 | 4.6 | 1.9 | 2.5 | 0.27 |
| YOR180C | 0.8 | 1.1 | 1.0 | 1.0 | 1.0 | 0.7 | 0.8 | 0.9 | 0.3 | 0.4 | 0.6 | 0.8 | 0.9 | 1.0 | 1.1 | 2.4 | 0.9 | 2.3 | 0.55 |
| YBR036C | 0.8 | 1.7 | 1.8 | 1.2 | 1.2 | 1.3 | 1.3 | 0.7 | 1.0 | 1.1 | 1.5 | 1.0 | 1.9 | 0.8 | 1.5 | 1.6 | 2.1 | 1.8 | 2.05 |
| YDR297W | 1.5 | 0.8 | 0.8 | 1.1 | 0.9 | 1.4 | 0.6 | 1.5 | 0.3 | 0.7 | 1.4 | 1.0 | 0.8 | 0.9 | 1.4 | 1.4 | 1.9 | 1.9 | 1.73 |
| YDR387C | 0.8 | 0.9 | 1.2 | 2.2 | 0.9 | 1.2 | 1.3 | 0.7 | 1.4 | 2.0 | 2.0 | 0.9 | 1.3 | 0.9 | 1.4 | 2.7 | 1.2 | 1.1 | 0.86 |
| YOL096C | 1.1 | 1.0 | 1.2 | 1.6 | 1.2 | 1.3 | 1.7 | 1.0 | 1.3 | 1.4 | 1.2 | 1.2 | 1.4 | 1.4 | 1.0 | 2.3 | 1.2 | 1.2 | 0.64 |
| YPR184W | 1.2 | 1.4 | 5.7 | 2.2 | 0.9 | 1.5 | 1.3 | 0.7 | 1.9 | 3.2 | 3.6 | 1.4 | 2.5 | 1.3 | 1.5 | 3.1 | 1.0 | 1.7 | 0.37 |
| YBR298C | 1.1 | 1.0 | 1.6 | 2.3 | 1.4 | 0.4 | 1.7 | 0.5 | 0.3 | 1.1 | 1.5 | 1.1 | 0.8 | 0.9 | 0.2 | 2.1 | 0.9 | 0.8 | 0.88 |
| YDL078C | 0.7 | 1.1 | 1.2 | 0.8 | 1.3 | 1.1 | 1.7 | 1.0 | 1.1 | 1.0 | 1.7 | 0.8 | 1.0 | 0.8 | 0.5 | 2.2 | 1.1 | 2.0 | 1.65 |
| YOL215C | 1.0 | 1.5 | 1.0 | 1.6 | 1.5 | 0.9 | 1.9 | 1.1 | 1.7 | 2.4 | 0.8 | 0.8 | 1.5 | 1.0 | 1.1 | 2.2 | 1.1 | 1.6 | 0.91 |

TABLE 7-continued

Metabolism protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YGL035C | 0.7 | 1.4 | 4.3 | 1.4 | 1.1 | 0.6 | 1.2 | 1.3 | 0.9 | 1.5 | 1.3 | 0.9 | 1.1 | 1.1 | 1.0 | 2.3 | 0.9 | 1.2 | 0.61 |
| YGR287C | 1.3 | 1.0 | 1.3 | 1.5 | 0.8 | 0.8 | 2.2 | 1.3 | 2.6 | 4.2 | 1.5 | 1.1 | 1.7 | 1.1 | 2.3 | 3.0 | 1.0 | 1.1 | 0.38 |
| YJL070C | 1.3 | 0.9 | 1.1 | 1.2 | 1.3 | 2.0 | 1.4 | 1.1 | 1.0 | 1.1 | 1.3 | 1.0 | 1.8 | 1.3 | 3.5 | 2.2 | 1.1 | 1.2 | 0.34 |
| YLR351C | 1.0 | 1.4 | 1.3 | 1.5 | 1.3 | 1.4 | 1.4 | 1.2 | 0.8 | 1.2 | 1.1 | 0.9 | 0.9 | 1.4 | 1.2 | 2.0 | 1.3 | 1.8 | 1.75 |
| YLR375W | 0.9 | 1.5 | 0.9 | 0.9 | 1.0 | 1.3 | 0.9 | 1.0 | 1.6 | 1.2 | 1.6 | 0.9 | 1.6 | 0.9 | 1.3 | 2.2 | 1.0 | 1.0 | 1.05 |
| YMR267W | 0.8 | 1.8 | 0.7 | 0.9 | 1.0 | 1.4 | 1.2 | 1.5 | 0.4 | 0.8 | 1.0 | 0.8 | 0.7 | 1.0 | 0.9 | 2.6 | 0.9 | 1.3 | 0.94 |
| YMR278W | 0.7 | 1.7 | 1.4 | 1.0 | 1.2 | 1.3 | 1.8 | 1.1 | 1.4 | 1.7 | 1.1 | 1.0 | 2.5 | 0.8 | 1.8 | 2.5 | 1.0 | 1.5 | 0.62 |
| YMR293C | 0.9 | 1.5 | 1.6 | 2.2 | 0.6 | 0.5 | 1.2 | 1.0 | 0.7 | 1.3 | 0.4 | 0.9 | 0.8 | 1.3 | 0.7 | 2.2 | 0.8 | 1.0 | 0.37 |
| YNR072W | 1.1 | 1.5 | 0.5 | 0.7 | 1.0 | 0.9 | 1.5 | 0.9 | 0.7 | 1.8 | 1.4 | 1.0 | 1.5 | 1.0 | 1.8 | 2.1 | 1.3 | 1.0 | 0.26 |
| YOR363C | 0.8 | 2.0 | 0.9 | 1.3 | 0.7 | 1.2 | 0.7 | 1.1 | 1.2 | 1.6 | 1.2 | 0.9 | 1.3 | 0.9 | 1.1 | 2.1 | 1.3 | 1.8 | 0.40 |

TABLE 8

Detoxification protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR453C | 1.1 | 2.7 | 4.4 | 3.0 | 0.7 | 1.7 | 1.0 | 1.3 | 4.5 | 6.1 | 2.3 | 0.9 | 1.4 | 3.8 | 2.3 | 5.6 | 1.0 | 1.5 | 1.53 |
| YLL060C | 12.5 | 4.2 | 2.3 | 2.6 | 0.9 | 1.4 | 2.0 | 5.8 | 13.0 | 23.2 | 14.1 | 1.1 | 1.8 | 10.6 | 1.5 | 3.6 | 1.9 | 2.3 | 0.57 |
| YBL064C | 2.6 | 2.8 | 3.9 | 1.7 | 0.8 | 5.2 | 2.5 | 2.4 | 4.5 | 3.8 | 2.9 | 1.7 | 4.1 | 5.0 | 1.3 | 5.0 | 1.2 | 2.3 | 1.67 |
| YBR008C | 3.0 | 2.4 | 4.9 | 0.7 | 0.9 | 1.0 | 0.9 | 2.8 | 54.6 | 21.1 | 9.4 | 0.8 | 2.0 | 4.1 | 0.8 | 3.1 | 2.0 | 1.2 | 0.37 |
| YOR153W | 1.6 | 0.9 | 5.1 | 1.1 | 1.0 | 7.4 | 2.6 | 0.5 | 3.2 | 1.2 | 1.0 | 4.0 | 11.8 | 0.3 | 3.6 | 1.6 | 2.5 | 3.1 | 1.91 |
| YHL047C | 0.6 | 4.4 | 1.0 | 1.0 | 1.2 | 8.4 | 16.8 | 1.5 | 1.2 | 11.9 | 1.0 | 2.6 | 3.8 | 0.5 | 1.1 | 2.3 | 1.2 | 1.2 | 0.74 |
| YCL035C | 2.0 | 2.3 | 1.5 | 1.7 | 1.5 | 5.1 | 2.7 | 1.4 | 1.9 | 2.3 | 2.1 | 1.5 | 2.8 | 2.5 | 1.9 | 5.5 | 2.6 | 4.2 | 1.74 |
| YGR197C | 1.1 | 2.4 | 2.5 | 1.0 | 0.7 | 0.5 | 1.3 | 0.8 | 16.7 | 3.2 | 1.1 | 1.2 | 2.4 | 1.5 | 1.0 | 1.5 | 1.7 | 1.9 | 0.37 |
| YHR055C | 4.4 | 1.8 | 0.8 | 1.2 | 2.7 | 1.6 | 1.1 | 2.1 | 3.9 | 3.3 | 1.8 | 1.2 | 3.0 | 1.5 | 0.5 | 0.8 | 0.9 | 0.6 | 3.96 |
| YNL239W | 1.0 | 2.4 | 2.4 | 1.2 | 1.2 | 1.8 | 2.1 | 1.3 | 2.5 | 6.0 | 1.9 | 1.5 | 3.6 | 1.3 | 1.7 | 1.5 | 1.1 | 1.4 | 0.68 |
| YNL241C | 1.3 | 2.5 | 4.3 | 1.0 | 0.8 | 0.9 | 3.2 | 0.9 | 3.4 | 7.4 | 3.0 | 2.0 | 4.9 | 1.1 | 7.0 | 2.8 | 1.0 | 1.0 | 0.68 |
| YBR293W | 1.9 | 3.1 | 1.0 | 1.8 | 0.8 | 0.9 | 0.9 | 0.9 | 5.5 | 2.4 | 1.1 | 1.0 | 3.0 | 1.4 | 3.1 | 1.6 | 1.0 | 0.9 | 0.94 |
| YDL100C | 1.0 | 1.2 | 1.1 | 0.8 | 1.0 | 2.1 | 1.6 | 1.7 | 5.4 | 3.2 | 2.8 | 1.5 | 2.5 | 1.4 | 1.0 | 1.3 | 1.2 | 1.4 | 2.60 |
| YER185W | 2.0 | 3.1 | 2.1 | 7.0 | 1.6 | 1.2 | 1.1 | 1.0 | 2.9 | 1.2 | 1.6 | 1.1 | 2.1 | 1.6 | 1.7 | 0.6 | 2.6 | 1.1 | 0.26 |
| YGL013C | 0.9 | 1.2 | 0.8 | 0.7 | 1.1 | 2.3 | 0.9 | 1.4 | 3.0 | 1.5 | 0.9 | 1.0 | 2.3 | 0.8 | 1.0 | 0.9 | 1.1 | 1.0 | 0.43 |
| YHR053C | 3.5 | 2.1 | 0.7 | 1.1 | 2.9 | 1.3 | 1.2 | 2.2 | 4.5 | 2.9 | 1.4 | 1.1 | 1.9 | 1.5 | 0.3 | 0.7 | 1.0 | 0.5 | 3.99 |
| YIR038C | 1.3 | 3.5 | 4.6 | 2.0 | 0.7 | 2.5 | 2.0 | 1.3 | 4.6 | 4.5 | 3.4 | 1.1 | 2.5 | 2.5 | 1.2 | 6.0 | 2.8 | 2.0 | 1.11 |
| YKL026C | 2.7 | 2.0 | 1.2 | 4.9 | 1.0 | 1.8 | 2.5 | 1.8 | 7.5 | 3.0 | 3.0 | 1.0 | 2.3 | 1.8 | 0.8 | 6.6 | 1.6 | 3.3 | 0.61 |
| YLL028W | 0.6 | 0.9 | 4.6 | 0.5 | 0.9 | 1.7 | 1.0 | 0.7 | 1.2 | 2.3 | 0.7 | 1.3 | 4.1 | 0.7 | 3.1 | 0.6 | 1.2 | 1.2 | 1.02 |
| YOR273C | 0.7 | 1.0 | 1.7 | 1.0 | 1.1 | 0.4 | 0.4 | 0.6 | 0.6 | 0.5 | 1.5 | 0.8 | 2.6 | 0.5 | 0.8 | 0.6 | 3.2 | 3.1 | 1.20 |
| YGR138C | 1.1 | 1.6 | 1.0 | 1.2 | 0.8 | 0.8 | 0.7 | 1.0 | 0.5 | 1.0 | 0.7 | 0.6 | 0.6 | 0.9 | 4.5 | 0.7 | 0.7 | 0.7 | 1.24 |
| YOR247W | 1.7 | 0.6 | 3.6 | 1.4 | 0.6 | 0.2 | 0.5 | 0.7 | 0.1 | 0.4 | 2.9 | 0.6 | 0.3 | 0.4 | 7.3 | 0.2 | 1.2 | 0.9 | 2.23 |
| YPL163C | 0.6 | 0.7 | 1.4 | 0.9 | 0.6 | 0.6 | 0.4 | 0.5 | 0.1 | 0.4 | 0.5 | 0.9 | 0.4 | 0.6 | 5.3 | 0.6 | 1.4 | 1.4 | 1.05 |
| YHL040C | 1.6 | 4.4 | 1.5 | 0.4 | 1.1 | 7.3 | 4.0 | 1.5 | 1.1 | 11.3 | 1.7 | 2.0 | 2.0 | 1.1 | 3.4 | 1.0 | 1.4 | 1.0 | 0.69 |
| YEL065W | 0.3 | 3.8 | 1.2 | 0.4 | 1.4 | 2.3 | 4.3 | 0.9 | 0.1 | 4.9 | 0.6 | 1.7 | 0.8 | 0.4 | 2.2 | 2.6 | 0.7 | 0.6 | 2.10 |
| YIR002C | 0.8 | 1.1 | 0.5 | 0.6 | 1.2 | 2.2 | 1.3 | 1.2 | 1.7 | 1.4 | 0.8 | 1.3 | 1.2 | 1.1 | 1.1 | 1.4 | 1.1 | 1.2 | 0.58 |
| YNL259C | 1.6 | 4.5 | 1.1 | 1.2 | 1.1 | 3.9 | 3.8 | 1.5 | 1.6 | 2.1 | 1.6 | 0.7 | 1.1 | 1.4 | 0.7 | 1.7 | 2.6 | 2.4 | 1.22 |
| YBR145W | 1.5 | 0.7 | 2.8 | 0.9 | 1.1 | 11.5 | 58.8 | 1.0 | 0.1 | 1.1 | 1.1 | 1.0 | 2.0 | 2.2 | 1.2 | 3.6 | 1.7 | 2.0 | 2.17 |
| YLR043C | 1.4 | 1.4 | 2.0 | 1.8 | 2.0 | 1.4 | 2.6 | 1.1 | 2.8 | 2.5 | 1.4 | 0.8 | 2.0 | 2.1 | 0.5 | 1.8 | 1.5 | 2.2 | 2.12 |
| YGR209C | 1.6 | 3.1 | 3.5 | 1.5 | 1.9 | 1.9 | 1.7 | 1.6 | 2.4 | 6.3 | 3.1 | 0.9 | 1.4 | 5.0 | 1.3 | 1.9 | 1.3 | 2.4 | 3.17 |
| YDL168W | 2.3 | 2.0 | 2.1 | 0.9 | 1.2 | 1.4 | 1.1 | 1.7 | 8.2 | 4.7 | 1.9 | 0.6 | 1.3 | 1.6 | 1.2 | 1.1 | 0.9 | 0.8 | 1.08 |
| YDR513W | 2.2 | 2.5 | 2.3 | 2.6 | 0.9 | 2.1 | 1.6 | 1.6 | 4.6 | 3.1 | 2.0 | 0.9 | 1.8 | 2.0 | 1.3 | 3.8 | 1.3 | 3.2 | 3.10 |
| YGR088W | 1.3 | 1.2 | 7.7 | 2.4 | 1.0 | 1.3 | 0.8 | 0.8 | 1.5 | 3.2 | 3.9 | 1.1 | 1.2 | 1.3 | 0.7 | 5.6 | 0.9 | 2.0 | 0.75 |
| YHR048W | 2.5 | 1.4 | 1.4 | 1.7 | 1.0 | 0.8 | 0.8 | 1.9 | 4.5 | 2.7 | 2.0 | 0.9 | 1.1 | 1.7 | 0.9 | 1.4 | 0.7 | 0.9 | 0.26 |
| YJL101C | 2.1 | 1.9 | 2.1 | 1.2 | 1.4 | 2.0 | 1.0 | 1.3 | 3.1 | 3.6 | 2.7 | 0.7 | 1.0 | 1.0 | 0.5 | 1.3 | 0.9 | 1.0 | 1.13 |
| YML116W | 4.1 | 1.3 | 1.5 | 1.4 | 1.2 | 0.9 | 1.4 | 2.2 | 1.4 | 3.1 | 4.3 | 0.5 | 0.8 | 2.0 | 1.9 | 1.0 | 1.0 | 1.0 | 0.94 |
| YMR038C | 1.9 | 1.7 | 1.8 | 0.8 | 1.5 | 1.0 | 1.1 | 1.9 | 2.4 | 2.6 | 2.7 | 0.9 | 1.7 | 1.1 | 0.6 | 1.5 | 1.2 | 1.3 | 1.76 |
| YBR244W | 0.6 | 1.4 | 2.0 | 0.9 | 1.7 | 1.0 | 0.6 | 1.0 | 1.4 | 3.0 | 1.5 | 0.5 | 0.4 | 3.7 | 0.4 | 0.7 | 1.2 | 1.2 | 3.42 |
| YCL069W | 0.9 | 15.7 | 0.9 | 0.8 | 0.9 |  | 1.4 | 1.3 | 1.2 | 6.9 | 1.0 | 0.9 | 0.8 | 1.3 | 1.4 | 0.9 | 1.0 | 1.0 | 0.25 |
| YKR105C | 0.8 | 0.9 | 0.9 | 1.5 | 1.0 | 1.2 | 1.0 | 1.3 | 1.0 | 5.2 | 0.0 | 0.8 | 2.5 | 1.2 | 1.5 | 0.7 | 0.8 | 1.0 | 0.26 |
| YOL158C | 0.7 | 4.0 | 2.4 | 0.9 | 1.2 | 2.0 | 1.6 | 0.7 | 1.7 | 6.1 | 0.7 | 0.9 | 1.4 | 1.0 | 0.9 | 1.2 | 1.4 | 1.7 | 1.30 |
| YDR256C | 0.8 | 1.4 | 0.7 | 1.3 | 1.2 | 0.5 | 0.6 | 0.8 | 5.2 | 2.0 | 1.4 | 0.8 | 1.1 | 1.6 | 1.0 | 4.3 | 1.0 | 2.0 | 0.30 |
| YGL254W | 1.2 | 1.1 | 0.8 | 0.6 | 1.1 | 0.7 | 1.3 | 1.4 | 3.1 | 1.8 | 1.1 | 1.2 | 2.4 | 1.3 | 1.1 | 1.4 | 0.8 | 1.2 | 0.53 |
| YKL064W | 0.6 | 0.9 | 0.4 | 0.8 | 1.2 | 1.5 | 1.1 | 0.9 | 2.4 | 1.6 | 0.7 | 0.7 | 1.6 | 1.1 | 0.7 | 1.4 | 1.3 | 1.3 | 0.60 |
| YLL057C | 2.2 | 59.9 | 1.8 | 0.9 | 1.1 | 1.0 | 1.6 | 1.4 | 121.8 | 2.9 | 1.3 | 0.7 | 1.4 | 1.1 | 1.4 | 0.9 | 3.0 | 1.3 | 0.19 |
| YPR200C | 47.7 | 1.7 | 0.8 | 5.0 | 1.6 | 0.8 | 1.3 | 1.4 | 4.7 | 3.8 | 2.0 | 0.4 | 0.6 | 2.0 | 0.7 | 1.2 | 1.1 | 1.0 | 0.27 |
| YJR104C | 1.4 | 1.8 | 2.9 | 1.2 | 1.5 | 1.4 | 1.1 | 1.5 | 1.9 | 2.8 | 2.6 | 0.9 | 0.9 | 2.3 | 2.9 | 0.9 | 1.1 |  | 3.50 |
| YKR106W | 1.3 | 0.8 | 2.1 | 1.4 | 1.2 | 1.6 | 0.9 | 1.3 | 10.5 | 7.4 | 1.8 | 0.8 | 1.4 | 1.7 |  | 2.8 | 0.9 | 0.8 | 0.16 |
| YOR031W | 2.6 | 1.7 | 1.3 | 3.4 | 1.4 | 0.9 | 1.3 | 0.9 | 0.7 | 1.3 | 1.2 | 0.8 | 1.8 | 1.5 | 1.4 | 6.2 | 1.7 | 2.4 | 0.52 |
| YHR008C | 1.3 | 6.9 | 4.8 | 1.8 | 0.6 | 1.0 | 0.7 | 0.9 | 1.7 | 2.4 | 2.1 | 0.7 | 1.2 | 1.6 | 1.7 | 2.2 | 0.9 | 1.0 | 1.04 |
| YML028W | 1.0 | 2.2 | 4.4 | 1.3 | 1.6 | 1.2 | 0.8 | 0.8 | 0.8 | 1.8 | 1.0 | 1.6 | 1.6 | 2.0 | 2.2 | 1.3 | 1.1 | 1.5 | 4.85 |

TABLE 8-continued

Detoxification protein genes

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YEL027W | 1.2 | 0.6 | 3.4 | 1.1 | 1.0 | 1.1 | 0.8 | 0.9 | 0.9 | 1.1 | 0.9 | 0.9 | 0.7 | 1.4 | 1.5 | 1.6 | 1.0 | 1.4 | 4.75 |
| YKR066C | 0.9 | 1.4 | 5.5 | 0.7 | 1.0 | 0.9 | 0.5 | 0.7 | 0.7 | 2.4 | 1.3 | 0.9 | 0.6 | 1.5 | 0.6 | 1.3 | 0.9 | 1.1 | 1.25 |
| YDR538W | 0.9 | 1.1 | 2.4 | 1.2 | 1.0 | 1.0 | 1.2 | 1.0 | 0.3 | 0.8 | 0.9 | 0.7 | 0.7 | 0.9 | 1.0 | 0.9 | 1.0 | 0.9 | 0.53 |
| YMR015C | 0.7 | 0.7 | 1.9 | 0.9 | 1.7 | 1.3 | 0.4 | 0.7 | 0.1 | 0.3 | 1.0 | 0.9 | 0.4 | 0.8 | 1.2 | 1.5 | 1.0 | 1.0 | 2.51 |
| YOR251C | 1.1 | 1.0 | 1.3 | 1.8 | 0.8 | 0.9 | 1.0 | 1.1 | 0.8 | 0.8 | 1.0 | 0.9 | 1.0 | 1.1 | 0.6 | 1.2 | 0.9 | 1.3 | 1.34 |
| YLR046C | 0.7 | 1.7 | 0.9 | 0.8 | 1.0 | 3.8 | 1.5 | 0.5 | 1.0 | 1.4 | 0.9 | 0.8 | 1.2 | 1.3 | 0.8 | 1.3 | 5.2 | 5.4 | 0.86 |
| YGR224W | 0.9 | 1.2 | 1.2 | 1.2 | 1.4 | 0.8 | 0.4 | 0.6 | 0.9 | 0.9 | 0.8 | 0.6 | 0.8 | 0.9 | 1.1 | 1.0 | 2.8 | 1.3 | 0.27 |
| YFL050C | 0.7 | 1.0 | 1.1 | 2.2 | 1.0 | 0.9 | 0.8 | 0.9 | 0.5 | 1.6 | 1.2 | 0.9 | 1.2 | 1.0 | 1.4 | 2.3 | 0.8 | 1.0 | 0.36 |
| YCR083W | 1.1 | 2.8 | 1.5 | 1.8 | 1.6 | 2.4 | 1.8 | 1.5 | 1.8 | 1.8 | 1.8 | 1.1 | 1.8 | 2.4 | 1.0 | 3.1 | 1.3 | 1.3 | 0.98 |

TABLE 9

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YKR076W | 5.0 | 2.6 | 3.5 | 2.2 | 1.0 | 4.7 | 4.9 | 6.2 | 43.4 | 43.1 | 18.6 | 1.5 | 5.1 | 14.7 | 3.2 | 9.6 | 1.8 | 2.7 | 0.27 |
| YNL335W | 1.2 | 0.7 | 1.5 | 2.3 | 1.5 | 1.6 | 1.3 | 1.7 | 1.6 | 5.3 | 1.1 | 0.8 | 0.9 | 4.6 | 1.7 | 1.0 | 1.2 | 1.1 | 0.22 |
| YBR173C | 1.1 | 2.4 | 3.4 | 1.6 | 0.7 | 1.3 | 1.6 | 1.2 | 6.0 | 5.1 | 2.5 | 1.7 | 3.8 | 3.0 | 15.4 | 2.1 | 0.9 | 1.6 | 1.15 |
| YFL022C | 0.8 | 0.9 | 1.5 | 0.6 | 0.7 | 0.9 | 0.3 | 0.8 | 0.5 | 0.5 | 1.2 | 0.6 | 0.6 | 3.1 | 1.1 | 1.3 | 0.9 | 0.8 | 1.07 |
| YGL158W | 1.1 | 2.8 | 1.9 | 12.9 | 1.0 | 0.4 | 1.3 | 1.3 | −0.4 | 0.9 | 0.2 | 1.3 | 1.0 | 2.3 | 2.3 | 8.2 | 0.8 | 1.1 | 0.18 |
| YHR139C | 3.0 | 4.6 | 6.8 | 9.3 | 1.3 | 1.9 | 1.5 | 1.3 | 107.2 | 46.6 | 3.5 | 1.6 | 7.0 | 2.5 | 1.9 | 17.1 | 1.4 | 1.3 | 0.34 |
| YGR213C | 5.4 | 2.9 | 1.0 | 6.8 | 1.2 | 4.1 | 7.0 | 2.0 | 7.5 | 6.9 | 1.6 | 10.6 | 30.4 | 1.0 | 6.5 | 5.2 | 12.8 | 8.5 | 0.22 |
| YKL165C | 0.5 | 2.0 | 1.1 | 0.6 | 0.9 | 0.6 | 2.1 | 1.5 | 0.4 | 0.4 | 0.3 | 2.4 | 3.2 | 0.8 | 2.1 | 1.2 | 0.9 | 1.0 | 1.08 |
| YBL005W-A | 1.0 | 0.9 | 0.5 | 0.9 | 1.3 | 1.2 | 1.4 | 1.0 | 0.8 | 1.5 | 0.8 | 1.6 | 2.9 | 1.4 | 0.9 | 1.1 | 1.3 | 1.0 | 0.48 |
| YBL041W | 1.2 | 1.4 | 0.9 | 1.0 | 1.6 | 1.7 | 1.6 | 1.7 | 2.8 | 2.6 | 1.6 | 1.6 | 2.6 | 2.0 | 1.3 | 2.3 | 1.3 | 2.0 | 3.03 |
| YBL078C | 2.3 | 2.7 | 1.3 | 2.6 | 0.7 | 2.4 | 3.1 | 1.6 | 12.3 | 15.2 | 4.6 | 3.1 | 5.0 | 3.6 | 2.5 | 4.4 | 1.8 | 2.8 | 0.65 |
| YCL020W | 1.1 | 2.5 | 0.5 | 1.1 | 0.5 | 1.0 | 1.5 | 1.7 | 0.9 | 2.4 | 1.3 | 1.5 | 3.0 | 1.7 | 2.5 | 1.3 | 0.9 | 1.3 | 1.46 |
| YDL007W | 0.8 | 1.4 | 1.3 | 0.9 | 1.0 | 1.1 | 1.2 | 1.4 | 3.8 | 2.4 | 1.3 | 1.1 | 2.4 | 1.4 | 1.4 | 0.8 | 0.8 | 1.5 | 2.43 |
| YDL097C | 0.9 | 1.7 | 0.9 | 1.2 | 0.8 | 1.3 | 1.6 | 1.5 | 4.5 | 2.3 | 1.5 | 1.3 | 4.0 | 1.4 | 1.1 | 1.1 | 1.0 | 1.3 | 2.06 |
| YDL126C | 0.5 | 1.4 | 2.3 | 0.7 | 0.9 | 1.2 | 1.5 | 0.8 | 2.7 | 2.0 | 1.4 | 1.3 | 4.3 | 0.6 | 1.7 | 0.7 | 0.9 | 0.9 | 3.24 |
| YER012W | 1.4 | 1.2 | 1.2 | 1.0 | 1.9 | 2.4 | 2.4 | 1.8 | 6.7 | 2.7 | 1.9 | 1.5 | 2.9 | 4.6 | 1.7 | 2.2 | 1.5 | 1.3 | 1.84 |
| YFR010W | 1.1 | 1.1 | 0.8 | 1.2 | 0.9 | 1.3 | 1.4 | 1.6 | 4.3 | 3.4 | 1.5 | 1.2 | 3.7 | 1.1 | 1.5 | 1.3 | 0.9 | 1.4 | 1.89 |
| YFR024C | 0.8 | 25.0 | 2.3 | 1.1 | 0.7 | 1.4 | 3.0 | 0.9 | 5.3 | 4.1 | 1.9 | 1.5 | 2.8 | 1.2 | 0.9 | 1.9 | 1.0 | 1.4 | 1.06 |
| YGL048C | 1.0 | 1.3 | 0.7 | 1.3 | 1.8 | 1.5 | 2.0 | 1.5 | 2.4 | 2.1 | 1.5 | 1.3 | 2.5 | 1.2 | 1.0 | 1.6 | 1.4 | 2.0 | 3.07 |
| YGL141W | 0.8 | 1.2 | 1.1 | 0.7 | 1.4 | 3.0 | 1.7 | 0.8 | 4.5 | 1.9 | 0.6 | 1.4 | 3.6 | 1.2 | 1.5 | 1.2 | 1.4 | 1.2 | 0.44 |
| YGL180W | 1.3 | 1.3 | 1.7 | 0.6 | 1.2 | 1.1 | 2.4 | 1.2 | 7.2 | 3.7 | 1.3 | 1.4 | 2.6 | 1.0 | 1.3 | 1.7 | 1.0 | 1.1 | 0.28 |
| YGR048W | 0.7 | 2.7 | 1.4 | 1.3 | 1.0 | 1.0 | 1.9 | 1.4 | 4.4 | 3.1 | 1.1 | 1.1 | 2.5 | 1.3 | 0.8 | 1.1 | 0.9 | 1.2 | 0.93 |
| YGR135W | 1.0 | 1.0 | 1.0 | 1.1 | 1.6 | 1.5 | 2.2 | 1.8 | 1.5 | 2.3 | 1.6 | 1.2 | 2.8 | 2.6 | 1.5 | 1.5 | 1.0 | 1.9 | 3.10 |
| YGR201C | 1.7 | 11.9 | 2.4 | 2.0 | 0.8 | 3.1 | 2.6 | 1.6 | 5.4 | 3.5 | 1.6 | 1.9 | 8.6 | 1.6 | 0.5 | 14.4 | 1.4 | 2.1 | 0.60 |
| YHL030W | 0.5 | 0.8 | 1.0 | 0.7 | 0.7 | 1.9 | 0.9 | 0.8 | 2.7 | 2.5 | 1.1 | 1.1 | 3.8 | 1.0 | 2.0 | 0.5 | 0.8 | 0.9 | 0.66 |
| YHR166C | 0.9 | 1.1 | 1.0 | 0.7 | 1.0 | 1.8 | 1.5 | 1.0 | 2.6 | 1.2 | 0.6 | 1.7 | 6.9 | 1.2 | 0.9 | 1.1 | 1.4 | 1.5 | 1.35 |
| YJR069C | 0.8 | 0.8 | 0.9 | 0.6 | 0.9 | 1.2 | 1.3 | 0.9 | 0.7 | 0.6 | 0.9 | 1.1 | 3.9 | 0.6 | 0.4 | 0.8 | 1.0 | 0.9 | 1.73 |
| YKL073W | 0.6 | 1.4 | 0.5 | 0.6 | 1.2 | 0.5 | 2.1 | 1.6 | 1.3 | 1.1 | 0.5 | 1.5 | 3.3 | 0.7 | 1.6 | 1.0 | 1.2 | 1.5 | 1.29 |
| YKL103C | 1.6 | 4.1 | 2.5 | 2.1 | 0.9 | 2.7 | 2.8 | 1.6 | 8.3 | 9.9 | 2.8 | 1.3 | 3.8 | 2.0 | 2.1 | 1.2 | 1.9 | 2.2 | 0.56 |
| YLR080W | 1.0 | 1.4 | 1.2 | 1.7 | 1.1 | 2.5 | 2.8 | 1.3 | 2.3 | 1.5 | 1.9 | 0.8 | 3.6 | 1.2 | 0.7 | 3.0 | 1.6 | 2.2 | 0.41 |
| YLR107W | 1.2 | 0.9 | 0.5 | 1.2 | 1.7 | 2.3 | 1.6 | 1.1 | 1.8 | 1.2 | 0.8 | 1.0 | 2.9 | 1.6 | 1.1 | 1.6 | 1.8 | 2.4 | 0.94 |
| YLR121C | 1.7 | 1.7 | 1.1 | 1.2 | 1.0 | 1.6 |  | 1.3 | 2.2 | 2.0 | 2.2 | 1.1 | 4.0 | 1.2 | 10.7 | 1.5 | 2.7 | 1.4 | 0.30 |
| YLR336C | 0.6 | 0.8 | 0.7 | 0.4 | 0.9 | 0.8 | 1.8 | 1.0 | −0.3 | 0.5 | 0.5 | 1.9 | 4.6 | 0.6 | 0.8 | 1.3 | 1.5 | 1.0 | 0.71 |
| YLR370C | 1.1 | 1.0 | 1.1 | 1.4 | 1.4 | 4.1 | 2.1 | 0.8 | 1.5 | 1.9 | 1.0 | 1.2 | 3.1 | 1.9 | 1.5 | 1.6 | 1.6 | 2.0 | 1.41 |
| YLR423C | 1.2 | 1.2 | 0.7 | 1.9 | 1.5 | 1.2 | 3.8 | 2.0 | 1.2 | 1.0 | 1.0 | 1.7 | 3.9 | 1.2 | 1.3 | 1.9 | 1.2 | 1.6 | 0.34 |
| YML092C | 1.1 | 3.1 | 2.4 | 1.1 | 0.9 | 1.9 | 1.2 | 1.2 | 6.4 | 4.0 | 2.5 | 1.2 | 2.3 | 1.6 | 1.4 | 2.2 | 1.3 | 1.5 | 1.72 |
| YML130C | 1.5 | 2.7 | 5.3 | 1.2 | 0.9 | 0.6 | 2.9 | 2.7 | 7.8 | 4.2 | 1.9 | 2.3 | 5.8 | 1.3 | 2.4 | 0.8 | 1.2 | 1.2 | 1.59 |
| YMR214W | 0.8 | 3.8 | 1.0 | 1.4 | 0.8 | 0.9 | 1.0 | 1.1 | 2.1 | 1.0 | 0.7 | 1.0 | 2.4 | 1.1 | 4.8 | 0.7 | 1.1 | 1.0 | 0.88 |
| YMR297W | 0.7 | 2.0 | 3.6 | 1.9 | 0.6 | 1.8 | 1.2 | 0.8 | 1.9 | 1.0 | 2.5 | 1.2 | 4.2 | 0.5 | 2.4 | 1.9 | 1.1 | 1.4 | 4.10 |
| YNL036W | 2.0 | 1.9 | 3.2 | 1.0 | 1.6 | 1.1 | 2.0 | 2.1 | 6.6 | 5.0 | 1.7 | 1.4 | 3.3 | 5.1 | 1.6 | 1.3 | 1.4 | 1.9 | 2.04 |
| YOL005C | 1.4 | 1.4 | 1.1 | 0.8 | 1.6 | 1.1 | 1.1 | 1.0 | 0.9 | 1.0 | 1.6 | 1.2 | 2.9 | 1.2 | 0.9 | 1.0 | 1.2 | 1.2 | 1.71 |
| YOR134W | 2.0 | 3.6 | 1.0 | 9.5 | 0.9 | 1.4 | 1.1 | 1.5 | 1.5 | 8.2 | 1.9 | 2.8 | 4.4 | 1.3 | 1.6 | 7.7 | 2.2 | 4.6 | 0.28 |
| YOR362C | 1.0 | 1.7 | 1.0 | 0.8 | 1.7 | 1.6 | 1.4 | 1.4 | 4.3 | 3.0 | 1.3 | 1.3 | 2.5 | 1.4 | 1.0 | 1.5 | 1.1 | 1.8 | 2.55 |
| YAR009C | 0.8 | 1.3 | 0.6 | 1.0 | 1.4 | 1.6 | 2.7 | 1.4 | 0.9 | 1.4 | 0.9 | 1.3 | 2.0 | 1.0 | 2.1 | 0.6 | 0.8 | 1.2 | 7.11 |
| YBL101C | 1.0 | 1.1 | 1.9 | 0.9 | 1.0 | 0.9 | 0.8 | 0.8 | 3.0 | 1.4 | 0.8 | 1.1 | 3.5 | 0.9 | 2.7 | 1.4 | 1.0 | 1.1 | 0.39 |
| YBR046C | 1.4 | 1.4 | 1.7 | 1.8 | 1.3 | 2.6 | 3.9 | 1.6 | 4.6 | 6.2 | 2.9 | 1.2 | 2.0 | 1.3 | 2.1 | 3.0 | 1.2 | 2.0 | 0.63 |
| YBR139W | 1.2 | 2.3 | 3.1 | 1.4 | 0.8 | 2.4 | 1.9 | 0.7 | 2.3 | 1.6 | 2.3 | 1.2 | 2.7 | 1.1 | 5.6 | 2.3 | 1.2 | 2.0 | 1.21 |
| YBR170C | 0.8 | 1.2 | 0.6 | 1.4 | 1.5 | 1.4 | 1.9 | 1.3 | 6.1 | 4.2 | 1.5 | 1.2 | 2.7 | 1.3 | 1.9 | 1.3 | 1.1 | 1.4 | 0.72 |
| YBR177C | 0.8 | 1.1 | 4.0 | 1.2 | 1.2 | 2.3 | 0.9 | 0.9 | 2.1 | 1.7 | 0.6 | 1.2 | 3.1 | 1.3 | 1.4 | 0.4 | 0.8 | 0.9 | 0.76 |
| YBR212W | 0.7 | 1.2 | 2.6 | 1.2 | 1.0 | 1.4 | 0.9 | 0.6 | 2.7 | 2.3 | 1.1 | 0.9 | 2.2 | 0.7 | 1.0 | 1.5 | 1.1 | 1.0 | 0.95 |
| YBR239C | 1.0 | 1.3 | 0.9 | 1.5 | 0.8 | 1.5 | 1.0 | 1.3 | 0.4 | 1.2 | 0.7 | 1.1 | 1.9 | 1.1 | 1.0 | 2.7 | 1.0 | 0.9 | 0.31 |
| YCL033C | 1.1 | 2.0 | 1.7 | 1.7 | 1.2 | 4.6 | 2.4 | 1.1 | 2.3 | 1.4 | 1.9 | 1.6 | 2.0 | 1.8 | 0.8 | 3.6 | 2.0 | 2.0 | 1.14 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YCR062W | 0.8 | 1.9 | 2.7 | 2.8 | 1.4 | 1.9 | 0.9 | 0.7 | 0.7 | 1.3 | 1.2 | 1.3 | 2.2 | 1.0 | 2.3 | 1.1 | 1.1 | 1.0 | 0.41 |
| YCR067C | 0.9 | 0.7 | 1.2 | 1.3 | 0.7 | 0.8 | 0.8 | 0.7 | 1.8 | 1.6 | 1.2 | 0.9 | 2.0 | 0.9 | 2.1 | 1.4 | 1.1 | 0.9 | 0.62 |
| YDL020C | 2.3 | 1.2 | 3.4 | 1.1 | 1.2 | 2.5 | 1.0 | 2.2 | 5.6 | 2.9 | 1.9 | 1.1 | 3.4 | 1.2 | 1.5 | 1.8 | 1.5 | 1.7 | 1.36 |
| YDR168W | 1.2 | 1.4 | 1.0 | 0.8 | 1.5 | 1.3 | 2.4 | 2.1 | 3.7 | 2.3 | 1.5 | 1.2 | 2.4 | 1.4 | 1.9 | 1.4 | 1.2 | 1.4 | 1.28 |
| YDR169C | 1.0 | 1.4 | 1.1 | 1.3 | 1.3 | 1.2 | 1.1 | 1.0 | 1.6 | 1.4 | 0.9 | 0.9 | 1.9 | 0.9 | 1.4 | 0.9 | 1.4 | 1.1 | 0.40 |
| YDR188W | 0.8 | 1.2 | 1.0 | 0.8 | 0.8 | 0.8 | 0.9 | 1.0 | 2.9 | 1.6 | 0.9 | 0.9 | 1.7 | 0.7 | 1.3 | 0.9 | 0.7 | 0.8 | 1.78 |
| YDR264C | 0.5 | 2.6 | 0.9 | 1.4 | 0.9 | 1.8 | 3.2 | 0.8 | 1.1 | 3.4 | 0.9 | 1.1 | 2.1 | 0.7 | 2.3 | 1.5 | 1.2 | 1.4 | 1.63 |
| YDR304C | 1.0 | 1.8 | 2.7 | 1.3 | 1.5 | 2.1 | 2.0 | 1.3 | 3.9 | 1.9 | 1.2 | 1.3 | 2.3 | 1.7 | 1.0 | 4.0 | 1.6 | 1.8 | 2.23 |
| YDR403W | 1.0 | 1.2 | 1.6 | 1.0 | 1.2 | 1.1 | 1.2 | 1.2 | 4.1 | 3.6 | 1.0 | 1.0 | 2.0 | 1.1 | 0.9 | 0.9 | 0.9 | 1.0 | 0.35 |
| YDR427W | 0.8 | 1.1 | 0.8 | 0.8 | 1.5 | 1.9 | 1.4 | 1.2 | 2.3 | 2.0 | 1.2 | 1.1 | 2.1 | 1.0 | 1.3 | 1.1 | 1.0 | 1.5 | 2.37 |
| YEL012W | 1.3 | 1.8 | 1.0 | 1.8 | 1.7 | 1.6 | 4.7 | 1.4 | 4.6 | 4.2 | 2.2 | 1.2 | 2.2 | 1.9 | 1.1 | 2.5 | 1.5 | 2.2 | 0.74 |
| YER009W | 1.3 | 0.6 | 2.4 | 1.2 | 1.2 | 2.0 | 2.8 | 1.0 | 0.7 | 1.0 | 1.4 | 1.1 | 2.0 | 1.6 | 0.9 | 1.5 | 2.0 | 2.1 | 3.35 |
| YER021W | 0.8 | 1.0 | 0.9 | 0.9 | 1.4 | 1.1 | 1.5 | 1.2 | 3.0 | 2.2 | 1.3 | 1.0 | 1.8 | 1.3 | 0.8 | 1.4 | 0.8 | 1.5 | 2.02 |
| YER094C | 1.0 | 1.3 | 0.9 | 1.1 | 1.9 | 1.1 | 1.8 | 1.3 | 2.3 | 1.7 | 1.3 | 1.1 | 2.1 | 1.5 | 0.8 | 1.5 | 1.3 | 1.8 | 3.01 |
| YER177W | 1.4 | 1.5 | 2.1 | 1.5 | 0.9 | 1.6 | 1.2 | 1.1 | 1.8 | 1.7 | 1.9 | 1.1 | 2.2 | 0.9 | 1.4 | 1.0 | 0.9 | 2.0 | 5.81 |
| YFL029C | 1.0 | 1.2 | 1.2 | 1.8 | 1.7 | 1.0 | 1.6 | 1.5 | 4.3 | 2.9 | 2.1 | 1.1 | 1.8 | 1.9 | 1.3 | 1.2 | 1.2 | 1.4 | 0.49 |
| YFL038C | 1.0 | 1.2 | 0.7 | 1.3 | 1.5 | 1.3 | 1.7 | 1.4 | 2.1 | 1.9 | 1.7 | 1.1 | 2.1 | 1.5 | 1.5 | 2.1 | 1.2 | 1.6 | 2.31 |
| YFR004W | 1.0 | 1.5 | 0.8 | 1.4 | 1.0 | 1.5 | 1.3 | 1.4 | 3.6 | 2.6 | 1.3 | 1.2 | 2.0 | 2.1 | 1.1 | 1.3 | 1.0 | 1.4 | 2.44 |
| YFR050C | 0.9 | 1.2 | 1.1 | 1.3 | 1.7 | 1.5 | 1.4 | 1.4 | 3.1 | 2.1 | 1.4 | 1.5 | 2.1 | 1.6 | 1.5 | 1.5 | 1.1 | 1.7 | 1.70 |
| YGL011C | 1.2 | 1.5 | 1.1 | 1.1 | 1.8 | 1.6 | 1.5 | 1.3 | 2.0 | 2.2 | 1.5 | 1.0 | 2.1 | 3.0 | 1.3 | 1.7 | 1.3 | 1.5 | 1.78 |
| YGL094C | 0.8 | 1.3 | 0.3 | 0.9 | 1.3 | 1.0 | 0.8 | 1.0 | 1.4 | 1.1 | 0.6 | 0.8 | 2.3 | 0.9 | 1.9 | 1.0 | 1.0 | 0.9 | 0.51 |
| YGL150C | 0.7 | 0.8 | 1.2 | 1.0 | 0.8 | 1.1 | 0.8 | 0.8 | 1.4 | 0.9 | 0.4 | 0.8 | 2.4 | 1.0 | 1.3 | 0.9 | 0.9 | 0.8 | 0.62 |
| YGL207W | 0.5 | 0.6 | 0.9 | 0.6 | 1.3 | 0.9 | 0.9 | 1.0 | 1.4 | 1.1 | 0.7 | 0.7 | 2.5 | 0.8 | 1.2 | 0.7 | 0.9 | 0.8 | 0.88 |
| YGR232W | 1.2 | 1.2 | 1.2 | 1.7 | 1.5 | 1.9 | 2.0 | 1.1 | 3.4 | 2.2 | 1.3 | 1.1 | 2.4 | 2.1 | 0.9 | 1.8 | 1.3 | 1.2 | 0.96 |
| YGR248W | 1.3 | 1.7 | 3.2 | 4.0 | 0.5 | 2.3 | 1.1 | 1.2 | 2.8 | 3.2 | 2.3 | 1.1 | 2.0 | 1.5 | 1.5 | 7.9 | 1.0 | 1.5 | 0.52 |
| YGR253C | 1.3 | 1.4 | 0.7 | 1.3 | 2.0 | 1.4 | 1.6 | 2.0 | 4.0 | 3.1 | 2.4 | 1.1 | 3.4 | 1.8 | 1.1 | 1.8 | 1.5 | 2.1 | 2.01 |
| YHR027C | 0.5 | 0.8 | 1.2 | 0.6 | 1.1 | 0.4 | 0.9 | 0.6 | 3.6 | 2.2 | 1.1 | 1.0 | 2.1 | 0.7 | 1.5 | 0.9 | 0.8 | 1.0 | 2.06 |
| YHR161C | 0.6 | 1.1 | 1.3 | 2.1 | 1.5 | 1.2 | 1.8 | 0.7 | 2.5 | 2.0 | 1.2 | 1.0 | 1.8 | 1.0 | 1.4 | 1.7 | 1.4 | 1.5 | 0.86 |
| YHR169W | 0.6 | 0.5 | 0.4 | 0.4 | 1.1 | 1.2 | 0.9 | 0.9 | 0.0 | 0.2 | 0.4 | 1.1 | 3.3 | 1.1 | 0.6 | 1.0 | 1.6 | 1.3 | 0.81 |
| YIL010W | 1.0 | 1.2 | 1.4 | 0.8 | 1.2 | 4.4 | 1.5 | 0.9 | 1.4 | 2.2 | 1.4 | 1.4 | 2.3 | 1.7 | 1.1 | 1.7 | 1.5 | 1.5 | 0.70 |
| YIL034C | 1.0 | 0.8 | 1.5 | 3.0 | 0.7 | 1.7 | 1.2 | 0.9 | 2.1 | 1.3 | 1.6 | 1.0 | 2.6 | 1.1 | 1.0 | 1.7 | 1.2 | 1.5 | 0.99 |
| YIL142W | 0.7 | 1.1 | 0.9 | 1.1 | 0.8 | 1.1 | 0.8 | 1.1 | 4.4 | 3.0 | 1.7 | 1.1 | 1.8 | 1.0 | 1.3 | 0.7 | 0.9 | 0.8 | 1.84 |
| YIR039C | 1.4 | 1.8 | 4.3 | 4.2 | 1.5 | 3.2 | 4.1 | 1.1 | 4.4 | 4.1 | 3.8 | 1.4 | 2.9 | 1.9 | 2.0 | 4.2 | 1.2 | 1.1 | 0.45 |
| YJL001W | 0.9 | 1.7 | 1.2 | 2.0 |  | 1.7 | 1.6 | 1.3 | 3.1 | 2.8 | 1.5 | 1.6 | 2.9 | 2.5 | 1.2 | 1.8 | 1.0 | 1.6 | 3.00 |
| YJL035C | 0.9 | 1.3 | 0.8 | 0.6 | 1.4 | 0.7 | 1.3 | 1.5 | 1.7 | 1.4 | 0.8 | 1.1 | 2.4 | 1.6 | 0.7 | 0.6 | 1.0 | 1.0 | 0.82 |
| YJL053W | 1.1 | 0.9 | 1.7 | 1.3 | 1.1 | 2.0 | 1.7 | 1.3 | 2.2 | 2.2 | 1.6 | 1.1 | 1.9 | 1.3 | 1.1 | 1.7 | 1.3 | 1.6 | 0.80 |
| YJL164C | 1.1 | 1.1 | 1.0 | 1.9 | 1.1 | 2.7 | 3.1 | 0.9 | 2.1 | 0.8 | 1.5 | 1.0 | 2.1 | 0.9 | 0.8 | 2.1 | 1.3 | 1.7 | 1.04 |
| YJL210W | 1.2 | 1.4 | 1.6 | 2.0 | 0.6 | 0.6 | 1.0 | 1.0 | 2.0 | 0.9 | 2.4 | 1.0 | 2.2 | 0.9 | 0.8 | 2.3 | 0.9 | 1.0 | 0.70 |
| YJR117W | 1.0 | 2.1 | 2.3 | 0.7 | 1.2 | 1.3 | 1.0 | 0.8 | 4.7 | 2.3 | 1.0 | 1.2 | 2.8 | 0.8 | 2.2 | 0.7 | 0.8 | 0.9 | 1.34 |
| YKL007W | 1.2 | 1.6 | 1.2 | 0.9 | 1.0 | 0.9 | 1.5 | 1.2 | 2.3 | 2.4 | 1.8 | 1.3 | 2.5 | 0.7 | 1.0 | 1.0 | 1.4 | 1.3 | 1.13 |
| YKL117W | 1.0 | 1.3 | 0.8 | 1.0 | 1.8 | 1.0 | 1.3 | 1.5 | 2.9 | 2.1 | 1.6 | 1.0 | 2.4 | 1.6 | 1.6 | 1.8 | 1.2 | 1.8 | 3.73 |
| YKL193C | 1.3 | 0.8 | 1.1 | 1.4 | 1.1 | 0.9 | 2.1 | 1.4 | 1.0 | 1.6 | 1.7 | 0.9 | 2.1 | 1.2 | 1.2 | 2.4 | 1.2 | 2.3 | 0.71 |
| YLR120C | 1.2 | 1.9 | 2.4 | 1.6 | 1.1 | 1.9 | 1.5 | 0.9 | 1.8 | 1.6 | 1.2 | 1.6 | 4.8 | 0.8 | 2.7 | 1.7 | 3.5 | 2.9 | 1.53 |
| YLR136C | 1.3 | 9.0 | 0.6 | 3.3 | 1.6 | 1.7 | 3.9 | 1.1 | 0.9 | 6.0 | 1.2 | 1.3 | 2.9 | 0.7 | 2.1 | 1.2 | 1.8 | 1.4 | 0.41 |
| YLR178C | 1.7 | 6.9 | 8.8 | 4.6 | 1.0 | 4.2 | 3.3 | 0.9 | 4.3 | 4.1 | 3.7 | 2.2 | 7.5 | 2.8 | 2.3 | 10.6 | 2.0 | 3.6 | 1.03 |
| YLR327C | 5.5 | 3.3 | 14.4 | 8.2 | 1.3 | 5.1 | 5.7 | 2.2 | 3.0 | 8.3 | 5.0 | 1.4 | 2.8 | 1.5 | 0.8 | 2.8 | 3.3 | 5.3 | 2.23 |
| YLR356W | 1.0 | 2.9 | 4.9 | 1.2 | 1.1 | 3.4 | 1.1 | 0.7 | 2.3 | 1.6 | 3.1 | 1.5 | 2.5 | 2.2 | 2.8 | 0.9 | 1.1 | 1.0 | 0.41 |
| YLR362W | 1.1 | 1.2 | 1.0 | 3.0 | 1.5 | 0.8 | 1.9 | 1.4 | 3.5 | 3.3 | 1.5 | 0.8 | 2.4 | 1.2 | 1.3 | 1.9 | 1.2 | 1.3 | 0.35 |
| YLR429W | 0.7 | 1.0 | 0.6 | 0.9 | 1.4 | 0.8 | 1.3 | 1.0 | 0.9 | 1.3 | 0.9 | 1.1 | 2.3 | 0.7 | 1.5 | 1.0 | 1.0 | 0.9 | 0.86 |
| YMR004W | 0.9 | 0.9 | 1.3 | 1.3 | 1.0 | 0.5 | 1.2 | 1.0 | 94.2 | 3.4 | 2.5 | 1.0 | 2.2 | 2.2 | 1.3 | 1.3 | 0.9 | 1.3 | 0.52 |
| YMR219W | 0.7 | 1.1 | 1.0 | 0.7 | 1.6 | 0.8 |  | 1.1 | 2.3 | 0.9 | 1.5 | 1.5 | 2.1 | 0.5 | 1.7 | 0.8 | 1.1 | 0.9 | 0.23 |
| YMR275C | 0.7 | 0.7 | 1.2 | 0.6 | 0.7 | 1.2 | 0.8 | 0.8 | 2.4 | 2.1 | 1.1 | 0.7 | 2.1 | 0.8 | 1.7 | 1.0 | 0.9 | 0.7 | 0.79 |
| YMR314W |  | 1.2 | 0.9 | 1.3 |  | 1.3 | 1.1 | 1.2 | 5.9 | 2.7 | 1.8 | 1.0 | 2.6 | 1.0 | 1.2 | 1.6 | 1.3 | 1.6 | 1.67 |
| YNL006W | 1.1 | 2.1 | 1.3 | 1.5 | 0.9 | 1.0 | 1.6 | 1.1 | 4.0 | 4.0 | 1.1 | 0.7 | 2.3 | 0.8 | 0.7 | 0.9 | 1.0 | 1.3 | 1.20 |
| YNL007C | 0.7 | 2.4 | 5.1 | 0.8 | 1.2 | 0.6 | 1.2 | 0.8 | 3.0 | 1.7 | 1.3 | 0.7 | 2.1 | 0.4 | 0.8 | 0.5 | 1.1 | 1.0 | 3.62 |
| YNL093W | 2.1 | 6.4 | 0.4 | 4.5 | 1.2 | 1.6 | 1.4 | 0.8 | 1.7 | 2.0 | 1.6 | 1.1 | 2.2 | 1.1 | 0.6 | 4.9 | 3.0 | 3.1 | 0.32 |
| YNL333W | 1.0 | 1.4 | 1.7 | 2.3 | 1.5 | 1.5 | 2.9 | 2.1 | 2.3 | 2.1 | 2.0 | 1.0 | 2.2 | 1.9 | 1.0 | 1.4 | 1.4 | 1.1 | 0.49 |
| YNR010W | 1.3 | 1.2 | 0.5 | 2.8 | 1.8 | 1.3 | 1.5 | 1.1 | 1.7 | 0.9 | 1.4 | 0.8 | 2.8 | 1.3 | 0.8 | 1.2 | 1.7 | 2.3 | 0.37 |
| YNR069C | 1.5 | 1.3 | 0.7 | 0.4 | 1.4 | 1.7 | 1.4 | 1.4 | 5.5 | 5.8 | 2.5 | 1.2 | 3.4 | 2.1 | 1.0 | 0.8 | 1.1 | 0.9 | 0.18 |
| YOL164W | 0.9 | 4.4 | 1.0 | 1.5 | 1.6 | 1.2 | 2.2 | 1.0 | 4.9 | 3.6 | 1.0 | 1.1 | 3.4 | 1.3 | 1.0 | 1.1 | 1.1 | 1.3 | 0.45 |
| YOR036W | 1.8 | 0.9 | 1.4 | 1.6 | 1.1 | 1.7 | 1.8 | 1.4 | 1.2 | 1.9 | 1.3 | 1.2 | 2.1 | 1.2 | 1.2 | 1.3 | 1.6 | 1.7 | 0.98 |
| YOR117W | 0.8 | 1.3 | 1.7 | 0.8 | 1.2 | 1.1 | 3.3 | 1.0 | 3.5 | 1.8 | 1.2 | 2.5 | 2.3 | 1.0 | 1.4 | 1.2 | 1.4 | 0.9 | 1.42 |
| YOR124C | 0.6 | 1.1 | 1.3 | 0.8 | 1.1 | 0.9 | 1.1 | 1.3 | 2.0 | 1.9 | 1.2 | 0.9 | 2.1 | 0.8 | 1.3 | 1.0 | 1.0 | 1.0 | 0.65 |
| YOR132W | 0.9 | 1.6 | 0.8 | 2.8 | 1.1 | 1.6 | 1.4 | 1.2 | 2.8 | 1.6 | 1.3 | 0.7 | 2.5 | 0.7 | 1.5 | 1.6 | 1.2 | 1.6 | 0.46 |
| YOR157C | 1.0 | 1.3 | 1.2 | 1.3 | 0.7 | 1.2 | 1.2 | 1.2 | 5.7 | 2.6 | 1.6 | 1.3 | 2.4 | 2.2 | 1.9 | 0.9 | 1.2 | 1.2 | 1.23 |
| YOR185C | 1.1 | 1.3 | 1.9 | 1.1 | 1.2 | 3.0 | 1.3 | 1.4 | 1.9 | 2.9 | 1.2 | 1.5 | 2.2 | 2.1 | 1.0 | 2.2 | 0.9 | 1.1 | 1.67 |
| YDR259C | 0.8 | 1.1 | 0.8 | 0.9 | 2.0 | 0.8 | 1.3 | 1.1 | 2.7 | 1.5 | 1.0 | 0.8 | 1.8 | 1.2 | 1.3 | 1.4 | 0.9 | 1.5 | 2.33 |
| YOR261C | 1.0 | 1.4 | 0.6 | 0.9 | 1.5 | 1.4 | 1.9 | 2.6 | 5.5 | 2.5 | 2.1 | 0.9 | 2.5 | 1.8 | 1.3 | 2.0 | 1.0 | 1.9 | 2.80 |
| YOR288C | 0.9 | 1.3 | 1.1 | 1.1 | 1.1 | 1.0 | 2.0 | 1.9 | 0.9 | 1.0 | 1.4 | 1.2 | 2.4 | 0.8 | 1.8 | 1.4 | 1.5 | 1.6 | 0.79 |
| YPL109C | 1.1 | 2.5 | 0.5 | 1.2 | 1.2 | 1.2 | 1.8 | 1.1 | 1.2 | 1.5 | -0.2 | 0.9 | 1.8 | 1.3 | 1.3 | 1.9 | 1.2 | 1.2 | 0.21 |
| YPL149W | 1.5 | 1.5 | 0.6 | 2.8 | 0.8 | 0.9 | 1.2 | 1.1 | 5.6 | 3.7 | 1.2 | 0.9 | 2.3 | 1.0 | 0.8 | 1.2 | 2.2 | 2.9 | 1.39 |
| YPL154C | 0.7 | 3.3 | 4.2 | 1.2 | 1.2 | 3.5 | 1.5 | 0.8 | 2.8 | 1.7 | 1.8 | 1.5 | 3.1 | 0.8 | 4.0 | 1.8 | 1.6 | 2.0 | 3.78 |
| YPR103W | 0.7 | 1.1 | 1.3 | 0.7 | 1.7 | 1.2 | 1.6 | 1.0 | 5.5 | 2.0 | 0.9 | 1.2 | 2.8 | 1.8 | 1.0 | 1.1 | 1.2 | 1.5 | 1.93 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPR108W | 0.8 | 1.0 | 1.3 | 0.6 | 1.3 | 1.5 | 1.6 | 1.6 | 3.7 | 2.8 | 1.8 | 1.0 | 2.6 | 1.0 | 1.3 | 1.2 | 1.0 | 1.3 | 2.25 |
| YCL027W | 0.7 | 2.0 | 1.0 | 1.0 | 1.2 | 1.3 | 1.0 | 0.6 | 0.7 | 16.3 | 0.9 | 0.8 | 1.1 | 1.2 | 3.6 | 1.1 | 0.7 | 0.8 | 0.30 |
| YDR055W | 1.7 | 2.1 | 2.2 | 2.8 | 1.7 | 3.9 | 1.5 | 1.6 | 0.8 | 2.4 | 2.2 | 1.4 | 3.1 | 0.9 | 5.7 | 3.4 | 2.0 | 1.9 | 1.55 |
| YEL042W | 0.6 | 0.9 | 1.7 | 0.9 | 0.7 | 0.5 | 0.5 | 0.7 | 0.2 | 0.3 | 1.6 | 1.0 | 0.4 | 0.6 | 4.8 | 0.6 | 0.7 | 0.8 | 1.21 |
| YGR136W | 0.9 | 1.2 | 1.3 | 0.7 | 1.2 | 1.1 | 1.5 | 1.3 | 2.1 | 2.2 | 1.3 | 1.2 | 1.7 | 1.1 | 2.6 | 2.2 | 1.3 | 1.8 | 1.42 |
| YHR142W | 1.5 | 0.8 | 2.1 | 0.8 | 1.3 | 1.2 | 0.9 | 1.3 | 0.4 | 0.9 | 1.1 | 1.3 | 1.2 | 1.2 | 4.8 | 1.0 | 1.3 | 1.3 | 1.17 |
| YJL073W | 0.8 | 0.8 | 2.5 | 0.7 | 1.2 | 2.0 |  | 1.0 | 1.7 | 0.7 | 0.5 | 1.0 | 1.6 | 1.1 | 2.6 | 0.8 | 1.1 | 1.0 | 0.43 |
| YJR004C | 0.2 | 0.8 | 3.4 | 0.6 | 1.1 | 1.2 | 0.4 | 0.4 | 0.3 | 0.7 | 0.7 | 0.8 | 0.3 | 0.7 | 3.2 | 0.3 | 0.4 | 0.4 | 2.12 |
| YKL039W | 0.8 | 1.1 | 2.4 | 0.8 | 0.7 | 4.9 | 2.0 | 0.8 | 1.3 | 3.3 | 1.0 | 0.9 | 1.9 | 0.8 | 3.1 | 1.5 | 1.2 | 1.3 | 1.13 |
| YLR250W | 1.5 | 1.0 | 1.0 | 1.4 | 1.4 | 1.1 | 1.9 | 1.3 | 2.7 | 2.4 | 1.4 | 1.0 | 1.2 | 2.5 | 2.6 | 2.1 | 1.4 | 2.2 | 2.90 |
| YOR181W | 1.0 | 0.9 | 1.1 | 1.4 | 0.7 | 0.9 | 0.7 | 0.7 | 0.6 | 0.5 | 1.0 | 0.8 | 1.2 | 0.9 | 3.4 | 1.0 | 1.1 | 0.6 | 0.39 |
| YOR198C | 1.0 | 0.7 | 1.4 | 1.0 | 0.8 | 0.9 | 1.6 | 1.3 | 2.4 | 1.4 | 1.4 | 1.5 | 1.8 | 1.1 | 3.8 | 0.8 | 1.1 | 1.5 | 1.76 |
| YPL089C | 1.2 | 1.0 | 0.5 | 1.8 | 1.4 | 0.8 | 0.9 | 0.8 | 0.4 | 2.5 | 0.9 | 0.7 | 1.3 | 0.8 | 2.6 | 0.9 | 1.5 | 1.1 | 0.37 |
| YBR214W | 0.9 | 2.1 | 5.7 | 2.0 | 1.1 | 0.8 | 1.1 | 0.7 | 2.2 | 3.5 | 3.2 | 1.2 | 2.1 | 0.9 | 5.1 | 1.3 | 1.1 | 1.2 | 0.51 |
| YDR085C | 1.9 | 1.8 | 1.6 | 3.4 | 0.9 | 2.1 | 4.1 | 2.0 | 0.4 | 2.3 | 1.7 | 1.6 | 1.1 | 1.6 | 3.1 | 2.3 | 1.3 | 1.8 | 0.37 |
| YDR259C | 1.4 | 1.0 | 0.4 | 1.4 | 1.0 | 0.5 | 2.8 | 1.4 | 1.0 | 1.8 | 1.2 | 1.0 | 2.0 | 1.5 | 2.9 | 0.9 | 1.0 | 0.8 | 0.28 |
| YDR388W | 0.7 | 0.7 | 1.2 | 1.0 | 0.7 | 1.0 | 1.1 | 0.8 | 1.4 | 0.9 | 1.6 | 0.8 | 1.7 | 0.6 | 2.6 | 1.0 | 1.2 | 1.3 | 0.99 |
| YDR432W | 0.5 | 0.8 | 1.0 | 1.4 | 1.6 | 0.6 | 0.5 | 0.5 | 0.7 | 0.8 | 0.6 | 0.7 | 1.4 | 0.5 | 2.6 | 0.6 | 0.7 | 0.7 | 2.38 |
| YDR481C | 0.7 | 2.3 | 1.3 | 0.7 | 1.0 | 0.9 | 0.7 | 1.0 | 1.9 | 1.6 | 1.2 | 0.9 | 1.5 | 0.9 | 3.5 | 1.3 | 1.2 | 1.4 | 1.43 |
| YDR510W | 1.0 | 1.3 | 1.5 | 1.3 | 0.7 | 1.0 | 1.6 | 1.5 | 2.7 | 2.5 | 1.6 | 1.4 | 2.0 | 1.9 | 2.2 | 1.5 | 1.1 | 1.5 | 1.57 |
| YGR189C | 1.1 | 0.9 | 1.5 | 3.5 | 0.7 | 0.5 | 0.6 | 1.0 | 0.3 | 0.9 | 1.5 | 1.3 | 1.2 | 0.9 | 9.3 | 0.6 | 2.3 | 1.7 | 1.51 |
| YIL123W | 1.0 | 0.5 | 1.2 | 1.5 | 0.6 | 0.5 | 0.5 | 0.6 | 0.1 | 0.2 | 1.2 | 0.8 | 0.4 | 0.3 | 4.8 | 0.7 | 1.3 | 1.0 | 1.67 |
| YIL140W | 0.7 | 1.0 | 1.5 | 1.4 | 0.8 | 0.5 | 0.5 | 0.7 | 0.7 | 0.6 | 0.9 | 1.0 | 0.5 | 0.9 | 3.3 | 0.6 | 0.7 | 1.0 | 0.62 |
| YKL096W | 1.4 | 0.6 | 8.1 | 1.6 | 0.6 | 0.6 | 0.2 | 0.5 | 0.0 | 0.5 | 3.5 | 0.3 | 0.1 | 0.5 | 2.3 | 0.4 | 0.5 | 0.7 | 2.04 |
| YLR391W |  | 0.7 | 2.9 | 0.8 | 1.2 | 1.5 | 0.7 | 0.7 | 0.4 | 0.7 | 1.4 | 1.0 | 0.9 | 0.5 | 3.9 | 1.3 | 1.4 | 0.9 | 1.72 |
| YMR094W | 1.0 | 0.5 | 1.3 | 1.7 | 0.9 | 0.5 | 0.8 | 1.0 | −0.1 | 0.9 | 1.0 | 0.9 | 1.4 | 2.8 | 6.6 | 1.0 | 1.0 | 1.0 | 0.23 |
| YMR104C | 1.9 | 14.3 | 2.2 | 2.6 | 0.7 | 1.9 | 1.5 | 0.9 | 0.6 | 3.2 | 1.1 | 1.0 | 1.5 | 1.1 | 2.5 | 2.3 | 2.8 | 1.9 | 0.51 |
| YMR276W | 0.6 | 1.4 | 1.5 | 0.7 | 1.3 | 0.8 | 1.1 | 0.8 | 1.8 | 1.7 | 1.9 | 1.2 | 1.9 | 1.2 | 3.3 | 0.9 | 1.2 | 0.7 | 0.47 |
| YOL013C | 0.9 | 1.0 | 1.0 | 1.5 | 0.7 | 1.1 | 1.7 | 1.0 | 0.8 | 1.0 | 1.4 | 1.1 | 1.8 | 0.9 | 2.7 | 1.3 | 1.1 | 1.4 | 0.65 |
| YOR355W | 0.7 | 0.6 | 1.1 | 0.8 | 1.0 | 1.6 | 1.1 | 0.8 | 0.1 | 0.8 | 1.2 | 0.9 | 1.1 | 0.6 | 3.2 | 0.8 | 0.8 | 0.9 | 0.98 |
| YCR071C | 1.1 | 0.7 | 0.9 | 0.8 | 1.2 | 2.5 | 1.4 | 0.9 | 0.6 | 1.2 | 1.1 | 1.1 | 1.3 | 1.7 | 1.1 | 1.5 | 1.2 | 1.3 | 0.96 |
| YDL008W | 1.1 | 1.0 | 1.0 | 1.1 | 1.8 | 2.7 | 2.0 | 1.2 | 2.3 | 3.0 | 0.9 | 1.2 | 2.0 | 2.2 | 0.7 | 1.3 | 1.5 | 1.6 | 0.95 |
| YDR115W | 1.3 | 0.9 | 0.6 | 1.5 | 1.4 | 2.3 | 1.6 | 1.3 | 1.1 | 1.0 | 1.2 | 0.9 | 1.1 | 1.5 | 0.8 | 2.2 | 1.2 | 1.4 | 1.50 |
| YER130C | 0.9 | 1.6 | 0.5 | 0.8 | 1.7 | 2.7 | 1.5 | 1.2 | 0.5 | 1.3 | 0.9 | 1.0 | 1.6 | 0.8 | 1.1 | 0.7 | 3.0 | 2.5 | 1.36 |
| YMR226C | 1.1 | 1.8 | 1.4 | 1.6 | 0.9 | 2.6 | 1.1 | 1.4 | 2.6 | 2.2 | 1.4 | 1.1 | 1.6 | 1.6 | 2.0 | 1.7 | 1.6 | 2.0 | 2.03 |
| YOR383C | 0.9 | 4.3 | 2.6 | 0.9 | 0.9 | 6.8 | 8.0 | 1.0 | 1.2 | 4.5 | 1.4 | 1.1 | 1.2 | 0.6 | 1.1 | 3.0 | 1.4 | 1.1 | 0.68 |
| YAR010C | 0.8 | 1.2 | 1.2 | 0.8 | 1.0 | 2.3 | 1.9 | 1.3 | 1.2 | 1.1 | 0.9 | 1.0 | 1.4 | 1.0 | 1.8 | 0.7 | 1.5 | 1.0 | 4.69 |
| YBL043W | 1.2 | 1.2 | 1.1 | 1.3 | 1.1 | 26.9 | 1.5 | 2.1 | 0.5 | 14.7 | 1.5 | 0.9 | 1.8 | 1.9 | 1.8 | 2.3 | 2.3 | 1.8 | 0.47 |
| YCR004C | 1.7 | 1.0 | 12.0 |  | 1.2 | 1.8 | 1.4 | 1.2 | 4.7 | 2.1 | 1.9 | 0.8 | 1.3 | 3.7 | 0.8 | 4.9 | 1.4 | 3.5 | 3.02 |
| YCR088W | 0.9 | 1.1 | 1.2 | 0.9 | 1.1 | 2.0 | 1.2 | 0.5 | 0.8 | 0.9 | 1.0 | 1.3 | 1.9 | 0.9 | 2.8 | 0.7 | 1.4 | 0.9 | 0.47 |
| YDL238C | 0.7 | 1.0 | 1.1 | 1.7 | 0.9 | 2.1 | 1.4 | 5.8 | 1.7 | 2.7 | 1.1 | 0.9 | 2.0 | 1.2 | 1.3 | 1.7 | 1.1 | 1.3 | 0.35 |
| YDR084C | 0.9 | 0.9 | 1.5 | 1.1 | 1.2 | 2.1 | 0.9 | 0.7 | 0.6 | 0.6 | 0.7 | 0.7 | 1.0 | 1.0 | 3.9 | 1.0 | 2.0 | 1.3 | 1.12 |
| YDR104C | 0.8 | 1.1 | 1.2 | 1.2 | 1.3 | 1.7 | 1.0 | 1.3 | 2.8 | 2.7 | 1.0 | 1.1 | 1.6 | 1.4 | 1.4 | 0.9 | 0.9 | 1.0 | 0.34 |
| YDR315C | 1.0 | 1.4 | 1.0 | 1.3 | 0.9 | 9.4 | 1.4 | 1.4 | 1.1 | 1.6 | 1.3 | 0.6 | 1.6 | 1.4 | 1.5 | 1.5 | 1.2 | 1.2 | 0.48 |
| YDR358W | 0.7 | 1.1 | 0.7 | 1.1 | 1.4 | 2.5 | 2.8 | 1.2 | 2.9 | 3.2 | 1.0 | 1.1 | 3.2 | 1.2 | 0.9 | 2.2 | 1.9 | 1.9 | 0.50 |
| YEL066W | 2.0 | 2.9 | 1.5 | 2.2 | 0.8 | 2.2 | 1.8 | 1.4 | 1.3 | 2.4 | 1.9 | 0.8 | 1.6 | 1.9 | 1.0 | 1.9 | 1.0 | 1.1 | 0.64 |
| YER039C | 1.0 | 1.2 | 1.0 | 4.1 | 1.5 | 1.6 | 1.3 | 0.7 | 1.2 | 0.8 | 1.2 | 0.9 | 2.1 | 1.2 | 1.2 | 1.8 | 1.7 | 1.1 | 0.42 |
| YER107C | 0.9 | 0.5 | 1.0 | 0.6 | 1.3 | 2.5 | 1.0 | 0.8 | 0.4 | 0.5 | 0.7 | 0.7 | 0.9 | 1.1 | 0.7 | 0.9 | 1.1 | 1.2 | 0.92 |
| YFL028C | 1.2 | 1.1 | 0.7 | 1.5 | 1.7 | 1.7 | 2.0 | 1.5 | 2.7 | 1.8 | 1.3 | 1.1 | 1.4 | 1.6 | 0.8 | 1.9 | 1.2 | 1.5 | 1.28 |
| YFL043C | 1.0 | 1.2 | 0.6 | 1.2 | 1.2 | 1.8 | 1.8 | 1.0 | 2.2 | 3.8 | 1.1 | 0.9 | 1.5 | 1.5 | 1.1 | 2.0 | 1.5 | 1.2 | 0.38 |
| YGL229C | 0.6 | 0.7 | 0.9 | 0.8 | 1.0 | 2.2 | 2.2 | 0.7 | 1.8 | 1.7 | 1.1 | 1.1 | 1.7 | 1.0 | 0.2 | 1.8 | 1.1 | 0.9 | 0.44 |
| YGR257C | 0.7 | 0.8 | 0.9 | 1.1 | 1.3 | 2.1 | 2.4 | 1.0 | 1.5 | 1.9 | 1.2 | 0.9 | 2.0 | 0.9 | 1.3 | 1.3 | 1.1 | 1.3 | 0.84 |
| YHR004C | 0.9 | 1.1 | 0.8 | 1.1 | 1.5 | 2.0 | 1.5 | 0.9 | 1.1 | 0.6 | 0.8 | 0.9 | 1.1 | 0.8 | 1.2 | 2.4 | 1.4 | 1.6 | 0.84 |
| YHR071W | 1.5 | 1.1 | 0.6 | 1.6 | 1.5 | 2.0 | 1.0 | 1.7 | 1.0 | 7.2 | 1.8 | 0.8 | 2.3 | 1.6 | 3.0 | 1.7 | 2.6 | 1.0 | 0.79 |
| YJL089W | 1.1 | 1.5 | 1.0 | 0.8 | 1.1 | 1.6 | 1.1 | 1.1 | 1.6 | 3.9 | 0.6 | 1.2 | 1.8 | 1.8 | 6.4 | 1.2 | 1.2 | 1.1 | 0.21 |
| YJL116C | 0.9 | 1.8 | 1.3 | 1.9 | 1.3 | 3.4 | 0.8 | 1.8 | 2.4 | 2.6 | 2.9 | 1.1 | 4.3 | 2.6 | 1.0 | 1.3 | 1.2 | 0.7 | 1.01 |
| YJR086W | 1.2 | 1.1 | 0.8 | 1.4 | 1.3 | 1.9 | 1.7 | 1.1 | 1.4 | 1.1 | 1.0 | 0.8 | 0.9 | 2.2 | 2.0 | 1.4 | 1.4 | 1.6 | 1.24 |
| YKL008C | 1.2 | 0.6 | 2.0 | 0.8 | 0.9 | 3.8 | 1.4 | 1.2 | 0.3 | 0.4 | 1.5 | 1.5 | 1.7 | 0.8 | 1.3 | 2.1 | 1.4 | 1.9 | 2.11 |
| YKL013C | 1.4 | 0.9 | 1.4 | 1.1 | 1.9 | 1.9 | 1.8 | 0.9 | 1.5 | 1.4 | 1.1 | 0.7 | 1.3 | 1.4 | 1.2 | 1.5 | 1.6 | 1.7 | 1.55 |
| YKL041W | 1.2 | 1.1 | 1.1 | 1.0 | 1.3 | 2.2 | 1.0 | 1.6 | 1.6 | 1.5 | 1.2 | 0.8 | 1.3 | 1.3 | 1.0 | 2.5 | 1.1 | 1.3 | 0.91 |
| YKL139W | 0.9 | 0.7 | 1.4 | 0.8 | 2.8 | 3.5 | 2.6 | 1.2 | 1.6 | 1.5 | 1.4 | 0.8 | 1.6 | 1.0 | 1.0 | 1.3 | 1.9 | 0.8 | 0.62 |
| YKR014C | 1.1 | 1.3 | 0.7 | 1.1 | 1.5 | 2.1 | 1.7 | 1.6 | 2.4 | 2.0 | 1.1 | 1.1 | 1.5 | 1.8 | 1.4 | 2.4 | 1.0 | 1.7 | 2.05 |
| YLR093C | 1.3 | 0.8 | 0.7 | 1.2 | 1.4 | 2.9 | 1.9 | 1.2 | 1.5 | 1.3 | 1.0 | 1.0 | 1.3 | 1.3 | 0.9 | 2.4 | 1.7 | 3.2 | 1.90 |
| YLR118C | 1.0 | 1.1 | 1.6 | 1.0 | 1.0 | 2.5 | 1.5 | 1.0 | 1.1 | 1.3 | 1.2 | 1.0 | 1.4 | 1.5 | 0.8 | 3.5 | 1.3 | 1.9 | 1.17 |
| YLR251W | 1.8 | 0.8 | 4.2 | 4.6 | 1.6 | 2.1 | 2.6 | 1.2 | 2.1 | 1.3 | 4.1 | 0.8 | 1.7 | 1.3 | 0.8 | 2.5 | 2.1 | 3.8 | 0.78 |
| YMR027W | 0.8 | 2.6 | 0.7 | 0.8 | 1.1 | 2.1 | 2.0 | 0.9 | 1.1 | 1.4 | 1.1 | 0.9 | 2.4 | 0.9 | 4.0 | 0.8 | 1.3 | 1.2 | 4.05 |
| YMR262W | 1.0 | 1.3 | 1.9 | 1.1 | 1.2 | 2.0 | 1.9 | 1.0 | 3.0 | 1.2 | 1.3 | 0.8 | 1.7 | 0.9 | 0.3 | 1.0 | 1.0 | 1.2 | 0.65 |
| YNL214W | 1.2 | 0.9 | 1.1 | 1.1 | 1.4 | 2.3 | 1.3 | 1.1 | 1.5 | 1.5 | 0.6 | 0.8 | 1.2 | 1.7 | 0.9 | 2.0 | 1.1 | 1.2 | 0.47 |
| YOR149C | 0.7 | 0.9 | 1.0 | 0.8 | 1.1 | 2.3 | 1.0 | 0.7 | 0.4 | 1.0 | 1.0 | 1.0 | 1.3 | 0.9 | 1.3 | 1.1 | 1.0 | 1.2 | 0.76 |
| YOR165W | 0.9 | 1.5 | 0.7 | 0.8 | 0.8 | 2.2 | 0.9 | 1.1 | 0.8 | 1.3 | 1.3 | 0.7 | 0.9 | 0.8 | 0.8 | 1.1 | 0.9 | 1.0 | 1.03 |
| YOR285W | 1.4 | 6.0 | 3.5 | 1.9 | 1.7 | 2.1 | 4.0 | 1.2 | 4.0 | 2.9 | 2.3 | 0.9 | 2.1 | 1.6 | 2.0 | 2.9 | 2.3 | 3.3 | 2.62 |
| YOR367W | 1.0 | 0.9 | 1.7 | 0.9 | 1.1 | 3.3 | 1.9 | 1.1 | 1.1 | 1.1 | 1.4 | 0.5 | 0.8 | 1.5 | 1.1 | 1.3 | 1.4 | 1.4 | 0.60 |
| YPL018W | 1.0 | 1.4 | 1.0 | 0.5 | 1.8 | 2.1 | 0.9 | 1.1 | 1.4 | 1.2 | 1.3 | 1.1 | 2.2 | 1.3 | 0.9 | 0.8 | 1.3 | 0.8 | 0.22 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YPL203W | 1.3 | 1.0 | 2.2 | 1.0 | 2.1 | 1.8 | 2.1 | 1.1 | 1.8 | 2.1 | 1.5 | 0.9 | 1.5 | 1.0 | 0.6 | 2.3 | 1.3 | 1.7 | 0.79 |
| YPL255W | 0.8 | 0.3 | 1.1 | 0.6 | 0.9 | 2.0 | 0.6 | 0.9 | 0.1 | 0.1 | 0.7 | 0.6 | 0.6 | 0.7 | 0.6 | 0.7 | 0.8 | 0.7 | 0.55 |
| YPR073C | 1.2 | 1.9 | 0.5 | 1.4 | 1.8 | 2.0 | 2.5 | 1.5 | 1.3 | 2.6 | 0.9 | 0.8 | 1.4 | 1.5 | 0.8 | 1.8 | 1.4 | 1.8 | 1.55 |
| YDR518W | 0.8 | 1.7 | 1.1 | 1.2 | 1.6 | 1.2 | 2.7 | 1.1 | 0.2 | 1.2 | 1.0 | 1.5 | 1.8 | 0.8 | 2.5 | 1.7 | 1.4 | 1.6 | 0.93 |
| YOR381W | 0.8 | 2.0 | 0.8 | 1.8 | 1.0 | 1.0 | 3.6 | 0.8 | 1.2 | 3.5 | 2.6 | 1.1 | 1.7 | 0.8 | 0.6 | 2.5 | 0.8 | 0.9 | 0.38 |
| YBR109C | 1.6 | 1.3 | 2.4 | 1.1 | 1.0 | 1.4 | 2.4 | 1.7 | 3.8 | 3.3 | 1.5 | 1.4 | 2.0 | 2.0 | 1.4 | 1.9 | 1.4 | 1.9 | 2.15 |
| YBR201W | 1.2 | 4.3 | 1.2 | 2.4 | 1.2 | 1.0 | 3.4 | 2.2 | 0.8 | 1.0 | 1.1 | 1.7 | 1.9 | 1.1 | 1.6 | 1.5 | 1.8 | 1.6 | 0.75 |
| YDR041W | 1.2 | 1.1 | 0.6 | 1.8 | 2.0 | 1.6 | 2.4 | 1.2 | 1.3 | 1.3 | 1.2 | 0.8 | 0.9 | 1.4 | 1.0 | 2.4 | 1.5 | 2.5 | 1.85 |
| YER136W | 0.9 | 1.1 | 1.1 | 1.4 | 1.6 | 1.3 | 2.1 | 1.3 | 1.4 | 1.6 | 1.7 | 0.9 | 1.3 | 0.8 | 1.2 | 1.6 | 1.3 | 1.7 | 2.31 |
| YER159C | 1.1 | 0.9 | 0.2 | 1.6 | 2.1 | 1.3 | 2.0 | 1.4 | 0.2 | 0.9 | 1.6 | 0.9 | 0.9 | 1.1 | 2.2 | 1.1 | 1.6 | 1.9 | 0.99 |
| YJL030W | 1.6 | 1.4 | 0.5 | 1.0 | 1.3 | 1.1 | 1.9 | 1.6 | 2.3 | 1.9 | 1.4 | 1.0 | 1.4 | 2.1 | 1.5 | 1.9 | 1.3 | 1.5 | 0.87 |
| YJR029W | 0.8 | 1.3 | 0.6 | 0.8 |  | 1.0 | 2.4 | 0.9 | 1.1 | 1.5 | 0.6 | 1.0 | 2.1 | 1.1 | 1.8 | 0.7 | 0.8 | 1.1 | 5.84 |
| YJR099W | 1.4 | 0.9 | 1.1 | 1.3 | 1.5 | 2.1 | 2.0 | 1.4 | 1.4 | 2.4 | 1.3 | 0.7 | 1.5 | 2.1 | 0.5 | 2.0 | 1.1 | 1.7 | 0.94 |
| YJR122W | 2.0 | 1.4 | 2.5 | 1.1 | 1.3 | 1.4 | 1.8 | 1.4 | 5.3 | 6.1 | 2.4 | 0.9 | 1.3 | 1.4 | 0.8 | 1.9 | 1.0 | 1.1 | 0.43 |
| YJR125C | 1.0 | 1.0 | 1.2 | 1.0 | 1.2 | 1.3 | 1.9 | 0.9 | 1.8 | 1.3 | 1.1 | 0.9 | 1.5 | 1.1 | 1.3 | 2.0 | 1.2 | 1.4 | 0.90 |
| YKL190W | 1.1 | 1.3 | 0.4 | 0.9 |  | 1.5 | 2.0 | 1.1 | 1.8 | 1.9 | 1.5 | 0.9 | 1.3 | 1.7 | 1.4 | 1.8 | 1.3 | 1.3 | 1.14 |
| YLL051C | 0.8 | 1.1 | 1.0 | 1.5 | 1.4 | 1.2 | 2.0 | 0.9 | 0.9 | 1.8 | 0.7 | 1.1 | 1.3 | 0.8 | 1.2 | 0.8 | 1.0 | 1.0 | 0.81 |
| YLR090W | 0.7 | 1.1 | 0.8 | 1.3 | 1.2 | 1.3 | 2.2 | 0.9 | 1.8 | 1.4 | 1.0 | 0.8 | 1.7 | 1.0 | 0.8 | 1.9 | 0.8 | 1.0 | 0.67 |
| YMR051C | 0.9 | 2.8 | 0.8 | 1.3 | 1.7 | 1.2 | 2.6 | 0.9 | 1.0 | 1.4 | 1.1 | 0.9 | 1.3 | 1.2 | 1.7 | 1.0 | 1.8 | 1.2 | 3.91 |
| YMR139W | 1.0 | 3.4 | 2.5 | 1.5 | 1.2 | 1.5 | 2.2 | 0.9 | 2.8 | 2.4 | 1.3 | 0.9 | 1.6 | 1.3 | 0.9 | 2.3 | 1.1 | 2.0 | 0.89 |
| YNL015W | 2.3 | 6.7 | 1.8 | 2.4 | 1.8 | 1.7 | 3.5 | 2.2 | 2.1 | 4.3 | 2.1 | 2.8 | 3.9 | 1.6 | 1.4 | 5.3 | 3.0 | 5.2 | 1.03 |
| YNL079C | 1.1 | 1.0 | 0.4 | 1.0 | 1.7 | 1.1 | 1.9 | 1.6 | 1.5 | 1.2 | 1.3 | 1.2 | 1.8 | 1.0 | 1.5 | 1.4 | 1.0 | 1.9 | 3.26 |
| YNL223W | 1.1 | 1.2 | 0.6 | 1.7 | 1.0 | 1.8 | 2.2 | 1.4 | 3.3 | 1.9 | 1.3 | 1.3 | 2.0 | 1.2 | 1.0 | 2.1 | 1.0 | 1.5 | 0.34 |
| YNR007C | 1.2 | 1.8 | 0.7 | 1.0 | 1.5 | 1.3 | 1.9 | 1.2 | 2.5 | 2.0 | 0.7 | 0.9 | 1.5 | 1.5 | 0.6 | 2.0 | 1.4 | 1.6 | 0.49 |
| YNR035C | 0.8 | 1.2 | 1.7 | 1.0 | 0.8 | 1.1 | 2.6 | 1.1 | 2.9 | 1.5 | 1.5 | 1.1 | 1.7 | 1.0 | 1.3 | 1.6 | 1.4 | 1.8 | 1.60 |
| YOL016C | 1.3 | 2.0 | 0.4 | 2.0 | 1.6 | 0.9 | 3.0 | 1.3 | 1.9 | 1.6 | 1.3 | 1.4 | 3.0 | 0.7 | 0.5 | 1.6 | 4.3 | 3.8 | 2.10 |
| YOL104C | 1.0 | 1.7 | 0.2 | 1.8 | 1.9 | 1.4 | 2.6 | 1.4 | 0.2 | 1.7 | 1.2 | 0.8 | 0.6 | 2.2 | 1.3 | 0.5 | 1.1 | 0.9 | 0.32 |
| YPR107C | 1.4 | 1.0 | 1.2 | 1.9 | 1.5 | 1.3 | 2.0 | 1.3 | 2.4 | 2.4 | 1.2 | 0.7 | 1.4 | 1.7 | 1.0 | 1.4 | 1.2 | 1.5 | 0.81 |
| YOL152W | 0.2 | 0.6 | 1.0 | 0.8 | 0.7 | 1.8 | 2.4 | 4.1 | 0.9 | 1.2 | 5.9 | 0.8 | 0.5 | 0.4 | 0.8 | 1.2 | 1.1 | 1.2 | 0.91 |
| YAL007C | 1.3 | 0.9 | 0.9 | 1.5 | 0.6 | 0.7 | 1.5 | 1.7 | 1.1 | 0.9 | 2.0 | 1.3 | 2.0 | 1.3 | 2.5 | 0.8 | 1.2 | 1.5 | 1.74 |
| YDL043C | 1.0 | 0.8 | 0.8 | 1.2 | 1.1 | 0.5 | 0.9 | 1.3 | 0.8 | 0.8 | 3.9 | 0.9 | 0.8 | 1.2 | 0.8 | 1.2 | 0.8 | 0.8 | 0.78 |
| YDL212W | 1.0 | 1.2 | 1.6 | 1.2 | 1.1 | 0.4 | 0.7 | 0.9 | 0.4 | 0.6 | 2.0 | 0.8 | 0.5 | 1.0 | 1.1 | 0.9 | 1.1 | 1.7 | 4.27 |
| YDR183W | 1.2 | 0.7 | 0.9 | 1.4 | 1.5 | 1.4 | 1.8 | 1.8 | 2.5 | 2.9 | 1.8 | 1.1 | 1.4 | 1.9 | 1.4 | 1.3 | 0.8 | 1.0 | 0.61 |
| YGL089C | 0.4 | 0.7 | 2.0 | 1.0 | 1.5 | 0.5 | 0.4 | 1.0 | 0.0 | 1.9 | 2.3 | 0.4 | 0.2 | 1.4 | 0.9 | 0.2 | 0.3 | 0.6 | 3.00 |
| YGL096W | 1.9 | 2.9 | 1.2 | 2.5 | 0.9 | 0.5 | 1.8 | 1.7 | 2.1 | 3.6 | 1.7 | 1.1 | 1.2 | 1.4 | 0.8 | 1.7 | 1.1 | 1.1 | 0.54 |
| YGR006W | 1.2 | 1.1 | 0.9 | 2.9 | 0.5 | 0.5 | 1.0 | 1.2 | 0.7 | 0.9 | 1.6 | 0.8 | 1.4 | 1.1 | 1.2 | 1.5 | 0.9 | 1.0 | 0.40 |
| YHL034C | 0.7 | 1.0 | 0.7 | 0.8 | 1.9 | 1.1 | 1.4 | 1.4 | 1.9 | 1.9 | 2.2 | 0.8 | 1.6 | 1.0 | 1.4 | 1.6 | 1.2 | 1.5 | 2.11 |
| YHR163W | 0.9 | 1.2 | 1.3 | 1.2 | 0.8 | 1.9 | 0.9 | 1.3 | 1.4 | 1.1 | 2.9 | 0.7 | 1.1 | 1.5 | 0.7 | 1.2 | 1.1 | 1.2 | 1.71 |
| YIR024C | 1.5 | 0.9 | 0.9 | 2.0 | 1.1 | 0.8 | 1.5 | 1.4 | 5.6 | 2.9 | 6.3 | 1.1 | 1.6 | 2.6 | 0.9 | 2.2 | 0.9 | 1.4 | 0.75 |
| YKL070W | 1.0 | 0.8 | 1.7 | 0.9 | 1.3 | 1.1 | 1.1 | 1.5 | 15.0 | 11.0 | 10.4 | 0.6 | 1.0 | 2.2 | 0.8 | 0.9 | 1.0 | 0.9 | 0.29 |
| YLL050C | 1.4 | 1.0 | 1.2 | 1.7 |  | 1.9 | 1.4 | 1.3 | 1.0 | 1.0 | 2.3 | 0.9 | 1.8 | 1.2 | 1.6 | 1.3 | 1.2 | 2.1 | 3.43 |
| YLR220W | 0.9 | 0.6 | 3.0 | 1.0 | 0.9 | 0.3 | 0.4 | 1.0 | 0.4 | 0.4 | 2.4 | 0.7 | 0.5 | 1.4 | 0.7 | 1.1 | 0.8 | 0.8 | 2.28 |
| YLR390W | 0.9 | 0.9 | 1.2 | 1.7 | 1.2 | 0.7 | 1.5 | 0.8 | 1.7 | 1.7 | 1.9 | 1.0 | 1.1 | 1.1 | 0.5 | 2.0 | 1.0 | 0.9 | 0.51 |
| YOL044W | 1.0 | 1.4 | 1.0 | 1.3 | 1.0 | 1.2 | 1.2 | 1.1 | 1.6 | 1.4 | 2.1 | 0.7 | 1.3 | 1.1 | 0.6 | 1.3 | 1.6 | 1.9 | 0.65 |
| YOL147C | 1.6 | 1.1 | 2.4 | 1.5 | 0.7 | 0.9 | 0.6 | 1.5 | 0.5 | 0.7 | 2.8 | 0.7 | 0.8 | 0.9 | 0.8 | 2.4 | 2.0 | 1.7 | 1.09 |
| YDR069C | 1.4 | 0.8 | 3.0 | 1.5 | 1.6 | 0.7 | 1.0 | 1.8 | 1.8 | 4.5 | 0.8 | 0.7 | 1.3 | 1.2 | 1.0 | 1.3 | 1.0 | 1.3 | 0.33 |
| YER131W | 1.5 | 0.3 | 0.9 | 0.7 | 1.6 | 0.9 | 0.6 | 2.0 | 0.0 | 0.6 | 1.0 | 0.9 | 0.2 | 0.8 | 0.9 | 0.4 | 0.9 | 0.9 | 5.32 |
| YGR044C | 0.8 | 1.3 | 0.7 | 1.2 | 1.1 | 1.4 | 1.3 | 1.8 | 0.9 | 0.8 | 2.1 | 0.8 | 1.4 | 1.0 | 0.5 | 3.3 | 1.1 | 2.6 | 1.43 |
| YMR240C | 1.1 | 0.6 | 2.5 | 0.7 | 1.4 | 0.8 | 1.1 | 2.3 | 0.5 | 1.1 | 1.4 | 0.6 | 0.8 | 1.1 | 1.0 | 1.1 | 1.1 | 1.1 | 0.39 |
| YBR105C | 1.7 | 1.5 | 0.9 | 2.0 | 0.8 | 1.8 | 2.0 | 1.2 | 1.1 | 3.3 | 1.1 | 1.2 | 1.1 | 1.7 | 1.4 | 1.3 | 1.3 | 1.1 | 0.96 |
| YBR182C | 2.0 | 1.9 | 1.0 | 2.4 | 1.4 | 1.0 | 1.7 | 1.3 | 0.6 | 3.2 | 1.5 | 1.3 | 1.2 | 1.2 | 3.1 | 1.1 | 3.4 | 1.6 | 0.41 |
| YBR186W | 1.0 | 1.0 | 1.1 | 1.7 | 1.0 | 0.5 | 0.9 | 0.9 | 1.0 | 2.4 | 0.9 | 0.8 | 0.7 | 1.1 | 0.9 | 1.2 | 0.7 | 1.0 | 0.31 |
| YEL052W | 1.1 | 1.0 | 2.0 | 2.0 | 1.3 | 1.2 | 1.2 | 1.2 | 3.0 | 3.4 | 1.7 | 1.1 | 1.5 | 1.1 | 0.7 | 2.1 | 0.9 | 1.0 | 0.90 |
| YER098W | 0.9 | 0.9 | 0.5 | 1.1 | 1.4 | 1.6 | 1.3 | 1.7 | 2.8 | 3.3 | 1.4 | 1.0 | 1.1 | 1.3 | 0.9 | 1.7 | 1.2 | 1.5 | 0.35 |
| YGL240W | 0.9 | 1.2 | 0.8 | 1.8 | 1.2 | 1.1 | 1.2 | 0.8 | 2.0 | 3.4 | 0.9 | 0.8 | 1.7 | 1.3 | 1.1 | 1.0 | 1.2 | 0.8 | 0.48 |
| YGR067C | 2.2 | 1.4 | 1.2 | 4.6 | 1.6 | 1.3 | 1.5 | 1.5 | 0.7 | 6.7 | 1.0 | 0.7 | 1.0 | 0.9 | 1.2 | 1.7 | 1.2 | 1.0 | 0.11 |
| YGR133W | 1.0 | 1.1 | 0.7 | 0.6 | 1.3 | 1.2 | 1.2 | 1.2 | 1.3 | 3.6 | 1.6 | 0.9 | 1.2 | 1.4 | 1.0 | 1.5 | 1.0 | 1.0 | 0.35 |
| YHR124W | 1.1 | 1.1 | 1.5 | 2.0 | 0.9 | 0.8 | 1.2 | 1.1 | 3.0 | 6.8 | 1.1 | 1.2 | 1.7 | 2.7 | 0.8 | 1.8 | 1.3 | 1.1 | 0.24 |
| YJL103C | 1.3 | 1.8 | 3.8 | 1.3 | 1.1 | 1.0 | 0.7 | 0.8 | 2.3 | 2.4 | 1.5 | 0.8 | 1.4 | 1.0 | 1.3 | 0.9 | 1.4 | 1.2 | 0.44 |
| YJR036C | 1.2 | 1.2 | 1.0 | 4.3 | 1.5 | 0.9 | 1.0 | 1.0 | 1.4 | 3.0 | 1.1 | 0.9 | 1.1 | 1.3 | 1.8 | 2.0 | 0.9 | 1.2 | 0.31 |
| YLR216C | 1.2 | 2.3 | 3.3 | 1.1 | 1.2 | 1.2 | 5.2 | 1.3 | 14.1 | 4.1 | 1.8 | 0.7 | 1.2 | 1.1 | 1.2 | 1.5 | 1.2 | 1.3 | 1.44 |
| YLR389C | 0.8 | 6.4 | 2.3 | 0.6 | 0.7 | 0.2 | 1.0 | 1.0 | 2.4 | 2.8 | 0.9 | 0.8 | 1.9 | 0.8 | 1.0 | 1.4 | 1.0 | 1.0 | 0.60 |
| YNL128W | 1.3 | 4.6 | 1.1 | 0.8 | 1.2 | 1.1 | 1.0 | 1.3 | 2.9 | 2.4 | 0.9 | 0.9 | 1.4 | 1.4 | 1.1 | 0.6 | 0.9 | 0.9 | 0.21 |
| YOL133W | 1.0 | 1.6 | 1.4 | 1.2 | 0.9 | 1.6 | 1.8 | 1.0 | 4.7 | 3.8 | 1.5 | 0.6 | 1.0 | 1.4 | 1.3 | 2.0 | 1.3 | 1.3 | 0.87 |
| YOR133W | 1.1 | 1.3 | 1.6 | 1.3 | 1.3 | 0.9 | 1.1 | 0.8 | 3.1 | 4.9 | 1.3 | 0.8 | 1.3 | 1.1 | 1.8 | 1.3 | 1.2 | 1.2 | 0.26 |
| YOR227W | 1.1 | 2.4 | 3.2 | 0.9 | 0.5 | 1.0 | 1.0 | 0.7 | 2.9 | 3.0 | 1.2 | 1.0 | 1.7 | 1.1 | 3.7 | 2.2 | 0.8 | 1.3 | 0.35 |
| YPR015C | 1.3 | 1.3 | 1.5 | 1.7 | 1.1 | 0.7 | 1.3 | 1.2 | 5.6 | 5.3 | 1.0 | 0.7 | 1.5 | 1.5 | 1.6 | 2.0 | 1.0 | 1.0 | 0.32 |
| YPR086W | 1.0 | 1.4 | 0.7 | 0.7 | 1.2 | 1.1 | 1.6 | 1.3 | 3.0 | 2.9 | 1.3 | 0.8 | 1.0 | 1.0 | 1.3 | 1.4 | 1.2 | 1.2 | 1.37 |
| YBL056W | 0.7 | 0.7 | 1.1 | 1.2 | 1.8 | 1.6 | 1.4 | 1.3 | 3.6 | 2.2 | 0.7 | 0.9 | 2.7 | 0.9 | 1.0 | 1.7 | 1.1 | 1.5 | 2.49 |
| YBR026C | 1.1 | 1.7 | 2.8 | 0.9 | 1.2 | 0.1 |  | 1.1 | 3.4 | 1.6 | 1.6 | 1.2 | 1.5 | 1.5 | 0.7 | 0.5 | 0.8 | 0.9 | 0.59 |
| YBR123C | 0.8 | 0.7 | 1.6 | 1.8 | 1.1 | 1.3 | 0.9 | 0.9 | 3.2 | 2.5 | 1.1 | 1.0 | 1.4 | 1.1 | 1.0 | 1.2 | 0.8 | 1.0 | 0.62 |
| YDR099W | 0.9 | 1.0 | 2.0 | 1.3 | 1.1 | 2.2 | 1.3 | 1.1 | 2.4 | 1.3 | 1.1 | 0.9 | 1.5 | 0.9 | 1.9 | 1.4 | 1.2 | 1.7 | 3.51 |
| YDR177W | 1.2 | 1.7 | 1.0 | 1.0 | 1.0 | 1.4 | 1.3 | 1.6 | 3.5 | 1.9 | 1.3 | 1.2 | 1.7 | 2.4 | 0.8 | 1.3 | 1.3 | 1.5 | 1.77 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YDR392W | 0.9 | 2.9 | 1.1 | 1.3 | 1.2 | 0.6 | 1.1 | 1.1 | 4.3 | 1.5 | 1.2 | 0.8 | 1.4 | 1.3 | 1.1 | 1.4 | 1.0 | 1.2 | 0.63 |
| YDR394W | 0.9 | 1.2 | 1.3 | 0.8 | 1.2 | 1.1 | 1.2 | 1.3 | 3.8 | 2.0 | 1.8 | 0.6 | 1.0 | 1.2 | 1.1 | 1.0 | 1.1 | 0.8 | 0.97 |
| YER184C | 2.3 | 1.6 | 1.1 | 2.3 | 1.0 | 0.6 | 0.9 | 1.1 | 4.6 | 3.2 | 1.3 | 0.8 | 1.6 | 1.4 | 1.4 | 1.2 | 1.6 | 2.3 | 0.29 |
| YFL059W | 1.2 | 1.4 | 1.2 | 2.2 | 1.1 | 1.0 | 1.3 | 1.5 | 4.1 | 4.2 | 1.5 | 1.2 | 2.3 | 2.4 | 0.9 | 1.6 | 1.3 | 1.1 | 0.57 |
| YGL185C | 1.3 | 1.9 | 1.9 | 1.9 | 0.8 | 0.8 | 1.9 | 1.5 | 4.1 | 2.3 | 1.5 | 1.5 | 1.7 | 1.5 | 0.9 | 15.8 | 1.3 | 1.6 | 0.23 |
| YHL019C | 1.1 | 0.8 | 1.2 | 0.6 | 1.0 | 1.2 | 1.1 | 1.0 | 2.1 | 1.4 | 1.3 | 0.8 | 0.8 | 0.8 | 1.2 | 1.3 | 1.0 | 1.0 | 0.55 |
| YHR012W | 1.1 | 1.0 | 1.2 | 1.0 |  | 1.6 | 1.2 | 1.2 | 4.9 | 2.2 | 1.5 | 0.9 | 1.7 | 1.7 | 1.0 | 1.0 | 1.2 | 1.4 | 1.11 |
| YHR028C | 0.8 | 1.2 | 1.4 | 0.8 | 1.0 | 0.9 | 1.2 | 0.8 | 3.7 | 2.2 | 1.4 | 0.7 | 0.6 | 1.1 | 1.1 | 0.7 | 1.0 | 1.0 | 0.92 |
| YHR109W | 0.8 | 1.0 | 0.0 | 0.7 | 1.3 | 1.4 | 1.4 | 1.2 | 2.4 | 1.8 | 0.7 | 1.0 | 1.4 | 1.5 | 0.9 | 1.3 | 0.9 | 1.1 | 0.22 |
| YHR156C | 1.3 | 1.3 | 0.9 | 2.1 | 1.9 | 1.0 | 1.2 | 1.3 | 3.6 | 1.9 | 0.6 | 0.7 | 1.0 | 1.9 | 1.2 | 1.4 | 0.9 | 1.3 | 0.47 |
| YIL159W | 1.1 | 1.6 | 1.3 | 0.7 | 1.2 | 2.3 | 0.6 | 1.1 | 5.9 | 1.6 | 0.8 | 0.9 | 1.5 | 2.0 | 1.0 | 0.7 | 0.9 | 0.8 | 0.29 |
| YJL154C | 0.6 | 2.7 | 0.7 | 0.6 | 1.2 | 1.3 | 1.5 | 1.0 | 2.3 | 2.0 | 0.5 | 0.9 | 1.6 | 0.8 | 1.2 | 1.2 | 1.2 | 1.1 | 0.62 |
| YJR110W | 1.0 | 0.6 | 1.0 | 1.4 | 1.3 | 0.9 | 0.9 | 1.1 | 4.9 | 2.3 | 1.2 | 0.7 | 0.9 | 1.1 | 1.2 | 1.1 | 0.8 | 1.0 | 0.58 |
| YKL025C | 0.7 | 1.1 | 1.1 | 0.9 | 1.1 | 0.9 | 0.9 | 0.9 | 2.8 | 1.7 | 1.1 | 0.8 | 1.3 | 0.9 | 1.2 | 1.1 | 0.9 | 1.0 | 0.54 |
| YKL171W | 0.9 | 1.3 | 1.2 | 2.1 | 0.9 | 0.4 | 0.9 | 0.8 | 8.2 | 1.8 | 2.8 | 1.1 | 1.5 | 1.1 | 1.2 | 2.1 | 0.9 | 1.2 | 0.45 |
| YKL196C | 1.2 | 1.1 | 0.5 | 0.9 | 1.3 | 0.9 | 1.5 | 1.3 | 4.3 | 2.0 | 1.6 | 1.0 | 1.8 | 2.5 | 1.9 | 1.9 | 1.3 | 2.0 | 2.41 |
| YKR068C | 1.2 | 1.5 | 1.0 | 1.8 | 1.1 | 1.4 | 1.4 | 1.3 | 2.4 | 1.9 | 1.0 | 1.0 | 1.1 | 1.6 | 0.8 | 1.4 | 1.4 | 1.7 | 1.72 |
| YLR144C | 0.8 | 1.5 | 4.0 | 1.3 | 0.7 | 0.9 | 0.7 | 1.1 | 2.8 | 1.5 | 1.0 | 0.7 | 2.3 | 1.2 | 1.9 | 1.7 | 1.0 | 1.0 | 0.44 |
| YML112W | 1.0 | 1.0 | 1.1 | 2.0 | 1.0 | 1.4 | 0.9 | 1.3 | 3.2 | 2.4 | 1.0 | 1.0 | 1.3 | 1.8 | 0.8 | 0.9 | 0.8 | 0.9 | 0.49 |
| YOL038W | 0.9 | 1.0 | 0.4 | 1.6 | 1.8 | 1.2 | 1.4 | 1.4 | 3.5 | 2.7 | 2.0 | 0.9 | 1.8 | 2.1 | 1.7 | 1.6 | 1.1 | 1.4 | 1.29 |
| YOR257W | 1.1 | 2.5 | 0.8 | 1.1 | 1.1 | 0.8 | 1.3 | 1.5 | 3.4 | 1.4 | 1.0 | 0.7 | 0.8 | 1.5 | 0.7 | 1.6 | 1.1 | 1.6 | 0.68 |
| YOR265W | 1.4 | 1.0 | 0.8 | 1.0 | 1.2 | 1.4 | 1.3 | 1.4 | 3.5 | 2.2 | 1.3 | 0.8 | 1.8 | 2.5 | 1.2 | 1.1 | 1.0 | 1.2 | 0.93 |
| YPL124W | 1.3 | 1.3 | 0.7 | 0.7 | 1.6 | 0.8 | 0.9 | 1.8 | 2.2 | 1.0 | 0.9 | 0.7 | 0.9 | 1.6 | 0.6 | 0.8 | 1.3 | 1.2 | 0.41 |
| YPR125W | 0.6 | 1.3 | 0.9 |  | 1.2 | 0.7 | 1.3 | 1.2 | 4.1 | 1.8 | 0.9 | 1.1 | 1.9 | 1.6 | 2.0 | 0.6 | 0.8 | 0.7 | 0.73 |
| YPR168W | 0.9 | 1.0 | 0.2 | 0.5 | 1.3 | 0.4 | 1.1 | 1.1 | 4.7 | 2.7 | 1.2 | 0.5 | 1.0 | 1.1 | 1.2 | 1.3 | 0.9 | 0.8 | 0.29 |
| YPR180W | 0.9 | 1.2 | 1.6 | 1.0 | 1.0 | 0.8 | 2.4 | 1.3 | 2.3 | 1.1 | 0.5 | 0.7 | 1.3 | 1.2 | 1.3 | 1.0 | 1.0 | 1.4 | 0.61 |
| YPR193C | 1.0 | 2.2 | 0.6 | 1.1 | 1.4 | 1.3 | 1.4 | 1.1 | 3.5 | 4.1 | 0.1 | 0.9 | 1.6 | 1.6 | 0.9 | 1.6 | 1.1 | 0.9 | 0.17 |
| YBR045C | 0.9 | 1.0 | 2.2 | 0.7 | 1.0 | 0.8 | 0.8 | 1.0 | 3.6 | 1.1 | 0.4 | 1.3 | 1.3 | 1.0 | 2.0 | 0.8 | 1.1 | 0.9 | 1.29 |
| YBR128C | 1.0 | 1.1 | 2.1 | 1.0 | 1.1 | 1.5 | 2.1 | 1.2 | 2.8 | 1.2 | 1.3 | 0.7 | 1.3 | 1.4 | 1.4 | 2.0 | 1.2 | 1.8 | 0.44 |
| YCL055W | 0.7 | 2.2 | 0.7 | 1.3 | 1.2 | 1.4 | 1.0 | 1.3 | 2.1 | 1.5 | 1.4 | 0.9 | 0.9 | 1.8 | 1.5 | 0.7 | 0.8 | 1.1 | 0.66 |
| YCR019W | 1.0 | 1.6 | 1.0 | 0.8 | 1.4 | 1.5 | 1.1 | 1.5 | 2.8 | 1.6 | 2.0 | 1.0 | 1.6 | 1.2 | 0.7 | 1.4 | 1.0 | 1.0 | 0.45 |
| YDL065C | 1.2 | 0.9 | 1.0 | 0.7 | 1.4 | 1.1 | 1.3 | 1.4 | 2.4 | 1.5 | 1.4 | 0.6 | 0.7 | 1.4 | 1.3 | 1.5 | 1.1 | 1.2 | 1.08 |
| YDL143W | 0.8 | 0.8 | 1.2 | 1.1 | 1.0 | 1.0 | 0.9 | 1.2 | 2.1 | 1.8 | 1.3 | 1.1 | 1.9 | 0.9 | 1.4 | 0.9 | 0.8 | 0.8 | 1.86 |
| YDL197C | 1.0 | 1.1 | 0.9 | 2.1 | 1.5 | 1.2 | 1.0 | 1.0 | 2.6 | 1.5 | 1.1 | 0.8 | 1.4 | 1.1 | 1.3 | 0.9 | 1.3 | 0.8 | 0.31 |
| YDL230W | 1.0 | 0.8 | 1.2 | 1.3 | 1.4 | 0.9 | 1.1 | 0.9 | 2.6 | 1.2 | 0.9 | 0.6 | 1.3 | 1.0 | 1.4 | 1.7 | 1.0 | 1.2 | 0.42 |
| YDR212W | 0.8 | 1.2 | 1.3 | 0.8 | 1.4 | 1.4 | 1.0 | 1.3 | 3.5 | 1.7 | 1.8 | 0.8 | 2.0 | 1.0 | 1.2 | 0.7 | 0.6 | 1.2 | 2.13 |
| YDR257C | 0.8 | 5.3 | 0.6 | 0.8 | 1.6 | 1.1 | 1.0 | 1.0 | 3.0 | 1.6 | 1.3 | 0.7 | 1.0 | 1.0 | 1.3 | 1.0 | 1.1 | 0.8 | 0.62 |
| YDR329C | 0.9 | 0.8 | 1.0 | 1.7 | 1.9 | 1.2 | 1.6 | 1.2 | 2.5 | 1.0 | 1.0 | 0.8 | 1.1 | 1.1 | 1.0 | 1.6 | 1.2 | 1.6 | 0.95 |
| YDR488C | 1.0 | 0.3 | 0.9 | 0.9 | 0.9 | 0.9 | 0.7 | 0.9 | 2.1 | 0.4 | 0.4 | 0.6 | 1.3 | 0.8 | 3.5 | 0.7 | 0.9 | 0.9 | 0.32 |
| YDR505C | 0.8 | 1.0 | 1.0 | 1.4 | 1.2 | 1.1 | 1.2 | 0.8 | 2.5 | 1.0 | 1.0 | 0.7 | 1.6 | 0.9 | 1.1 | 1.6 | 1.0 | 1.5 | 0.84 |
| YDR506C | 0.9 | 0.7 | 1.3 | 0.7 | 0.9 | 0.9 | 0.6 | 1.0 | 1.9 | 1.4 | 1.1 | 0.9 | 0.3 | 0.5 | 0.9 | 0.4 | 0.6 | 0.5 | 1.90 |
| YDR515W | 0.9 | 1.1 | 0.8 | 0.8 | 1.5 | 0.8 | 0.6 | 1.4 | 5.8 | 2.7 | 1.0 | 0.8 | 0.7 | 0.8 | 1.3 | 0.5 | 0.7 | 0.5 | 1.02 |
| YEL005C | 1.1 | 1.3 | 0.8 | 1.1 | 1.6 | 1.9 | 2.0 | 1.2 | 2.3 | 1.6 | 1.6 | 0.8 | 1.2 | 1.7 | 0.8 | 3.4 | 1.1 | 1.4 | 0.45 |
| YER048C | 0.8 | 1.2 | 0.4 | 1.4 | 1.8 | 1.9 | 1.9 | 1.6 | 2.3 | 1.1 | 1.6 | 0.8 | 1.1 | 1.0 | 0.6 | 1.8 | 1.3 | 1.6 | 1.08 |
| YER078C | 0.9 | 0.8 | 1.8 | 0.8 | 0.9 | 1.4 | 1.3 | 1.1 | 2.3 | 1.5 | 1.3 | 1.0 | 1.5 | 1.0 | 0.9 | 1.0 | 0.9 | 0.9 | 0.49 |
| YER089C | 0.5 | 0.5 | 1.4 | 1.1 | 0.8 | 0.6 | 0.9 | 0.5 | 2.0 | 2.3 | 1.2 | 0.7 | 1.3 | 0.6 | 1.0 | 0.8 | 0.7 | 0.6 | 0.75 |
| YER100W | 1.1 | 1.1 | 0.7 | 0.7 | 0.9 | 0.5 | 0.6 | 1.2 | 2.3 | 1.6 | 1.1 | 0.8 | 0.7 | 0.8 | 1.0 | 1.1 | 1.1 | 0.7 | 0.95 |
| YFR051C | 0.5 | 1.1 | 2.2 | 0.5 | 0.5 | 0.2 | 1.0 | 0.8 | 2.5 | 1.4 | 1.3 | 1.2 | 1.5 | 0.8 | 3.0 | 0.8 | 1.1 | 0.9 | 0.53 |
| YGL093W | 0.8 | 0.9 | 1.2 | 0.6 | 0.9 | 1.0 | 0.8 | 0.8 | 4.5 | 1.6 | 1.1 | 0.6 | 0.7 | 0.8 | 1.4 | 1.0 | 0.9 | 1.2 | 0.56 |
| YGL105W | 0.9 | 0.8 | 1.1 | 0.8 | 1.3 | 1.5 | 0.7 | 1.2 | 1.8 | 1.4 | 1.4 | 1.1 | 1.0 | 1.1 | 0.9 | 1.0 | 0.8 | 0.9 | 3.01 |
| YGL166W | 1.0 | 1.4 | 0.6 | 1.5 | 1.3 | 1.0 | 1.5 | 1.2 | 1.8 | 2.4 | 1.0 | 1.1 | 1.9 | 1.1 | 0.9 | 1.2 | 2.1 | 1.9 | 0.73 |
| YGL215W | 0.7 | 1.2 | 1.2 | 0.9 | 1.0 | 0.9 | 1.0 | 0.7 | 2.2 | 1.8 | 0.8 | 0.7 | 1.0 | 0.8 | 1.0 | 1.2 | 0.7 | 0.9 | 1.31 |
| YGL216W | 0.7 | 1.3 | 0.8 | 1.0 | 1.2 | 1.5 | 1.0 | 1.0 | 2.6 | 0.5 | 0.5 | 1.0 | 1.4 | 1.0 | 1.1 | 0.8 | 1.1 | 0.9 | 0.37 |
| YGL221C | 1.1 | 1.2 | 1.0 | 1.1 | 0.9 | 2.2 | 1.3 | 1.6 | 3.4 | 1.9 | 1.4 | 1.1 | 1.7 | 1.7 | 0.7 | 1.3 | 1.1 | 1.4 | 1.64 |
| YGR186W | 0.9 | 0.7 | 0.4 | 1.1 | 1.5 | 0.7 | 1.3 | 1.3 | 2.6 | 1.9 | 1.0 | 0.6 | 1.1 | 1.1 | 1.3 | 1.4 | 1.3 | 1.2 | 0.79 |
| YGR270W | 0.9 | 1.0 | 0.8 | 0.8 | 0.7 | 0.9 | 0.9 | 0.9 | 2.3 | 1.3 | 0.7 | 0.8 | 1.3 | 0.9 | 1.6 | 1.0 | 0.9 | 0.9 | 0.51 |
| YGR274C | 0.7 | 0.5 | 0.3 | 0.9 | 1.8 | 0.7 | 1.3 | 1.2 | 2.2 | 1.8 | 0.9 | 0.7 | 1.1 | 0.8 | 1.2 | 0.7 | 1.1 | 1.0 | 0.62 |
| YHR082C | 0.7 | 1.1 | 1.6 | 0.9 | 1.6 | 0.8 | 1.1 | 0.8 | 2.6 | 1.7 | 0.9 | 0.7 | 1.7 | 0.9 | 1.4 | 0.7 | 1.1 | 0.9 | 0.60 |
| YHR160C | 1.0 | 0.5 | 1.6 | 1.6 | 1.0 | 1.0 | 1.1 | 1.2 | 2.3 | 1.6 | −0.2 | 0.8 | 1.8 | 1.2 | 2.1 | 4.4 | 1.0 | 1.5 | 0.32 |
| YHR171W | 1.2 | 0.8 | 1.1 | 1.2 | 1.3 | 2.0 | 1.9 | 0.9 | 2.1 | 1.6 | 1.2 | 0.8 | 1.3 | 1.0 | 0.7 | 1.6 | 1.2 | 1.5 | 0.41 |
| YHR205W | 0.7 | 1.3 | 0.6 | 0.8 | 1.3 | 1.0 | 0.7 | 0.5 | 2.0 | 0.6 | 0.9 | 0.9 | 1.7 | 0.9 | 1.5 | 0.8 | 0.9 | 0.8 | 0.34 |
| YIL062C | 1.1 | 1.0 | 1.3 | 1.2 | 1.2 | 0.9 | 0.4 | 1.1 | 2.8 | 2.3 | 1.7 | 0.8 | 1.1 | 2.0 | 0.9 | 0.4 | 1.1 | 1.1 | 1.72 |
| YIL075C | 0.5 | 0.7 | 1.5 | 0.6 | 1.1 | 0.8 | 0.8 | 0.7 | 1.9 | 2.3 | 0.8 | 0.8 | 0.7 | 0.8 | 1.6 | 0.8 | 0.8 | 0.8 | 1.54 |
| YIR009W | 0.8 | 0.8 | 0.9 | 2.8 | 1.5 | 1.4 | 1.3 | 1.3 | 2.6 | 1.5 | 1.1 | 0.7 | 0.8 | 1.6 | 1.1 | 1.0 | 1.7 | 1.0 | 0.48 |
| YIR018W | 1.2 | 1.0 | 0.9 | 1.1 | 1.4 | 2.0 | 1.5 | 1.5 | 4.0 | 2.1 | 1.2 | 1.1 | 1.5 | 1.2 | 1.5 | 1.0 | 1.6 | 1.1 | 0.44 |
| YJR091C | 0.8 | 1.2 | 2.6 | 1.4 | 1.4 | 0.8 | 1.1 | 0.8 | 2.4 | 2.3 | 1.8 | 0.8 | 1.4 | 0.8 | 1.4 | 0.7 | 1.2 | 0.9 | 0.57 |
| YKL079W | 0.9 | 0.8 | 1.5 | 1.0 | 1.4 | 0.8 | 1.7 | 1.2 | 2.3 | 2.0 | 1.3 | 0.9 | 1.2 | 0.9 | 1.1 | 1.6 | 1.1 | 1.2 | 0.64 |
| YKR102W | 0.8 | 1.6 | 1.4 | 0.8 | 0.9 |  |  | 0.7 | 2.4 | 1.4 | 3.3 | 0.8 | 2.7 | 1.8 | 1.1 | 1.5 | 1.5 | 0.9 | 0.19 |
| YLL054C | 1.2 | 0.6 | 0.5 | 1.2 | 1.2 | 1.4 | 1.9 | 1.1 | 1.1 | 2.4 | 1.4 | 0.5 | 0.7 | 1.7 | 1.2 | 0.9 | 0.9 | 1.0 | 0.33 |
| YLR200W | 1.4 | 0.9 | 0.5 | 1.2 | 1.7 | 1.2 | 1.9 | 1.4 | 2.2 | 2.6 | 1.1 | 0.9 | 1.3 | 2.3 | 0.9 | 1.2 | 1.1 | 1.5 | 1.12 |
| YLR248W | 0.9 | 0.7 | 1.1 | 1.4 | 1.9 | 1.2 | 1.2 | 1.1 | 2.3 | 1.1 | 1.0 | 0.7 | 1.2 | 0.9 | 1.2 | 1.7 | 1.1 | 1.7 | 1.58 |
| YLR266C | 0.9 | 1.3 | 0.7 | 1.5 | 0.7 | 1.0 | 1.6 | 1.1 | 2.2 | 2.6 | 1.1 | 1.0 | 1.3 | 1.0 | 0.8 | 1.7 | 0.8 | 1.4 | 0.74 |
| YML088W | 0.9 | 1.6 | 0.3 | 0.5 | 1.5 | 0.7 | 1.1 | 1.1 | 4.0 | 2.2 | 0.5 | 1.0 | 1.3 | 1.1 | 1.4 | 0.8 | 0.8 | 0.8 | 0.58 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YMR091C | 1.0 | 0.7 | 0.8 | 1.0 | 0.7 | 0.8 | 0.8 | 1.3 | 2.1 | 1.3 | 0.9 | 0.8 | 0.9 | 1.5 | 0.9 | 1.3 | 0.9 | 1.2 | 1.03 |
| YMR110C | 1.0 | 1.4 | 1.8 | 1.9 | 1.3 | 2.1 | 1.9 | 0.9 | 2.3 | 1.6 | 1.6 | 0.9 | 1.8 | 0.8 | 0.9 | 2.7 | 1.5 | 2.5 | 1.63 |
| YMR255W | 1.2 | 1.4 | 0.7 | 1.8 | 1.3 | 0.9 | 1.5 | 1.4 | 2.8 | 2.4 | 1.2 | 0.9 | 1.1 | 1.6 | 1.0 | 1.3 | 1.5 | 2.0 | 0.97 |
| YNL039W | 0.7 | 0.8 | 0.3 | 0.4 | 2.1 | 0.8 | 1.1 | 1.2 | 2.1 | 1.8 | 0.4 | 0.9 | 0.8 | 0.8 | 1.3 | 1.3 | 0.9 | 1.1 | 0.61 |
| YNL077W | 1.5 | 1.1 | 2.3 | 1.2 | 1.5 | 0.9 | 1.2 | 1.0 | 4.4 | 5.1 | 1.0 | 0.7 | 1.5 | 0.5 | 0.3 | 0.6 | 1.3 | 1.0 | 0.78 |
| YNL083W | 0.8 | 1.4 | 1.3 | 1.2 | 0.8 | 0.7 | 0.9 | 1.1 | 3.1 | 1.6 | 0.9 | 0.9 | 1.2 | 0.9 | 0.8 | 1.8 | 0.8 | 1.1 | 0.37 |
| YNL147W | 1.3 | 2.4 | 0.6 | 0.7 | 2.0 | 1.5 | 1.4 | 1.8 | 2.1 | 2.9 | 1.2 | 0.8 | 1.0 | 2.0 | 1.2 | 1.7 | 1.0 | 1.6 | 1.32 |
| YNR006W | 1.1 | 1.8 | 0.5 | 0.9 | 1.5 | 0.9 | 1.5 | 0.9 | 2.2 | 2.3 | 0.8 | 0.9 | 1.6 | 0.9 | 1.2 | 1.1 | 1.8 | 1.2 | 0.40 |
| YNR034W | 0.9 | 1.4 | 5.3 | 1.6 | 1.0 | 0.9 | 1.3 | 1.0 | 3.0 | 2.1 | 1.3 | 0.9 | 1.4 | 0.9 | 1.1 | 2.3 | 0.7 | 1.1 | 0.64 |
| YNR047W | 0.7 | 1.0 | 1.7 | 0.5 | 1.1 | 1.0 | 1.0 | 0.8 | 2.0 | 1.2 | 0.6 | 0.9 | 1.5 | 0.9 | 1.2 | 1.5 | 0.9 | 1.0 | 0.44 |
| YOR023C | 0.7 | 1.2 | 1.3 | 0.8 | 1.2 | 1.8 | 1.1 | 0.6 | 3.5 | 1.3 | 0.9 | 1.1 | 1.9 | 0.9 | 1.6 | 0.8 | 1.1 | 0.8 | 0.37 |
| YOR058C | 2.0 | 1.4 | 2.0 | 0.6 | 0.9 | 0.9 | 0.8 | 1.7 | 6.4 | 4.5 | 1.4 | 0.7 | 1.7 | 1.7 | 1.1 | 1.6 | 0.9 | 1.0 | 0.31 |
| YOR069W | 0.8 | 1.6 | 0.7 | 1.3 | 1.0 | 0.5 | 1.2 | 1.1 | 1.9 | 1.4 | 2.8 | 0.9 | 1.1 | 1.3 | 1.4 | 1.5 | 0.8 | 1.1 | 0.69 |
| YOR229W | 0.9 | 0.9 | 1.0 | 0.8 | 1.5 | 1.3 | 1.1 | 0.8 | 2.5 | 0.8 | 0.7 | 0.8 | 1.3 | 1.0 | 1.2 | 0.9 | 0.9 | 1.0 | 0.58 |
| YOR256C | 1.0 | 0.8 | 0.9 | 1.5 | 1.7 | 0.9 | 1.4 | 1.1 | 2.7 | 1.8 | 1.7 | 0.7 | 1.6 | 1.1 | 1.1 | 1.5 | 1.2 | 1.5 | 0.53 |
| YPL020C | 1.1 | 0.7 | 0.7 | 1.3 | 0.8 | 0.8 | 1.1 | 1.1 | 2.3 | 1.6 | 1.1 | 0.9 | 1.1 | 1.1 | 1.6 | 1.2 | 1.3 | 1.4 | 0.91 |
| YPL105C | 0.6 | 0.8 | 0.6 | 0.7 | 1.1 | 1.2 | 0.7 | 1.0 | 3.4 | 1.4 | 0.6 | 0.7 | 1.0 | 0.6 | 1.1 | 0.5 | 0.8 | 0.6 | 0.80 |
| YPR066W | 1.2 | 2.2 | 1.1 | 2.2 | 1.3 | 0.7 | 1.3 | 0.8 | 2.3 | 1.9 | 0.9 | 0.8 | 1.4 | 1.2 | 0.7 | 1.6 | 1.1 | 1.2 | 0.41 |
| YPR081C | 0.9 | 1.0 | 1.0 | 1.1 | 0.8 | 1.1 | 1.1 | 1.0 | 4.2 | 2.6 | 0.9 | 1.0 | 1.4 | 1.1 | 1.3 | 1.8 | 0.9 | 1.3 | 0.34 |
| YPR140W | 0.9 | 1.2 | 0.8 | 1.8 | 0.9 | 3.0 | 1.9 | 1.1 | 2.1 | 1.3 | 0.8 | 0.8 | 1.3 | 1.4 | 1.7 | 2.4 | 0.8 | 1.3 | 0.47 |
| YPR155C | 0.9 | 2.5 | 1.5 | 1.4 | 0.9 | 0.9 | 1.4 | 1.0 | 2.0 | 1.3 | 0.9 | 0.9 | 1.3 | 1.2 | 0.5 | 3.4 | 0.8 | 1.6 | 0.40 |
| YPR185W | 0.7 | 0.9 | 0.3 | 0.4 | 1.1 | 0.9 | 1.2 | 1.0 | 2.5 | 1.7 | 0.9 | 0.8 | 1.7 | 1.0 | 1.1 | 1.3 | 1.3 | 1.1 | 0.68 |
| YBR076W | 2.3 | 1.1 | 1.4 | 5.0 | 0.9 | 0.8 | 1.0 | 0.7 | 0.4 | 1.8 | 0.8 | 0.9 | 1.9 | 1.2 | 1.1 | 0.5 | 1.4 | 1.2 | 0.36 |
| YDR373W | 1.7 | 0.8 | 0.5 | 1.3 | 1.8 | 0.9 | 1.4 | 1.9 | 2.5 | 2.8 | 1.7 | 0.5 | 1.0 | 2.1 | 1.6 | 1.4 | 1.2 | 1.6 | 1.08 |
| YFR014C | 2.1 | 2.4 | 0.8 | 2.6 | 0.7 | 0.8 | 1.4 | 1.3 | 1.0 | 1.6 | 1.8 | 0.9 | 1.3 | 1.0 | 0.6 | 2.3 | 1.2 | 2.9 | 0.94 |
| YHR136C | 2.4 | 13.6 | 1.4 | 2.1 | 2.4 | 1.4 | 0.5 | 1.3 | 0.1 | 2.0 | 2.0 | 1.2 | 0.3 | 1.7 | 0.5 | 1.3 | 1.6 | 2.5 | 1.33 |
| YIL129C | 0.8 | 5.8 | 1.0 | 1.2 |  | 0.3 |  |  | 2.1 | 1.8 | 1.5 |  | 1.9 | 0.9 | 1.0 | 1.0 | 1.3 | 0.8 | 0.25 |
| YMR077C | 1.1 | 3.9 | 1.1 | 1.8 | 1.0 | 0.5 | 1.4 | 1.7 | 1.9 | 2.5 | 1.5 | 0.9 | 0.8 | 1.6 | 1.7 | 2.3 | 0.9 | 1.3 | 0.59 |
| YBR264C | 1.2 | 3.7 | 1.5 | 1.5 | 0.7 | 0.9 | 1.3 | 1.2 | 0.9 | 1.1 | 1.0 | 1.0 | 0.9 | 1.6 | 1.1 | 1.8 | 0.9 | 1.3 | 0.61 |
| YPL177C | 1.2 | 3.7 | 0.9 | 1.3 | 0.7 | 0.8 | 0.8 | 1.3 | 0.5 | 1.0 | 1.4 | 0.8 | 0.8 | 1.3 | 0.6 | 1.9 | 1.2 | 1.1 | 0.75 |
| YGL056C | 0.7 | 3.5 | 1.3 | 1.0 | 0.6 | 0.4 | 1.0 | 0.9 | 0.4 | 0.6 | 0.0 | 1.1 | 0.8 | 1.1 | 1.2 | 1.5 | 0.9 | 1.1 | 0.47 |
| YBL101W-A | 1.0 | 5.7 | 0.7 | 0.6 | 1.0 | 1.4 | 1.3 | 1.5 | 1.2 | 2.1 | 1.2 | 1.1 | 2.0 | 1.5 | 2.1 | 1.1 | 1.3 | 1.2 | 1.24 |
| YER072W | 1.6 | 2.3 | 1.6 | 1.3 | 1.2 | 1.5 | 0.7 | 1.2 | 0.5 | 1.1 | 1.7 | 1.1 | 0.6 | 1.5 | 0.9 | 1.1 | 1.7 | 1.7 | 1.69 |
| YMR112C | 1.2 | 4.2 | 0.9 | 1.2 | 1.0 | 0.7 | 1.5 | 1.6 | 1.4 | 1.3 | 0.9 | 1.0 | 0.9 | 1.8 | 0.9 | 1.4 | 1.1 | 1.6 | 0.57 |
| YJR058C | 1.3 | 2.0 | 1.3 | 1.5 | 1.1 | 1.6 | 1.3 | 1.2 | 1.9 | 2.6 | 1.2 | 0.7 | 0.8 | 1.8 | 0.8 | 1.2 | 1.3 | 1.2 | 1.00 |
| YML055W | 1.7 | 2.3 | 0.6 | 2.0 | 0.9 | 1.2 | 1.7 | 1.7 | 1.0 | 1.4 | 1.4 | 1.0 | 1.7 | 1.9 | 0.6 | 1.4 | 1.2 | 1.5 | 1.08 |
| YDR080W | 0.9 | 1.8 | 0.5 | 0.6 | 1.2 | 1.5 | 1.6 | 1.2 | 1.7 | 2.6 | 1.2 | 1.0 | 2.0 | 1.1 | 1.2 | 1.7 | 1.2 | 1.3 | 0.68 |
| YNR030W | 0.6 | 2.1 | 2.2 | 0.7 | 0.8 | 1.2 | 1.0 | 0.6 | 1.0 | 1.4 | 1.2 | 0.8 | 1.5 | 0.6 | 1.1 | 0.4 | 0.9 | 0.8 | 1.19 |
| YNL196C | 1.1 | 1.8 | 1.4 | 1.3 | 0.9 | 1.2 | 1.0 | 0.7 | 0.5 | 2.2 | 0.7 | 1.0 | 2.2 | 1.2 | 0.8 | 2.1 | 1.1 | 1.2 | 0.50 |
| YOR148C | 1.4 | 1.4 | 0.5 | 1.8 | 0.9 | 0.9 | 1.2 | 1.5 | 0.8 | 0.8 | 1.3 | 0.9 | 1.4 | 1.4 | 1.0 | 1.3 | 1.0 | 1.3 | 1.08 |
| YER029C | 1.0 | 1.6 | 0.4 | 1.9 | 1.7 | 1.2 | 1.1 | 1.5 | 1.4 | 1.1 | 0.8 | 0.9 | 0.9 | 1.4 | 1.1 | 1.7 | 0.9 | 1.3 | 1.20 |
| YLR360W | 0.9 | 2.0 | 0.5 | 0.7 | 1.9 | 1.4 | 1.7 | 1.3 | 0.9 | 1.3 | 0.9 | 0.9 | 0.7 | 1.1 | 0.8 | 2.1 | 1.2 | 1.4 | 0.53 |
| YGR239C | 1.3 | 1.3 | 0.7 | 1.3 | 1.2 | 2.3 | 1.2 | 1.5 | 0.5 | 3.8 | 1.4 | 1.0 | 1.0 | 1.4 | 1.3 | 1.1 | 1.1 | 1.3 | 0.49 |
| YDL229W | 0.9 | 1.9 | 0.4 | 0.6 | 1.2 | 1.0 | 1.3 | 1.2 | 1.4 | 0.9 | 1.6 | 0.9 | 1.0 | 1.3 | 1.2 | 1.0 | 1.2 | 1.1 | 0.76 |
| YJR027W | 0.8 | 1.9 | 0.8 | 0.7 |  | 1.5 | 2.0 | 1.0 | 1.2 | 1.3 | 1.1 | 0.8 | 1.3 | 1.1 | 2.3 | 0.7 | 0.7 | 1.1 | 4.88 |
| YKL198C | 1.2 | 1.4 | 0.8 | 0.2 | 0.9 | 1.0 | 1.2 | 0.6 | 0.0 | 0.8 | 1.4 | 0.7 | 1.9 | 6.6 | 2.6 | 0.7 | 1.0 | 0.8 | 0.17 |
| YBR031W | 1.1 | 0.8 | 4.1 | 1.4 | 1.4 | 0.7 | 0.5 | 1.0 | 0.1 | 1.0 | 0.9 | 1.0 | 0.3 | 0.4 | 0.9 | 0.7 | 1.0 | 0.8 | 7.58 |
| YBR118W | 1.3 | 0.8 | 2.9 | 1.2 | 1.0 | 1.3 | 0.5 | 0.9 | 1.0 | 0.8 | 0.8 | 0.7 | 1.6 | 0.6 | 1.2 | 0.9 |  |  | 8.91 |
| YCR106W | 0.9 | 1.1 | 2.8 | 1.1 | 0.8 | 1.4 | 0.9 | 0.8 | 2.0 | 1.2 | 1.2 | 0.8 | 1.2 | 0.8 | 1.3 | 1.2 | 1.1 | 1.2 | 0.76 |
| YDR012W | 0.9 | 0.8 | 3.9 | 1.2 | 1.1 | 0.9 | 0.5 | 1.1 | 0.3 | 0.7 | 0.9 | 1.2 | 0.2 | 0.4 | 0.8 | 0.7 | 1.0 | 0.7 | 7.07 |
| YDR134C | 1.0 | 0.7 | 3.9 | 1.9 | 0.8 | 1.1 | 0.4 | 0.6 | 0.1 | 0.5 | 1.9 | 0.6 | 0.4 | 0.5 | 0.8 | 0.9 | 0.7 | 1.1 | 5.84 |
| YDR276C | 1.5 | 1.6 | 6.1 | 1.4 | 0.7 | 1.1 | 1.0 | 1.1 | 1.1 | 2.7 | 1.4 | 0.9 | 1.1 | 1.3 | 2.2 | 3.6 | 1.3 | 2.4 | 2.48 |
| YGR279C | 0.9 | 0.7 | 3.6 | 1.0 | 1.2 | 1.6 | 0.8 | 0.6 | 0.3 | 0.7 | 0.9 | 0.7 | 0.3 | 0.4 | 1.3 | 0.8 | 1.0 | 0.8 | 3.77 |
| YJL059W | 1.0 | 1.7 | 3.1 | 0.8 | 0.9 | 1.6 | 1.1 | 0.8 | 1.7 | 1.6 | 1.8 | 1.0 | 1.6 | 1.3 | 0.9 | 0.8 | 1.1 | 1.0 | 0.39 |
| YKL056C | 1.3 | 0.7 | 2.6 | 1.4 | 1.7 | 0.9 | 0.5 | 1.0 | 0.1 | 0.7 | 1.1 | 0.8 | 0.1 | 0.7 | 0.9 | 0.6 | 0.8 | 1.2 | 6.68 |
| YKL097W-A | 1.5 | 1.3 | 4.2 | 1.3 | 1.2 | 0.9 | 0.2 | 0.7 | 0.0 | 0.4 | 1.6 | 0.7 | 0.2 | 0.6 | 2.0 | 0.8 | 1.1 | 1.4 | 4.01 |
| YNL209W | 0.9 | 0.9 | 2.7 | 0.9 | 1.3 | 0.9 | 0.5 | 1.1 | 0.2 | 0.8 | 0.9 | 0.9 | 0.5 | 0.6 | 0.9 | 0.3 | 0.6 | 0.6 | 8.06 |
| YNL307C | 0.8 | 0.6 | 3.1 | 1.3 | 1.0 | 1.9 | 0.9 | 0.9 | 1.0 | 0.9 | 1.0 | 1.0 | 1.0 | 0.7 | 0.6 | 1.0 | 1.0 | 1.3 | 2.79 |
| YPR028W | 1.0 | 1.1 | 4.0 | 1.7 | 1.0 | 1.4 | 0.8 | 0.7 | 0.5 | 0.8 | 1.4 | 0.6 | 1.7 | 0.8 | 0.9 | 1.3 | 1.2 | 1.7 | 4.06 |
| YPR149W | 1.0 | 1.1 | 5.9 | 1.7 | 1.7 | 1.6 | 2.1 | 0.6 | 1.2 | 1.8 | 1.1 | 0.7 | 1.4 | 1.3 | 1.0 | 2.2 | 1.1 | 1.1 | 2.65 |
| YAL016W | 0.8 | 1.0 | 2.8 | 0.9 | 0.9 | 0.9 | 1.1 | 1.0 | 1.2 | 1.9 | 0.9 | 0.8 | 1.4 | 0.9 | 1.1 | 1.1 | 0.8 | 1.3 | 1.00 |
| YBR283C | 0.6 | 0.7 | 1.9 | 1.2 | 1.4 | 2.2 | 0.8 | 0.8 | 1.5 | 1.2 | 2.0 | 0.8 | 0.8 | 0.6 | 1.4 | 0.9 | 0.9 | 0.9 | 2.62 |
| YBR286W | 0.7 | 1.4 | 3.8 | 1.2 | 1.3 | 1.5 | 1.3 | 0.9 | 1.2 | 1.6 | 1.0 | 1.1 | 1.8 | 1.5 | 1.3 | 2.6 | 0.8 | 1.6 | 2.98 |
| YCL008C | 0.8 | 1.1 | 1.8 | 1.2 | 1.2 | 0.9 | 0.9 | 0.7 | 0.9 | 1.4 | 0.9 | 0.9 | 1.0 | 0.9 | 1.4 | 0.6 | 0.9 | 0.9 | 0.47 |
| YCR069W | 1.0 | 1.2 | 2.0 | 0.9 | 1.1 | 1.4 | 1.1 | 0.7 | 0.8 | 0.7 | 1.3 | 1.4 | 1.6 | 1.0 | 2.4 | 1.2 | 1.2 | 1.3 | 0.97 |
| YDL061C | 1.4 | 0.5 | 2.9 | 0.9 | 1.3 | 1.1 | 0.5 | 1.0 | 0.0 | 0.5 | 1.4 | 1.0 | 0.1 | 0.7 | 1.0 | 0.6 | 1.1 | 1.0 | 4.40 |
| YDR151C | 1.3 | 1.0 | 2.3 | 1.8 | 0.8 | 0.7 | 0.8 | 1.5 | 2.6 | 2.8 | 2.1 | 0.9 | 2.8 | 1.1 | 0.6 | 1.2 | 0.8 | 1.1 | 0.96 |
| YDR382W | 1.3 | 0.5 | 2.4 | 1.2 | 1.1 | 0.6 | 0.4 | 1.2 | 0.0 | 0.4 | 1.2 | 0.7 | 0.1 | 0.7 | 1.1 | 0.4 | 1.0 | 1.0 | 6.40 |
| YDR385W | 0.6 | 0.4 | 3.5 | 0.9 | 1.1 | 0.5 | 0.4 | 0.7 | 0.2 | 0.5 | 0.9 | 0.9 | 0.3 | 0.5 | 0.8 | 0.3 | 0.6 | 0.4 | 7.27 |
| YDR407C | 0.7 | 1.0 | 2.0 | 0.7 | 0.8 | 1.2 | 1.4 | 0.9 | 1.5 | 1.7 | 1.2 | 1.0 | 1.3 | 0.8 | 1.3 | 1.0 | 0.9 | 0.9 | 0.52 |
| YGL206C | 0.4 | 3.5 | 2.0 | 0.5 | 0.6 | 0.8 | 0.8 | 0.5 | 0.7 | 0.7 | 0.9 | 0.7 | 1.1 | 0.8 | 1.3 | 0.6 | 0.8 | 1.0 | 1.04 |
| YGR172C | 0.6 | 1.3 | 2.5 | 1.3 | 0.6 | 0.9 | 1.0 | 0.8 | 0.4 | 1.1 | 0.8 | 0.8 | 0.7 | 1.1 | 1.9 | 1.0 | 1.1 | 1.1 | 0.94 |
| YIL015W | 1.1 | 1.7 | 2.0 | 2.5 | 0.9 | 0.4 | 0.9 | 0.9 | 0.3 | 1.1 | 0.8 | 0.9 | 0.8 | 5.9 | 1.1 | 0.8 | 0.8 | 1.0 | 0.17 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YIL018W | 1.0 | 0.4 | 2.3 | 1.4 |  | 0.9 | 0.4 | 0.8 | 0.0 | 0.3 | 1.2 | 0.6 | 0.0 | 0.6 | 0.6 | 0.4 | 0.8 | 0.8 | 6.27 |
| YJL138C | 1.0 | 0.7 | 2.3 | 1.4 | 0.9 | 0.8 | 0.8 | 1.2 | 0.2 | 0.7 | 1.2 | 0.8 | 0.3 | 0.7 | 0.9 | 0.6 | 0.9 | 1.0 | 7.38 |
| YJL191W | 1.0 | 0.4 | 2.2 | 0.7 |  | 1.3 | 1.0 | 0.8 | 0.0 | 0.4 | 1.1 | 1.0 | 0.9 | 1.1 | 0.7 | 2.2 | 1.0 | 1.0 | 1.86 |
| YJR047C | 1.1 | 0.8 | 2.6 | 1.1 | 1.1 | 1.1 | 0.4 | 0.9 | 0.7 | 0.5 | 1.1 | 0.9 | 0.9 | 0.9 | 0.6 | 0.8 | 0.8 | 0.9 | 5.29 |
| YJR119C | 0.9 | 1.0 | 2.0 | 1.0 | 0.9 | 1.4 | 1.1 | 1.6 | 0.5 | 1.3 | 1.1 | 0.9 | 1.2 | 1.3 | 1.5 | 1.0 | 0.7 | 0.9 | 0.30 |
| YJR123W | 1.2 | 0.6 | 2.2 | 1.0 | 1.3 | 1.0 | 0.4 | 1.2 | 0.0 | 0.5 | 0.9 | 0.8 | 0.1 | 0.6 | 1.1 | 0.4 | 0.8 | 0.9 | 7.84 |
| YJR145C | 0.8 | 0.7 | 2.3 | 1.3 |  | 0.4 | 0.4 | 1.0 | 0.0 | 0.4 | 0.8 | 0.6 | 0.0 | 0.6 | 0.8 | 0.5 | 0.8 | 0.9 | 4.82 |
| YLR110C | 1.4 | 0.8 | 2.7 | 1.2 | 1.7 | 0.9 | 0.4 | 0.8 | 0.3 | 0.8 | 3.2 | 0.7 | 0.5 | 0.5 | 1.7 | 0.8 | 0.9 | 1.1 | 3.99 |
| YLR264W | 1.1 | 0.4 | 2.2 | 1.0 | 1.1 | 0.7 | 0.4 | 1.0 | 0.0 | 0.3 | 0.8 | 1.1 | 0.3 | 1.2 | 1.2 | 0.5 | 1.0 | 1.1 | 3.91 |
| YLR340W | 0.8 | 0.4 | 2.6 | 1.0 | 0.6 | 0.7 | 0.3 | 0.9 | 0.0 | 0.5 | 1.4 | 0.9 | 0.1 | 0.5 | 1.3 | 0.2 | 0.9 | 0.7 | 6.55 |
| YLR388W | 1.6 | 0.4 | 1.9 | 1.0 | 2.5 | 0.7 | 0.5 | 1.2 | 0.2 | 0.7 | 1.0 | 0.6 | 0.1 | 0.8 | 0.6 | 0.5 | 0.8 | 1.0 | 4.48 |
| YMR092C | 0.6 | 1.2 | 1.9 | 1.3 | 0.8 | 0.9 | 1.2 | 0.9 | 1.5 | 1.7 | 1.2 | 0.9 | 1.7 | 0.8 | 1.1 | 1.2 | 0.9 | 1.3 | 1.43 |
| YMR101C | 1.1 | 1.8 | 1.9 | 2.9 | 0.9 | 0.4 | 0.9 | 0.8 | −4.0 | 1.6 | −0.3 | 0.7 | 0.8 | 1.1 | 1.0 | 0.9 | 0.7 | 0.8 | 0.16 |
| YNL069C | 1.2 | 0.3 | 2.8 | 2.3 | 0.7 | 0.4 | 0.3 | 1.0 | 0.0 | 0.4 | 1.0 | 0.6 | 0.1 | 0.9 | 1.0 | 0.3 | 0.8 | 0.6 | 4.03 |
| YNL135C | 1.1 | 0.9 | 2.0 | 1.4 | 1.7 | 0.9 | 0.8 | 0.5 | 0.7 | 0.5 | 0.7 | 0.8 | 0.9 | 0.5 | 1.0 | 1.4 | 1.2 | 1.7 | 3.05 |
| YOL039W | 1.2 | 0.3 | 3.9 | 0.7 | 1.3 | 0.4 | 0.3 | 1.0 | 0.0 | 0.9 | 1.1 | 0.7 | 0.1 | 0.5 | 0.8 | 0.4 | 0.7 | 0.7 | 4.94 |
| YOL120C | 1.0 | 0.3 | 2.3 | 0.8 | 1.5 | 0.3 | 0.4 | 0.8 | 0.0 | 0.3 | 1.0 | 0.7 | 0.1 | 0.6 | 0.6 | 0.3 | 0.6 | 0.8 | 4.42 |
| YOR230W | 1.2 | 2.3 | 3.0 | 1.0 | 0.9 | 1.1 | 0.6 | 0.6 | 0.6 | 0.7 | 1.6 | 1.4 | 1.5 | 0.7 | 0.6 | 1.6 | 1.2 | 1.6 | 1.76 |
| YOR298W | 0.9 | 0.9 | 3.2 | 0.5 | 1.5 | 0.9 | 0.6 | 0.7 | 0.6 | 1.0 | 0.1 | 0.7 | 1.1 | 2.1 | 1.2 | 0.1 | 1.0 | 0.8 | 0.41 |
| YPL048W | 0.7 | 0.7 | 2.6 | 1.2 | 0.7 | 0.6 | 0.6 | 0.8 | 1.6 | 0.6 | 1.7 | 1.0 | 0.9 | 0.6 | 1.5 | 1.3 | 1.2 | 1.0 | 2.11 |
| YPL179W | 1.0 | 1.5 | 2.4 | 1.0 | 1.1 | 1.6 | 1.2 | 0.8 | 1.2 | 1.1 | 1.1 | 1.0 | 1.3 | 0.8 | 1.2 | 1.4 | 1.3 | 1.3 | 1.38 |
| YPL218W | 1.5 | 0.9 | 2.5 | 1.7 | 1.1 | 1.5 | 1.3 | 1.4 | 1.1 | 1.2 | 1.1 | 1.2 | 1.0 | 1.5 | 1.1 | 1.7 | 1.1 | 1.8 | 2.98 |
| YPL220W | 1.3 | 0.9 | 2.3 | 1.4 | 1.1 | 1.3 | 0.6 | 1.2 | 0.0 | 0.5 | 1.3 | 0.5 | 0.1 | 0.6 | 0.6 | 0.5 | 1.1 | 1.1 | 8.33 |
| YPR080W | 1.3 | 1.3 | 2.8 | 1.2 | 1.4 | 1.4 | 0.9 | 1.3 | 0.7 | 1.1 | 1.0 | 1.0 | 1.3 | 0.6 | 1.5 | 0.6 | 1.1 | 1.0 | 8.03 |
| YPR181C | 0.5 | 0.8 | 2.3 | 0.6 | 1.0 | 2.0 | 1.3 | 0.5 | 1.0 | 0.7 | 1.3 | 1.0 | 1.7 | 2.4 | 1.5 | 1.6 | 1.8 | 1.6 | 1.84 |
| YBR290W | 1.3 | 1.4 | 0.8 | 3.0 | 1.0 | 1.1 | 1.4 | 1.5 | 2.0 | 1.8 | 1.2 | 1.0 | 1.7 | 1.4 | 0.9 | 1.3 | 1.2 | 2.1 | 1.34 |
| YCR091W | 1.3 | 1.1 | 0.6 | 2.2 | 1.3 | 1.3 | 1.3 | 1.1 | 0.8 | 1.2 | 0.8 | 1.1 | 1.3 | 1.3 | 0.7 | 2.7 | 1.3 | 1.4 | 0.22 |
| YFL026W | 1.0 | 0.8 | 1.2 | 5.0 | 1.4 | 1.0 | 1.2 | 1.3 | 0.6 | 1.5 | 1.3 | 0.8 | 1.1 | 1.1 | 1.0 | 1.0 | 1.0 | 1.0 | 0.27 |
| YOR003W | 0.9 | 1.1 | 1.3 | 3.3 | 1.6 | 1.1 | 1.1 | 0.9 | 1.6 | 1.3 | 0.7 | 0.8 | 1.0 | 1.2 | 2.8 | 1.3 | 1.0 | 1.1 | 0.30 |
| YCR038C | 0.9 | 1.1 | 0.9 | 2.5 | 0.9 | 0.9 | 0.9 | 0.9 | 0.7 | 0.7 | 1.1 | 0.8 | 1.0 | 1.1 | 0.7 | 1.0 | 0.9 | 1.1 | 0.31 |
| YDL119C | 1.0 | 0.8 | 0.6 | 2.2 | 0.9 | 0.6 | 1.3 | 1.1 | 1.3 | 1.1 | 1.5 | 0.9 | 1.1 | 1.2 | 0.5 | 1.2 | 1.0 | 1.0 | 0.77 |
| YDL220C | 0.9 | 1.3 | 1.1 | 1.6 | 1.2 | 1.8 | 1.1 | 0.8 | 0.2 | 1.3 | 0.8 | 1.0 | 1.6 | 0.9 | 1.6 | 0.8 | 1.1 | 0.9 | 0.24 |
| YDR125C | 1.1 | 0.9 | 1.0 | 1.7 | 1.1 | 0.8 | 1.0 | 1.2 | 0.7 | 1.9 | 1.0 | 0.8 | 0.9 | 1.0 | 0.8 | 1.7 | 0.9 | 1.2 | 0.35 |
| YDR225W | 1.0 | 0.6 | 0.6 | 1.6 | 1.9 | 0.5 | 0.4 | 0.8 | 0.3 | 0.7 | 2.7 | 0.4 | 0.2 | 0.8 | 0.1 | 0.8 | 1.1 | 1.8 | 5.54 |
| YER066W | 0.9 | 0.7 | 0.9 | 2.1 | 1.5 | 1.3 | 1.3 | 0.7 | 1.7 | 1.4 | 1.5 | 0.7 | 0.9 | 1.1 | 0.5 | 3.3 | 1.1 | 1.1 | 0.66 |
| YER076C | 0.8 | 0.9 | 1.2 | 1.9 | 1.1 | 0.6 | 0.8 | 0.7 | 0.2 | 1.2 | 0.7 | 0.7 | 1.1 | 0.9 | 0.8 | 1.3 | 1.0 | 1.0 | 0.33 |
| YFR006W | 0.9 | 1.8 | 1.1 | 3.4 | 0.7 | 0.8 | 1.4 | 1.0 | −1.6 | 0.7 | 1.2 | 1.0 | 0.9 | 0.9 | 0.8 | 1.2 | 0.9 | 1.3 | 1.54 |
| YGL208W | 0.9 | 1.8 | 1.1 | 2.2 | 0.7 | 0.6 | 1.1 | 0.7 | 1.4 | 1.3 | 1.3 | 0.8 | 1.5 | 0.9 | 1.8 | 3.1 | 0.8 | 1.3 | 0.32 |
| YGR023W | 1.0 | 0.9 | 1.1 | 4.2 | 1.0 | 1.2 | 1.0 | 1.2 | 1.2 | 3.2 | 2.4 | 0.9 | 1.4 | 1.3 | 1.1 | 0.9 | 1.2 | 1.5 | 0.69 |
| YGR108W | 0.9 | 3.9 | 0.3 | 3.6 | 0.8 | 0.1 | 0.3 | 0.5 | 0.0 | 0.1 | 0.5 | 0.4 | 0.3 | 0.8 | 0.2 | 0.4 | 0.7 | 1.0 | 0.93 |
| YHR195W | 1.1 | 1.5 | 0.6 | 2.4 | 1.5 | 1.0 | 1.3 | 1.6 | 1.8 | 0.8 | 1.4 | 0.9 | 1.2 | 1.2 | 0.7 | 3.7 | 1.0 | 1.5 | 1.12 |
| YIL050W | 1.0 | 1.3 | 1.3 | 2.4 | 0.9 | 0.7 | 1.1 | 1.2 | 1.3 | 1.9 | 0.9 | 1.0 | 1.0 | 1.3 | 0.6 | 2.7 | 1.0 | 1.1 | 0.52 |
| YJR050W | 1.0 | 0.6 | 0.7 | 2.1 | 1.2 | 1.4 | 1.1 | 1.8 | 2.0 | 1.3 | 0.8 | 0.8 | 1.9 | 1.3 | 0.9 | 1.5 | 0.9 | 1.1 | 0.85 |
| YKL093W | 1.0 | 1.6 | 1.4 | 3.6 | 0.8 | 0.8 | 0.7 | 0.9 | 1.5 | 1.6 | 0.9 | 0.9 | 1.2 | 1.1 | 0.8 | 2.9 | 0.8 | 1.0 | 0.38 |
| YMR053C | 1.1 | 1.0 | 0.8 | 2.1 | 0.9 | 1.3 | 0.9 | 1.0 | 2.2 | 1.4 | 1.3 | 0.9 | 1.5 | 1.3 | 2.4 | 2.3 | 1.1 | 1.6 | 0.31 |
| YNL139C | 0.8 | 1.1 | 0.8 | 2.0 | 1.9 | 1.0 | 1.0 | 0.9 | 0.6 | 0.7 | 0.8 | 0.5 | 1.2 | 0.7 | 1.4 | 1.1 | 1.1 | 1.0 | 0.47 |
| YOR122C | 1.0 | 0.7 | 1.8 | 1.9 | 1.7 | 1.3 | 1.2 | 1.0 | 1.1 | 0.9 | 1.5 | 0.8 | 1.0 | 1.2 | 1.6 | 1.5 | 1.0 | 2.2 | 3.06 |
| YOR312C | 1.2 | 0.4 | 1.0 | 1.9 | 0.7 | 0.6 | 0.6 | 1.2 | 0.0 | 0.3 | 0.8 | 0.7 | 0.1 | 0.7 | 0.7 | 0.5 | 1.2 | 1.0 | 5.24 |
| YOR327C | 2.3 | 1.8 | 0.5 | 1.9 | 1.0 | 1.4 | 1.4 | 1.9 | 1.4 | 2.2 | 2.1 | 1.0 | 2.1 | 1.5 | 0.9 | 1.5 | 2.2 | 2.1 | 1.46 |
| YPL001W | 0.9 | 0.9 | 1.0 | 2.5 | 1.7 | 0.7 | 1.0 | 1.2 | 0.7 | 1.0 | 1.3 | 0.7 | 0.8 | 1.3 | 1.3 | 0.8 | 0.9 | 1.2 | 0.74 |
| YPL230W | 1.2 | 1.7 | 1.8 | 4.0 | 0.8 | 1.0 | 1.1 | 1.0 | 0.9 | 2.7 | 3.1 | 1.0 | 2.0 | 1.3 | 0.7 | 2.0 | 1.0 | 1.6 | 0.47 |
| YER025W | 0.6 | 0.7 | 0.6 | 0.6 | 1.5 | 1.0 | 1.5 | 1.1 | 0.4 | 0.6 | 1.2 | 0.7 | 0.6 | 2.1 | 0.8 | 2.6 | 1.8 | 2.3 | 1.96 |
| YHR185C | 0.9 | 1.1 | 1.4 | 0.7 | 1.4 | 1.0 | 1.3 | 0.8 | −0.6 | 0.9 | 0.7 | 0.8 | 0.4 | 1.7 | 1.3 | 3.2 | 1.4 | 3.0 | 1.64 |
| YIL076W | 1.3 | 0.6 | 1.1 | 1.0 | 1.8 | 0.6 | 0.5 | 1.3 | 1.0 | 1.4 | 1.1 | 0.8 | 0.8 | 1.4 | 1.0 | 0.8 | 1.2 | 2.5 | 3.73 |
| YMR238W | 1.9 | 1.3 | 1.1 | 1.3 | 1.5 | 1.3 | 1.2 | 0.9 | 1.3 | 1.4 | 1.2 | 1.0 | 1.5 | 1.2 | 2.3 | 1.4 | 2.2 | 2.4 | 1.36 |
| YBR009C | 1.6 | 0.8 | 0.4 | 1.7 | 1.4 | 1.0 | 0.5 | 1.2 | 0.6 | 0.6 | 0.8 | 0.5 | 0.4 | 1.1 | 0.2 | 0.4 | 1.0 | 2.4 | 7.00 |
| YBR010W | 1.0 | 0.8 | 0.5 | 2.0 | 0.8 | 1.1 | 0.8 | 1.3 | 0.5 | 0.7 | 1.0 | 0.7 | 0.4 | 1.0 | 0.3 | 0.8 | 1.1 | 2.3 | 7.25 |
| YCL067C | 1.2 | 1.1 | 0.3 | 1.7 | 1.1 | 1.7 | 1.3 | 1.7 | 1.4 | 1.9 | 1.6 | 1.0 | 1.4 | 2.1 | 2.2 | 1.7 | 0.8 | 2.2 | 3.15 |
| YCR096C | 1.1 | 0.9 | 0.4 | 1.6 | 2.1 | 1.2 | 1.7 | 1.5 | 1.2 | 1.6 | 1.4 | 1.0 | 1.0 | 2.1 | 2.1 | 1.8 | 1.0 | 2.1 | 2.34 |
| YDL137W | 1.4 | 1.1 | 1.2 | 1.2 | 1.8 | 1.0 | 2.0 | 1.1 | 1.1 | 1.3 | 1.5 | 1.6 | 1.7 | 1.4 | 1.3 | 2.3 | 1.3 | 2.2 | 4.95 |
| YDL192W | 1.4 | 1.0 | 0.6 | 1.2 | 1.4 | 1.0 | 1.7 | 1.5 | 0.8 | 0.6 | 1.3 | 1.1 | 0.9 | 1.2 | 1.3 | 1.3 | 1.1 | 2.3 | 5.57 |
| YDR224C | 1.1 | 0.7 | 0.8 | 0.9 | 1.2 | 1.0 | 0.8 | 1.4 | 1.1 | 1.3 | 1.1 | 0.7 | 0.5 | 1.7 | 0.3 | 1.1 | 1.2 | 2.3 | 5.62 |
| YDR378C | 1.3 | 1.3 | 1.4 | 1.3 | 1.0 | 1.0 | 1.4 | 1.5 | 0.5 | 1.3 | 0.8 | 0.9 | 0.8 | 1.4 | 0.8 | 1.0 | 1.7 | 2.2 | 2.40 |
| YMR197C | 1.3 | 1.6 | 1.4 | 1.9 | 1.1 | 1.6 | 1.5 | 1.4 | 1.9 | 2.5 | 1.0 | 1.1 | 1.5 | 4.1 | 1.7 | 1.9 | 1.2 | 2.2 | 1.20 |
| YOL109W | 2.0 | 2.0 | 1.5 | 1.8 | 1.0 | 1.3 | 1.2 | 1.5 | 0.1 | 1.1 | 1.0 | 0.8 | 0.5 | 1.4 | 1.0 | 0.8 | 1.6 | 2.2 | 4.13 |
| YPL010W | 1.0 | 1.1 | 0.9 | 1.0 | 1.4 | 1.0 | 1.9 | 1.5 | 1.7 | 1.5 | 1.3 | 1.1 | 1.1 | 1.3 | 1.2 | 1.3 | 1.3 | 2.0 | 3.25 |
| YHR132C | 0.8 | 0.7 | 1.7 | 1.4 | 1.0 | 0.7 | 0.8 | 0.8 | 0.9 | 1.1 | 1.1 | 0.8 | 1.2 | 0.9 | 1.4 | 2.3 | 0.8 | 1.3 | 1.52 |
| YJL141C | 1.0 | 0.8 | 1.0 | 1.6 | 1.5 | 1.1 | 1.1 | 0.9 | 1.2 | 1.3 | 1.2 | 0.8 | 1.4 | 0.8 | 0.8 | 2.2 | 1.4 | 1.6 | 0.94 |
| YKR098C | 1.0 | 1.1 | 1.2 | 1.7 | 1.1 | 1.8 | 1.7 | 1.3 | 1.4 | 2.7 | 1.9 | 1.1 | 1.4 | 1.4 | 0.9 | 3.9 | 1.1 | 1.6 | 0.55 |
| YLR206W | 0.7 | 1.6 | 1.4 | 1.1 | 1.1 | 0.5 | 0.7 | 0.8 | 1.5 | 1.0 | 1.3 | 0.8 | 1.4 | 0.8 | 2.4 | 2.3 | 1.1 | 1.2 | 0.72 |
| YAL055W | 1.2 | 1.0 | 0.9 | 1.0 | 1.4 | 1.3 | 1.5 | 1.9 | 1.0 | 1.4 | 1.3 | 1.2 | 1.5 | 1.6 | 1.1 | 2.6 | 1.3 | 1.3 | 0.62 |
| YAR062W | 1.2 | 1.8 | 1.4 | 0.7 | 1.0 | 0.6 | 1.3 | 0.9 | 0.4 | 0.9 | −1.1 | 0.8 | 1.2 | 1.1 | 1.3 | 2.4 | 0.9 | 1.0 | 0.32 |
| YBL102W | 0.8 | 1.0 | 1.4 | 1.2 | 0.9 | 2.5 | 1.6 | 0.8 | 2.3 | 1.1 | 1.2 | 0.9 | 1.7 | 1.1 | 1.1 | 2.0 | 2.4 | 1.5 | 1.26 |

TABLE 9-continued

Genes belonging to other category

The level of expressed mRNA in the presence of chemical substance/The level of expressed mRNA in the absence of chemical substance

| yeast genes | (1) | (2) | (3) | (4) | (5) | (6) | (7) | (8) | (9) | (10) | (11) | (12) | (13) | (14) | (15) | (16) | (17) | (18) | Intensity |
|---|---|---|---|---|---|---|---|---|---|---|---|---|---|---|---|---|---|---|---|
| YBR161W | 1.2 | 0.8 | 2.3 | 0.7 | 1.1 |  | 3.0 | 0.9 | 0.4 | 0.4 | 1.1 | 0.6 | 1.0 | 0.9 | 1.5 | 2.1 | 1.5 | 2.2 | 0.72 |
| YCR039C | 1.9 | 2.1 | 0.3 | 0.9 | 1.9 | 1.5 | 1.4 | 1.6 | 1.8 | 2.2 | 1.2 | 0.8 | 1.0 | 1.7 | 1.9 | 2.1 | 1.0 | 2.1 | 1.73 |
| YDL018C | 1.3 | 0.9 | 0.9 | 1.1 | 1.8 | 1.4 | 1.2 | 1.3 | 1.0 | 1.0 | 0.9 | 0.7 | 1.0 | 1.5 | 1.1 | 3.1 | 1.5 | 1.7 | 0.84 |
| YDR022C | 1.1 | 1.2 | 0.8 | 0.9 | 1.5 | 2.2 | 1.8 | 1.4 | 0.9 | 1.4 | 0.9 | 0.7 | 1.3 | 2.1 | 1.0 | 2.1 | 1.3 | 1.2 | 0.47 |
| YDR181C | 1.1 | 1.2 | 0.8 | 1.4 | 0.9 | 0.7 | 1.0 | 1.2 | 2.0 | 0.9 | 0.8 | 0.7 | 0.7 | 1.3 | 1.2 | 2.0 | 0.8 | 1.2 | 0.48 |
| YGR036C | 0.9 | 0.8 | 0.9 | 1.1 | 1.3 | 1.3 | 1.0 | 0.8 | 0.9 | 0.9 | 0.9 | 1.0 | 1.3 | 1.0 | 0.7 | 2.0 | 1.3 | 1.1 | 1.12 |
| YGR120C | 1.2 | 1.8 | 0.5 | 1.0 | 1.8 | 1.5 | 1.6 | 1.3 | 0.3 | 1.2 | 1.1 | 0.7 | 0.5 | 1.0 | 1.2 | 1.9 | 1.1 | 1.2 | 0.36 |
| YGR131W | 0.8 | 2.1 | 1.9 | 1.1 | 0.9 | 1.9 | 1.1 | 1.1 | 1.9 | 5.8 | 1.1 | 0.5 | 1.4 | 2.0 | 0.8 | 2.6 | 1.3 | 1.0 | 0.41 |
| YGR167W | 1.1 | 1.1 | 0.6 | 1.5 | 0.9 | 1.7 | 1.4 | 1.4 | 1.4 | 1.9 | 1.1 | 1.1 | 1.6 | 1.7 | 1.6 | 2.8 | 1.3 | 1.7 | 1.79 |
| YHL024W | 1.2 | 0.8 | 1.6 | 1.1 | 1.5 | 1.2 | 1.3 | 0.8 | 2.1 | 3.6 | 1.1 | 1.6 | 1.6 | 2.1 | 2.9 | 3.8 | 1.4 | 1.4 | 0.58 |
| YJL113W | 1.2 | 1.9 | 1.2 | 1.2 |  | 0.7 | 1.2 | 1.3 | 1.3 | 2.1 | 1.2 | 0.7 | 0.9 | 1.3 | 1.7 | 2.1 | 0.9 | 1.5 | 0.41 |
| YJL146W | 1.3 | 1.9 | 1.2 | 2.0 | 0.8 | 0.7 | 1.3 | 1.0 | 1.0 | 1.7 | −1.1 | 1.1 | 0.8 | 1.5 | 1.2 | 1.8 | 1.0 | 1.3 | 0.30 |
| YJR019C | 0.8 | 1.8 | 1.9 | 1.6 | 1.1 | 0.8 | 0.9 | 0.7 | 1.1 | 0.6 | 2.4 | 1.1 | 1.4 | 0.8 | 1.1 | 2.6 | 1.8 | 1.4 | 0.33 |
| YJR049C | 1.0 | 1.2 | 1.0 | 1.0 | 0.7 | 0.6 | 1.0 | 1.2 | 1.4 | 1.4 | 1.6 | 1.0 | 2.1 | 1.2 | 1.2 | 1.7 | 0.9 | 1.2 | 0.44 |
| YLR078C | 0.9 | 1.1 | 0.7 | 1.4 |  | 0.8 | 1.2 | 1.1 | 0.8 | 1.1 | 2.9 | 1.0 | 0.8 | 1.2 | 0.6 | 2.2 | 1.2 | 1.2 | 1.02 |
| YNR037C | 0.9 | 0.9 | 0.9 | 1.7 | 1.2 | 0.7 | 1.7 | 1.1 | 1.3 | 1.7 | 1.5 | 0.7 | 2.0 | 1.2 | 0.8 | 1.9 | 1.4 | 1.6 | 1.34 |
| YOR028C | 1.4 | 0.7 | 1.1 | 2.3 | 1.6 | 1.0 | 1.2 | 1.5 | 1.2 | 2.0 | 1.5 | 0.6 | 0.8 | 1.3 | 1.1 | 3.7 | 0.8 | 1.7 | 0.78 |

The tables show that the expressed mRNA of about 700 of 2400 unknown yeast genes was induced by any one of chemical substances such as heavy metals, agricultural chemicals, surfactants (Table 1), as well as the expressed mRNA of 167 mitochondria-located genes (Table 2), 52 DNA repair genes (Table 3), 161 energy genes (Table 4), 142 transport facilitation protein genes (Table 5), 90 stress protein genes (Table 6), 142 metabolism genes (Table 7), 60 detoxification genes (Table 8), and 507 genes belonging to other category (Table 9). Here, when the value of the following is 2 or more, then it is considered significant:

The level of expressed *mRNA* in the presence of chemical substance
The level of expressed *mRNA* in the absence of chemical substance.

kind of toxic chemical substances are predicted. Thus, it is desired that the production of marker proteins is lower in the absence of chemical substances, and the production of marker proteins is higher in the presence of chemical substances. Under the circumstance, yeast gene as used in promoter assay is selected, of which intensity (level of expressed gene in control cells/average level of expressed whole genes) is preferably 1.5 or less, more preferably 1 or less, even more preferably 0.5 or less, and of which expression magnification (expressed mRNA in the presence of chemical substance/expressed mRNA in the absence of chemical substance) is preferably 3 or more, more preferably 10 or more, even more preferably 20 or more.

Example 2

Primers for PCR to amplify the polynucleotide comprising the promoter of yeast gene YKL071w were prepared. Primers were designed using a primer design software, Oligo4.0-S, Sequencher I Mackintosh version. The base sequence of the upper primer was:

CGCAATAATACTGGAAACATCAA (SEQ ID No: 7), whereas the base sequence of the lower primer was:
ATCGACTTTGTTTGCTTAGAAT (SEQ ID No: 8).

The inventors of the present application understood that the induction of certain yeast genes by toxic substances is caused by the activation of the promoters of the genes by the toxic substances. Thus, the inventors prepared a vector that comprised a polynucleotide sequence comprising the promoter of the yeast gene, which sequence is operably linked to a polynucleotide encoding a marker protein; and transformed yeast cells with the vector. Such cells enable us to detect readily toxic substances by detecting the expressed marker proteins (hereinafter, such detection may be referred to as "promoter assay"). The working examples hereinafter illustrate the preparation of such vectors, transformation of yeast cells by use of said vectors, and the detection of toxic substances by use of the transformed cells.

Promoter assay is a method for determining variations of the level of intracellular genes without destroying cells on the basis of the level of expressed marker genes instead of the expressed mRNA. The gene selected to detect a chemical substance is expressed in the absence of chemical substances, and thus a marker protein also occurs in the absence of chemical substances. In the method according to the present invention, the behavior of yeast genes on the addition of test materials is determined on the basis of the level of expressed marker protein so that the presence or the absence, and the For PCR, yeast chromosome (*Saccharomyces cerevisiae* S288C, Cat. 40802, Research Genetics, Inc.) was used as template, and the commercially available kit (KOD DNA Polymerase; Code KOD-101, Toyobo) was used as reagents.

Type YEp shuttle vector pYES2 (pYES2, Cat no: V825-20, Invitrogen Corporation, USA), which can be replicated both in *E. coli*, and yeast was used as vector (R. W. Old, S. B. Primrose Principles of Gene Manipulation 5th Ed., BAIFU-KAN CO., LTD, pp 138-165, pp. 234-263, 2000). The portion of vector pQBI 63 (Cat no. 54-0082, Wako Pure Chemical Industries, Ltd.) corresponding to a marker protein GFP was used as the polynucleotide encoding GFP (SEQ ID No: 6). First, the GFP polynucleotide was inserted into the multiple cloning sites of pYES2 to give a vector. Thereafter, the GALL promoter of pYES2 was replaced with the polynucleotide comprising the promoter sequence of the intended yeast gene YKL071w (SEQ ID No: 1) to give an intended plasmid vector. Suitable restriction enzymes were selected, and the insertion of the polynucleotide comprising GFP and the promoter sequence was conducted.

Next, the yeast Saccharomyces cerevisiae W303 was transformed with the resultant plasmid vector according to the following procedures:

1) Incubating the yeast Saccharomyces cerevisiae W303 in 200 ml of SD medium under shaking until OD 660 reaches 0.5;

2) Suspending the collected cells in 5 ml of TE-buffer;

3) Adding 250 μL of 2.5M lithium acetate;

4) Dispending each 300 μl, adding 1 μl of above plasmid vector thereto, then incubating the suspensions at 30° C. for 30 minutes;

5) Adding 700 μl of 50% PEG4000, and incubating the mixture under shaking at 30° C. for 60 minutes;

6) Giving heat shock (420C, 5 minutes), and then immediately cooling the mixture;

7) Washing the mixture twice with 1M sorbitol; and

8) Seeding it on agar plates made of minimum essential medium.

The transformations were confirmed on selective medium (SD medium (Yeast nitrogen base without amino acids (Difco 0919-15)+glucose+amino acids (adenine, histidine, tryptophan)). Colonies that were grown on agar plate of selective medium were further checked for auxotrophy for amino acids.

The transformed yeast cells named SC-YKL071w-pQBI has been deposited as the International Deposition at National Institute of Advanced Industrial Science and Technology, International Patent Organism Depositary of Tsukuba Central 6, 1-1-1 Higashi, Tsukuba, Ibaraki, Japan under Accession No. FERM BP-8161 on Aug. 19, 2002.

Example 3

Primers for PCR to amplify the polynucleotide comprising the promoter of yeast gene YCR102c were prepared. Primers were designed using a primer design software, Oligo4.0-S, Sequencher I Mackintosh version. The base sequence of the upper primer was:
AGGTGCGATAGTGGGGAATAAGA (SEQ ID No: 9), whereas the base sequence of the lower primer was:
GGTTTCTGGAATTGCAACTTGC (SEQ ID No: 10).

For PCR, yeast chromosome (Saccharomyces cerevisiae S288C, Cat. 40802, Research Genetics, Inc.) was used as template, and the commercially available kit (KOD DNA Polymerase; Code KOD-101, Toyobo) was used as reagents.

Type YEp shuttle vector pYES2 (pYES2, Cat no: V825-20, Invitrogen Corporation, USA), which can be replicated both in E. coli, and yeast was used as vector (R. W. Old, S. B. Primrose Principles of Gene Manipulation 5th Ed., BAIFU-KAN CO., LTD, pp 138-165, pp. 234-263, 2000). The portion of vector pQBI 63 (Cat no. 54-0082, Wako Pure Chemical Industries, Ltd.) corresponding to a marker protein GFP was used as the polynucleotide encoding GFP (SEQ ID No: 6). First, the GFP polynucleotide was inserted into the multiple cloning sites of pYES2 to give a vector. Thereafter, the GALL promoter of pYES2 was replaced with the polynucleotide comprising the promoter sequence of the intended yeast gene YCR102c (SEQ ID No: 2) to give an intended plasmid vector. Suitable restriction enzymes were selected, and the insertion of the polynucleotide comprising GFP and the promoter sequence was conducted.

Next, the yeast Saccharomyces cerevisiae W303 was transformed with the resultant plasmid vector according to the following procedures:

1) Incubating the yeast Saccharomyces cerevisiae W303 in 200 ml of SD medium under shaking until OD 660 reaches 0.5;

2) Suspending the collected cells in 5 ml of TE-buffer;

3) Adding 250 μL of 2.5M lithium acetate;

4) Dispending each 300 μl, adding 10 μl of above plasmid vector thereto, then incubating the suspensions at 30° C. for 30 minutes;

5) Adding 700 μl of 50% PEG4000, and incubating the mixture under shaking at 30° C. for 60 minutes;

6) Giving heat shock (42° C., 5 minutes), and then immediately cooling the mixture;

7) Washing the mixture twice with 1M sorbitol; and

8) Seeding it on agar plates made of minimum essential medium.

The transformations were confirmed on selective medium (SD medium (Yeast nitrogen base without amino acids (Difco 0919-15)+glucose+amino acids (adenine, histidine, tryptophan)). Colonies that were grown on agar plate of selective medium were further checked for auxotrophy for amino acids.

The transformed yeast cells named SC-YCR102c-pQBI has been deposited as the International Deposition at National Institute of Advanced Industrial Science and Technology, International Patent Organism Depositary of Tsukuba Central 6, 1-1-1 Higashi, Tsukuba, Ibaraki, Japan under Accession No. FERM BP-8159 on Aug. 19, 2002.

Example 4

Primers for PCR to amplify the polynucleotide comprising the promoter of yeast gene YOR382w were prepared. Primers were designed using a primer design software, Oligo4.0-S, Sequencher I Mackintosh version. The base sequence of the upper primer was:
GCTTTTCTCGCTTCGTTATCACC (SEQ ID No: 11), whereas the base sequence of the lower primer was:
TATTATTGTTTTGTGATGGCTT (SEQ ID No: 12).

For PCR, yeast chromosome (Saccharomyces cerevisiae S288C, Cat. 40802, Research Genetics, Inc.) was used as template, and the commercially available kit (KOD DNA Polymerase; Code KOD-101, Toyobo) was used as reagents.

Type YEp shuttle vector pYES2 (pYES2, Cat no: V825-20, Invitrogen Corporation, USA), which can be replicated both in E. coli, and yeast was used as vector (R. W. Old, S. B. Primrose Principles of Gene Manipulation 5th Ed., BAIFU-KAN CO., LTD, pp 138-165, pp. 234-263, 2000). The portion of vector pQBI 63 (Cat no. 54-0082, Wako Pure Chemical Industries, Ltd.) corresponding to a marker protein GFP was used as the polynucleotide encoding GFP (SEQ ID No: 6). First, the GFP polynucleotide was inserted into the multiple cloning sites of pYES2 to give a vector. Thereafter, the GALL promoter of pYES2 was replaced with the polynucleotide comprising the promoter sequence of the intended yeast gene YOR382w (SEQ ID No: 3) to give an intended plasmid vector. Suitable restriction enzymes were selected, and the insertion of the polynucleotide comprising GFP and the promoter sequence was conducted.

Next, the yeast *Saccharomyces cerevisiae* W303 was transformed with the resultant plasmid vector according to the following procedures:

1) Incubating the yeast *Saccharomyces cerevisiae* W303 in 200 ml of SD medium under shaking until OD 660 reaches 0.5;

2) Suspending the collected cells in 5 ml of TE-buffer;

3) Adding 250 μL of 2.5M lithium acetate;

4) Dispending each 300 μl, adding 10 μl of above plasmid vector thereto, then incubating the suspensions at 30° C. for 30 minutes;

5) Adding 700 μl of 50% PEG4000, and incubating the mixture under shaking at 30° C. for 60 minutes;

6) Giving heat shock (42° C., 5 minutes), and then immediately cooling the mixture;

7) Washing the mixture twice with 1M sorbitol; and

8) Seeding it on agar plates made of minimum essential medium.

The transformations were confirmed on selective medium (SD medium (Yeast nitrogen base without amino acids (Difco 0919-15)+glucose+amino acids (adenine, histidine, tryptophan)). Colonies that were grown on agar plate of selective medium were further checked for auxotrophy for amino acids.

The transformed yeast cells named SC-YOR382W-pQBI has been deposited as the International Deposition at National Institute of Advanced Industrial Science and Technology, International Patent Organism Depositary of Tsukuba Central 6, 1-1-1 Higashi, Tsukuba, Ibaraki, Japan under Accession No. FERM BP-8160 on Aug. 19, 2002.

Example 5

Primers for PCR to amplify the polynucleotide comprising the promoter of yeast gene YLL057c were prepared. Primers were designed using a primer design software, Oligo4.0-S, Sequencher I Mackintosh version. The base sequence of the upper primer was:
GCTAACGAACAGGATGGTATTGA (SEQ ID No: 13), whereas the base sequence of the lower primer was:
ATTTTAACTGGGTTACTGTGCT (SEQ ID No: 14).

For PCR, yeast chromosome (*Saccharomyces cerevisiae* S288C, Cat. 40802, Research Genetics, Inc.) was used as template, and the commercially available kit (KOD DNA Polymerase; Code KOD-101, Toyobo) was used as reagents.

Type YEp shuttle vector pYES2 (pYES2, Cat no: V825-20, Invitrogen Corporation, USA), which can be replicated both in *E. coli*, and yeast was used as vector (R. W. Old, S. B. Primrose Principles of Gene Manipulation 5th Ed., BAIFU-KAN CO., LTD, pp 138-165, pp. 234-263, 2000). The portion of vector pQBI 63 (Cat no. 54-0082, Wako Pure Chemical Industries, Ltd.) corresponding to a marker protein GFP was used as the polynucleotide encoding GFP (SEQ ID No: 6).

First, the GFP polynucleotide was inserted into the multiple cloning sites of pYES2 to give a vector. Thereafter, the GAL1 promoter of pYES2 was replaced with the polynucleotide comprising the promoter sequence of the intended yeast gene YLL057c (SEQ ID No: 4) to give an intended plasmid vector. Suitable restriction enzymes were selected, and the insertion of the polynucleotide comprising GFP and the promoter sequence was conducted.

Next, the yeast *Saccharomyces cerevisiae* W303 was transformed with the resultant plasmid vector according to the following procedures:

1) Incubating the yeast *Saccharomyces cerevisiae* W303 in 200 ml of SD medium under shaking until OD 660 reaches 0.5;

2) Suspending the collected cells in 5 ml of TE-buffer;

3) Adding 250 μL of 2.5M lithium acetate;

4) Dispending each 300 μl, adding 10 μl of above plasmid vector thereto, then incubating the suspensions at 30° C. for 30 minutes;

5) Adding 700 μl of 50% PEG4000, and incubating the mixture under shaking at 30° C. for 60 minutes;

6) Giving heat shock (42° C., 5 minutes), and then immediately cooling the mixture;

7) Washing the mixture twice with 1M sorbitol; and

8) Seeding it on agar plates made of minimum essential medium.

The transformations were confirmed on selective medium (SD medium (Yeast nitrogen base without amino acids (Difco 0919-15)+glucose+amino acids (adenine, histidine, tryptophan)). Colonies that were grown on agar plate of selective medium were further checked for auxotrophy for amino acids.

The transformed yeast cells named SC-YLL057C-pQBI was deposited at National Institute of Advanced Industrial Science and Technology, International Patent Organism Depositary of Tsukuba Central 6, 1-1-1 Higashi, Tsukuba, Ibaraki, Japan under Accession No. FERM P-18439 on Jul. 27, 2001, and then transferred into the International Deposition under Budapest Treaty as FERM BP-8158 on Aug. 19, 2002.

Example 6

Primers for PCR to amplify the polynucleotide comprising the promoter of yeast gene YLR303w were prepared. Primers were designed using a primer design software, Oligo4.0-S, Sequencher I Mackintosh version. The base sequence of the upper primer was:
TCGTTTTCTACTTTCTTCTGCTG (SEQ ID No: 15), whereas the base sequence of the lower primer was:
TGTATGGATGGGGGTAATAGAA (SEQ ID No: 16).

For PCR, yeast chromosome (*Saccharomyces cerevisiae* S288C, Cat. 40802, Research Genetics, Inc.) was used as template, and the commercially available kit (KOD DNA Polymerase; Code KOD-101, Toyobo) was used as reagents.

Type YEp shuttle vector pYES2 (pYES2, Cat no: V825-20, Invitrogen Corporation, USA), which can be replicated both in *E. coli*, and yeast was used as vector (R. W. Old, S. B. Primrose Principles of Gene Manipulation 5th Ed., BAIFU-KAN CO., LTD, pp 138-165, pp. 234-263, 2000). The portion of vector pQBI 63 (Cat no. 54-0082, Wako Pure Chemical Industries, Ltd.) corresponding to a marker protein GFP was used as the polynucleotide encoding GFP (SEQ ID No: 6). First, the GFP polynucleotide was inserted into the multiple cloning sites of pYES2 to give a vector. Thereafter, the GAL1 promoter of pYES2 was replaced with the polynucleotide comprising the promoter sequence of the intended yeast gene YLR303w (SEQ ID No: 5) to give an intended plasmid vector. Suitable restriction enzymes were selected, and the insertion of the polynucleotide comprising GFP and the promoter sequence was conducted.

Next, the yeast *Saccharomyces cerevisiae* W303 was transformed with the resultant plasmid vector according to the following procedures:

1) Incubating the yeast *Saccharomyces cerevisiae* W303 in 200 ml of SD medium under shaking until OD 660 reaches 0.5;

2) Suspending the collected cells in 5 ml of TE-buffer;

3) Adding 250 μL of 2.5M lithium acetate;

4) Dispending each 300 μl, adding 10 μl of above plasmid vector thereto, then incubating the suspensions at 30° C. for 30 minutes;

5) Adding 700 μl of 50% PEG4000, and incubating the mixture under shaking at 30° C. for 60 minutes;

6) Giving heat shock (42° C., 5 minutes), and then immediately cooling the mixture;

7) Washing the mixture twice with 1M sorbitol; and

8) Seeding it on agar plates made of minimum essential medium.

The transformations were confirmed on selective medium (SD medium (Yeast nitrogen base without amino acids (Difco 0919-15)+glucose+amino acids (adenine, histidine, tryptophan)). Colonies that were grown on agar plate of selective medium were further checked for auxotrophy for amino acids.

The transformed yeast cells named SC-YLR303W-pQBI was deposited at National Institute of Advanced Industrial Science and Technology, International Patent Organism Depositary of Tsukuba Central 6, 1-1-1 Higashi, Tsukuba, Ibaraki, Japan under Accession No. FERM P-18438 on Jul. 27, 2001, and then transferred into the International Deposition under Budapest Treaty as FERM BP-8157 on Aug. 19, 2002.

Example 7

The cells of SC-YKL071W-pQBI as prepared in Example 2 were contacted to one of the following compounds. The yeast cells SC-YKL071W-pQBI were incubated at 25° C. in SD medium (Yeast nitrogen base without amino acids (Difco 0919-15)+glucose+amino acids (adenine, histidine, tryptophan)). One of toxic chemical substances as shown below was added to the cells at logarithmic growth phase, and then the cells were further incubated for two hours. Cells were incubated without any chemical substance in the same condition, and was used as control.

(1) benzo(a)pyrene, (2) bisphenol-A, (3) (2-ethylhexyl)phthalate, (4) 2,5-dichlorophenol, (5) 2,4-dichlorophenoxyacetic acid, (6) formaldehyde, (7) methylmercury chloride, (8) 4-nitroquinolin-N-oxide, (9) p-nonylphenol, (10) pentachlorophenol, (11) sodium arsenite, (12) Tetramethylthiuram disulfide, (13) tributyltin chloride, (14) 2,4,5-trichlorophenol, (15) Trp-P-2 (acetate), (16) paraquat, (17) cadmium chloride, (18) γ-hexachlorocyclohexane, (19) malathon, (20) manganese ethylenebis(dithiocarbamate), (21) nickel (II) chloride, (22) potassium bichromate, (23) triphenyltin chloride, (24) phenol, (25) S-4-Chlorobenzyl-N,N-diethylthiocarbamate, (26) hexachlorophene, (27) triclosan, (28) mercury(II) chloride, (29) copper sulfate (II), (30) potassium cyanide, and (31) dimethylsulfoxide.

After contacted, the yeast cells were washed once with physiological saline, and then immobilized with a physiological saline containing 5% formalin, after which the fluorescence was determined by flow cytometry (EPICS XL: BECKMAN COULTER). Fluorometric range of the control was first defined. When the number of the cells having a higher fluorescence than the control was under 1%, "−" was indicated as not showing any fluorescence, whereas when the number was between 1% and 2%, and 2% or more, then "+" and "++" were indicated as showing a fluorescence, respectively. The results are shown in Table 10.

TABLE 10

| Chemical substances | Concentrations | Fluorescens |
|---|---|---|
| (1) benzo(a)pyrene | 0.2 mM | − |
| (2) bisphenol-A | 0.4 mM | − |
| (3) (2-ethylhexyl)phthalate | 83.3 mM | − |
| (4) 2,5-dichlorophenol | 0.3 mM | − |
| (5) 2,4-dichlorophenoxyacetic acid | 0.3 mM | − |
| (6) formaldehyde | 0.2 mM | − |
| (7) methylmercury chloride | 0.2 μM | − |
| (8) 4-nitroquinolin-N-oxide | 0.6 μM | − |
| (9) p-nonylphenol | 10 μM | − |
| (10) pentachlorophenol | 50 μM | − |
| (11) sodium arsenite | 0.3 mM | − |
| (12) Tetramethylthiuram disulfide | 20 μM | + |
| (13) tributyltin chloride | 0.4 μM | − |
| (14) 2,4,5-trichlorophenol | 30 mM | − |
| (15) Trp-P-2 (acetate) | 0.2 mM | − |
| (16) paraquat | 16.7 mM | − |
| (17) cadmium chloride | 40 μM | − |
| (18) γ-hexachlorocyclohexane | 6.7 mM | − |
| (19) malathon | 22.2 mM | − |
| (20) manganese ethylenebis (dithiocarbamate) | 0.8 mM | − |
| (21) nickel (II) chloride | 3.3 mM | − |
| (22) potassium bichromate | 0.3 mM | − |
| (23) triphenyltin chloride | 10 μM | − |
| (24) phenol | 5.6 mM | − |
| (25) S-4-Chlorobenzyl-N,N-diethylthiocarbamate | 0.7 mM | − |
| (26) hexachlorophene | 30 μM | − |
| (27) triclosan | 730 μM | − |
| (28) mercury (II) chloride | 50 μM | − |
| (29) copper sulfate (II) | 3.3 mM | − |
| (30) potassium cyanide | 16.7 mM | − |
| (31) dimethylsulfoxide | 3.7% | − |

Table 10 shows that tetramethylthiuram disulfide induced the expression of GFP.

Example 8

The cells of SC-YCR102C-pQBI as prepared in Example 3 were contacted to one of the following compounds. The yeast cells SC-YCR102C-pQBI were incubated at 25° C. in SD medium (Yeast nitrogen base without amino acids (Difco 0919-15)+glucose+amino acids (adenine, histidine, tryptophan)). One of toxic chemical substances as shown below was added to the cells at logarithmic growth phase, and then the cells were further incubated for two hours. Cells were incubated without any chemical substance in the same condition, and was used as control.

(1) benzo(a)pyrene, (2) bisphenol-A, (3) (2-ethylhexyl)phthalate, (4) 2,5-dichlorophenol, (5) 2,4-dichlorophenoxyacetic acid, (6) formaldehyde, (7) methylmercury chloride, (8) 4-nitroquinolin-N-oxide, (9) p-nonylphenol, (10) pentachlorophenol, (11) sodium arsenite, (12) Tetramethylthiuram disulfide, (13) tributyltin chloride, (14) 2,4,5-trichlorophenol, (15) Trp-P-2 (acetate), (16) paraquat, (17) cadmium chloride, (18) γ-hexachlorocyclohexane, (19) malathon, (20) manganese ethylenebis(dithiocarbamate), (21) nickel (II) chloride, (22) potassium bichromate, (23) triphenyltin chloride, (24) phenol, (25) S-4-Chlorobenzyl-N,N-diethylthiocarbamate, (26) hexachlorophene, (27) triclosan, (28) mercury(II) chloride, (29) copper sulfate (II), (30) potassium cyanide, and (31) dimethylsulfoxide.

After contacted, the yeast cells were washed once with physiological saline, and then immobilized with a physiological saline containing 5% formalin, after which the fluorescence was determined by flow cytometry (EPICS XL: BECKMAN COULTER). Fluorometric range of the control was first defined. When the number of the cells having a higher fluorescence than the control was under 1%, "−" was indicated as not showing any fluorescence, whereas when the number was between 1% and 2%, and 2% or more, then "+" and "++" were indicated as showing a fluorescence, respectively. The results are shown in Table 11.

TABLE 11

| Chemical substances | Concentrations | Fluorescence |
| --- | --- | --- |
| (1) benzo(a)pyrene | 0.2 mM | − |
| (2) bisphenol-A | 0.4 mM | − |
| (3) (2-ethylhexyl)phthalate | 83.3 mM | − |
| (4) 2,5-dichlorophenol | 0.3 mM | − |
| (5) 2,4-dichlorophenoxyacetic acid | 0.3 mM | − |
| (6) formaldehyde | 0.2 mM | − |
| (7) methylmercury chloride | 0.2 μM | − |
| (8) 4-nitroquinolin-N-oxide | 0.6 μM | − |
| (9) p-nonylphenol | 10 μM | − |
| (10) pentachlorophenol | 50 μM | − |
| (11) sodium arsenite | 0.3 mM | − |
| (12) Tetramethylthiuram disulfide | 20 μM | + |
| (13) tributyltin chloride | 0.4 μM | − |
| (14) 2,4,5-trichlorophenol | 30 mM | − |
| (15) Trp-P-2 (acetate) | 0.2 mM | − |
| (16) paraquat | 16.7 mM | − |
| (17) cadmium chloride | 40 μM | − |
| (18) γ-hexachlorocyclohexane | 6.7 mM | − |
| (19) malathon | 22.2 mM | − |
| (20) manganese ethylenebis(dithiocarbamate) | 0.8 mM | − |
| (21) nickel (II) chloride | 3.3 mM | − |
| (22) potassium bichromate | 0.3 mM | − |
| (23) triphenyltin chloride | 10 μM | − |
| (24) phenol | 5.6 mM | − |
| (25) S-4-Chlorobenzyl-N,N-diethylthiocarbamate | 0.7 mM | − |
| (26) hexachlorophene | 30 μM | − |
| (27) triclosan | 730 μM | − |
| (28) mercury (II) chloride | 50 μM | − |
| (29) copper sulfate (II) | 3.3 mM | − |
| (30) potassium cyanide | 16.7 mM | − |
| (31) dimethylsulfoxide | 3.7% | − |

Table 11 shows that tetramethylthiuram disulfide induced the expression of GFP.

Example 9

The cells of SC-YOR382W-pQBI as prepared in Example 4 were contacted to one of the following compounds. The yeast cells SC-YOR382W-pQBI were incubated at 25° C. in SD medium (Yeast nitrogen base without amino acids (Difco 0919-15)+glucose+amino acids (adenine, histidine, tryptophan)). One of toxic chemical substances as shown below was added to the cells at logarithmic growth phase, and then the cells were further incubated for two hours. Cells were incubated without any chemical substance in the same condition, and was used as control.

(1) benzo(a)pyrene, (2) bisphenol-A, (3) (2-ethylhexyl)phthalate, (4) 2,5-dichlorophenol, (5) 2,4-dichlorophenoxyacetic acid, (6) formaldehyde, (7) methylmercury chloride, (8) 4-nitroquinolin-N-oxide, (9) p-nonylphenol, (10) pentachlorophenol, (11) sodium arsenite, (12) Tetramethylthiuram disulfide, (13) tributyltin chloride, (14) 2,4,5-trichlorophenol, (15) Trp-P-2 (acetate), (16) paraquat, (17) cadmium chloride, (18) γ-hexachlorocyclohexane, (19) malathon, (20) manganese ethylenebis(dithiocarbamate), (21) nickel (II) chloride, (22) potassium bichromate, (23) triphenyltin chloride, (24) phenol, (25) S-4-Chlorobenzyl-N,N-diethylthiocarbamate, (26) hexachlorophene, (27) triclosan, (28) mercury(II) chloride, (29) copper sulfate (II), (30) potassium cyanide, and (31) dimethylsulfoxide.

After contacted, the yeast cells were washed once with physiological saline, and then immobilized with a physiological saline containing 5% formalin, after which the fluorescence was determined by flow cytometry (EPICS XL: BECKMAN COULTER). Fluorometric range of the control was first defined. When the number of the cells having a higher fluorescence than the control was under 1%, "−" was indicated as not showing any fluorescence, whereas when the number was between 1% and 2%, and 2% or more, then "+" and "++" were indicated as showing a fluorescence, respectively. The results are shown in Table 12.

TABLE 12

| Chemical substances | Concentrations | Fluorescence |
| --- | --- | --- |
| (1) benzo(a)pyrene | 0.2 mM | − |
| (2) bisphenol-A | 0.4 mM | − |
| (3) (2-ethylhexyl)phthalate | 83.3 mM | − |
| (4) 2,5-dichlorophenol | 0.3 mM | ++ |
| (5) 2,4-dichlorophenoxyacetic acid | 0.3 mM | − |
| (6) formaldehyde | 0.2 mM | − |
| (7) methylmercury chloride | 0.2 μM | − |
| (8) 4-nitroquinolin-N-oxide | 0.6 μM | ++ |
| (9) p-nonylphenol | 10 μM | ++ |
| (10) pentachlorophenol | 50 μM | − |
| (11) sodium arsenite | 0.3 mM | − |
| (12) Tetramethylthiuram disulfide | 20 μM | − |
| (13) tributyltin chloride | 0.4 μM | − |
| (14) 2,4,5-trichlorophenol | 30 mM | ++ |
| (15) Trp-P-2 (acetate) | 0.2 mM | ++ |
| (16) paraquat | 16.7 mM | − |
| (17) cadmium chloride | 40 μM | − |
| (18) γ-hexachlorocyclohexane | 6.7 mM | − |
| (19) malathon | 22.2 mM | ++ |
| (20) manganese ethylenebis(dithiocarbamate) | 0.8 mM | ++ |
| (21) nickel (II) chloride | 3.3 mM | ++ |
| (22) potassium bichromate | 0.3 mM | ++ |
| (23) triphenyltin chloride | 10 μM | − |
| (24) phenol | 5.6 mM | ++ |
| (25) S-4-Chlorobenzyl-N,N-diethylthiocarbamate | 0.7 mM | − |
| (26) hexachlorophene | 30 μM | − |
| (27) triclosan | 730 μM | − |
| (28) mercury(II) chloride | 50 μM | − |
| (29) copper sulfate (II) | 3.3 mM | − |
| (30) potassium cyanide | 16.7 mM | − |
| (31) dimethylsulfoxide | 3.7% | ++ |

Table 12 shows that 2,4-dichlorophenoxyacetic acid, 4-nitroquinolin-N-oxide, p-nonylphenol, 2,4,5-trichlorophenol, Trp-P-2 (acetate), malathon, manganese ethylenebis(dithiocarbamate), nickel (II) chloride, potassium bichromate, phenol, and dimethylsulfoxide induced the expression of GFP.

Example 10

The cells of SC-YLL057C-pQBI as prepared in Example 5 were contacted to one of the following compounds. The yeast cells SC-YLL057C-pQBI were incubated at 25° C. in SD medium (Yeast nitrogen base without amino acids (Difco 0919-15)+glucose+amino acids (adenine, histidine, tryptophan)). One of toxic chemical substances as shown below was added to the cells at logarithmic growth phase, and then the cells were further incubated for two hours. Cells were incubated without any chemical substance in the same condition, and was used as control.

(1) benzo(a)pyrene, (2) bisphenol-A, (3) (2-ethylhexyl)phthalate, (4) 2,5-dichlorophenol, (5) 2,4-dichlorophenoxyacetic acid, (6) formaldehyde, (7) methylmercury chloride, (8) 4-nitroquinolin-N-oxide, (9) p-nonylphenol, (10) pentachlorophenol, (11) sodium arsenite, (12) Tetramethylthiuram disulfide, (13) tributyltin chloride, (14) 2,4,5-trichlorophenol, (15) Trp-P-2 (acetate), (16) paraquat, (17) cadmium chloride, (18) γ-hexachlorocyclohexane, (19) malathon, (20) manganese ethylenebis(dithiocarbamate), (21) nickel (II) chloride, (22) potassium bichromate, (23) triphenyltin chloride, (24) phenol, (25) S-4-Chlorobenzyl-N,N-diethylthiocarbamate, (26) hexachlorophene, (27) triclosan, (28) mercury(II) chloride, (29) copper sulfate (II), (30) potassium cyanide, and (31) dimethylsulfoxide.

After contacted, the yeast cells were washed once with physiological saline, and then immobilized with a physiological saline containing 5% formalin, after which the fluorescence was determined by flow cytometry (EPICS XL: BECKMAN COULTER). Fluorometric range of the control was first defined. When the number of the cells having a higher fluorescence than the control was under 1%, "−" was indicated as not showing any fluorescence, whereas when the number was between 1% and 2%, and 2% or more, then "+" and "++" were indicated as showing a fluorescence, respectively. The results are shown in Table 13.

TABLE 13

| Chemical substances | Concentrations | Fluorescence |
|---|---|---|
| (1) benzo(a)pyrene | 0.2 mM | − |
| (2) bisphenol-A | 0.4 mM | − |
| (3) (2-ethylhexyl)phthalate | 83.3 mM | − |
| (4) 2,5-dichlorophenol | 0.3 mM | − |
| (5) 2,4-dichlorophenoxyacetic acid | 0.3 mM | ++ |
| (6) formaldehyde | 0.2 mM | − |
| (7) methylmercury chloride | 0.2 μM | − |
| (8) 4-nitroquinolin-N-oxide | 0.6 μM | − |
| (9) p-nonylphenol | 10 μM | − |
| (10) pentachlorophenol | 50 μM | − |
| (11) sodium arsenite | 0.3 mM | ++ |
| (12) Tetramethylthiuram disulfide | 20 μM | − |
| (13) tributyltin chloride | 0.4 μM | − |
| (14) 2,4,5-trichlorophenol | 30 mM | − |
| (15) Trp-P-2 (acetate) | 0.2 mM | − |
| (16) paraquat | 16.7 mM | − |
| (17) cadmium chloride | 40 μM | ++ |
| (18) γ-hexachlorocyclohexane | 6.7 mM | − |
| (19) malathon | 22.2 mM | − |
| (20) manganese ethylenebis(dithiocarbamate) | 0.8 mM | − |
| (21) nickel (II) chloride | 3.3 mM | − |
| (22) potassium bichromate | 0.3 mM | − |
| (23) triphenyltin chloride | 10 μM | − |
| (24) phenol | 5.6 mM | − |

TABLE 13-continued

| Chemical substances | Concentrations | Fluorescence |
|---|---|---|
| (25) S-4-Chlorobenzyl-N,N-diethylthiocarbamate | 0.7 mM | − |
| (26) hexachlorophene | 30 μM | − |
| (27) triclosan | 730 μM | − |
| (28) mercury(II) chloride | 50 μM | − |
| (29) copper sulfate (II) | 3.3 mM | − |
| (30) potassium cyanide | 16.7 mM | ++ |
| (31) dimethylsulfoxide | 3.7% | − |

Table 13 shows that 2,4-dichlorophenoxyacetic acid, sodium arsenite, cadmium chloride, and potassium cyanide induced the expression of GFP.

Example 11

The cells of SC-YCR303W-pQBI as prepared in Example 6 were contacted to one of the following compounds. The yeast cells SC-YCR303W-pQBI were incubated at 25° C. in SD medium (Yeast nitrogen base without amino acids (Difco 0919-15)+glucose+amino acids (adenine, histidine, tryptophan)). One of toxic chemical substances as shown below was added to the cells at logarithmic growth phase, and then the cells were further incubated for two hours. Cells were incubated without any chemical substance in the same condition, and was used as control.

(1) benzo(a)pyrene, (2) bisphenol-A, (3) (2-ethylhexyl)phthalate, (4) 2,5-dichlorophenol, (5) 2,4-dichlorophenoxyacetic acid, (6) formaldehyde, (7) methylmercury chloride, (8) 4-nitroquinolin-N-oxide, (9) p-nonylphenol, (10) pentachlorophenol, (11) sodium arsenite, (12) Tetramethylthiuram disulfide, (13) tributyltin chloride, (14) 2,4,5-trichlorophenol, (15) Trp-P-2 (acetate), (16) paraquat, (17) cadmium chloride, (18) γ-hexachlorocyclohexane, (19) malathon, (20) manganese ethylenebis(dithiocarbamate), (21) nickel (II) chloride, (22) potassium bichromate, (23) triphenyltin chloride, (24) phenol, (25) S-4-Chlorobenzyl-N,N-diethylthiocarbamate, (26) hexachlorophene, (27) triclosan, (28) mercury(II) chloride, (29) copper sulfate (II), (30) potassium cyanide, and (31) dimethylsulfoxide.

After contacted, the yeast cells were washed once with physiological saline, and then immobilized with a physiological saline containing 5% formalin, after which the fluorescence was determined by flow cytometry (EPICS XL: BECKMAN COULTER). Fluorometric range of the control was first defined. When the number of the cells having a higher fluorescence than the control was under 1%, "−" was indicated as not showing any fluorescence, whereas when the number was between 1% and 2%, and 2% or more, then "+" and "++" were indicated as showing a fluorescence, respectively. The results are shown in Table 14.

TABLE 14

| Chemical substances | Concentrations | Fluorescence |
|---|---|---|
| (1) benzo(a)pyrene | 0.2 mM | ++ |
| (2) bisphenol-A | 0.4 mM | − |
| (3) (2-ethylhexyl)phthalate | 83.3 mM | − |
| (4) 2,5-dichlorophenol | 0.3 mM | − |
| (5) 2,4-dichlorophenoxyacetic acid | 0.3 mM | ++ |
| (6) formaldehyde | 0.2 mM | ++ |
| (7) methylmercury chloride | 0.2 μM | − |
| (8) 4-nitroquinolin-N-oxide | 0.6 μM | − |
| (9) p-nonylphenol | 10 μM | − |
| (10) pentachlorophenol | 50 μM | − |

TABLE 14-continued

| Chemical substances | Concentrations | Fluorescence |
|---|---|---|
| (11) sodium arsenite | 0.3 mM | ++ |
| (12) Tetramethylthiuram disulfide | 20 μM | − |
| (13) tributyltin chloride | 0.4 μM | − |
| (14) 2,4,5-trichlorophenol | 30 mM | − |
| (15) Trp-P-2 (acetate) | 0.2 mM | − |
| (16) paraquat | 16.7 mM | − |
| (17) cadmium chloride | 40 μM | ++ |
| (18) γ-hexachlorocyclohexane | 6.7 mM | − |
| (19) malathon | 22.2 mM | − |
| (20) manganese ethylenebis (dithiocarbamate) | 0.8 mM | + |
| (21) nickel (II) chloride | 3.3 mM | − |
| (22) potassium bichromate | 0.3 mM | − |
| (23) triphenyltin chloride | 10 μM | − |
| (24) phenol | 5.6 mM | − |

TABLE 14-continued

| Chemical substances | Concentrations | Fluorescence |
|---|---|---|
| (25) S-4-Chlorobenzyl-N,N-diethylthiocarbamate | 0.7 mM | − |
| (26) hexachlorophene | 30 μM | − |
| (27) triclosan | 730 μM | − |
| (28) mercury (II) chloride | 50 μM | ++ |
| (29) copper sulfate (II) | 3.3 mM | − |
| (30) potassium cyanide | 16.7 mM | ++ |
| (31) dimethylsulfoxide | 3.7% | − |

Table 14 shows that benzo(a)pyrene, 2,4-dichlorophenoxyacetic acid, formaldehyde, sodium arsenite, cadmium chloride, manganese ethylenebis(dithiocarbamate), mercury (II) chloride, and potassium cyanide induced the expression of GFP.

The invention claimed is:

1. A process for detecting a toxic compound in a test material, wherein said toxic compound is selected from the group consisting of 2,5-dichlorophenol, 4-nitroquinolin-N-oxide, p-nonylphenol, 2,4,5-trichlorophenol, Trp-P-2(acetate), malathon, manganese ethylenebis (dithiocarbamate), nickel (II) chloride, potassium bichromate, phenol and dimethylsulfoxide, wherein said process comprises:

(1) contacting the test material to a cell that is transformed with a polynucleotide or with a vector comprising said polynucleotide, wherein said polynucleotide comprises a polynucleotide sequence operably linked to a polynucleotide encoding a marker protein, and wherein said polynucleotide sequence comprises SEQ ID NO: 3; and (2) detecting said toxic compound via an expression of mRNA encoding a marker protein, wherein the mRNA expression is a result of said toxic compound activating expression of the gene within SEQ ID NO: 3.

2. The process according to claim 1, wherein the expression of mRNA is confirmed by the expression of a marker protein.

3. The process according to claim 1, wherein the expression of mRNA is detected by northern blotting.

4. The process according to claim 1, wherein said mRNA is amplified by reverse transcription-PCR (RT-PCR), and the expression of mRNA is detected.

* * * * *

UNITED STATES PATENT AND TRADEMARK OFFICE
CERTIFICATE OF CORRECTION

| | | |
|---|---|---|
| PATENT NO. | : 7,704,692 B1 | Page 1 of 1 |
| APPLICATION NO. | : 11/758288 | |
| DATED | : April 27, 2010 | |
| INVENTOR(S) | : Hitoshi Iwahashi et al. | |

It is certified that error appears in the above-identified patent and that said Letters Patent is hereby corrected as shown below:

On the title page, Item (73), that part of the Assignee name reading "Daiken Industries, Ltd." should read --Daikin Industries, Ltd.--.

Signed and Sealed this

Nineteenth Day of October, 2010

David J. Kappos
*Director of the United States Patent and Trademark Office*